(12) United States Patent
Chassaing et al.

(10) Patent No.: US 8,569,495 B2
(45) Date of Patent: Oct. 29, 2013

(54) ANTHELMINTIC AGENTS AND THEIR USE

(75) Inventors: Christophe Pierre Alain Chassaing, Schwabenheim (DE); Jörg Schröder, Schwabenheim (DE); Thomas Simon Ilg, Schwabenheim (DE); Manfred Uphoff, Schwabenheim (DE); Thorsten Meyer, Schwabenheim (DE)

(73) Assignee: Intervet International B.V., Boxmeer (NL)

( * ) Notice: Subject to any disclaimer, the term of this patent is extended or adjusted under 35 U.S.C. 154(b) by 276 days.

(21) Appl. No.: 12/808,897

(22) PCT Filed: Dec. 16, 2008

(86) PCT No.: PCT/EP2008/067621
§ 371 (c)(1),
(2), (4) Date: Oct. 19, 2010

(87) PCT Pub. No.: WO2009/077527
PCT Pub. Date: Jun. 25, 2009

(65) Prior Publication Data
US 2011/0021506 A1    Jan. 27, 2011

Related U.S. Application Data

(60) Provisional application No. 61/014,242, filed on Dec. 17, 2007.

(30) Foreign Application Priority Data

Feb. 25, 2008   (EP) .................................... 08101961

(51) Int. Cl.
C07D 295/00    (2006.01)
A61K 31/497    (2006.01)
A61K 31/4965   (2006.01)

(52) U.S. Cl.
USPC .... 544/386; 544/392; 514/252.1; 514/255.01

(58) Field of Classification Search
USPC ........................................................ 544/386
See application file for complete search history.

(56) References Cited

U.S. PATENT DOCUMENTS 4,247,710 A  *  1/1981  Fahrenholtz et al. .......... 560/55

FOREIGN PATENT DOCUMENTS

WO         WO9714689 A1  *  4/1997

OTHER PUBLICATIONS

Sparatore, A. et al., Pharm. Pharmacol. Commun. 2000, 6: 421-425.*
Shalif, A. et al. JACS vol. 129, pp. 3490-3491. Published 2007.*

* cited by examiner

*Primary Examiner* — Paul Zarek
*Assistant Examiner* — George W Kosturko

(57) ABSTRACT

This invention is directed to compounds and salts that are generally useful as anthelmintic agents or as intermediates in processes for making anthelmintic agents. This invention also is directed to processes for making the compounds and salts, pharmaceutical compositions and kits comprising the compounds and salts, uses of the compounds and salts to make medicaments, and treatments comprising the administration of the compounds and salts to animals in need of the treatments.

31 Claims, No Drawings

ANTHELMINTIC AGENTS AND THEIR USE

CROSS-REFERENCE TO RELATED PATENT APPLICATIONS

This patent claims priority to U.S. Provisional Patent Appl. No. 61/014,242 (filed Dec. 17, 2007); and European Patent Appl. No. 08101961.4 (filed Feb. 25, 2008). The entire text of both patent applications is incorporated by reference into this patent.

FIELD OF THE INVENTION

This invention relates to compounds (and salts thereof) that are generally useful as anthelmintic agents or as intermediates in processes for making anthelmintic agents. This invention also relates to processes for making the compounds and salts, pharmaceutical compositions and kits comprising the compounds and salts, uses of the compounds and salts to make medicaments, and treatments comprising the administration of the compounds and salts to animals in need of the treatments.

BACKGROUND OF THE INVENTION

Parasitic diseases in humans and animals cause substantial suffering and economic losses throughout the world. Thus, control of parasitic infections remains an important global endeavor. The causative organisms include endoparasites, such as nematodes, cestodes, and trematodes. These organisms can infect, for example, the stomach, intestinal tract, lymphatic system, tissues, liver, lungs, heart, and brain.

There are many known drugs (or "anthelmintic agents") available to treat various endoparasitic infections. These reportedly include, for example, various avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); a thiazole benzimidazole derivatives (e.g., thiabendazole and cambendazole); carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzoenedisulphonamides (e.g., clorsulon); pyrazinaisoquinoline (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); and paraherquamides. See, e.g., McKellar, Q. A., et al., "Veterinary anthelmintics: old and new," *Review: Trends in Parasitology,* 20(10), 456-61 (October 2004).

While many endoparasitic infections can be treated with known drugs, evolutionary development of resistance by the parasites can render such drugs obsolete over time. See, e.g., Jabbar, A., et al., "Anthelmintic resistance: the state of play revisited," *Life Sciences,* 79, 2413-31 (2006). In addition, known drugs may have other deficiencies, such as limited spectrum of activity and the need for repeated treatments. Thus, there still exists a need for new anthelmintic agents to ensure safe, effective, and convenient treatment of a wide range of endoparasitic infections over a long period of time.

The following disclosure describes a group of such agents, as well as methods for making and using them.

SUMMARY OF THE INVENTION

Briefly, this invention is related to compounds (and salts thereof) that can generally be used as anthelmintic agents. The compounds correspond in structure to Formula I:

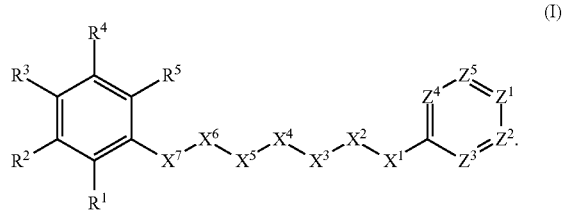

(I)

In Formula (I), each of $R^1$, $R^2$, $R^3$, $R^4$, and $R^5$ is independently selected from the group consisting of hydrogen, halogen, cyano, alkyl, alkoxy, nitro, aminosulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, amino sulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl are optionally substituted with one or more substituents independently selected from the group consisting of halogen, cyano, alkyl, alkoxy, haloalkyl, haloalkoxy, alkylsulfanyl, and haloalkylsulfanyl.

$X^1$ is selected from the group consisting of —O—, —C(O)—, —S—, —S(O)—, —S(O)$_2$—, and —NH—. The —NH— is optionally substituted with a substituent selected from the group consisting of alkyl, alkenyl, alkynyl, alkoxyalkyl, carbocyclyl, and carbocyclylalkyl. Any such substituent is optionally substituted with one or more independently selected halogen.

$X^2$ is selected from the group consisting of straight-chain $C_3$-$C_5$-alkyl, straight-chain $C_3$-$C_5$-alkenyl, straight-chain $C_3$-$C_5$-alkynyl, and $C_4$-$C_6$-carbocyclyl. The straight-chain $C_3$-$C_5$-alkyl, straight-chain $C_3$-$C_5$-alkenyl, straight-chain $C_3$-$C_5$-alkynyl, and $C_4$-$C_6$-carbocyclyl are optionally substituted with one or more independently selected alkyl.

$X^3$ is selected from the group consisting of —CH$_2$—, —O—, —C(O)—, —S—, —S(O)—, —S(O)$_2$—, and —NH—. The —CH$_2$— is optionally substituted with up to two substituents independently selected from the group consisting of alkyl and carbocyclyl. The —NH— is optionally substituted with a substituent selected from the group consisting of alkyl, alkenyl, alkynyl, alkoxyalkyl, carbocyclyl, and carbocyclylalkyl. Any such substituent of —NH— is optionally substituted with one or more independently selected halogen.

$X^4$ is selected from the group consisting of —CH$_2$— and —NH—. The —CH$_2$— is optionally substituted with up to two substituents independently selected from the group consisting of alkyl, haloalkyl, and alkenyl. The —NH— is optionally substituted with a substituent selected from the group consisting of alkyl, alkenyl, alkynyl, alkoxy alkyl, carbocyclyl, and carbocyclylalkyl. Any such substituent of —NH— is optionally substituted with one or more independently selected halogen.

$X^5$ is selected from the group consisting of —CH$_2$—, —O—, —C(S)—, —C(O)—, —S(O)—, and —S(O)$_2$—.

The —CH$_2$— is optionally substituted with up to two substituents independently selected from the group consisting of alkyl and carbocyclyl.

X$^6$ is a linker. The linker is a hydrocarbon group, except: (a) the linker comprises one or more nitrogen atoms, and (b) one or more of the carbons in the hydrocarbon optionally are substituted with one or more substituents independently selected from the group consisting of oxo, thiocarbonyl, halogen, hydroxy, and alkoxy. The linker comprises at least one chain of from 3 to 6 atoms that bridges X$^5$ to X$^7$. From 1 to 2 of the chain atoms are nitrogen. The linker has no chain of less than 3 atoms that bridges X$^5$ and X$^7$.

X$^7$ is selected from the group consisting of a bond, —O—, —C(O)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$—. The —NH— is optionally substituted with alkyl. The —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$— are optionally substituted with one or more independently selected alkyl.

Z$^1$ is selected from the group consisting of N and CH. The CH is substituted with a substituent selected from the group consisting of halogen, nitro, cyano, aminosulfonyl, alkyl, alkoxy, alkoxycarbonyl, alkylsulfanyl, alkylsulfinyl, alkylsulfonyl, aryl, arylsulfanyl, arylsulfinyl, arylsulfonyl, heteroaryl, heteroarylsulfanyl, heteroarylsulfinyl, and heteroarylsulfonyl. The alkyl, alkoxy, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl; and the aminosulfonyl is optionally substituted with up to two independently selected alkyl.

Z$^2$ is selected from the group consisting of N and CH. The CH is optionally substituted with a substituent selected from the group consisting of cyano, halogen, nitro, alkyl, alkoxy, haloalkyl, and haloalkylsulfanyl.

Each of Z$^3$, Z$^4$, and Z$^5$ is independently selected from the group consisting of N and CH. The CH is optionally substituted with a substituent selected from the group consisting of halogen, cyano, nitro, alkyl, alkoxy, alkylsulfanyl, haloalkyl, haloalkoxy, and haloalkylsulfanyl.

This invention also is directed, in part, to methods for making the above-described compounds and salts of this invention.

This invention also is directed, in part, to pharmaceutical compositions. The pharmaceutical compositions comprise at least one compound or salt of this invention, and at least one excipient.

This invention also is directed, in part, to methods for treating a disease in an animal, particularly a parasitic infection. The methods comprise administering at least one compound or salt of this invention to the animal.

This invention also is directed, in part, to a use of at least one compound or salt of this invention to prepare a medicament for treating a disease (e.g., a parasitic infection) in an animal.

This invention also is directed, in part, to a kit. The kit comprises at least one compound or salt of this invention. In addition, the kit comprises at least one other component, such as another ingredient (e.g., an excipient or active ingredient), instructions and/or an apparatus for combining the compound or salt with another ingredient, instructions and/or an apparatus for administering the compound or salt, and/or a diagnostic tool.

Further benefits of Applicants' invention will be apparent to one skilled in the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

I. Compounds Of This Invention

The compounds of this invention generally correspond in structure to Formula (I):

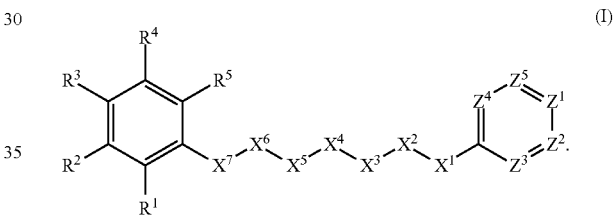

The substituents in Formula (I) are defined as follows:

A. Preferred Embodiments of R$^1$, R$^2$, R$^3$, R$^4$, and R$^5$

Each of R$^1$, R$^2$, R$^3$, R$^4$, and R$^5$ is independently selected from the group consisting of hydrogen, halogen, cyano, alkyl, alkoxy, nitro, aminosulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, amino sulfonyl, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl are optionally substituted with one or more substituents independently selected from the group consisting of halogen, cyano, alkyl, alkoxy, haloalkyl, haloalkoxy, alkylsulfanyl, and haloalkylsulfanyl.

In some embodiments, each of R$^1$, R$^2$, R$^3$, R$^4$, and R$^5$ is independently selected from the group consisting of hydrogen, halogen, cyano, alkyl, alkoxy, nitro, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl are optionally substituted with one or more substituents independently selected from the group consisting of halogen, cyano, alkyl, alkoxy, haloalkyl, haloalkoxy, alkylsulfanyl, and haloalkylsulfanyl.

In some embodiments, $R^1$, $R^2$, $R^3$, $R^4$, and $R^5$ are each independently selected from the group consisting of hydrogen, halogen, cyano, $C_1$-$C_6$-alkyl, $C_1$-$C_6$-alkoxy, nitro, $C_1$-$C_6$-alkoxycarbonyl, $C_1$-$C_6$-alkylsulfanyl, aryl, aryloxy, aryl-$C_1$-$C_6$-alkoxy, arylsulfanyl, aryl-$C_1$-$C_6$-alkylsulfanyl, heteroaryl, heteroaryloxy, heteroaryl-$C_1$-$C_6$-alkoxy, heteroarylsulfanyl, and heteroaryl-$C_1$-$C_6$-alkylsulfanyl. The $C_1$-$C_6$-alkyl, $C_1$-$C_6$-alkoxy, $C_1$-$C_6$-alkoxycarbonyl, $C_1$-$C_6$-alkylsulfanyl, aryl, aryloxy, aryl-$C_1$-$C_6$-alkoxy, arylsulfanyl, aryl-$C_1$-$C_6$-alkylsulfanyl, heteroaryl, heteroaryloxy, heteroaryl-$C_1$-$C_6$-alkoxy, heteroarylsulfanyl, and heteroaryl-$C_1$-$C_6$-alkylsulfanyl are optionally substituted with one or more substituents independently selected from the group consisting of halogen, cyano, $C_1$-$C_6$-alkyl, $C_1$-$C_6$-alkoxy, halo-$C_1$-$C_6$-alkyl, halo-$C_1$-$C_6$-alkoxy, $C_1$-$C_6$-alkylsulfanyl, and halo-$C_1$-$C_6$-alksulfanyl. In some such embodiments, each aryl is phenyl, and each heteroaryl is a 5- to 6-member heteroaryl.

In some embodiments, $R^1$, $R^2$, $R^3$, $R^4$, and $R^5$ are each independently selected from the group consisting of hydrogen, halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy.

In some embodiments, $R^1$, $R^2$, $R^3$, $R^4$, and $R^5$ are each independently selected from the group consisting of hydrogen, halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen and halo-$C_1$-$C_6$-alkyl.

In some embodiments, $R^1$, $R^2$, $R^3$, $R^4$, and $R^5$ are each independently selected from the group consisting of hydrogen, chloro, fluoro, cyano, nitro, methyl, tert-butyl, n-propyl, trifluoromethyl, ethyl, methoxy, ethoxy, trifluoromethoxy, trifluoromethylsulfanyl, iso-butoxy, phenyl, phenoxy, benzyloxy, and 4-trifluoromethylbenzyloxy.

In some embodiments, $R^1$, $R^2$, $R^3$, $R^4$, and $R^5$ are each independently selected from the group consisting of hydrogen, halogen, cyano, and $C_1$-$C_6$-alkyl. In some such embodiments, $R^1$, $R^2$, $R^3$, $R^4$, and $R^5$ are each independently selected from the group consisting of hydrogen, fluoro, chloro, cyano, methyl, ethyl, n-propyl, and tert-butyl.

In some embodiments, $R^1$, $R^2$, $R^3$, $R^4$, and $R^5$ are each independently selected from the group consisting of hydrogen and halogen. In some such embodiments, $R^1$, $R^2$, $R^3$, $R^4$, and $R^5$ are each independently selected from the group consisting of hydrogen, chloro, and fluoro. In other embodiments, $R^1$, $R^2$, $R^3$, $R^4$, and $R^5$ are each independently selected from the group consisting of hydrogen and fluoro. In still other embodiments, $R^1$, $R^2$, $R^3$, $R^4$, and $R^5$ are each independently selected from the group consisting of hydrogen and chloro.

In some embodiments, $R^1$, $R^2$, $R^3$, $R^4$, and $R^5$ are each independently selected from the group consisting of hydrogen and cyano.

In some embodiments, $R^1$, $R^2$, $R^3$, $R^4$, and $R^5$ are each independently selected from the group consisting of hydrogen and trifluoromethyl.

In some embodiments, $R^1$, $R^2$, $R^3$, $R^4$, and $R^5$ are each independently selected from the group consisting of hydrogen, phenyl, and $C_1$-$C_6$-alkylphenyl.

In some embodiments, $R^1$, $R^2$, $R^3$, $R^4$, and $R^5$ are each independently selected from the group consisting of hydrogen and $C_1$-$C_6$-alkyl. In some such embodiments, $R^1$, $R^2$, $R^3$, $R^4$, and $R^5$ are each independently selected from the group consisting of hydrogen, methyl, ethyl, n-propyl, and tert-butyl. In other embodiments, $R^1$, $R^2$, $R^3$, $R^4$, and $R^5$ are each independently selected from the group consisting of hydrogen and methyl. In other embodiments, $R^1$, $R^2$, $R^3$, $R^4$, and $R^5$ are each independently selected from the group consisting of hydrogen and ethyl. In other embodiments, $R^1$, $R^2$, $R^3$, $R^4$, and $R^5$ are each independently selected from the group consisting of hydrogen and n-propyl. In still other embodiments, $R^1$, $R^2$, $R^3$, $R^4$, and $R^5$ are each independently selected from the group consisting of hydrogen and tert-butyl.

In some embodiments, one of $R^1$, $R^2$, $R^3$, $R^4$, and $R^5$ is hydrogen; and the remaining four of $R^1$, $R^2$, $R^3$, $R^4$, and $R^5$ are each other than hydrogen. In some such embodiments, $R^3$ is one of the substituents that is other than hydrogen.

In some embodiments, two of $R^1$, $R^2$, $R^3$, $R^4$, and $R^5$ are each hydrogen; and the remaining three of $R^1$, $R^2$, $R^3$, $R^4$, and $R^5$ are each other than hydrogen. In some such embodiments, $R^3$ is one of the substituents that is other than hydrogen. For example, in some such embodiments, $R^2$, $R^3$, and $R^4$ are the three substituents that are each other than hydrogen. In other embodiments, $R^1$, $R^3$, and $R^5$ are the substituents that are each other than hydrogen. In still other embodiments, $R^1$, $R^3$, and $R^4$ are the substituents that are each other than hydrogen.

In some embodiments, three of $R^1$, $R^2$, $R^3$, $R^4$, and $R^5$ are each hydrogen; and the remaining two of $R^1$, $R^2$, $R^3$, $R^4$, and $R^5$ are each other than hydrogen. In some such embodiments, $R^3$ is one of the substituents that is other than hydrogen. For example, in some such embodiments, $R^2$ and $R^3$ are the two substituents that are each other than hydrogen. In other embodiments, $R^1$ and $R^3$ are the two substituents that are each other than hydrogen. In other embodiments, $R^1$ and $R^2$ are the two substituents that are each other than hydrogen.

In some embodiments, four of $R^1$, $R^2$, $R^3$, $R^4$, and $R^5$ are each hydrogen; and the remaining one of $R^1$, $R^2$, $R^3$, $R^4$, and $R^5$ is other than hydrogen. In some such embodiments, $R^3$ is the substituent that is other than hydrogen.

In some embodiments, all of $R^1$, $R^2$, $R^3$, $R^4$, and $R^5$ are each hydrogen.

In some embodiments, $R^3$ is selected from the group consisting of halogen, cyano, alkyl, alkoxy, nitro, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, alkoxycarbonyl, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl are optionally substituted with one or more substituents independently selected from the group consisting of halogen, cyano, alkyl, alkoxy, haloalkyl, haloalkoxy, alkylsulfanyl, and haloalkylsulfanyl.

In some embodiments, $R^3$ is selected from the group consisting of halogen, cyano, $C_1$-$C_6$-alkyl, $C_1$-$C_6$-alkoxy, nitro, $C_1$-$C_6$-alkoxycarbonyl, $C_1$-$C_6$-alkylsulfanyl, aryl, aryloxy, aryl-$C_1$-$C_6$-alkoxy, arylsulfanyl, aryl-$C_1$-$C_6$-alkylsulfanyl, heteroaryl, heteroaryloxy, heteroaryl-$C_1$-$C_6$-alkoxy, heteroarylsulfanyl, and heteroaryl-$C_1$-$C_6$-alkylsulfanyl. The $C_1$-$C_6$-alkyl, $C_1$-$C_6$-alkoxy, $C_1$-$C_6$-alkoxycarbonyl, $C_1$-$C_6$-alkylsulfanyl, aryl, aryloxy, aryl-$C_1$-$C_6$-alkoxy, arylsulfanyl, aryl-$C_1$-$C_6$-alkylsulfanyl, heteroaryl, heteroaryloxy, heteroaryl-$C_1$-$C_6$-alkoxy, heteroarylsulfanyl, and heteroaryl-$C_1$-$C_6$-alkylsulfanyl are optionally substituted with one or more substituents independently selected from the group consisting of halogen, cyano, $C_1$-$C_6$-alkyl, $C_1$-$C_6$-alkoxy, halo- $C_1$-$C_6$-alkyl, halo-$C_1$-$C_6$-alkoxy, $C_1$-$C_6$-alkylsulfanyl, and halo-$C_1$-$C_6$-alksulfanyl. In some such embodiments, each aryl is phenyl, and each heteroaryl is a 5- to 6-member heteroaryl.

In some embodiments, $R^3$ is selected from the group consisting of halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy.

In some embodiments, $R^3$ is selected from the group consisting of halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen and halo-$C_1$-$C_6$-alkyl.

In some embodiments, $R^3$ is selected from the group consisting of chloro, fluoro, cyano, nitro, methyl, tert-butyl, n-propyl, trifluoromethyl, ethyl, methoxy, ethoxy, trifluoromethoxy, trifluoromethylsulfanyl, iso-butoxy, phenyl, phenoxy, benzyloxy, and 4-trifluoromethylbenzyloxy.

In some embodiments, $R^3$ is chloro.
In some embodiments, $R^3$ is fluoro.
In some embodiments, $R^3$ is cyano.
In some embodiments, $R^3$ is methyl.
In some embodiments, $R^3$ is ethyl.
In some embodiments, $R^3$ is n-propyl.
In some embodiments, $R^3$ is tent-butyl.
In some embodiments, $R^3$ is trifluoromethyl.

B. Preferred Embodiments of $X^1$ $X^1$ is selected from the group consisting of —O—, —C(O)—, —S—, —S(O)—, —S(O)$_2$—, and —NH—. Here, the —NH— is optionally substituted with a substituent selected from the group consisting of alkyl, alkenyl, alkynyl, alkoxyalkyl, carbocyclyl, and carbocyclylalkyl. Any such substituent is optionally substituted with one or more independently selected halogen.

In some embodiments, $X^1$ is selected from the group consisting of —O—, —C(O)—, —S—, —S(O)—, —S(O)$_2$—, and —NH—. Here, the —NH— is optionally substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. Any such substituent is optionally substituted with one or more independently selected halogen.

In some embodiments, $X^1$ is —O—. In such embodiments, the compound is encompassed by the following formula:

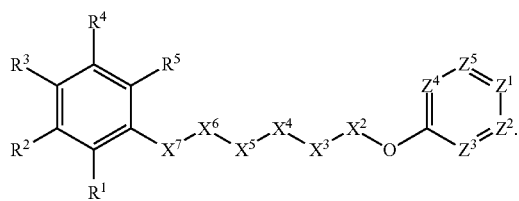

In some embodiments, $X^1$ is —NH— optionally substituted with $C_1$-$C_6$-alkyl. To illustrate, in some such embodiments, $X^1$ is —NH—. In such embodiments, the compound is encompassed by the following formula:

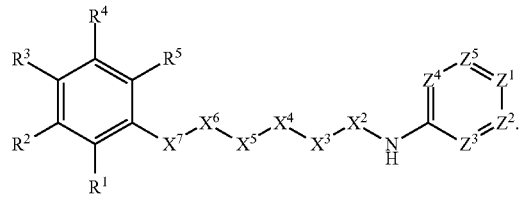

In other embodiments, for example, $X^1$ is —N(CH$_3$)—. Here, the compound is encompassed by the following formula:

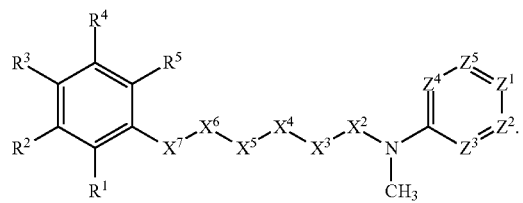

C. Preferred Embodiments of $X^2$ $X^2$ is selected from the group consisting of straight-chain $C_3$-$C_5$-alkyl, straight-chain $C_3$-$C_5$-alkenyl, straight-chain $C_3$-$C_5$-alkynyl, and $C_4$-$C_6$-carbocyclyl. The straight-chain $C_3$-$C_5$-alkyl, straight-chain $C_3$-$C_5$-alkenyl, straight-chain $C_3$-$C_5$-alkynyl, and $C_4$-$C_6$-carbocyclyl are optionally substituted with one or more independently selected alkyl. In some such embodiments, the straight-chain $C_3$-$C_5$-alkyl, straight-chain $C_3$-$C_5$-alkenyl, straight-chain $C_3$-$C_5$-alkynyl, and $C_4$-$C_6$-carbocyclyl are optionally substituted with one or more independently selected $C_1$-$C_6$-alkyl.

In some embodiments, $X^2$ is selected from the group consisting of straight-chain $C_3$-$C_5$-alkyl, straight-chain $C_3$-$C_5$-alkenyl, and straight-chain $C_3$-$C_5$-alkynyl. The straight-chain $C_3$-$C_5$-alkyl, straight-chain $C_3$-$C_5$-alkenyl, straight-chain and $C_3$-$C_5$-alkynyl are optionally substituted with one or more independently selected $C_1$-$C_6$-alkyl.

In some embodiments, $X^2$ is straight-chain $C_3$-$C_4$-alkyl optionally substituted with one or more independently selected $C_1$-$C_6$-alkyl.

In some embodiments, $X^2$ is straight-chain $C_3$-alkyl (i.e., n-propyl). In these embodiments, the compound is encompassed by the following formula:

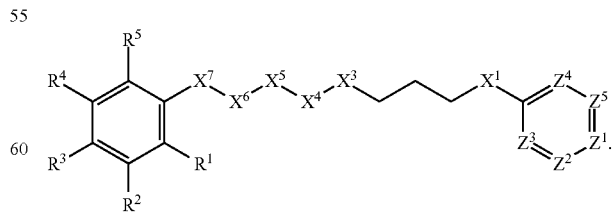

In some embodiments, $X^2$ is straight-chain $C_4$-alkyl (i.e., n-butyl). In these embodiments, the compound is encompassed by the following formula:

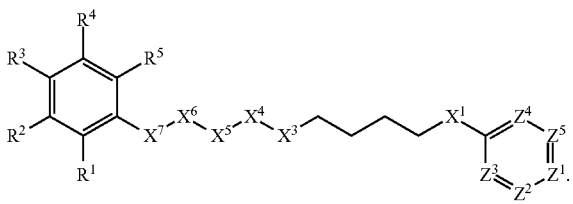

In some embodiments, $X^2$ is straight-chain $C_3$-$C_4$-alkenyl optionally substituted with one or more independently selected $C_1$-$C_6$-alkyl.

In some embodiments, $X^2$ is straight-chain $C_3$-$C_4$-alkenyl.

In some embodiments, $X^2$ is straight-chain $C_3$-$C_4$-alkynyl optionally substituted with one or more independently selected $C_1$-$C_6$-alkyl.

In some embodiments, $X^2$ is straight-chain $C_3$-$C_4$-alkynyl.

In some embodiments, $X^2$ is $C_4$-$C_6$ carbocyclyl optionally substituted with one or more independently selected $C_1$-$C_6$-alkyl.

In some embodiments, $X^2$ is a ring structure selected from the group consisting of cyclobutyl, cyclopentyl, cyclopentenyl, cyclohexyl, and phenyl. Any such group is optionally substituted with one or more independently selected $C_1$-$C_6$-alkyl.

In some embodiments, $X^2$ is cyclobutyl. In some such embodiments, the compound is encompassed by the following formula:

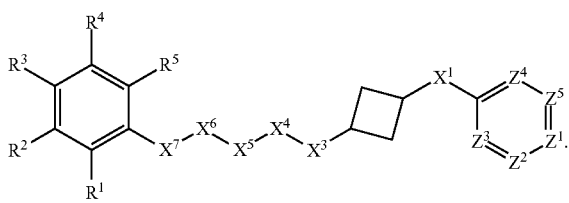

In some embodiments, $X^2$ is cyclopentyl. In some such embodiments, the compound is encompassed by the following formula:

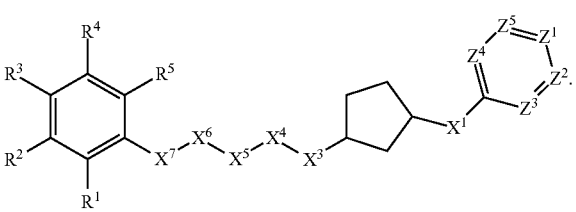

In some embodiments, $X^2$ is cyclohexyl. In some such embodiments, the compound is encompassed by the following formula:

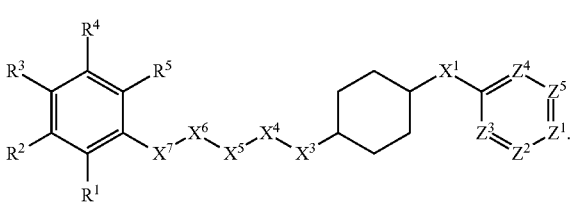

D. Preferred Embodiments of $X^3$ $X^3$ is selected from the group consisting of —O—, —C(O)—, —S—, —S(O)—, —S(O)$_2$—, —CH$_2$—, and —NH—. The —CH$_2$— is optionally substituted with up to two substituents independently selected from the group consisting of alkyl and carbocyclyl. The —NH— is optionally substituted with a substituent selected from the group consisting of alkyl, alkenyl, alkynyl, alkoxyalkyl, carbocyclyl, and carbocyclylalkyl. Any such substituent of —NH— is optionally substituted with one or more independently selected halogen.

In some embodiments, $X^3$ is selected from the group consisting of —O—, —C(O)—, —S—, —S(O)—, —S(O)$_2$—, —CH$_2$—, and —NH—. The —CH$_2$— is optionally substituted with up to two substituents independently selected from the group consisting of $C_1$-$C_6$-alkyl and cycloalkyl (e.g., $C_3$-$C_6$-cycloalkyl, such as cyclopropyl). The —NH— is optionally substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. Any such substituent of —NH— is optionally substituted with one or more independently selected halogen.

In some embodiments, $X^3$ is —O—. In such embodiments, the compound is encompassed by the following formula:

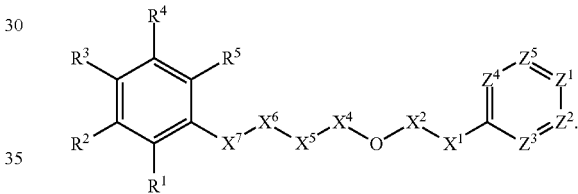

In some embodiments, $X^3$ is —CH$_2$—. In those embodiments, the compound is encompassed by the following formula:

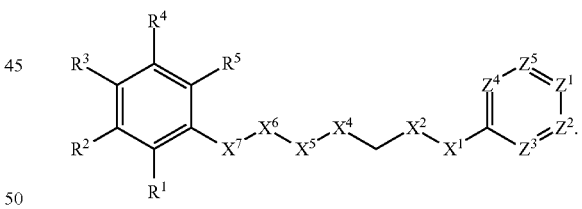

E. Preferred Embodiments of $X^4$ $X^4$ is selected from the group consisting of —CH$_2$— and —NH—. The —CH$_2$— is optionally substituted with up to two substituents independently selected from the group consisting of alkyl, haloalkyl, and alkenyl. The —NH— is optionally substituted with a substituent selected from the group consisting of alkyl, alkenyl, alkynyl, alkoxyalkyl, carbocyclyl, and carbocyclylalkyl. Any such substituent of —NH— is optionally substituted with one or more independently selected halogen.

In some embodiments, $X^4$ is selected from the group consisting of —CH$_2$— and —NH—. The —CH$_2$— is optionally substituted with up to two substituents independently selected from the group consisting of alkyl and alkenyl. The —NH— is optionally substituted with a substituent selected from the group consisting of alkyl, alkenyl, alkynyl, alkoxyalkyl, carbocyclyl, and carbocyclylalkyl. Any such substituent of —NH— is optionally substituted with one or more independently selected halogen.

In some embodiments, $X^4$ is selected from the group consisting of —CH$_2$— and —NH—. The —CH$_2$— is optionally substituted with up to two substituents independently selected from the group consisting of $C_1$-$C_6$-alkyl and $C_2$-$C_6$-alkenyl. The —NH— is optionally substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. Any such substituent of —NH— is optionally substituted with one or more independently selected halogen.

In some embodiments, $X^4$ is —CH$_2$—. In such embodiments, the compound is encompassed by the following formula:

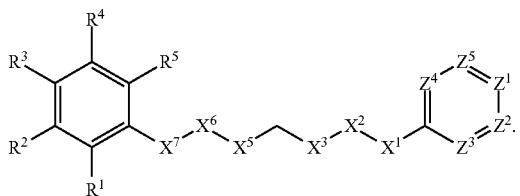

In some embodiments, $X^4$ is —CH$_2$— substituted with up to two independently selected $C_1$-$C_6$-alkyl. For example, in some embodiments, $X^4$ is —CH$_2$-substituted with methyl. In such embodiments, the compound is encompassed by the following formula:

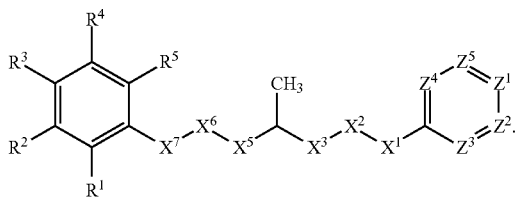

In other embodiments, $X^4$ is —CH$_2$— substituted with two methyl groups. In such embodiments, the compound is encompassed by the following formula:

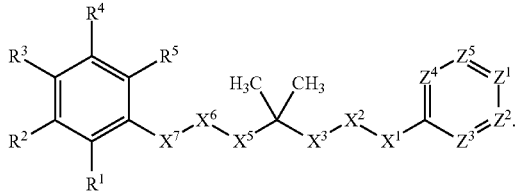

In some embodiments, $X^4$ is —CH$_2$— substituted with up to two independently selected $C_1$-$C_6$-haloalkyl. For example, in some embodiments, $X^4$ is —CH$_2$-substituted with trifluoromethyl. In such embodiments, the compound is encompassed by the following formula:

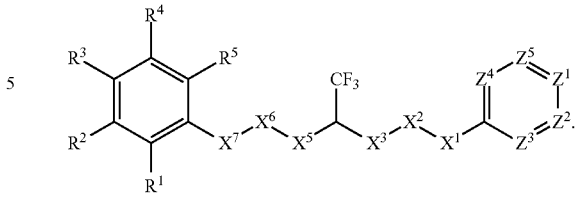

In other embodiments, $X^4$ is —CH$_2$— substituted with two trifluoromethyl groups. In such embodiments, the compound is encompassed by the following formula:

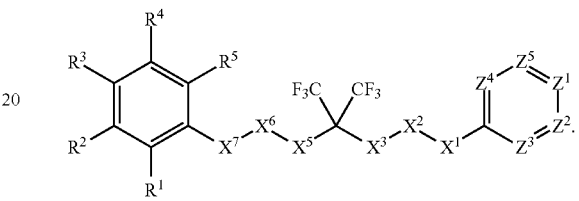

In some embodiments, $X^4$ is —NH—. In such embodiments, the compound is encompassed by the following formula:

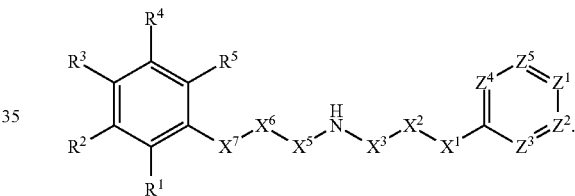

In some embodiments, $X^4$ is —NH— substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. In some such embodiments, $X^4$ is —NH— substituted with $C_1$-$C_6$-alkyl. For example, in some embodiments, $X^4$ is —N(CH$_3$)—. In those embodiments, the compound is encompassed by the following formula:

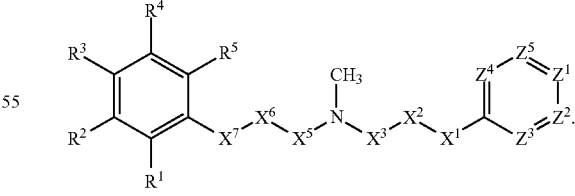

In some embodiments, $X^3$ is —C(O)—, and $X^4$ is —NH— substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. In some such embodiments, $X^3$ is —C(O)—, and $X^4$ is —NH—. In those embodiments, the compound is encompassed by the following formula:

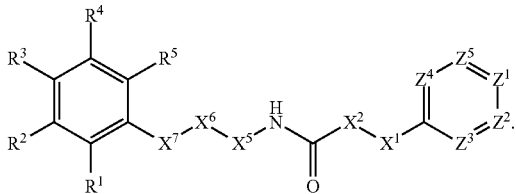

In other embodiments, $X^3$ is —C(O)—, and $X^4$ is —NH— substituted with $C_1$-$C_6$-alkyl. For example, in some such embodiments, $X^4$ is —N(CH$_3$)—. In those embodiments, the compound is encompassed by the following formula:

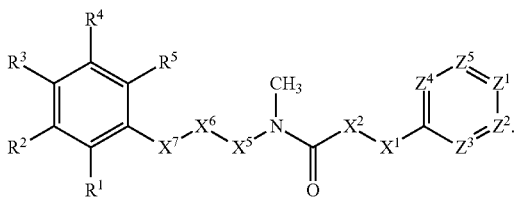

F. Preferred Embodiments of $X^5$ $X^5$ is selected from the group consisting of —O—, —CH$_2$—, —C(S)—, —C(O)—, —S(O)—, and —S(O)$_2$—. The —CH$_2$— is optionally substituted with up to two substituents independently selected from the group consisting of alkyl and carbocyclyl.

In some embodiments, $X^5$ is selected from the group consisting of —O—, —CH$_2$—, —C(S)—, —C(O)—, —S(O)—, and —S(O)$_2$—. The —CH$_2$— is optionally substituted with up to two substituents independently selected from the group consisting of $C_1$-$C_6$-alkyl and cycloalkyl (e.g., $C_3$-$C_6$-cycloalkyl, such as cyclopropyl).

In some embodiments, $X^5$ is —C(O)—. In those embodiments, the compound is encompassed by the following formula:

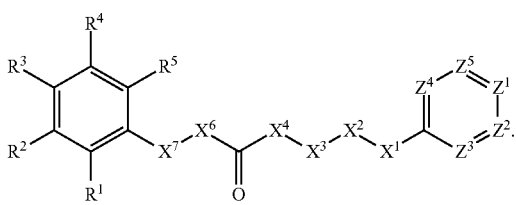

In other embodiments, $X^5$ is —C(S)—. In those embodiments, the compound is encompassed by the following formula:

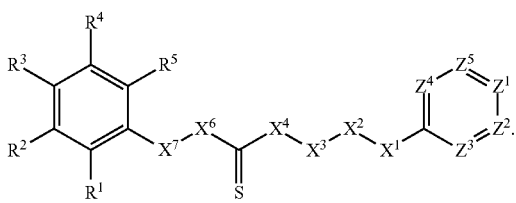

In still other embodiments, $X^5$ is —S(O)$_2$—. In those embodiments, the compound is encompassed by the following formula:

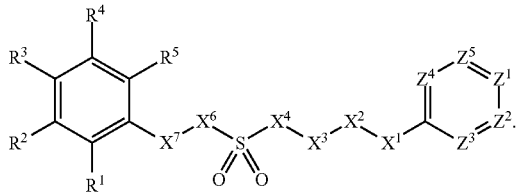

In still yet other embodiments, $X^5$ is —CH$_2$—. In such embodiments, the compound is encompassed by the following formula:

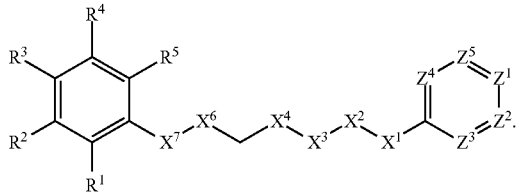

In some embodiments, $X^5$ is —C(O)—, and $X^4$ is —NH— substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl. In some such embodiments, $X^5$ is —C(O)—, and $X^4$ is —NH—. In those embodiments, the compound is encompassed by the following formula:

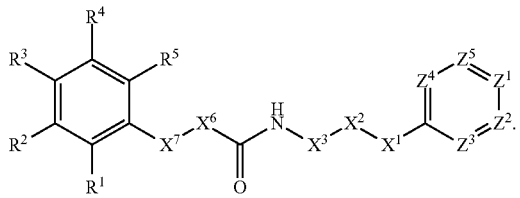

In other embodiments, $X^5$ is —C(O)—, and $X^4$ is —NH— substituted with $C_1$-$C_6$-alkyl. For example, in some such embodiments, $X^4$ is —N(CH$_3$)—. In those embodiments, the compound is encompassed by the following formula:

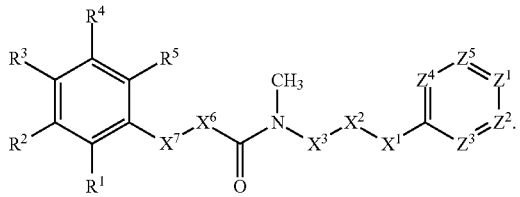

In general, no greater than one of $X^5$ and $X^3$ is optionally substituted —CH$_2$—.

G. Preferred Embodiments of $X^6$ $X^6$ is a linker. The linker is a hydrocarbon group, except: (a) the linker comprises one or more nitrogen atoms, and (b) one or more of the carbons in the hydrocarbon optionally are substituted with one or more substituents independently selected from the group consisting of oxo, halogen, hydroxy, and alkoxy. The linker comprises at least one chain of from 3 to 6 atoms that bridges $X^5$ to $X^7$. From 1 to 2 of the chain atoms are nitrogen. The linker has no chain of less than 3 atoms that bridges $X^5$ and $X^7$.

In some embodiments, the linker is a hydrocarbon group, except: (a) the linker comprises one or more nitrogen atoms, and (b) one or more of the carbons in the hydrocarbon optionally are substituted with one or more substituents independently selected from the group consisting of oxo, halogen, hydroxy, and $C_1$-$C_6$-alkoxy.

In some embodiments, the linker is a hydrocarbon group, except: (a) the linker comprises one or more nitrogen atoms, and (b) one or more of the carbons in the hydrocarbon optionally are substituted with oxo.

In some embodiments, the linker is a hydrocarbon group, except: (a) the linker comprises one or more nitrogen atoms, and (b) one carbon in the hydrocarbon is substituted with oxo.

In some embodiments, the linker is a hydrocarbon group, except for comprising one or more nitrogen atoms.

In some embodiments, the linker comprises no greater than one nitrogen atom.

In other embodiments, the linker comprises no greater and no less than two nitrogen atoms.

In some embodiments, the linker comprises at least one chain of from 3 to 5 atoms that bridges $X^5$ to $X^7$.

In some embodiments, the linker comprises at least one 3-atom chain that bridges $X^5$ to $X^7$.

In some embodiments, the linker comprises at least one 4-atom chain that bridges $X^5$ to $X^7$. In some such embodiments, the linker has no chain of less than 4 atoms that bridges $X^5$ to $X^7$.

In some embodiments, the linker comprises at least one 5-atom chain that bridges $X^5$ to $X^7$. In some such embodiments, the linker has no chain of less than 5 atoms that bridges $X^5$ to $X^7$.

In some embodiments, the linker comprises at least one 6-atom chain that bridges $X^5$ to $X^7$. In some such embodiments, the linker has no chain of less than 6 atoms that bridges $X^5$ to $X^7$.

In some embodiments, $X^6$ is selected from the group of linkers consisting of those shown in Table I:

TABLE I

Example of $X^6$ Linkers

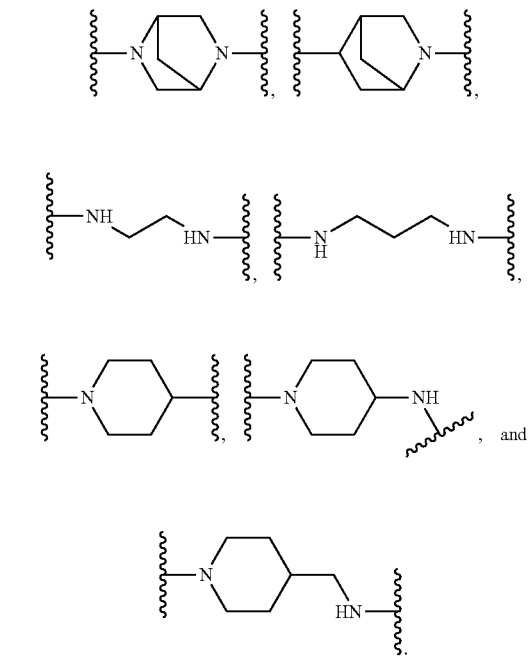

TABLE I-continued

Example of $X^6$ Linkers

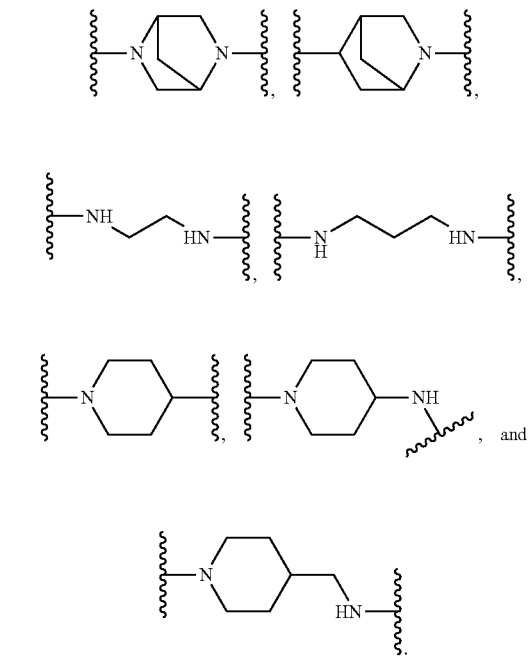

Any such group is optionally substituted with one or more substituents independently selected from the group consisting of halogen, $C_1$-$C_6$-alkyl, hydroxy, $C_1$-$C_6$-alkoxy, oxo, and thiocarbonyl.

In some embodiments, the linker comprises at least one 3-atom chain that bridges $X^5$ to $X^7$. To illustrate, the following are some of the structures from Table I that exemplify such linkers:

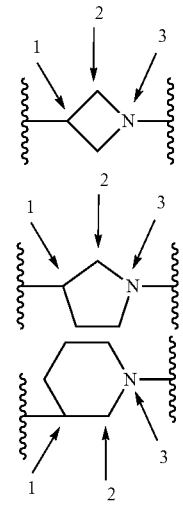

In some embodiments, the linker comprises at least one 4-atom chain that bridges $X^5$ to $X^7$. To illustrate, the following are some of the structures from Table I that exemplify such linkers:

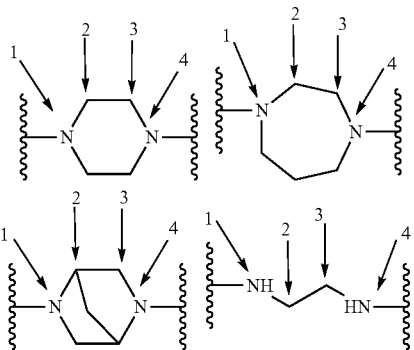

In some embodiments, the linker comprises at least one 5-atom chain that bridges $X^5$ to $X^7$. To illustrate, the following are some of the structures from Table I that exemplify such linkers:

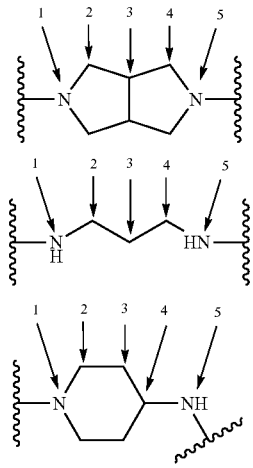

In some embodiments, the linker comprises at least one 6-atom chain that bridges $X^5$ to $X^7$. To illustrate, the following is a structure from Table I that exemplifies such a linker

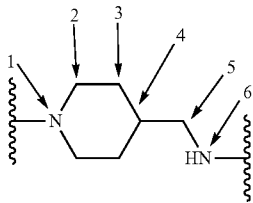 [SMILES: *NCC1CCN(*)CC1]

In some embodiments, the structures in Table I are not substituted with any $C_1$-$C_6$-alkyl or oxo.

In some embodiments, $X^6$ does not comprise a ring. In some such embodiments, $X^6$ is a linker selected from the group consisting of:

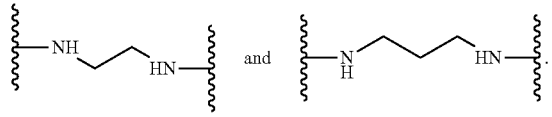 [SMILES: *NCCN* ; *NCCCN*]

Any such group is optionally substituted with one or more substituents independently selected from the group consisting of $C_1$-$C_6$-alkyl and oxo.

In some embodiments, $X^6$ is one of the single- or double-ring structures in Table I. The ring(s) is/are optionally substituted with one or more substituents independently selected from the group consisting of halogen, hydroxy, $C_1$-$C_6$-alkyl, $C_1$-$C_6$-alkoxy, oxo, and thiocarbonyl.

In some embodiments, $X^6$ is one of the 4- to 7-member single ring structures in Table I. The ring is optionally substituted with one or more substituents independently selected from the group consisting of halogen, hydroxy, $C_1$-$C_6$-alkyl, $C_1$-$C_6$-alkoxy, oxo, and thiocarbonyl.

In some embodiments, $X^6$ is one of the 4- to 7-member single ring structures in Table I. The ring is optionally substituted with one or more substituents independently selected from the group consisting of halogen, hydroxy, $C_1$-$C_6$-alkyl, $C_1$-$C_6$-alkoxy, and oxo.

In some embodiments, $X^6$ is one of the 4- to 7-member single ring structures in Table I. The ring is optionally substituted with one or more substituents independently selected from the group consisting of $C_1$-$C_6$-alkyl and oxo.

In some embodiments, $X^6$ is:

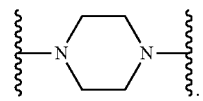

In those embodiments, the compound is encompassed by the following formula:

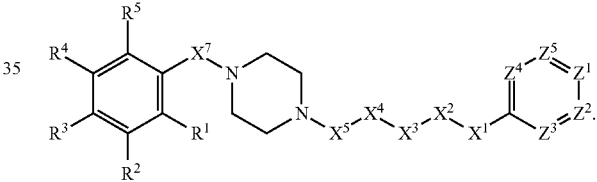

In some embodiments, $X^6$ is:

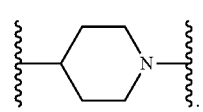

In such embodiments, the compound is encompassed by the following formula:

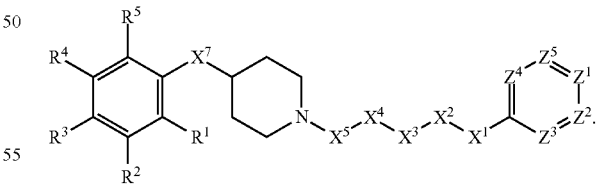

In some embodiments, $X^6$ is:

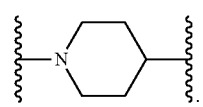

In such embodiments, the compound is encompassed by the following formula:

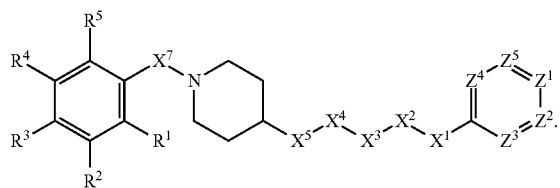

In some such embodiments, $X^5$ is —C(O)—, and the compound is encompassed by the following formula:

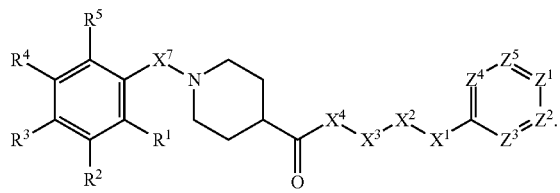

In other embodiments, $X^5$ is —C(O)—, $X^4$ is —N(H)—, and the compound is encompassed by the following formula:

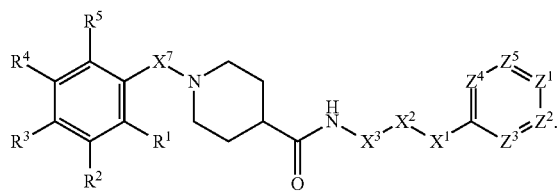

In still other embodiments, $X^5$ is —C(O)—, $X^4$ is —N(CH$_3$)—, and the compound is encompassed by the following formula:

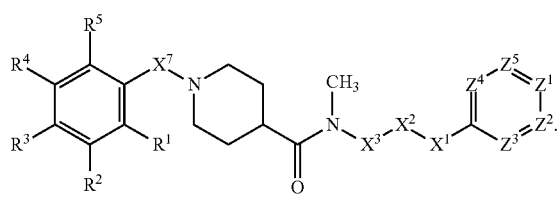

In some embodiments, $X^6$ is:

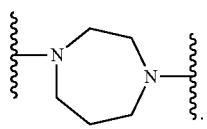

In such embodiments, the compound is encompassed by the following formula:

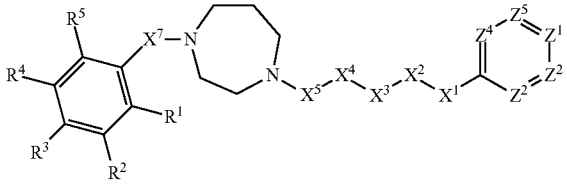

In some embodiments, $X^6$ is:

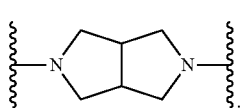

In such embodiments, the compound is encompassed by the following formula:

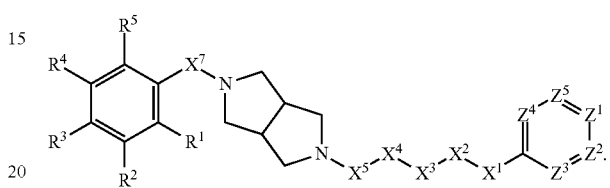

In some embodiments, $X^6$ is:

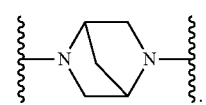

In such embodiments, the compound is encompassed by the following formula:

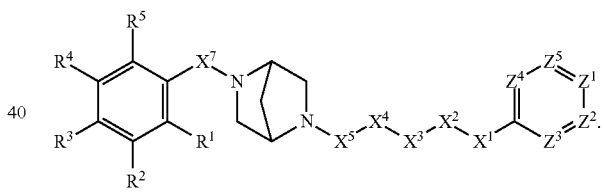

In some embodiments, $X^6$ is:

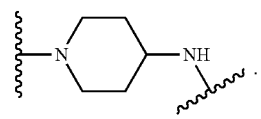

In such embodiments, the compound is encompassed by the following formula:

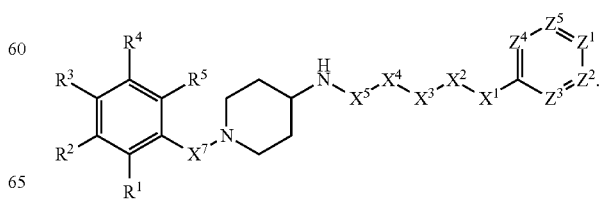

In some embodiments, $X^6$ is:

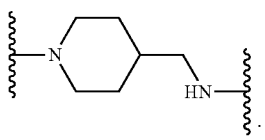 [SMILES: *NCC1CCN(*)CC1]

In such embodiments, the compound is encompassed by the following formula:

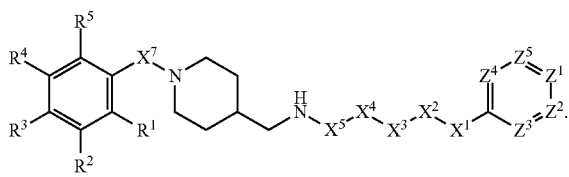

In some embodiments, one or more carbon atoms in the linker are substituted with one or two substituents independently selected from the group consisting of halogen, hydroxy, $C_1$-$C_6$-alkyl, $C_1$-$C_6$-alkoxy, oxo, and thiocarbonyl.

In some embodiments, one or more carbon atoms in the linker are substituted with one or two substituents independently selected from the group consisting of halogen, hydroxy, $C_1$-$C_6$-alkyl, $C_1$-$C_6$-alkoxy, and oxo.

In some embodiments, $X^6$ is one of the single- or double-ring structures in Table I, and one or two of the ring atoms in the ring structure are substituted with a substituent independently selected from the group consisting of methyl and oxo. To illustrate, in some embodiments, the a ring atom is substituted with an oxo substituent. The linker in such an instance may be, for example:

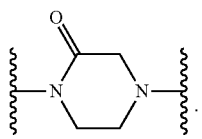 [SMILES: *N1CCN(*)C(=O)C1]

Here, the compound is encompassed by the following formula:

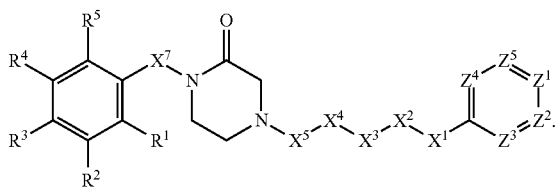

In other embodiments, for example, one or two of the ring atoms are substituted with methyl. To illustrate, the linker in such an instance may be, for example:

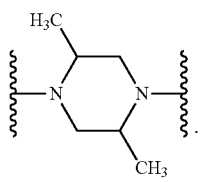

Here, the compound is encompassed by the following formula:

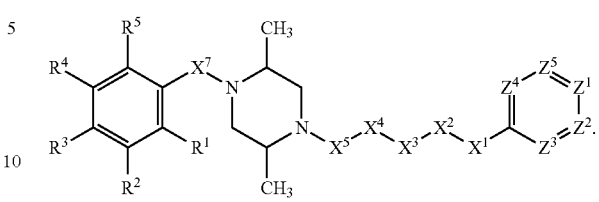

To further illustrate, the linker may alternatively be, for example:

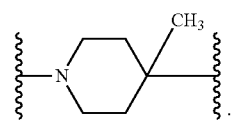 [SMILES: *N1CCC(*)(C)CC1]

Here, the compound is encompassed by the following formula:

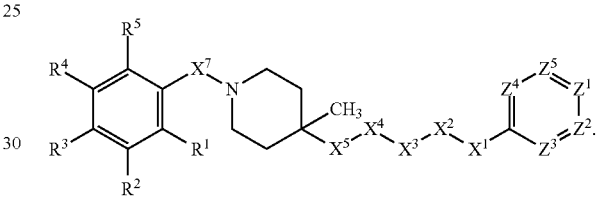

In some such embodiments, for example, $X^5$ is —C(O)—. In those embodiments, the compound is encompassed by the following formula:

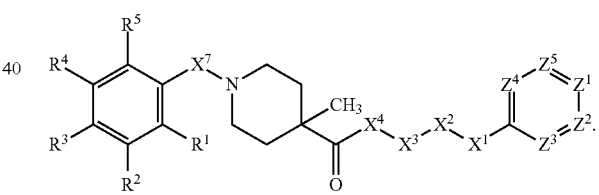

H. Preferred Embodiments of $X^7$ $X^7$ is selected from the group consisting of a bond, —O—, —C(O)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$—. The —NH— is optionally substituted with alkyl. And the —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$— are optionally substituted with one or more independently selected alkyl.

In some embodiments, $X^7$ is selected from the group consisting of a bond, —O—, —C(O)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —$CH_2$—$S(O)_2$—. The —NH— is optionally substituted with $C_1$-$C_6$-alkyl. And the —$CH_2$—, —$CH_2CH_2$—, —C(O)—$CH_2$—, —$CH_2$—C(O)—, —O—$CH_2$—, —$CH_2$—O—, —NH—$CH_2$—, —$CH_2$—NH—, —S—$CH_2$—, —$CH_2$—S—, —S(O)—$CH_2$—, —$CH_2$—S(O)—, —$S(O)_2$—$CH_2$—, and —$CH_2$—$S(O)_2$— are optionally substituted with one or more independently selected $C_1$-$C_6$-alkyl.

In some embodiments, $X^7$ is a bond. In such embodiments, the compound is encompassed by the following formula:

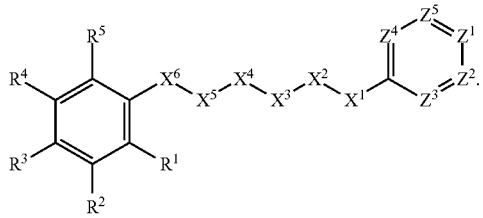

I. Preferred Embodiments of $Z^1$, $Z^2$, $Z^3$, $Z^4$, and $Z^5$ $Z^1$ is selected from the group consisting of N and CH. The CH is substituted with a substituent selected from the group consisting of halogen, nitro, cyano, aminosulfonyl, alkyl, alkoxy, alkoxycarbonyl, alkylsulfanyl, alkylsulfinyl, alkylsulfonyl, aryl, arylsulfanyl, arylsulfinyl, arylsulfonyl, heteroaryl, heteroarylsulfanyl, heteroarylsulfinyl, and heteroarylsulfonyl. The alkyl, alkoxy, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl. The aminosulfonyl is optionally substituted with up to two independently selected alkyl.

In some embodiments, $Z^1$ is selected from the group consisting of N and CH. The CH is substituted with a substituent selected from the group consisting of halogen, nitro, cyano, aminosulfonyl, $C_1$-$C_6$-alkyl, $C_1$-$C_6$-alkoxy, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, aryl, arylsulfanyl, arylsulfinyl, arylsulfonyl, heteroaryl, heteroarylsulfanyl, heteroarylsulfinyl, and heteroarylsulfonyl. The $C_1$-$C_6$-alkyl, $C_1$-$C_6$-alkoxy, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, $C_1$-$C_6$-alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and $C_1$-$C_6$-alkyl. The aminosulfonyl is optionally substituted with up to two independently selected $C_1$-$C_6$-alkyl. In some such embodiments, each aryl is phenyl, and each heteroaryl is a 5- to 6-member heteroaryl.

In some embodiments, $Z^1$ is N. Such embodiments are encompassed by the following structure:

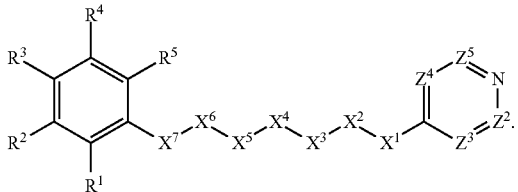

In some embodiments, $Z^1$ is CH substituted with a substituent selected from the group consisting of halogen, nitro, cyano, $C_1$-$C_6$-alkoxy, and $C_1$-$C_6$-alkylsulfanyl. The $C_1$-$C_6$-alkoxy and $C_1$-$C_6$-alkylsulfanyl are optionally substituted with one or more independently selected halogen.

In some embodiments, $Z^1$ is CH substituted with an electron-withdrawing substituent. Such substituents include, for example, halogen, nitro, cyano, halo-$C_1$-$C_6$-alkyl, halo-$C_1$-$C_6$-alkoxy, and halo-$C_1$-$C_6$-alkylsulfanyl.

In some embodiments, $Z^1$ is CH substituted with a halogen. For example, in some such embodiments, $Z^1$ is CH substituted with chloro. These embodiments are encompassed by the following structure:

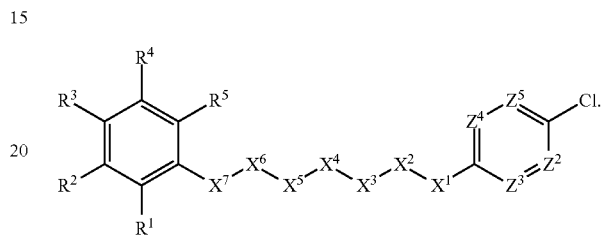

In some embodiments, $Z^1$ is CH substituted with nitro. Such embodiments are encompassed by the following structure:

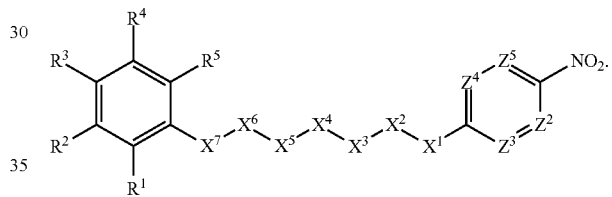

In some embodiments, $Z^1$ is CH substituted with cyano. Such embodiments are encompassed by the following structure:

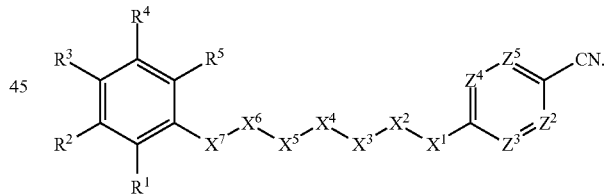

In some embodiments, $Z^1$ is CH substituted with halo-$C_1$-$C_6$-alkoxy. For example, in some such embodiments, $Z^1$ is CH substituted with fluoro-$C_1$-$C_6$-alkoxy. To illustrate, $Z^1$ can be, for example, CH substituted trifluoromethoxy such that the compound is encompassed by the following structure:

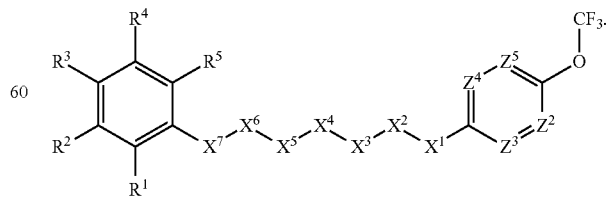

In some embodiments, $Z^1$ is CH substituted with halo-$C_1$-$C_6$-alkylsulfanyl. For example, in some such embodiments, $Z^1$ is CH substituted with fluoro-$C_1$-$C_6$-alkylsulfanyl. To illustrate, $Z^1$ can be, for example, CH substituted trifluoromethylsulfanyl such that the compound is encompassed by the following structure:

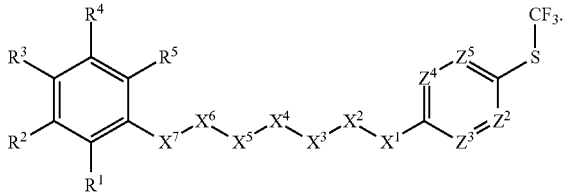

$Z^2$ is selected from the group consisting of N and CH. The CH is optionally substituted with a substituent selected from the group consisting of cyano, halogen, nitro, alkyl, alkoxy, haloalkyl, and haloalkylsulfanyl.

In some embodiments, $Z^2$ is selected from the group consisting of N and CH. The CH is optionally substituted with a substituent selected from the group consisting of cyano, halogen, nitro, $C_1$-$C_6$-alkyl, $C_1$-$C_6$-alkoxy, halo-$C_1$-$C_6$-alkyl, and halo-$C_1$-$C_6$-alkylsulfanyl.

In some embodiments, $Z^2$ is N. Such embodiments are encompassed by the following structure:

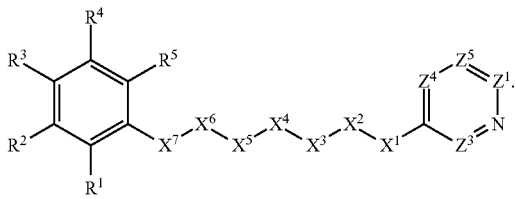

In some embodiments, $Z^2$ is CH substituted with a substituent selected from the group consisting of cyano, halogen, nitro, $C_1$-$C_6$-alkyl, $C_1$-$C_6$-alkoxy, halo-$C_1$-$C_6$-alkyl, and halo-$C_1$-$C_6$-alkylsulfanyl.

In some embodiments, $Z^2$ is CH substituted with halo-$C_1$-$C_6$-alkyl. In some such embodiments, for example, $Z^2$ is CH substituted with trifluoromethyl. Such embodiments are encompassed by the following structure:

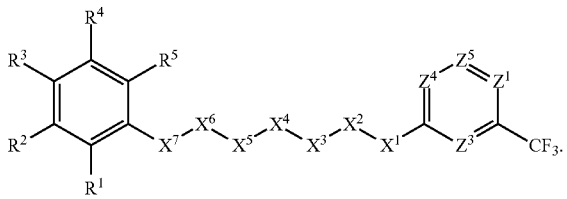

Each of $Z^3$, $Z^4$, and $Z^5$ is independently selected from the group consisting of N and CH. The CH is optionally substituted with a substituent selected from the group consisting of halogen, cyano, nitro, alkyl, alkoxy, alkylsulfanyl, haloalkyl, haloalkoxy, and haloalkylsulfanyl.

Each of $Z^3$, $Z^4$, and $Z^5$ is independently selected from the group consisting of N and CH. The CH is optionally substituted with a substituent selected from the group consisting of halogen, cyano, nitro, $C_1$-$C_6$-alkyl, $C_1$-$C_6$-alkoxy, $C_1$-$C_6$-alkylsulfanyl, halo-$C_1$-$C_6$-alkyl, halo-$C_1$-$C_6$-alkoxy, and halo-$C_1$-$C_6$-alkylsulfanyl.

In some embodiments, one of $Z^3$, $Z^4$, and $Z^5$ is CH.

In some embodiments, two of $Z^3$, $Z^4$, and $Z^5$ are each independently selected from the group consisting of N and CH optionally substituted with $C_1$-$C_6$-alkyl.

In some embodiments, one of $Z^3$, $Z^4$, and $Z^5$ is CH; and the remaining two of $Z^3$, $Z^4$, and $Z^5$ are each independently selected from the group consisting of N and CH optionally substituted with $C_1$-$C_6$-alkyl.

In some embodiments, one of $Z^3$, $Z^4$, and $Z^5$ is CH; and the remaining two of $Z^3$, $Z^4$, and $Z^5$ are each independently selected from the group consisting of N, CH, and $C(CH_3)$.

In some embodiments, two of $Z^3$, $Z^4$, and $Z^5$ are each CH.

In some embodiments, all of $Z^3$, $Z^4$, and $Z^5$ are each CH. Such embodiments are encompassed by the following structure:

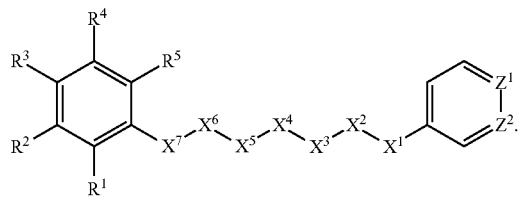

In some embodiments, two of $Z^1$, $Z^2$, $Z^3$, $Z^4$, and $Z^5$ are each N. In other embodiments, only one of $Z^1$, $Z^2$, $Z^3$, $Z^4$, and $Z^5$ is N. And, in yet other embodiments, none of $Z^1$, $Z^2$, $Z^3$, $Z^4$, and $Z^5$ are N.

J. Examples of Various Specific Preferred Embodiments

In some embodiments of this invention, the compound is defined as corresponding in structure to the following formula:

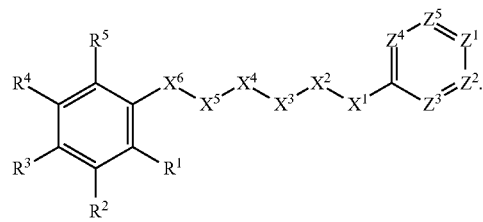

In some such embodiments:
Two of $R^1$, $R^2$, $R^3$, $R^4$, and $R^5$ are each hydrogen. The remaining three of $R^1$, $R^2$, $R^3$, $R^4$, and $R^5$ are each independently selected from the group consisting of hydrogen, halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen and halo-$C_1$-$C_6$-alkyl.

$X^1$ is selected from the group consisting of —O— and —NH—. The —NH— is optionally substituted with $C_1$-$C_6$-alkyl.

$X^2$ is selected from the group consisting of cyclobutyl, cyclopentyl, and cyclohexyl.

$X^3$ is selected from the group consisting of —$CH_2$—, —O—, and —C(O)—.

$X^4$ is selected from the group consisting of —CH$_2$— and —NH—. The —CH$_2$— is optionally substituted with up to two independently selected C$_1$-C$_6$-alkyl. The —NH— is optionally substituted with C$_1$-C$_6$-alkyl.

$X^5$ is selected from the group consisting of —CH$_2$—, —C(S)—, —C(O)—, and —S(O)$_2$—.

$X^6$ is selected from the group of linkers consisting of:

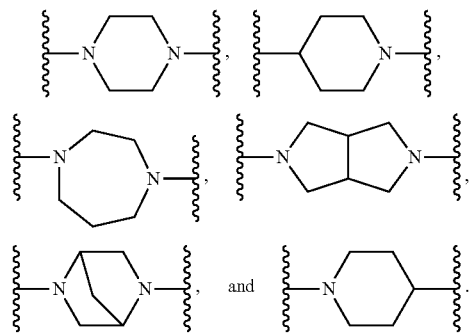

Here, any such group is optionally substituted with up to two substituents independently selected from the group consisting of C$_1$-C$_6$-alkyl and oxo.

$Z^1$ is CH substituted with a substituent selected from the group consisting of halogen, nitro, cyano, C$_1$-C$_6$-alkoxy, and C$_1$-C$_6$-alkylsulfanyl. The C$_1$-C$_6$-alkoxy and C$_1$-C$_6$-alkylsulfanyl are optionally substituted with one or more independently selected halogen.

$Z^2$ is CH optionally substituted with halo-C$_1$-C$_6$-alkyl.

One of $Z^3$, $Z^4$, and $Z^5$ is CH. The remaining two of $Z^3$, $Z^4$, and $Z^5$ are independently selected from the group consisting of N and CH, wherein the CH is optionally substituted with C$_1$-C$_6$-alkyl.

Compounds encompassed by these embodiments include, for example:

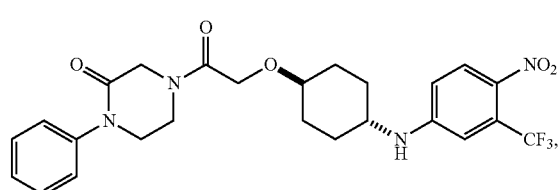

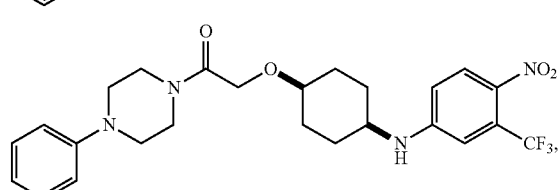

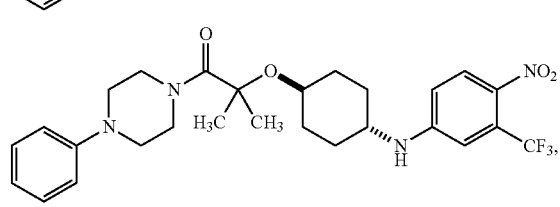

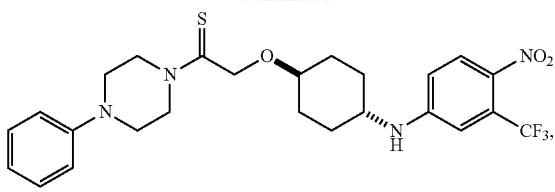

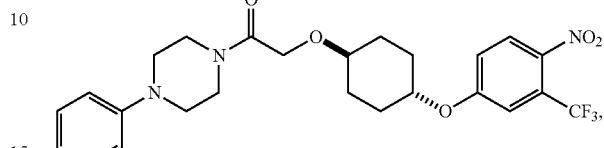

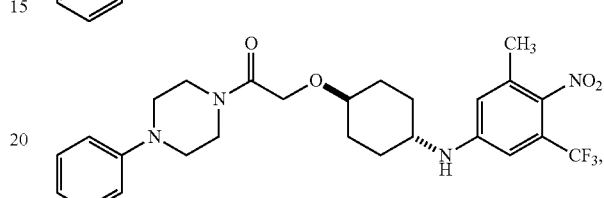

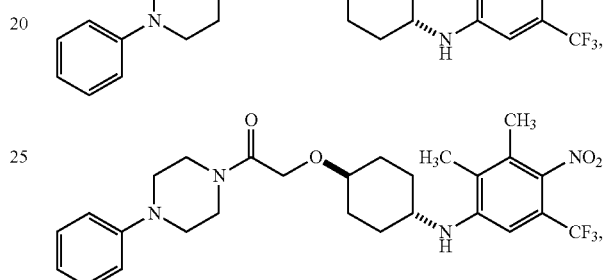

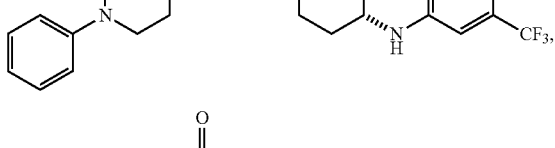

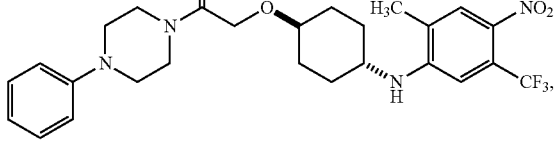

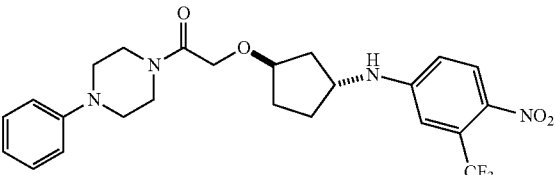

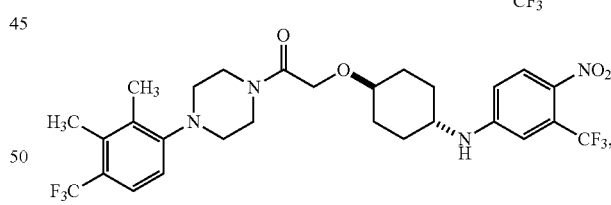

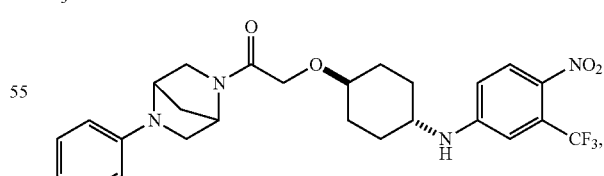

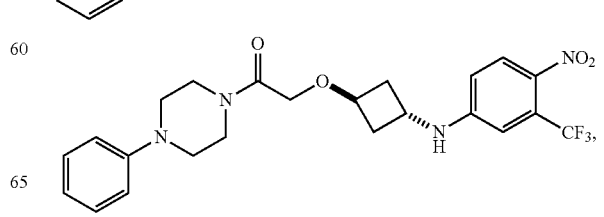

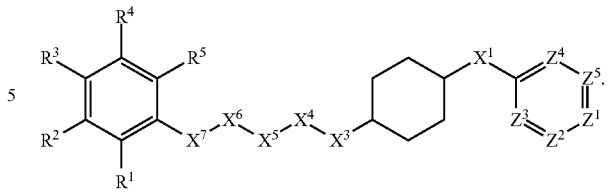

In some such embodiments:
Two of $R^1$, $R^2$, $R^3$, $R^4$, and $R^5$ are each hydrogen. The remaining three of $R^1$, $R^2$, $R^3$, $R^4$, and $R^5$ are each independently selected from the group consisting of hydrogen, halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen and halo-$C_1$-$C_6$-alkyl.

$X^1$ is —NH— optionally substituted with $C_1$-$C_6$-alkyl.

$X^3$ is selected from the group consisting of —$CH_2$—, —O—, and —C(O)—.

$X^4$ is selected from the group consisting of —$CH_2$— and —NH—. The —$CH_2$— is optionally substituted with up to two independently selected $C_1$-$C_6$-alkyl. The —NH— is optionally substituted with $C_1$-$C_6$-alkyl.

$X^5$ is selected from the group consisting of —$CH_2$— and —C(O)—.

$X^6$ is selected from the group of linkers consisting of:

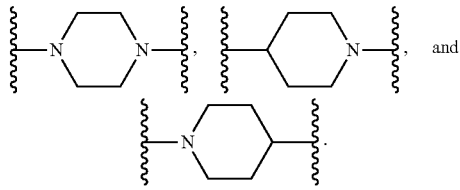

Any such group is optionally substituted with up to two substituents independently selected from the group consisting of $C_1$-$C_6$-alkyl and oxo.

$Z^1$ is CH substituted with a substituent selected from the group consisting of halogen, nitro, cyano, $C_1$-$C_6$-alkoxy, and $C_1$-$C_6$-alkylsulfanyl. The $C_1$-$C_6$-alkoxy and $C_1$-$C_6$-alkylsulfanyl are optionally substituted with one or more independently selected halogen.

$Z^2$ is CH optionally substituted with halo-$C_1$-$C_6$-alkyl.

$Z^3$, $Z^4$, and $Z^5$ are each CH.

In some of these embodiments, $X^7$ is a bond such that the compound corresponds in structure to the following formula:

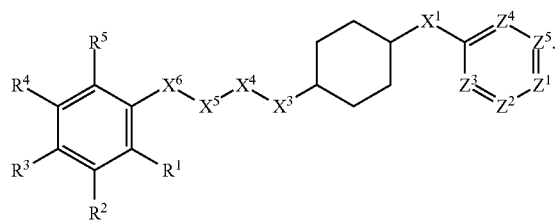

Compounds encompassed by these embodiments include, for example:

In some embodiments of this invention, the compound is defined as corresponding in structure to the following formula:

31
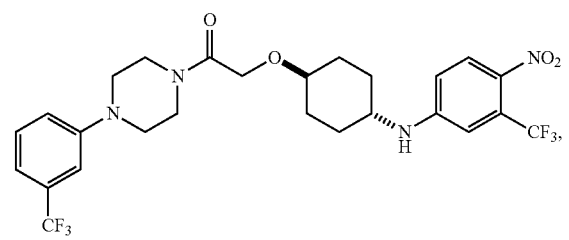
32
-continued
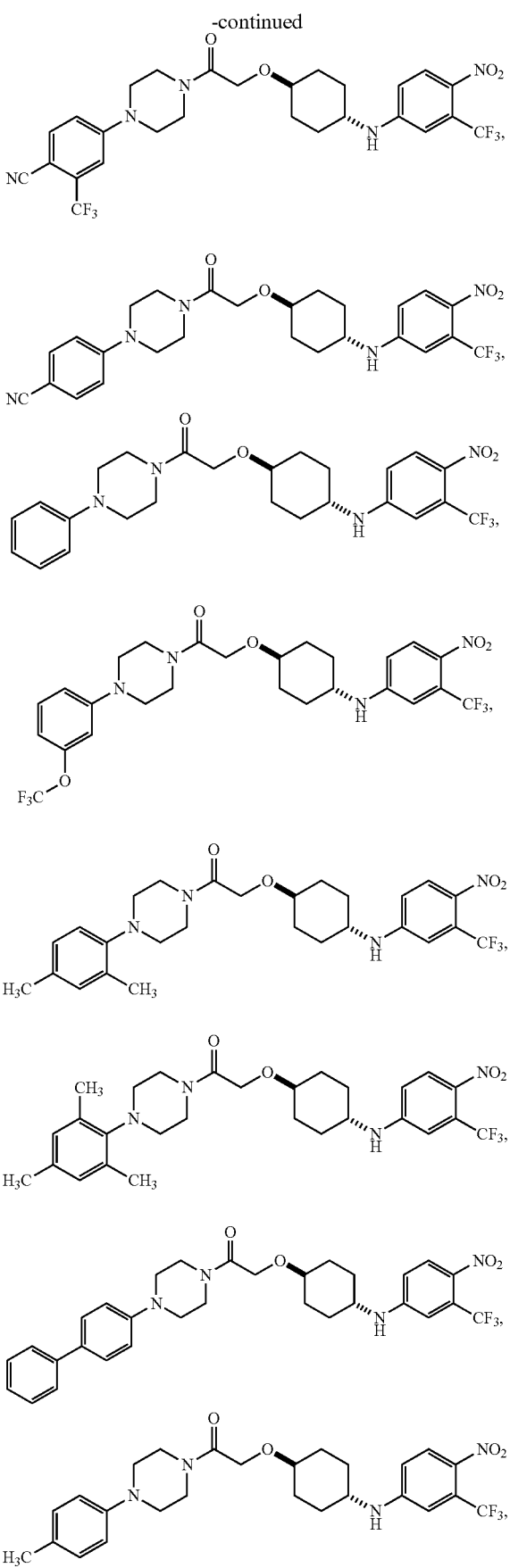

-continued
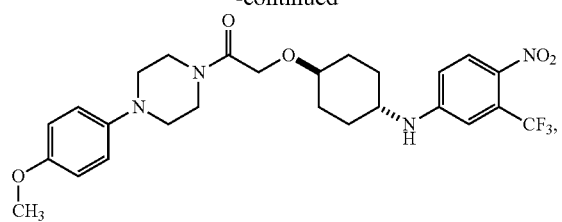
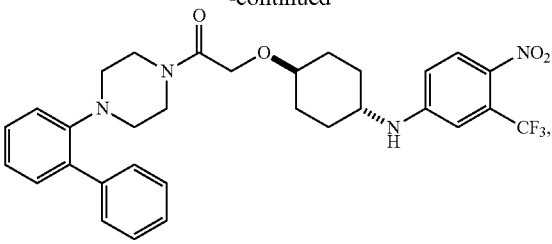
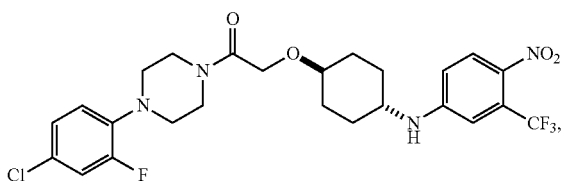
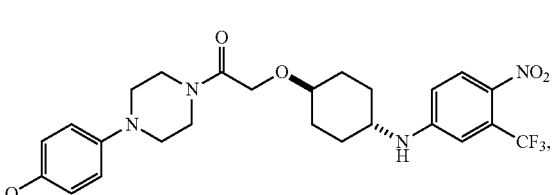
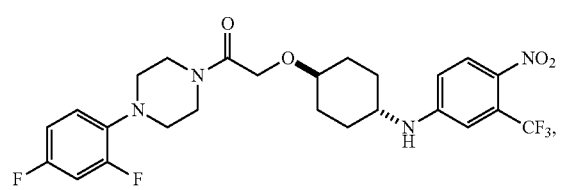
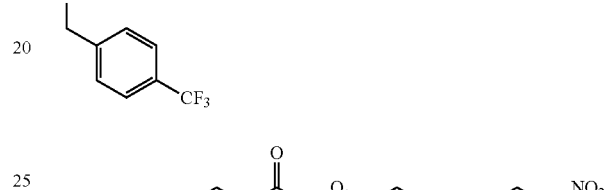
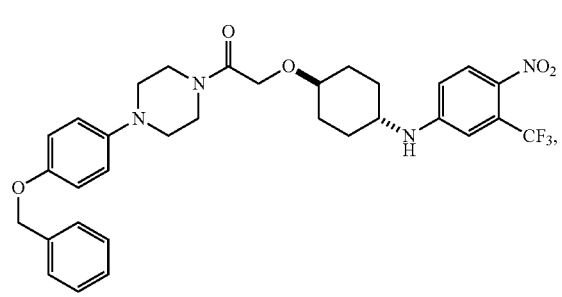
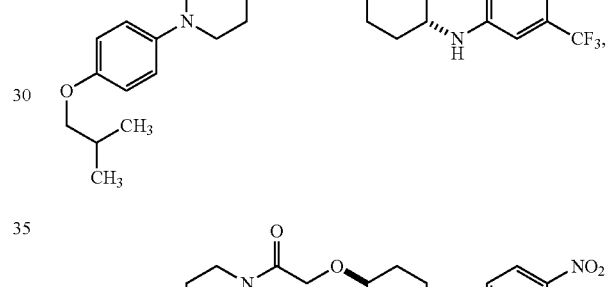
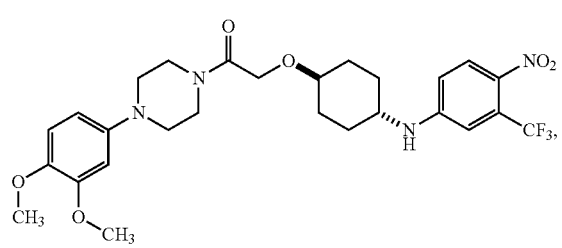
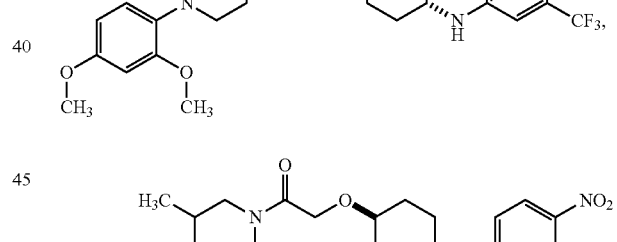
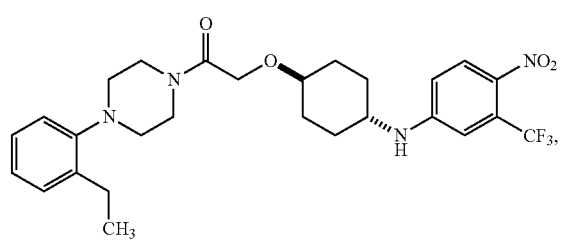
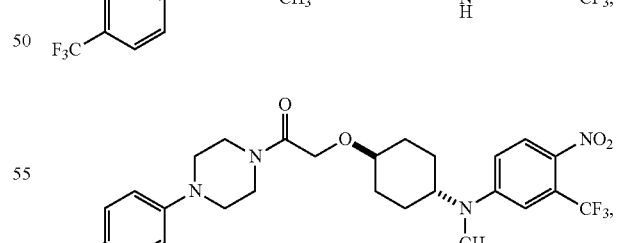
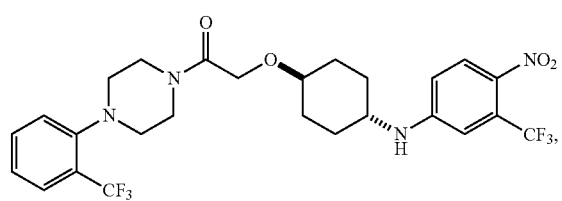
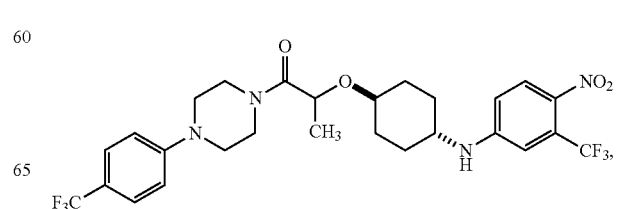

-continued
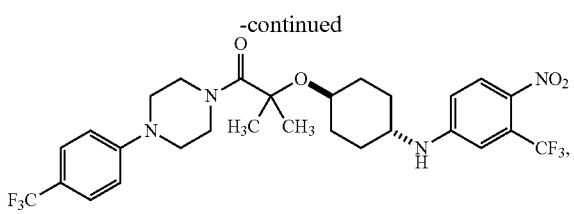
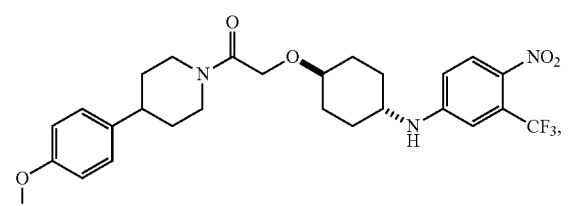
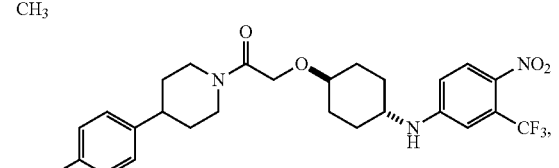
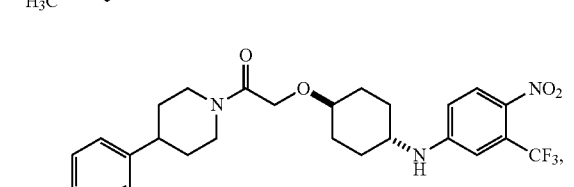
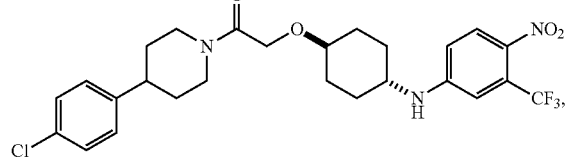
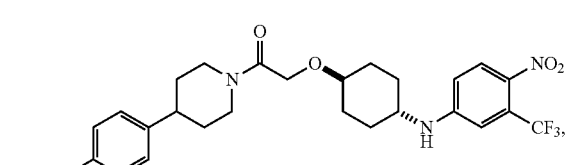
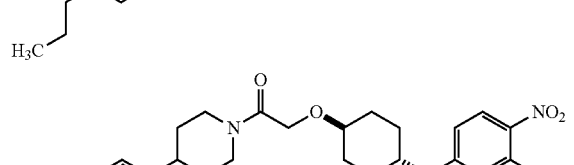
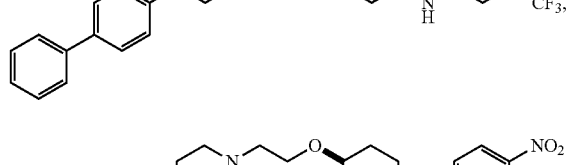
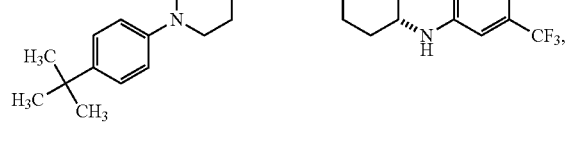
-continued
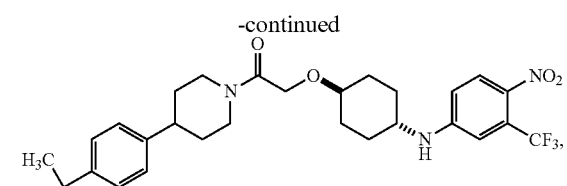
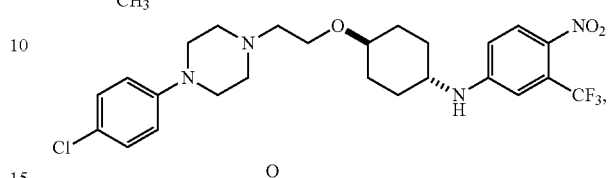
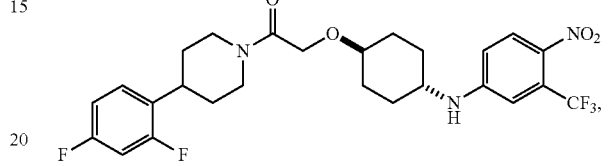
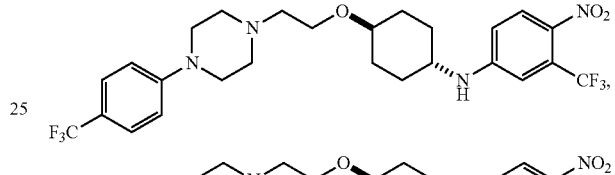
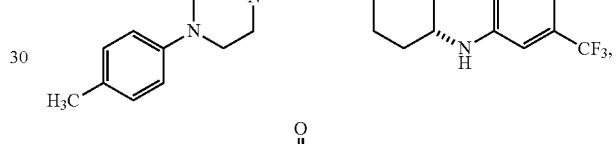
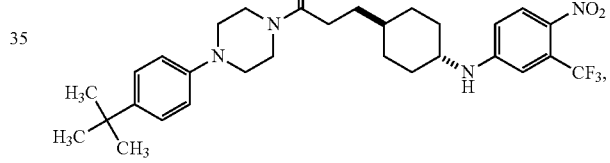
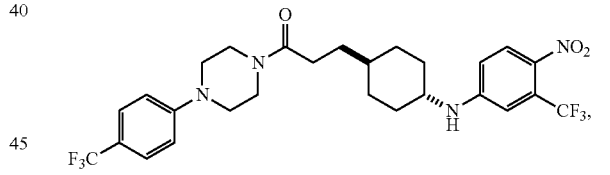
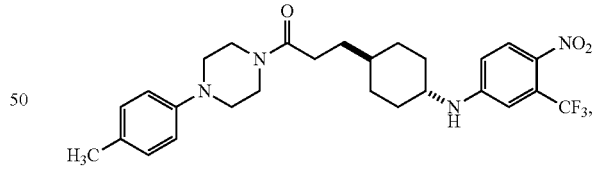
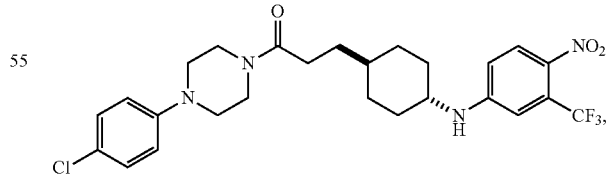
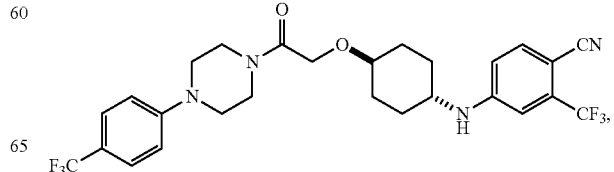

-continued
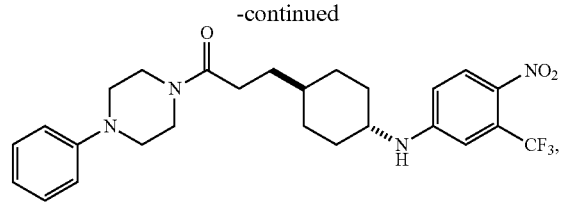
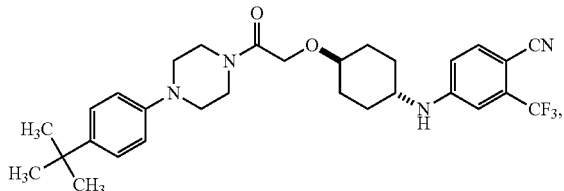
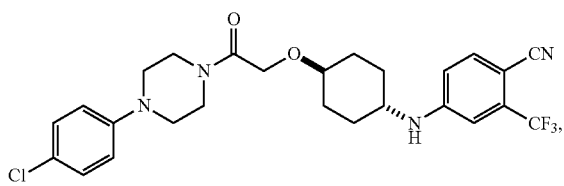
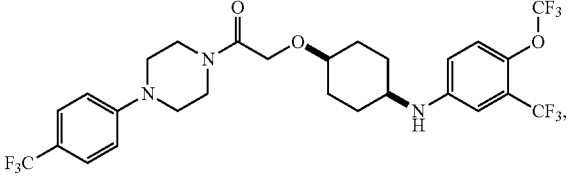
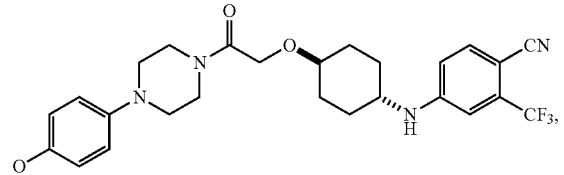
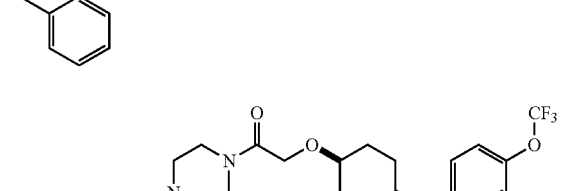
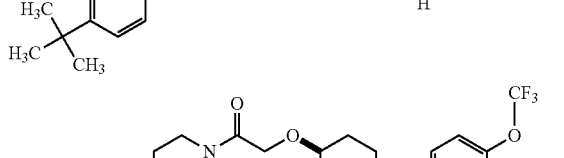
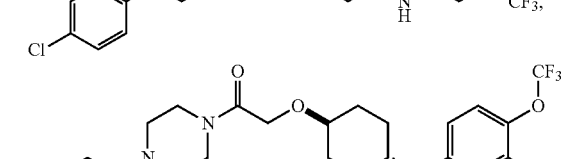
-continued
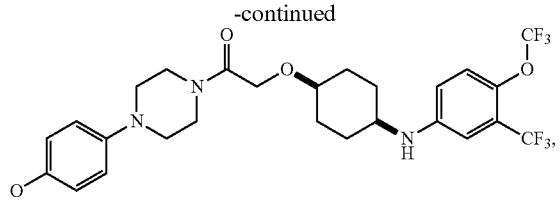
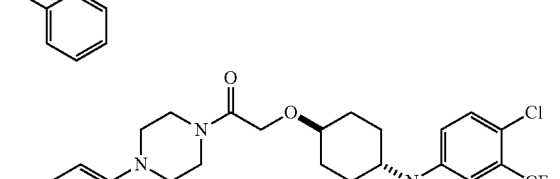
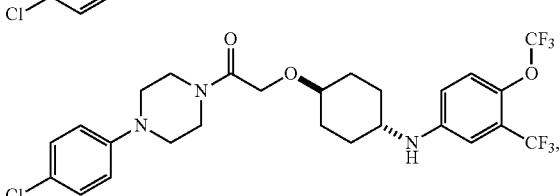
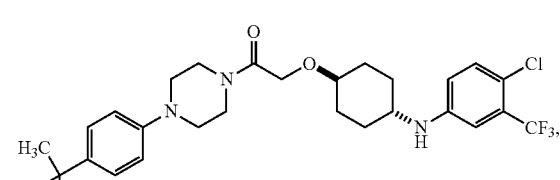
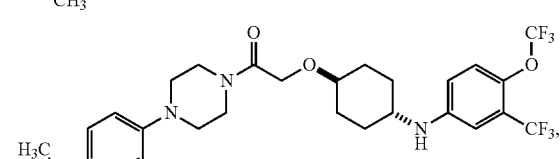
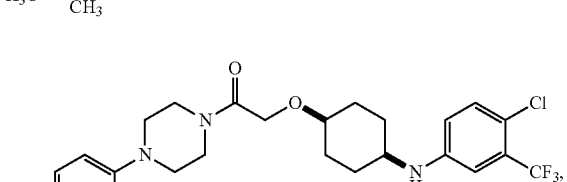
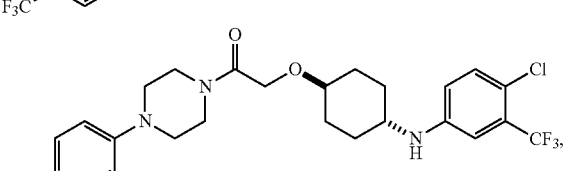
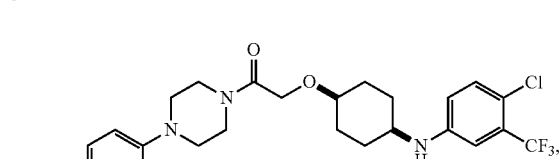

-continued
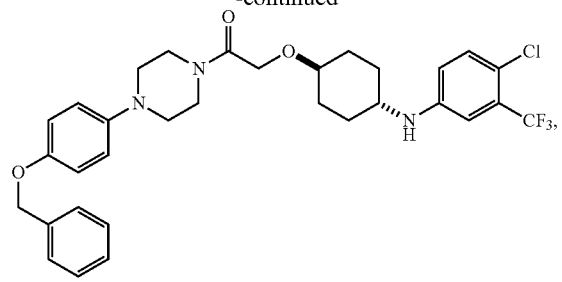
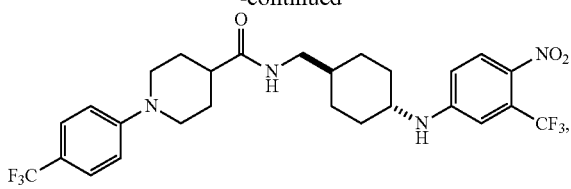
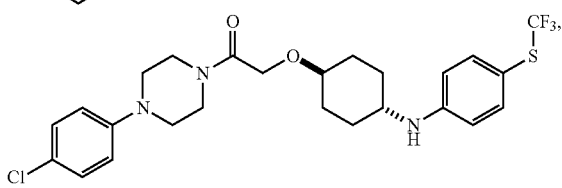
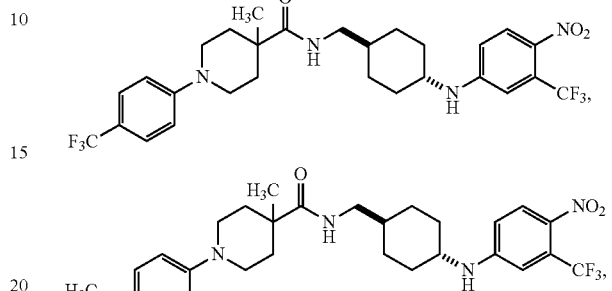
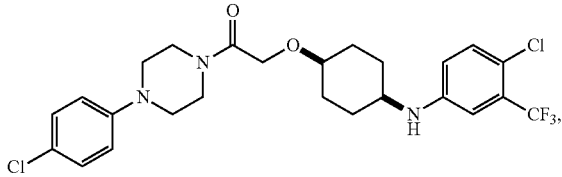
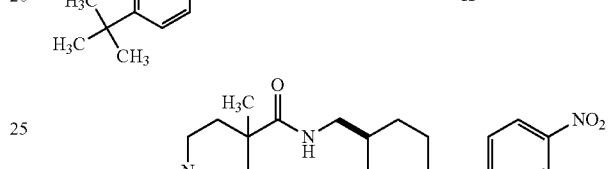
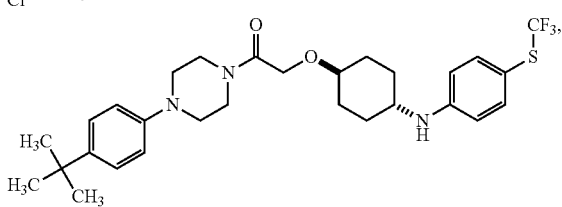
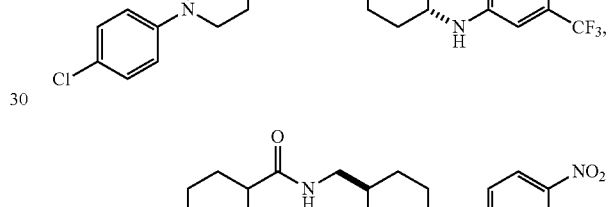
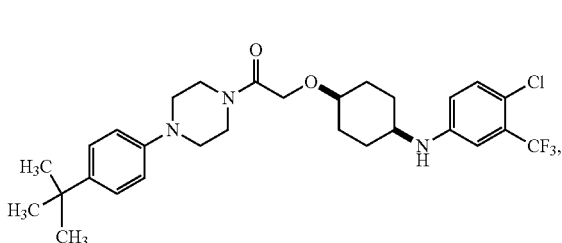
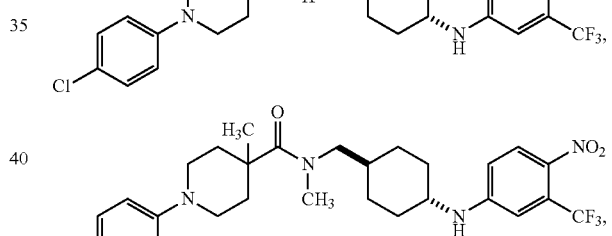
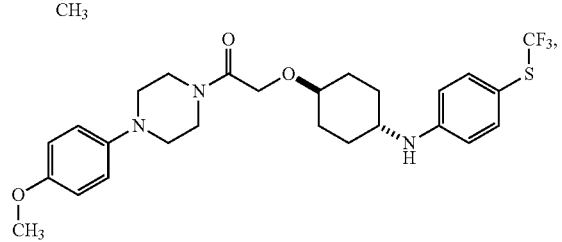
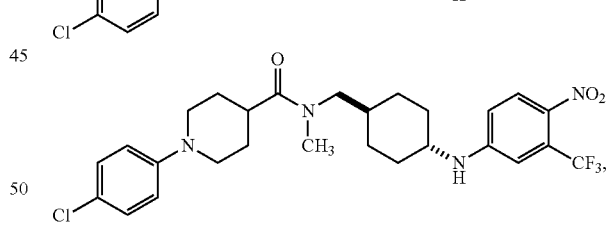
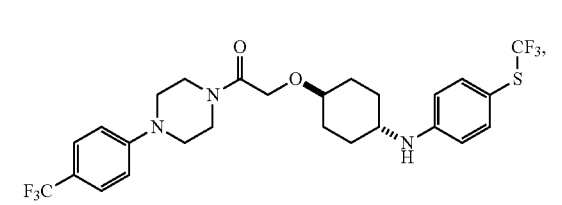
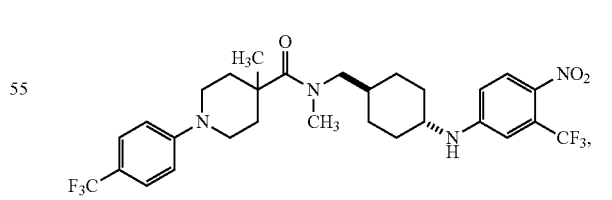
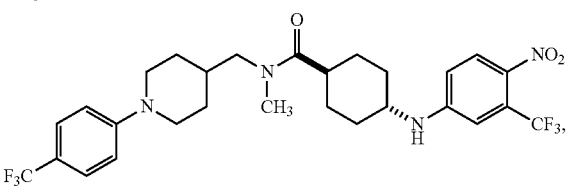
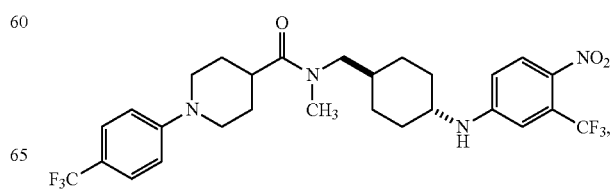

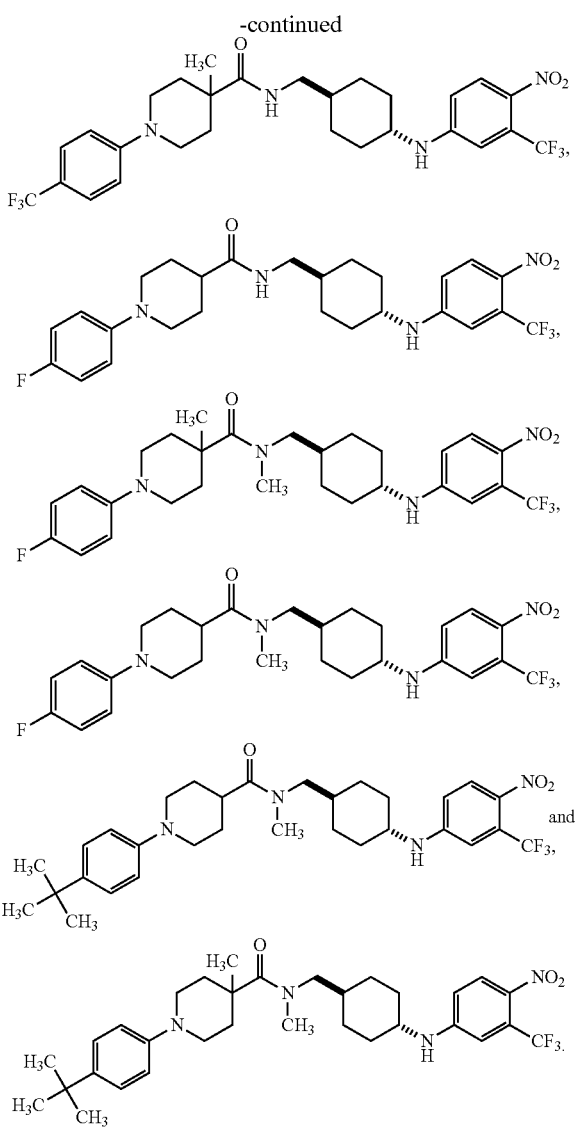

In some embodiments of this invention, the compound is defined as corresponding in structure to the following formula:

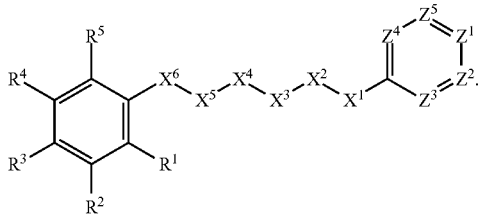

In some such embodiments:
Three of $R^1$, $R^2$, $R^3$, $R^4$, and $R^5$ are each independently selected from the group consisting of hydrogen, chloro, fluoro, cyano, nitro, methyl, tent-butyl, n-propyl, trifluoromethyl, ethyl, methoxy, ethoxy, trifluoromethoxy, trifluoromethylsulfanyl, iso-butoxy, phenyl, phenoxy, benzyloxy, and 4-trifluoromethylbenzyloxy. The remaining two of $R^1$, $R^2$, $R^3$, $R^4$, and $R^5$ are each hydrogen.

$X^1$ is selected from the group consisting of —O—, —NH—, and —N(CH$_3$)—.

$X^2$ is selected from the group consisting of cyclobutyl, cyclopentyl, and cyclohexyl.

$X^3$ is selected from the group consisting of —CH$_2$—, —O—, and —C(O)—.

$X^4$ is selected from the group consisting of —CH$_2$—, —C(H)(CH$_3$)—, —C(CH$_3$)$_2$—, —NH—, and —N(CH$_3$)—.

$X^5$ is selected from the group consisting of —CH$_2$—, —C(S)—, —C(O)—, and —S(O)$_2$—.

$X^6$ is selected from the group of linkers consisting of:

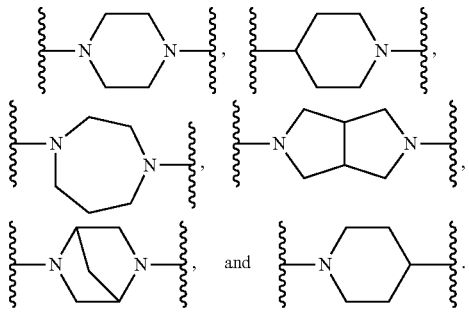

Any such group is optionally substituted with up to two substituents independently selected from the group consisting of methyl and oxo.

$Z^1$ is CH substituted with a substituent selected from the group consisting of chloro, nitro, cyano, trifluoromethoxy, and trifluoromethylsulfanyl.

$Z^2$ is CH optionally substituted with trifluoromethyl.

Two of $Z^3$, $Z^4$, and $Z^5$ are independently selected from the group consisting of N, CH, and C(CH$_3$). The remaining one of $Z^3$, $Z^4$, and $Z^5$ is CH.

In some embodiments of this invention, the compound is defined as corresponding in structure to the following formula:

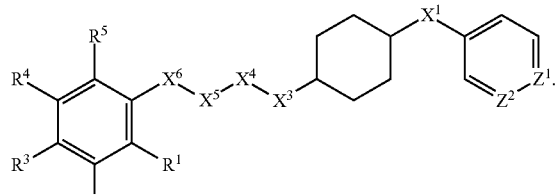

In some such embodiments:
Three of $R^1$, $R^2$, $R^3$, $R^4$, and $R^5$ are each independently selected from the group consisting of hydrogen, chloro, fluoro, cyano, nitro, methyl, tent-butyl, n-propyl, trifluoromethyl, ethyl, methoxy, ethoxy, trifluoromethoxy, trifluoromethylsulfanyl, iso-butoxy, phenyl, phenoxy, benzyloxy, and 4-trifluoromethylbenzyloxy. The remaining two of $R^1$, $R^2$, $R^3$, $R^4$, and $R^5$ are each hydrogen.

$X^1$ is selected from the group consisting of —NH— and —N(CH$_3$)—.

$X^3$ is selected from the group consisting of —CH$_2$—, —O—, and —C(O)—.

$X^4$ is selected from the group consisting of —CH$_2$, —C(H)(CH$_3$)—, —C(CH$_3$)$_2$—, —NH—, and —N(CH$_3$)—.

$X^5$ is selected from the group consisting of —CH$_2$— and —C(O)—.

$X^6$ is selected from the group of linkers consisting of:

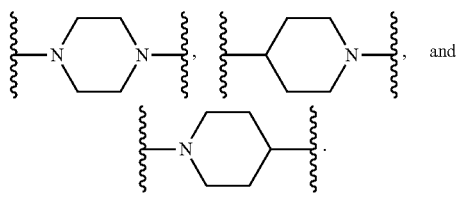

Any such group is optionally substituted with up to two methyl groups.

$Z^1$ is CH substituted with a substituent selected from the group consisting of chloro, nitro, cyano, trifluoromethoxy, and trifluoromethylsulfanyl.

$Z^2$ is CH optionally substituted with trifluoromethyl.

In some embodiments of this invention, the compound is defined as corresponding in structure to a formula selected from the group consisting of:

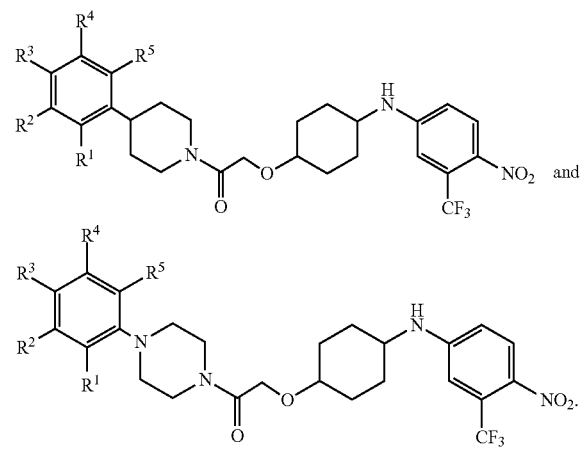

In some such embodiments:

- $R^3$ is selected from the group consisting of halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy.
- At least two of $R^1$, $R^2$, $R^4$, and $R^5$ are each hydrogen. The remaining two of $R^1$, $R^2$, $R^4$, and $R^5$ are each independently selected from the group consisting of hydrogen, halogen, cyano, $C_1$-$C_6$-alkyl, $C_1$-$C_6$-alkoxy, phenyl, phenoxy, and benzyloxy. The $C_1$-$C_6$-alkyl, $C_1$-$C_6$-alkoxy, phenyl, phenoxy, and benzyloxy are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy.

In some embodiments of this invention, the compound is defined as corresponding in structure to the following formula:

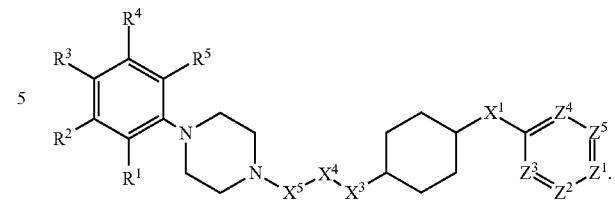

In some embodiments of this invention, the compound is defined as corresponding in structure to the following formula:

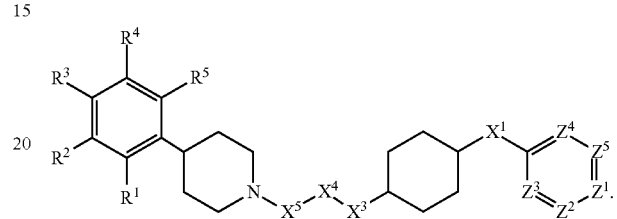

In some embodiments of this invention, the compound corresponds in structure to the following formula:

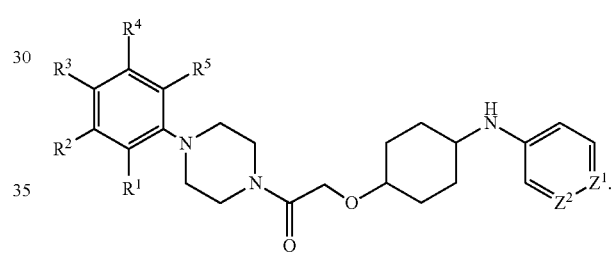

In some embodiments of this invention, the compound corresponds in structure to the following formula:

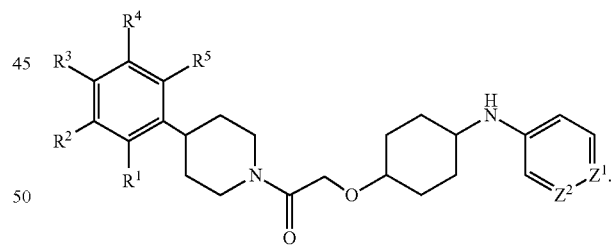

In some embodiments, the compound is defined as corresponding in structure to the following formula:

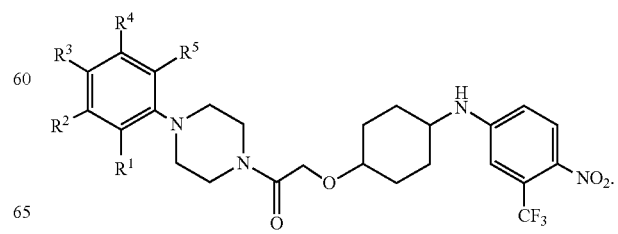

In some embodiments, the compound is defined as corresponding in structure to one of the following formulas:

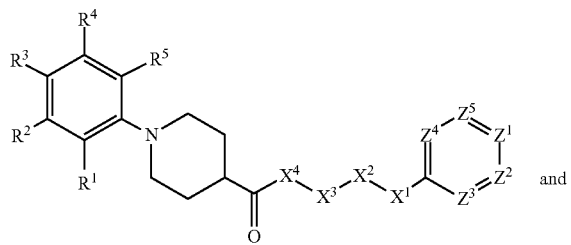

and

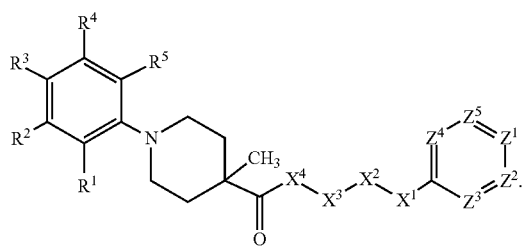

In some such embodiments, $X^4$ is —NH— optionally substituted with $C_1$-$C_6$-alkyl.

In some embodiments, the compound is selected from the group consisting of:

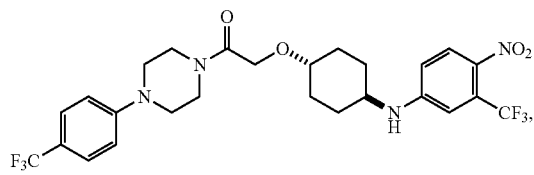

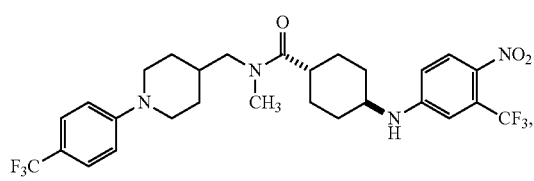

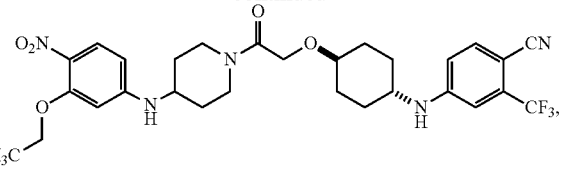

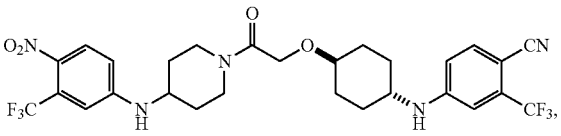

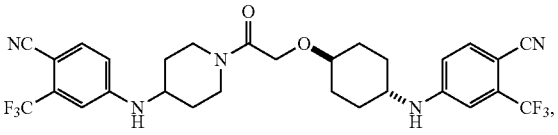

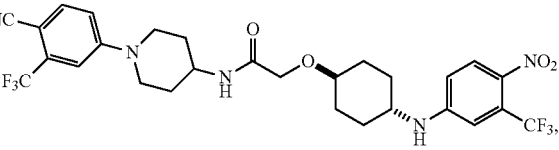

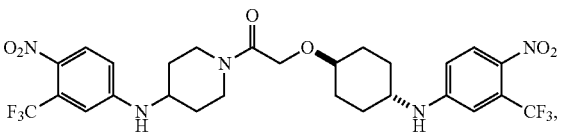

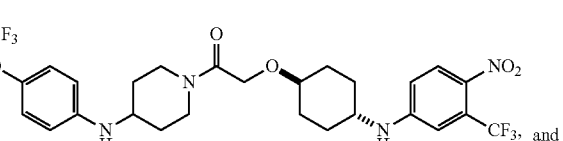

and

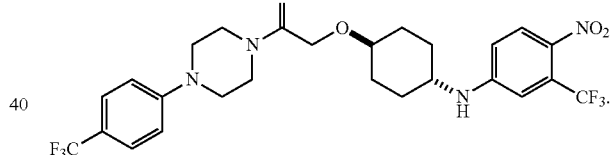

These compounds exhibited a lack undesirable toxicity levels in at least one toxicity study conducted by Applicants. In some embodiments, the compound is selected from the group consisting of:

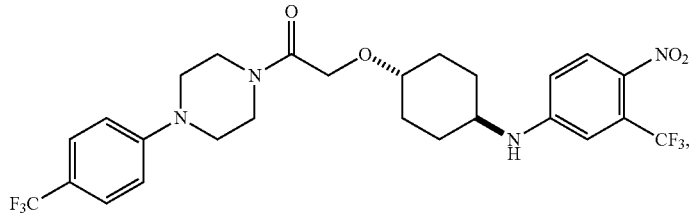

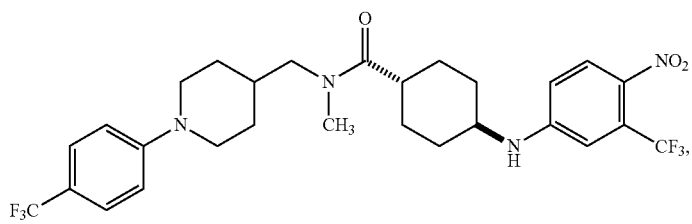

-continued

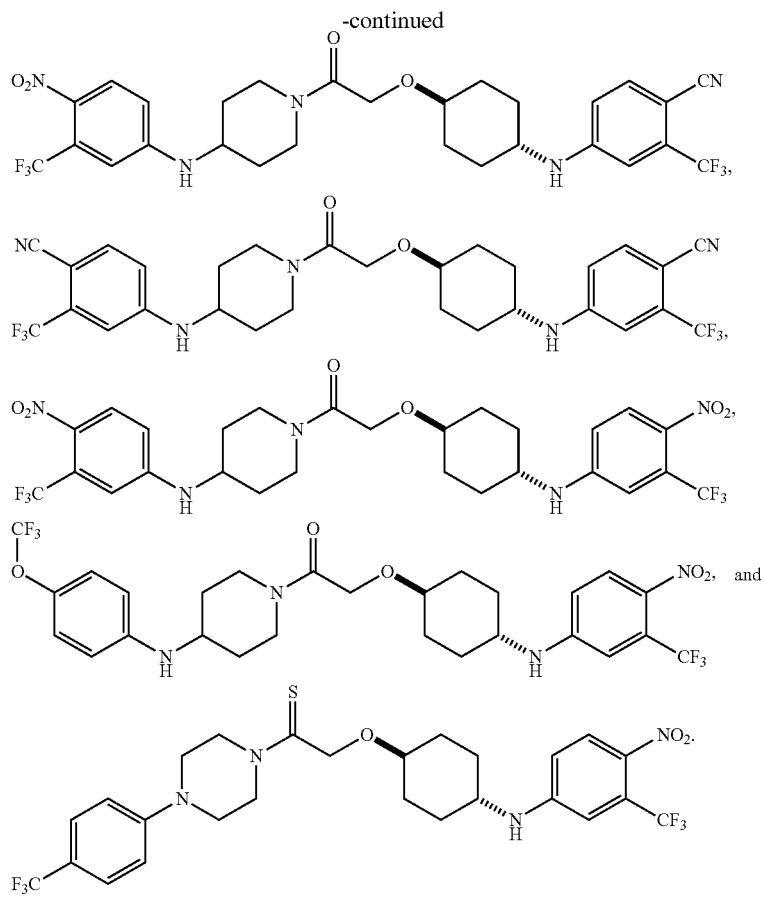

K. Isomers

In some embodiments, a compound of this invention may have two or more conformational structures. For example, the following compound can have a cis or trans configuration:

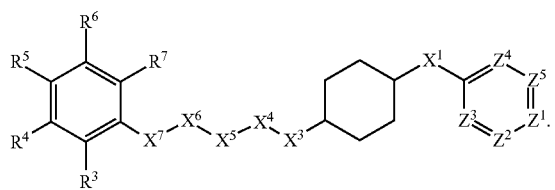

In some embodiments, this compound has the trans configuration such that the compound is encompassed by following formula:

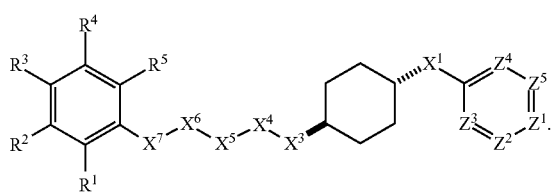

In other embodiments, the compound has the cis configuration such that the compound is encompassed by the following formula:

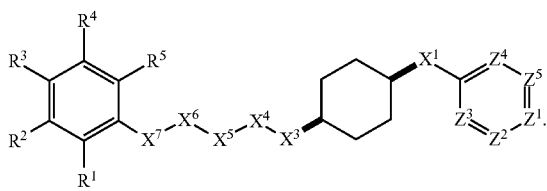

Unless otherwise stated, a compound structure that does not indicate a particular conformation is intended to encompass compositions of all the possible conformational isomers of the compound, as well as compositions comprising fewer than all the possible conformational isomers.

In some embodiments, the compound of this invention is a chiral compound.

In some embodiments, the compound of this invention is a non-chiral compound.

II. Salts of Compounds of this Invention

A salt of the above-described compounds may be advantageous due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the compound. Acid and base salts can typically be formed by, for example, mixing the compound with an acid or base, respectively, using various known methods in the art. To the extent a salt of the compound is intended to be administered in vivo (i.e., to an animal) for a therapeutic benefit, the salt preferably is pharmaceutically acceptable.

In general, an acid addition salt can be prepared by reacting a free base compound with an approximately stoichiometric amount of an inorganic or organic acid. Examples of often suitable inorganic acids for making pharmaceutically acceptable salts include hydrochloric, hydrobromic, hydroiodic, nitric, carbonic, sulfuric, and phosphoric acid. Examples of often suitable organic acids for making pharmaceutically acceptable salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

III. Treatment Methods Using Compounds and Salts of this Invention

Compounds and salts of this invention may generally be used as anthelmintics. In accordance with this invention, it has been discovered that these compounds and salts are particularly useful for treating nematode infections, such as infections by *Trichostrongylus axei, Trichostrongylus colubriformis, Haemonchus contortus, Ascaridia galli*, and/or *Oesophagostomum dentatum*. It is contemplated that the compounds and salts of this invention may be used to treat a range of animals, especially mammals. Such mammals include, for example, humans. Other mammals include, for example, farm or livestock mammals (e.g., swine, bovines, sheep, goats, etc.), laboratory mammals (e.g., mice, rats, jirds, etc.), companion mammals (e.g., dogs, cats, equines, etc.), and wild and zoo mammals (e.g., buffalo, deer, etc.). In some embodiments, the compounds and salts are used to treat goats. In other embodiments, the compounds and salts are used to treat sheep. It is contemplated that the compounds and salts of this invention also are suitable to treat non-mammals, such as birds (e.g., turkeys, chickens, etc.) and fish (e.g., salmon, trout, koi, etc.).

In some embodiments, one or more compounds or salts of this invention are used to treat an infection by a nematode (for example, *H. contortus*) that is resistant to one or more other anthelmintic agents. In some embodiments, the compound or salt is active against a nematode (for example, *H contortus*) resistant to one or more of the following: an avermectin (e.g., ivermectin, selamectin, doramectin, abamectin, and eprinomectin); a milbemycin (moxidectin and milbemycin oxime); a pro-benzimidazole (e.g., febantel, netobimin, and thiophanate); a benzimidazole derivative, such as a thiazole benzimidazole derivative (e.g., thiabendazole and cambendazole) or a carbamate benzimidazole derivative (e.g., fenbendazole, albendazole (oxide), mebendazole, oxfendazole, parbendazole, oxibendazole, flubendazole, and triclabendazole); an imidazothiazole (e.g., levamisole and tetramisole); a tetrahydropyrimidine (morantel and pyrantel), an organophosphate (e.g., trichlorphon, haloxon, dichlorvos, and naphthalophos); a salicylanilide (e.g., closantel, oxyclozanide, rafoxanide, and niclosamide); a nitrophenolic compound (e.g., nitroxynil and nitroscanate); benzoenedisulphonamide (e.g., clorsulon); a pyrazinaisoquinoline (e.g., praziquantel and epsiprantel); a heterocyclic compound (e.g., piperazine, diethylcarbamazine, dichlorophen, and phenothiazine); an arsenical (e.g., thiacetarsamide, melorsamine, and arsenamide); cyclooctadepsipeptide (e.g., emodepside); and a paraherquamide. In some such embodiments, for example, the compound or salt is active against a nematode (for example, *H contortus*) resistant to an avermectin, such as ivermectin. In other embodiments, the compound or salt is alternatively or additionally active against a nematode (for example, *H contortus*) resistant to a benzimidazole derivative, such as fenbendazole. In other embodiments, the compound or salt is alternatively or additionally active against a nematode (for example, *H contortus*) resistant to levamisole. And, in other embodiments, the compound or salt is alternatively or additionally active against a nematode (for example, *H contortus*) resistant to pyrantel.

The compounds and salts of this invention may be administered orally. For example, the compound or salt may be added to the intended recipient's feed, either directly or as part of a premix. The compound or salt alternatively may be administered as, for example, a separate solid dosage form (e.g., a tablet, a hard or soft capsule, granules, powders, etc.), paste, or liquid dosage form (e.g., a solution, suspension, syrup, etc.).

A dosage form may comprise one or more suitable excipients. Such excipients generally include, for example, sweetening agents, flavoring agents, coloring agents, preservative agents, inert diluents (e.g., calcium carbonate, sodium carbonate, lactose, calcium phosphate, sodium phosphate, or kaolin), granulating and disintegrating agents (e.g., corn starch or alginic acid), binding agents (e.g., gelatin, acacia, or carboxymethyl cellulose), and lubricating agents (e.g., magnesium stearate, stearic acid, or talc). Liquid compositions will generally comprise a solvent, such as, for example, one or more of dimethylformamide, N,N-dimethylacetamide, pyrrolidone, N-methylpyrrolidone, polyethyleneglycol, diethyleneglycolmonoethyl ester, dimethylsulfoxide, andethyl lactate. The solvent preferably has sufficient chemical properties and quantity to keep the compound or salt solubilized under normal storage conditions. In some instances, it may be desirable for the compositions to comprise one or more preservatives. The presence of a preservative may, for example, allow for the compositions to be stored for longer periods. Every excipient in the composition preferably is pharmaceutically acceptable.

It is contemplated that the compounds and salts of this invention may alternatively be administered via non-oral routes, such as rectally, via inhalation (e.g., via a mist or aerosol), transdermally (e.g., via a transdermal patch), or parenterally (e.g., subcutaneous injection, intravenous injection, intramuscular injection, etc.).

In general, the compositions of this invention are administered in a dosage form that provides a therapeutically effective amount of the compound or salt to the site of infection. A "therapeutically effective amount" is an amount that is sufficient to ameliorate, suppress, or eradicate a target pathogen(s) infection. Generally, the therapeutically effective amount is defined as the amount necessary to achieve a concentration efficacious to control the target pathogen(s) at the site of infection. The concentration at the site of infection is preferably at least equal to the $MIC_{90}$ level (minimum inhibitory concentration, i.e., the concentration that inhibits the growth of 90% of the target pathogen) of the compound or salt thereof for the target pathogen. To the extent the compound or salt is administered with another active ingredient(s) (e.g., one or more other anthelmintics), the dosage preferably comprises an amount of the compound or salt that, together with the amount of other active ingredient(s), constitutes a therapeutically effective amount.

A single administration of the compound or salt is typically sufficient to treat a nematode infection. Although such a single dose is typically preferred, it is contemplated that multiple doses can be used. When the compound or salt is orally administered, the total dose to treat an infection is generally greater than about 0.01 mg/kg (i.e., milligram of compound or salt per kilogram body weight). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 1 to about 15 mg/kg, from about 8 to about 12 mg/kg, or about 10 mg/kg. The same dose range may be suitable for other routes of administration. For example, in some embodiments, the same dose range is used for subcutaneous administration. The desired dose, however, may be less in some instances where the compound or salt is administered parenterally, particularly intravenously. For example, in some such embodiments, the dose is from about 0.01 to about 50 mg/kg, from about 0.01 to about 15 mg/kg, or from about 0.1 to about 10. For sheep, for example, a suitable intravenous dose may be from about 0.01 to about 10 mg/kg, from about 0.1 to about 5 mg/kg, or about 1 mg/kg.

If the compound or salt is administered parenterally via an injection, the concentration of the compound or salt in the dosage form preferably is sufficient to provide the desired therapeutically effective amount of the compound or salt in a volume that is acceptable for parenteral administration.

Factors affecting the preferred dosage may include, for example, the type (e.g., species and breed), age, size, sex, diet, activity, and condition of the intended recipient; the administration route; pharmacological considerations, such as the activity, efficacy, pharmacokinetic, and toxicology profiles of the particular composition administered; and whether the compound or salt is being administered as part of a combination of active ingredients. Thus, the preferred amount of the compound or salt can vary, and, therefore, can deviate from the typical dosages set forth above. Determining such dosage adjustments is generally within the skill of those in the art.

This invention also is directed to kits that are, for example, suitable for use in performing the methods of treatment described above. The kit comprises a therapeutically effective amount of at least one compound or salt of this invention, and an additional component. The additional component(s) may be, for example, one or more of the following: another ingredient (e.g., an excipient or active ingredient), instructions for combining the compound or salt with another ingredient, an apparatus for combining the compound or salt with another ingredient and/or administering the compound or salt, instructions for using an apparatus to combine the compound or salt with another ingredient and/or administer the compound or salt, or a diagnostic tool.

EXAMPLES

The following examples are merely illustrative, and not limiting to the remainder of this disclosure in any way.

Example 1

Protocols for Analyzing Compounds Prepared in Accordance with this Invention

Applicants prepared a plethora of compounds of this invention. The identities and purities were characterized and verified using various analytical high performance liquid chromatography ("HPLC") and mass spectroscopy ("MS") protocols. These protocols are discussed below.

System I

In some instances, the compound analysis was conducted using an HPLC/MSD 1100 (Agilent, Santa Clara, Calif., USA) having a binary pump (G1312A) with a degasser (G1379A), a well plate sampler (G1367A), a column oven (G1316A), a diode array detector (G1315B), a mass detector (G1946D SL) with an ESI-source, and an evaporating light detector (Sedex 75). Four different columns and detection methods were used with this system:

Protocol I-A

The column used for this protocol was a Zorbax SB-C18 (Agilent), having a 4.6 mm diameter, a 30 mm length, and 3.5 µm packing. The column was operated at 30° C. (ambient temperature). The injection volume was 5.0 µL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 0.2 | 90 | 10 |
| 4.2 | 2 | 98 |
| 5.5 | 2 | 98 |

The samples were diluted in a 1:1 mixture of solvents A and B before analysis. The detection methods were UV at 210 and 254 nm; ESI/MS (100-1000 m/z), positive ions; and ELSD (Sedex 75).

Protocol I-B

The column used for this protocol was an Atlantis dC18 (Waters, Milford, Mass., USA), having a 4.6 mm diameter, a 50 mm length, and 3 μm packing. The column was operated at 30° C. The injection volume was 2.0 μL, the flow rate was 1.0 ml/min, and the run time was 10 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 95 | 5 |
| 1.0 | 95 | 5 |
| 5.0 | 2 | 98 |
| 7.0 | 2 | 98 |

The samples were diluted in a 1:1 mixture of solvents A and B before analysis. The detection methods were UV at 210 and 254 nm; ESI/MS (100-1000 m/z), positive ions; and ELSD (Sedex 75).

Protocol I-C

The column used for this protocol was an Atlantis dC18, having a 4.6 mm diameter, a 50 mm length, and 3 μm packing. The column was operated at 30° C. The injection volume was 2.0 μL, the flow rate was 1.5 ml/min, and the run time was 6 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 0.5 | 90 | 10 |
| 3.0 | 2 | 98 |
| 4.0 | 2 | 98 |

The samples were diluted in a 1:1 mixture of solvents A and B before analysis. The detection methods were UV at 210 and 254 nm; ESI/MS (85-1000 m/z), positive ions; and ELSD (Sedex 75).

Protocol I-D

The column used for this protocol was a Zorbax SB-C18 (Agilent), having a 4.6 mm diameter, a 30 mm length, and 3.5 μm packing. The column was operated at 30° C. (ambient temperature). The injection volume was 5.0 μL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 50 | 50 |
| 0.2 | 50 | 50 |
| 4.2 | 2 | 98 |
| 5.5 | 2 | 98 |

The samples were diluted in a 1:1 mixture of solvents A and B before analysis. The detection methods were UV at 210 and 254 nm; ESI/MS (100-1000 m/z), positive ions; and ELSD (Sedex 75).

System II

In some instances, the compound analysis was conducted using an LC/MSD Trap 1100 (Agilent, Santa Clara, Calif., USA) having a binary pump (G1312A) with a degasser (G1379A), a well plate sampler (G1367A), a column oven (G1316A), a diode array detector (G1315B), a mass detector (G2445D SL) with an APCI-source, and an evaporating light detector (Alltech ELSD2000). Three different columns and detection methods were used with this system:

Protocol II-A

The column used for this protocol was a Zorbax SB-C18 (Agilent), having a 4.6 mm diameter, a 30 mm length, and 3.5 μm packing. The column was operated at 30° C. The injection volume was 5.0 μL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 0.2 | 90 | 10 |
| 4.2 | 2 | 98 |
| 5.5 | 2 | 98 |

The samples were diluted in a 1:1 mixture of solvents A and B before analysis. The detection methods were UV at 210 and 254 nm; and APCI/MS (80-1000 m/z), positive ions.

Protocol II-B

The column used for this protocol was an XBridge C18 (Waters), having a 4.6 mm diameter, a 50 mm length, and 2.5 μm packing. The column was operated at 40° C. The injection volume was 2.0 μL, the flow rate was 1.0 ml/min, and the run time was 10 min (equilibration included). Two eluents were used with the following gradients:

| Time (min) | Solvent A (%) water/ammonia, 99.9/0.1 (v/v) | Solvent B (%) acetonitrile |
|---|---|---|
| 0.0 | 75 | 25 |
| 5.0 | 0 | 100 |
| 7.0 | 0 | 100 |
| 7.5 | 75 | 25 |

The samples were diluted in a 1:1 mixture of solvents A and B before analysis. The detection methods were UV at 254 and 210 nm; and APCI/MS (100-1500 m/z), positive ions.

Protocol II-C

The column used for this protocol was a Gemini® C18 (Phenomenex Inc., CA) having a 4.6 mm diameter, a 50 mm length, and 5.0 μm packing. The column was operated at 35° C. The injection volume was 2.0 μL, and the flow rate was 1.0 ml/min. Two eluents were used with the following gradients:

| Time (min) | Solvent A (%) water/formic acid, 99.9/0.1 (v/v) | Solvent B (%) acetonitrile/formic acid, 99.9/0.1 (v/v) |
| --- | --- | --- |
| 0.0 | 98 | 2 |
| 3.5 | 2 | 98 |
| 6.0 | 2 | 98 |

The samples were diluted in a 1:1 mixture of solvents A and B before analysis. The detection methods were UV at 270 nm; and APCI/MS (100-800 m/z), positive and negative ions.

Example 2

Preparation of 1-(4-trifluormethyl-phenyl)-2,5-dimethylpiperazine intermediate (also known as trans-2,5-dimethyl-1-(4-trifluoromethyl-phenyl)-piperazine)

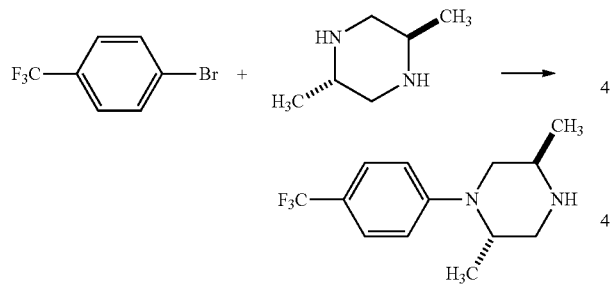

4-Bromobenzotrifluoride (1.35 g, 6.0 mmol), trans-2,5-dimethylpiperazine (582 mg, 5.1 mmol), tris-(dibenzylideneacetone)-dipalladium (240 mg, 0.26 mmol), 2-(dicyclohexylphosphino)-biphenyl (252 mg, 0.72 mmol) were dissolved in toluene (6 mL). A molar solution of lithium bis(trimethylsilyl)-amide (12 mL, 12 mmol) was then added. The resulting mixture was heated to 85° C. and stirred at that temperature for 6.5 hr. The mixture was then cooled to room temperature and diluted with diethyl ether (20 mL). The precipitate was separated by filtration, and the filtrate was concentrated under vacuum. Purification by column chromatography on silica gel (dichloromethane/methanol 1:0, 8:2) afforded the desired product as a brown oil (760 mg, 58% yield).

In many instances, the method of Example 2 can be adapted to make other compounds that are useful as intermediates for making the compounds and salts of this invention. An illustrative generic scheme is as follows:

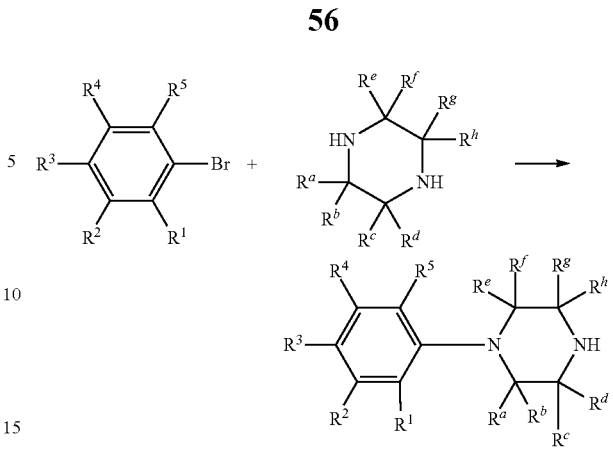

Here, $R^1$, $R^2$, $R^3$, $R^4$, and $R^5$ are as defined above for the compounds of this invention. $R^a$, $R^b$, $R^c$, $R^d$, $R^e$, $R^f$, $R^g$, and $R^h$ are each independently selected from the group consisting of hydrogen, halogen, hydroxy, alkyl, and alkoxy, with at least one of them being hydrogen Determining the suitability of the method (and any necessary routine adaptations) for making a particular intermediate is generally within the skill of those in the art after reading this patent.

Example 3

Preparation of 1-chloracetyl-4-(4-trifluormethyl-phenyl)-2,5-dimethylpiperazine intermediate (also known as 2-chloro-1-[trans-2,5-dimethyl-4-(4-trifluoromethyl-phenyl)-piperazin-1-yl]ethanone)

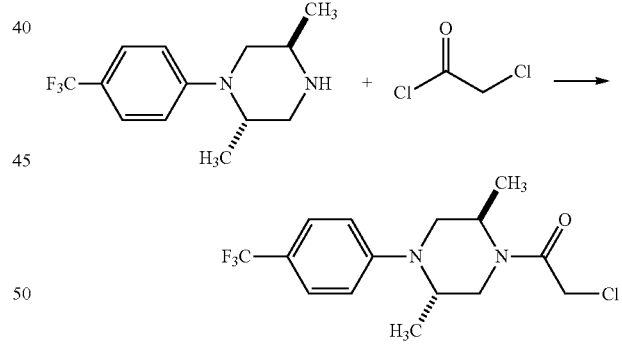

1-(4-Trifluormethyl-phenyl)-2,5-dimethylpiperazine (760 mg, 2.94 mmol, prepared in accordance with Example 2) and triethylamine (820 μL, 5.88 mmol) were dissolved in dichloromethane (5 mL). Chloroacetyl chloride (234 μL, 2.94 mmol) was then slowly added under stirring. After stirring for an additional 20 min at room temperature, the mixture was diluted with dichloromethane (10 mL), washed with water (10 mL), and washed with saturated aqueous sodium hydrogencarbonate (10 mL). The organic layer was collected, dried over magnesium sulfate, filtered, and concentrated under vacuum. The desired product was isolated as a light yellow oil (340 mg, 35% yield).

Example 4

Preparation of 1-chloracetyl-4-(4-trifluoromethyl-phenyl)-piperazine intermediate (also known as 2-chloro-1-[4-(4-trifluoromethyl-phenyl)-piperazin-1-yl]ethanone)

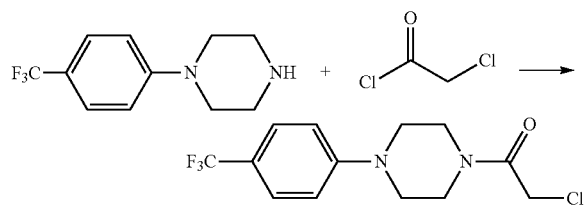

1-(4-Trifluormethyl-phenyl)-piperazine (283 mg, 1 mmol) and triethylamine (220 µL, 2 mmol) were dissolved in dichloromethane (8 mL). Chloroacetyl chloride (110 µL, 1 mmol) was then slowly added under stirring. After stirring for an additional 10 min at room temperature, the mixture was diluted with dichloromethane (10 mL), washed with water (10 mL), and washed with saturated aqueous sodium hydrogencarbonate (10 mL). The organic layer was collected, dried over magnesium sulfate, filtered, and concentrated under vacuum. The desired product was isolated as a light yellow oil (292 mg, 95% yield).

In many instances, the methods of Examples 3 and 4 can be adapted to make other compounds that are useful as intermediates for making the compounds and salts of this invention. An illustrative generic scheme is as follows:

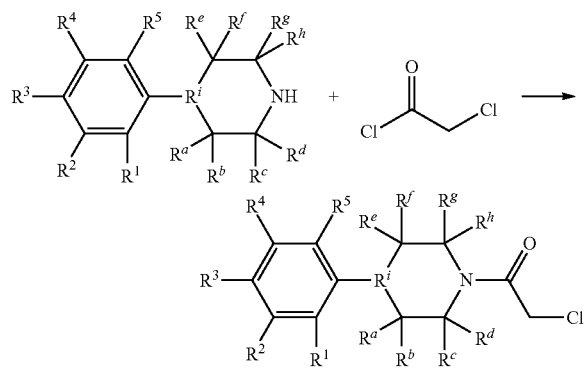

Here, $R^1$, $R^2$, $R^3$, $R^4$, and $R^5$ are as defined above for the compounds of this invention. $R^a$, $R^b$, $R^c$, $R^d$, $R^e$, $R^f$, $R^g$, and $R^h$ are each independently selected from the group consisting of hydrogen, halogen, hydroxy, alkyl, and alkoxy. And $R^i$ is either

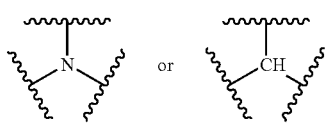

optionally substituted with halogen, hydroxy, alkyl, and alkoxy. Determining the suitability of the methods (and any necessary routine adaptations) for making a particular intermediate is generally within the skill of those in the art after reading this patent.

Example 5

Preparation of trans-4-(4-nitro-3-trifluoromethyl-phenylamino)-cyclohexanol Intermediate

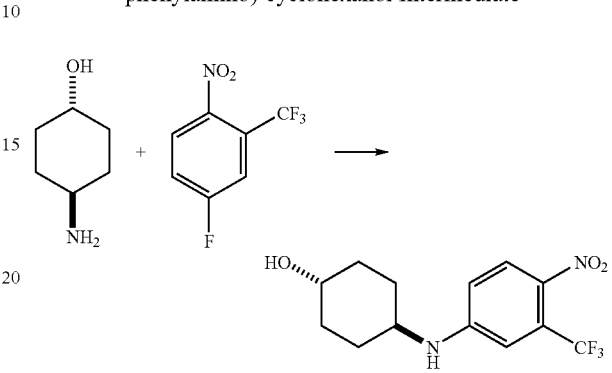

5-Fluoro-2-nitrobenzotrifluoride (400 mg, 1.91 mmol) and trans-4-aminocyclohexanol (220 mg, 1.91 mmol) were dissolved in dimethylsulfoxide (10 mL). The resulting mixture was heated at 95° C. for 3.5 hr. After cooling at room temperature, the mixture was diluted with dichloromethane (15 mL) and washed with water (3×10 mL). The organic phase was collected and dried over sodium sulfate, filtered, and concentrated under vacuum. The crude product was re-crystallized from petrol ether. The desired product was then isolated as a yellow solid (490 mg, 84% yield).

In many instances, the method of Example 5 can be adapted to make other compounds that are useful as intermediates for making the compounds and salts of this invention. An illustrative generic scheme is as follows:

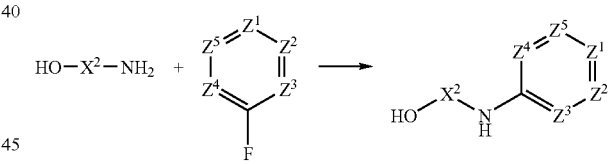

Here, $X^2$, $Z^1$, $Z^2$, $Z^3$, $Z^4$, and $Z^5$ are as defined above for the compounds of this invention. Another illustrative generic scheme is as follows:

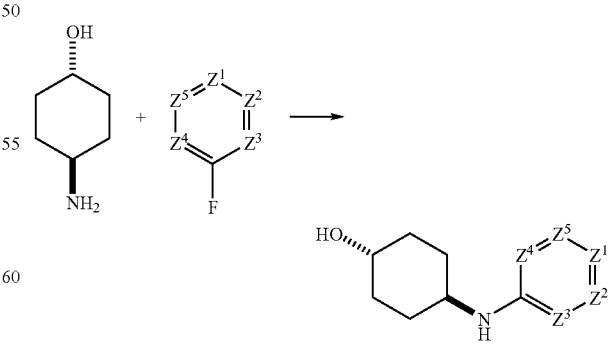

Determining the suitability of the method (and any necessary routine adaptations) for making a particular intermediate is generally within the skill of those in the art after reading this patent.

Example 6

Preparation of 4-(trans-4-hydroxy-cyclohexylamino)-2-trifluoromethyl-benzonitrile Intermediate

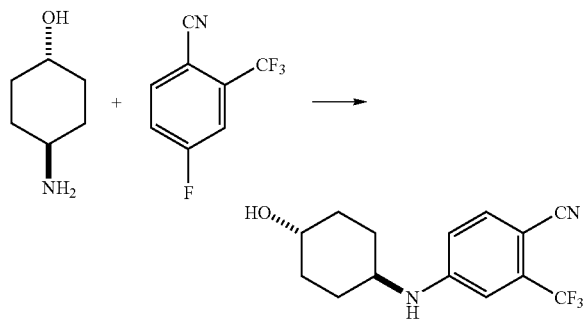

Potassium carbonate (304 mg, 2.2 mmol) was dissolved in a minimum amount of water. Next, 4-fluoro-2-trifluoromethylbenzonitrile (378 mg, 2.0 mmol) and trans-4-aminocyclohexanol (460 mg, 4.0 mmol) dissolved in acetonitrile (10 mL) were added. The resulting mixture was then heated at 80° C. for 3 days. After cooling at room temperature, the mixture was concentrated under vacuum, taken up in ethyl acetate (15 mL), washed with saturated aqueous ammonium chloride (2×10 mL), and washed with water (10 mL). The organic phase was collected and dried over sodium sulfate, filtered, and concentrated under vacuum. The desired product was isolated as a colorless solid (456 mg, 80% yield).

Example 7

Preparation of 1-benzyl-4-(4-phenoxy-phenyl)-piperidin-4-ol Intermediate

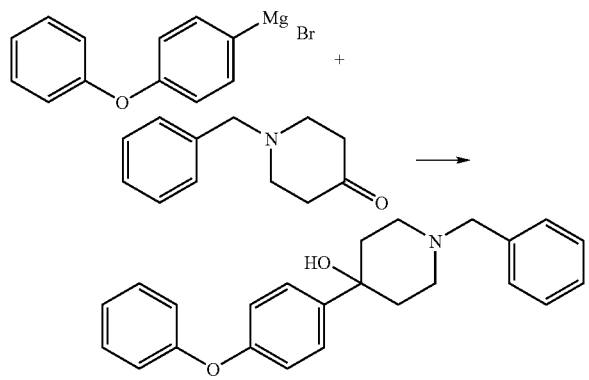

A 0.5 M solution of 4-phenoxy-phenylmagnesium bromide in tetrahydrofuran (30 mL, 15 mmol) was introduced into a flame-dried flask placed under an argon atmosphere. A solution of 1-benzyl-4-piperidone (2.84 g, 15 mmol) in dry tetrahydrofuran (12 mL) was then added dropwise, while the temperature was maintained at less than 20° C. with an ice bath. After completion of the addition, the mixture was allowed to reach room temperature and further stirred for 2 hr. Ice was then added to the mixture, and 1 N HCl was then added until the resulting precipitate was completely dissolved. The reaction was then diluted with diethyl ether (100 mL) and washed with water (50 mL). The aqueous layer was extracted with diethyl ether (2×50 mL), and the combined organic layers were sequentially washed with saturated aqueous sodium hydrogencarbonate (2×50 mL) and water (50 mL), dried over magnesium sulfate, filtered, and concentrated under vacuum. The crude product was purified by column chromatography on silica gel (dichloromethane and then diethyl ether). The desired product was then isolated as a colorless solid (1.74 g, 33% yield).

In many instances, the method of Example 7 can be adapted to make other compounds that are useful as intermediates for making the compounds and salts of this invention. An illustrative generic scheme is as follows:

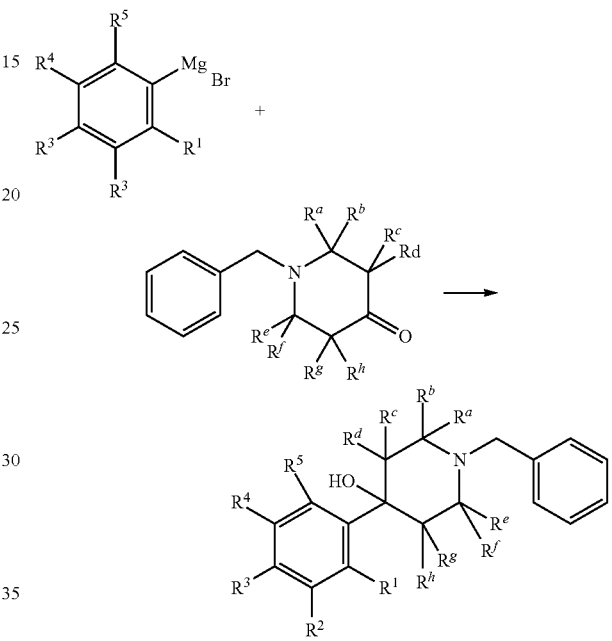

Here, $R^1$, $R^2$, $R^3$, $R^4$, and $R^5$ are as defined above for the compounds of this invention. And $R^a$, $R^b$, $R^c$, $R^d$, $R^e$, $R^f$, $R^g$, and $R^h$ each are independently selected from the group consisting of hydrogen, halogen, hydroxy, alkyl, and alkoxy, with at least one of them being hydrogen. Another illustrative generic scheme is as follows:

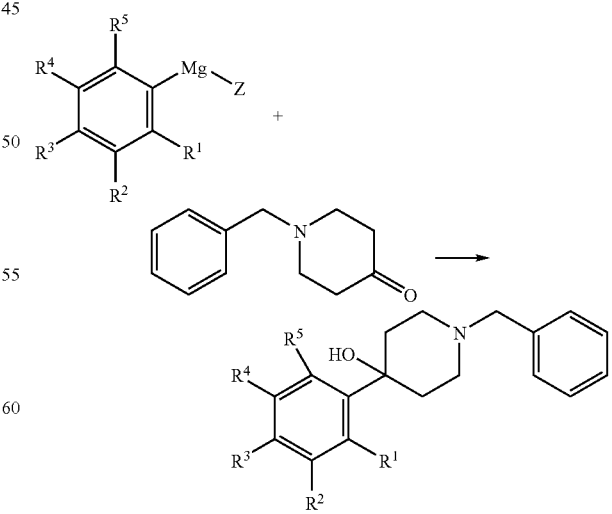

Here, Z may be, for example, halogen, such as bromo. Determining the suitability of the method (and any necessary routine adaptations) for making a particular intermediate is generally within the skill of those in the art after reading this patent.

Example 8

Preparation of 4-(4-phenoxy-phenyl)-piperidine Intermediate

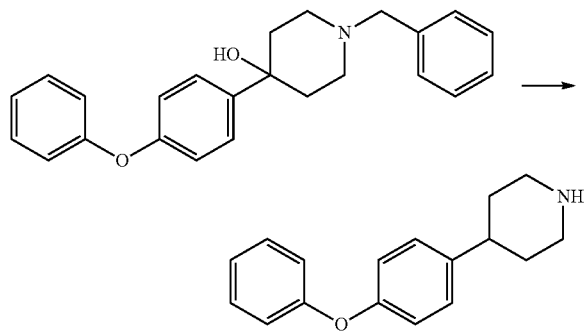

1-Benzyl-4-(4-phenoxy-phenyl)-piperidin-4-ol (3.47 g, 9.6 mmol, prepared in accordance with Example 7) was combined with trifluoroacetic acid (6 mL). The resulting mixture was irradiated at 130° C. in a mono-mode microwave oven for 15 min. The mixture was then concentrated under vacuum, and the obtained residue was triturated with diethyl ether (20 mL). After the solvent was removed under vacuum, the isolated product (6.6 g) was dissolved in methanol (350 mL). To this mixture was added 10% Pd/C was added (800 mg). The resulting suspension was reacted under $H_2$ pressure (4 bar) for 5 hr at 75° C. After removing the catalyst by filtration, the filtrate was concentrated under vacuum. The obtained residue was triturated with diethyl ether (50 mL), and the precipitate was filtered and dried under vacuum. The desired product was obtained as a light yellow solid (3.26 g, 92% yield).

In many instances, the method of Example 8 can be adapted to make other compounds that are useful as intermediates for making the compounds and salts of this invention. An illustrative generic scheme is as follows:

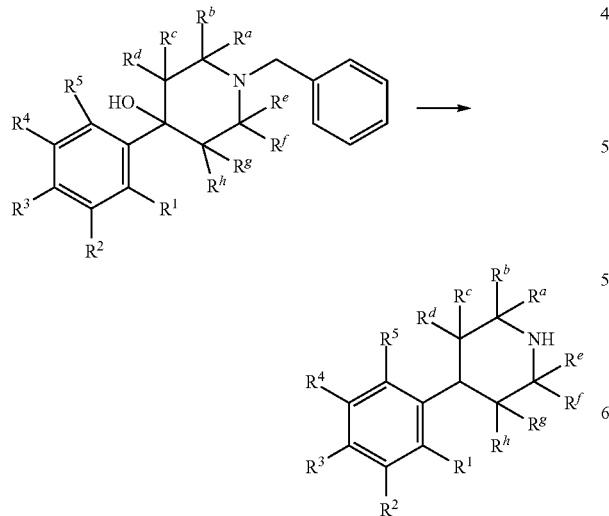

Here, $R^1$, $R^2$, $R^3$, $R^4$, and $R^5$ are as defined above for the compounds of this invention.

And $R^a$, $R^b$, $R^c$, $R^d$, $R^e$, $R^f$, $R^g$, and $R^h$ are independently selected from the group consisting of hydrogen, halogen, hydroxy, alkyl, and alkoxy. An illustrative generic scheme is as follows:

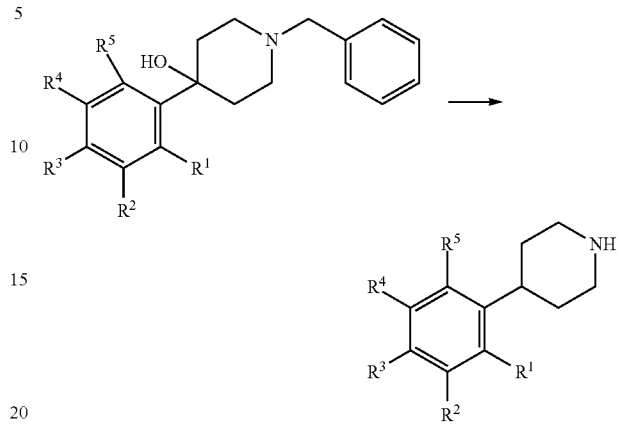

Determining the suitability of the method (and any necessary routine adaptations) for making a particular intermediate is generally within the skill of those in the art after reading this patent.

Example 9

Preparation of 4-(4-butyl-phenyl)-piperidine Intermediate

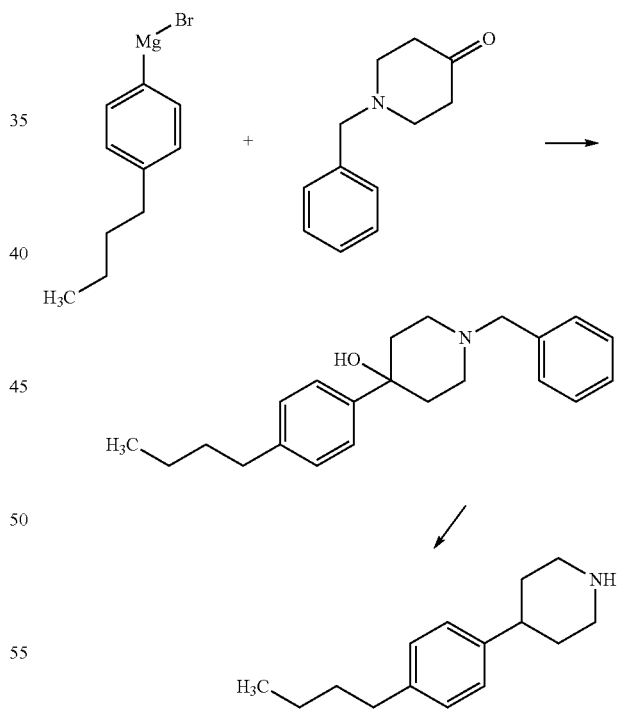

4-(4-Butyl-phenyl)-piperidine was prepared using a two-step procedure. In the first step, 1-benzyl-4-(4-butyl-phenyl)-piperidin-4-ol was prepared from (4-butyl-phenyl)magnesium bromide and 1-benzyl-4-piperidone using the procedure illustrated in Example 7, and in the second step, the 1-benzyl-4-(4-butyl-phenyl)-piperidin-4-ol was converted to 4-(4-butyl-phenyl)-piperidine using the procedure illustrated in Example 8. This afforded a quantitative yield of the product as a yellow oil.

Example 10

Preparation of 1-[trans-2,5-dimethyl-4-(4-trifluoromethyl-phenyl)-piperazin-1-yl]-2-[trans-4-(4-nitro-3-trifluoromethyl-phenylamino)-cyclohexyloxy]-ethanone

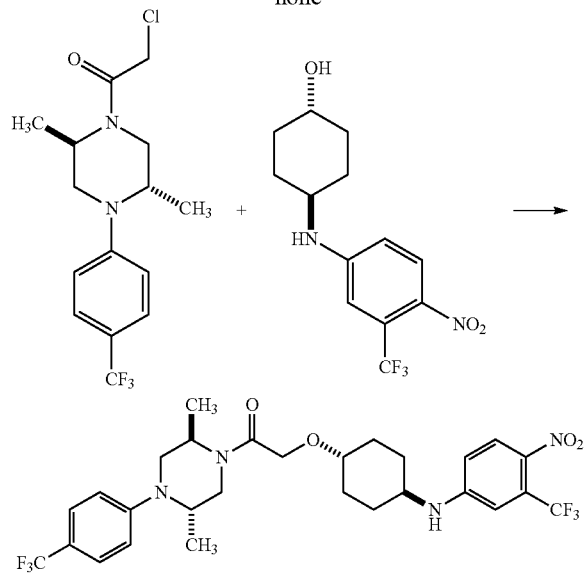

Trans-4-(4-nitro-3-trifluoromethyl-phenylamino)-cyclohexanol (118 mg, 0.39 mmol, prepared in accordance with Example 5) was placed under an inert atmosphere, dissolved in dry dimethylformamide (2 mL). A molar solution of lithium bis(trimethylsilyl)-amide (774 µL, 0.77 mmol) was added to the resulting mixture. The mixture was then stirred for 15 min at room temperature. Afterward, a solution of 2-chloro-1-[trans-2,5-dimethyl-4-(4-trifluoromethyl-phenyl)-piperazin-1-yl]-ethanone (130 mg, 0.39 mmol, prepared in accordance with Example 3) in tetrahydrofuran (1 mL) was added. The resulting mixture was stirred at room temperature until the conversion stopped. Next, the mixture was diluted with diethylether (10 mL). The mixture was then washed with water (5 mL), and then saturated aqueous sodium hydrogencarbonate (5 mL). The organic phase was collected, dried over magnesium sulfate, filtered, and concentrated under vacuum. The crude product isolated was purified by preparative HPLC. Following lyophilization of the fractions of interest, the desired product was isolated as a yellow solid (24 mg, 10% yield). The structure was confirmed using Protocol II-A. Calculated mass=603; observed mass=603; HPLC retention time=4.69 min.

Example 11

Preparation of 2-[trans-4-(4-nitro-3-trifluoromethyl-phenylamino)-cyclohexyloxy]-1-[4-(4-trifluoromethyl-phenyl)-piperazin-1-yl]-ethanone

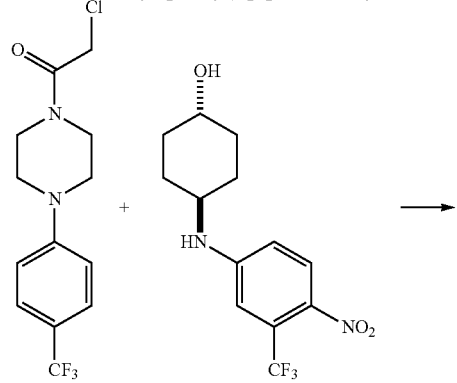

-continued

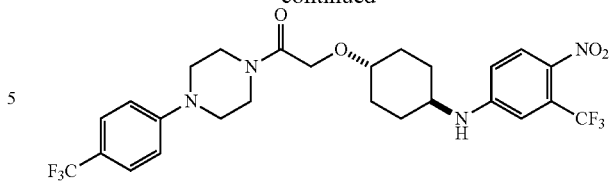

2-Chloro-1-[4-(4-trifluoromethyl-phenyl)-piperazin-1-yl]-ethanone (26 mg, 0.09 mmol, prepared in accordance with Example 4), trans-4-(4-nitro-3-trifluoromethyl-phenylamino)-cyclohexanol (26 mg, 0.09 mmol, prepare in accordance with Example 5), and sodium hydride (10 mg, 60% in oil, 0.26 mmol) were placed under an inert atmosphere. Tetrahydrofuran (1 mL) was added under stirring. Next, dimethylformamide (300 µL) was added under stirring. The resulting mixture was stirred for 40 min at room temperature and then diluted with dichloromethane (5 mL). The mixture was washed with water (5 mL) and then washed with saturated aqueous sodium hydrogencarbonate (5 mL). The organic phase was collected, dried over magnesium sulfate, filtered, and concentrated under vacuum. The crude product was purified by preparative HPLC. Following lyophilization of the fractions of interest, the desired product was isolated as a yellow solid (21 mg, 43% yield). The structure was confirmed using Protocol II-A. Calculated mass=575; observed mass=575; HPLC retention time=4.51 min.

In many instances, the methods of Examples 10 and 11 can be adapted to make other compounds (and salts thereof) of this invention. An illustrative generic scheme is as follows:

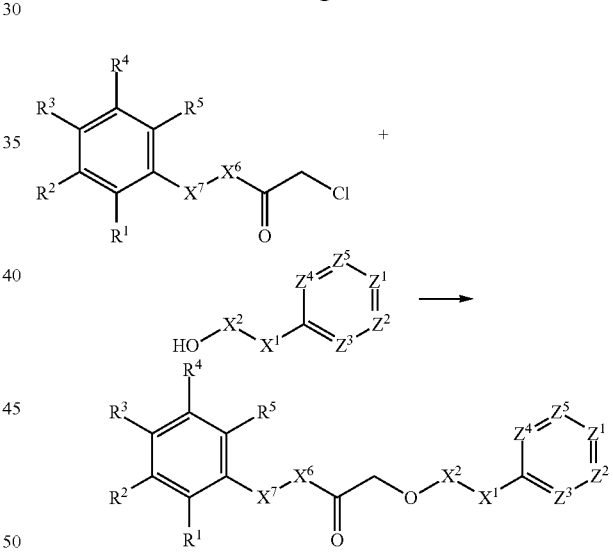

Here, $R^1$, $R^2$, $R^3$, $R^4$, $R^5$, $X^1$, $X^2$, $X^6$, $X^7$, $Z^1$, $Z^2$, $Z^3$, $Z^4$, and $Z^5$ are as defined above for the compounds of this invention. Another illustrative generic scheme is as follows:

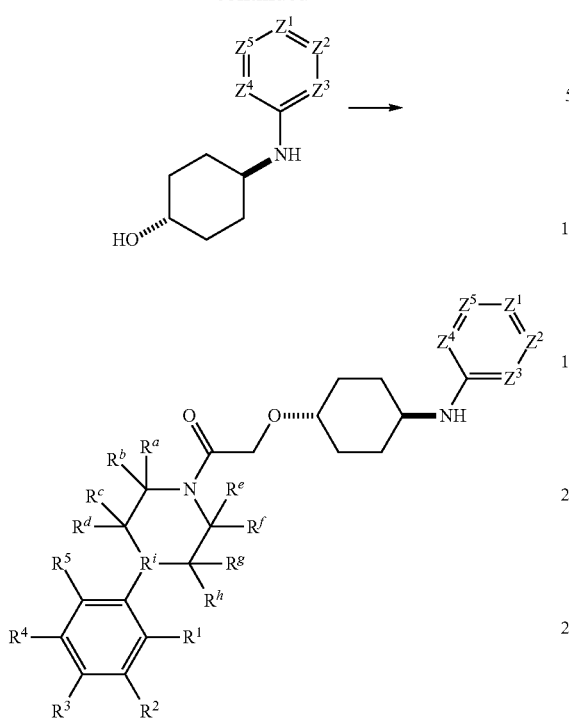

Here, $R^a$, $R^b$, $R^c$, $R^d$, $R^e$, $R^f$, $R^g$, and $R^h$ are independently selected from the group consisting of hydrogen, halogen, hydroxy, alkyl, and alkoxy. And $R^i$ is either

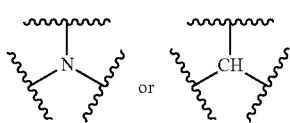

optionally substituted with halogen, hydroxy, alkyl, and alkoxy. Another illustrative generic scheme is as follows:

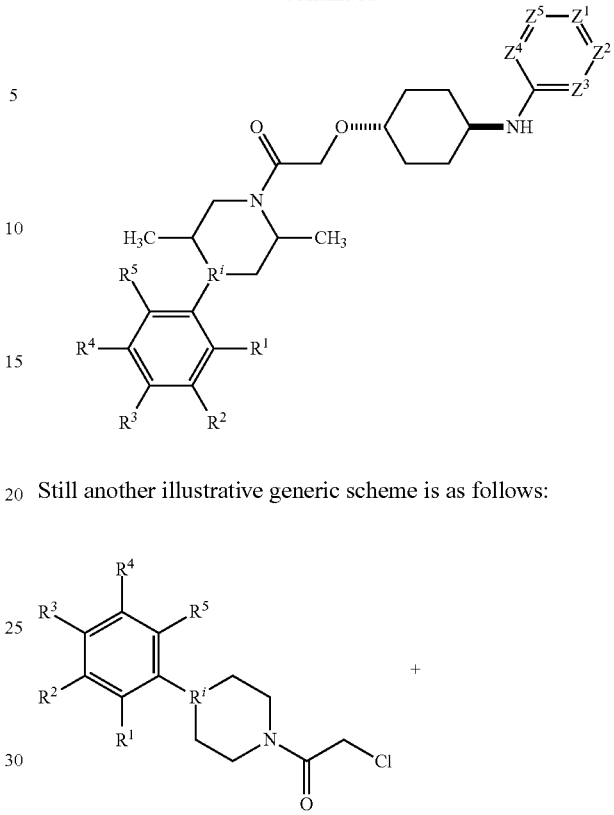

Still another illustrative generic scheme is as follows:

Determining the suitability of the methods (and any necessary routine adaptations) for making a particular compound (or salt thereof) is generally within the skill of those in the art after reading this patent.

Example 12

Preparation of 2-{trans-4-[methyl(4-nitro-3-trifluoromethyl-phenyl)-amino]-cyclohexyloxy}-1-[4-(4-trifluoromethyl-phenyl)-piperazin-1-yl]-ethanone

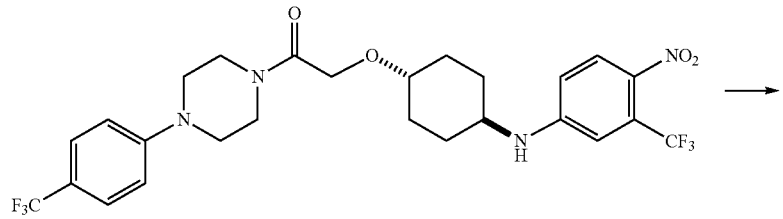

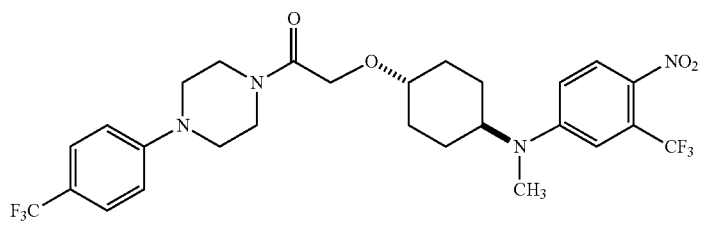

2-[Trans-4-(4-nitro-3-trifluoromethyl-phenylamino)-cyclohexyloxy]-1-[4-(4-trifluoromethyl-phenyl)-piperazin-1-yl]-ethanone (172 mg, 0.30 mmol, prepared in accordance with Example 11) and sodium hydride (12 mg, 0.30 mmol) were placed under an inert atmosphere. Dry tetrahydrofuran (3 mL) was then added. After gas evolution ceased, methyl iodide (20 μL, 0.31 mmol) was added under stirring to the dark orange colored solution. The resulting mixture was stirred at room temperature. After an hour, HPLC-MS monitoring of the reaction showed about 75% conversion to the desired product. More methyl iodide was added (5 μL, 0.08 mmol), and the mixture was stirred for an additional 30 min. HPLC-MS showed 85% conversion. The mixture was quenched with saturated aqueous ammonium chloride (10 mL) and extracted with ethyl acetate (25 mL). The organic layer was separated, washed with water (10 mL), dried over magnesium sulfate, filtered, and concentrated under vacuum. A yellow oil was isolated. The oil was purified by preparative HPLC. Following lyophilization of the fractions of interest, the desired product was isolated as a yellow solid (106 mg, 59% yield). The structure was confirmed using Protocol I-A. Calculated mass=589; observed mass=589; HPLC retention time=4.69 min.

In many instances, the method of Example 12 can be adapted to make other compounds (and salts thereof) of this invention. An illustrative generic scheme is as follows:

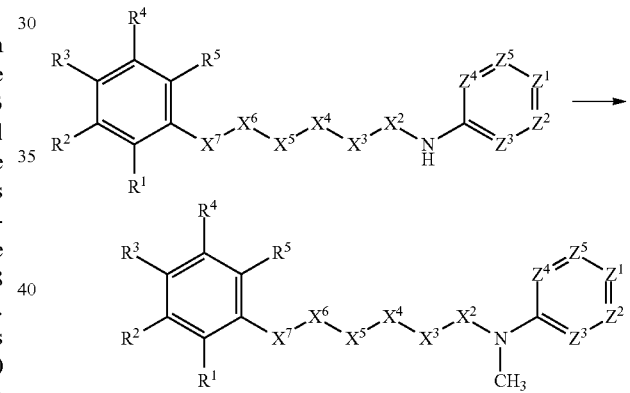

Here, $R^1$, $R^2$, $R^3$, $R^4$, $R^5$, $X^2$, $X^3$, $X^4$, $X^5$, $X^6$, $X^7$, $Z^1$, $Z^2$, $Z^3$, $Z^4$, and $Z^5$ are as defined above for the compounds of this invention. Determining the suitability of the method (and any necessary routine adaptations) for making a particular compound (or salt thereof) is generally within the skill of those in the art after reading this patent.

Example 13

Preparation of 2-[trans-4-(4-nitro-3-trifluoromethyl-phenylamino)-cyclohexyloxy]-1-[4-(4-trifluoromethyl-phenyl)-piperazin-1-yl]-propan-1-one

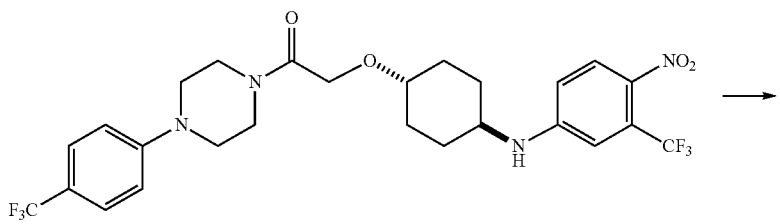

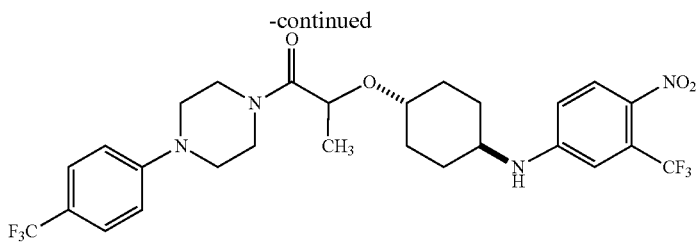

To a solution of diisopropylamine (0.28 mL, 2.0 mmol) in dry tetrahydrofuran (3 mL) at 5° C. was added n-butyllithium (2.5 M solution in hexanes, 1 mL, 2.5 mmol). The resulting mixture was allowed to stir for 30 min. Meanwhile, 2-[trans-4-(4-nitro-3-trifluoromethyl-phenylamino)-cyclohexyloxy]-1-[4-(4-trifluoromethyl-phenyl)-piperazin-1-yl]-ethanone (287 mg, 0.5 mmol, prepared in accordance with Example 11) was dissolved in dry tetrahydrofuran (2 mL). The solution was then cooled to −35° C. To the cooled solution was added an aliquot from the freshly prepared lithium diisopropylamide solution (1.8 mL). Stirring was continued for another 30 min. Methyliodide (37 μL, 0.6 mmol) was then added, and the mixture was allowed to attain −10° C. over 1 hr. Saturated ammonium chloride solution was then added (3 mL), and the mixture warmed to room temperature and acidified to a pH of 3 with 1 N HCl. The aqueous solution was then extracted with ethyl acetate (2×15 mL), and the combined organic layers were washed with brine (2×5 mL), dried over magnesium sulfate, and concentrated. Purification by column chromatography (Ethyl acetate/cyclohexanes, 4:1) afforded the desired product as an orange solid (152 mg, 52% yield). The structure was confirmed using Protocol I-B. Calculated mass=589; observed mass=589; HPLC retention time=5.82 min.

In many instances, the method of Example 13 can be adapted to make other compounds (and salts thereof) of this invention. An illustrative generic scheme is as follows:

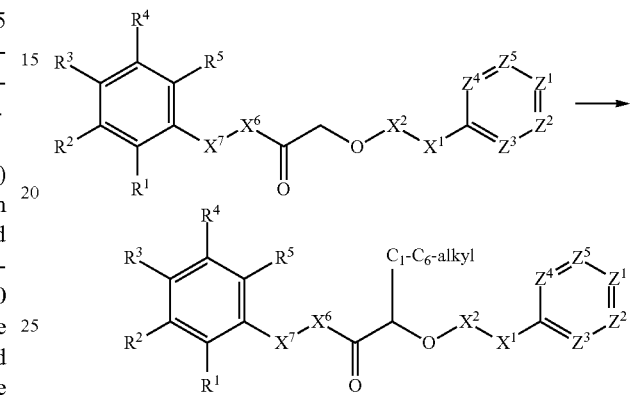

Here, $R^1$, $R^2$, $R^3$, $R^4$, $R^5$, $X^1$, $X^2$, $X^6$, $X^7$, $Z^1$, $Z^2$, $Z^3$, $Z^4$, and $Z^5$ are as defined above for the compounds of this invention. Determining the suitability of the method (and any necessary routine adaptations) for making a particular compound (or salt thereof) is generally within the skill of those in the art after reading this patent.

Example 14

Preparation of 2-methyl-2-[trans-4-(4-nitro-3-trifluoromethyl-phenylamino)-cyclohexyloxy]-1-[4-(4-trifluoromethyl-phenyl)-piperazin-1-yl]-propan-1-one

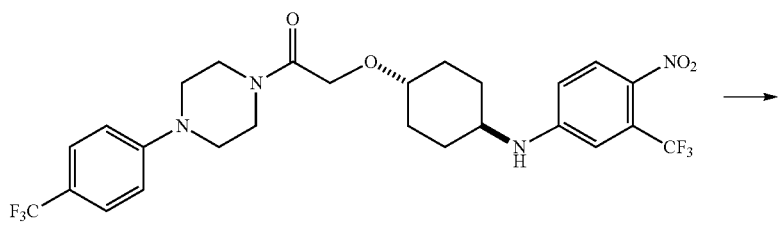

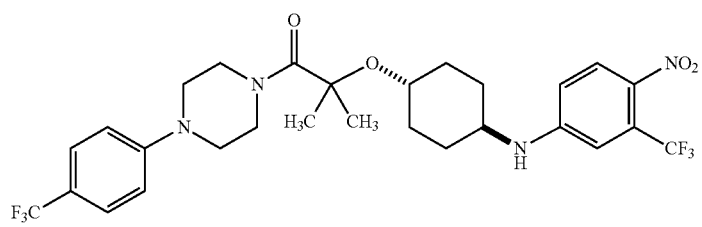

To a solution of diisopropylamine (1.12 mL, 8.0 mmol) in dry tetrahydrofuran (12 mL) at 5° C. was added n-butyllithium (2.5 M solution in hexanes, 3.2 mL, 8.0 mmol). The resulting mixture was allowed to stir for 30 min. Meanwhile, 2-[trans-4-(4-nitro-3-trifluoromethyl-phenylamino)-cyclohexyloxy]-1-[4-(4-trifluoromethyl-phenyl)-piperazin-1-yl]-ethanone (574 mg, 1.0 mmol, prepared in accordance with Example 11) was dissolved in dry tetrahydrofuran (16 mL), and the solution was cooled to −35° C. To this solution was added an aliquot from the freshly prepared lithium diisopropylamide solution (4.5 mL). Stirring was then continued for another 30 min. Next, methyliodide (75 μL, 1.2 mmol) was added, and the mixture was allowed to attain −10° C. over 1 hr. The mixture was then re-cooled to −35° C., and another aliquot from the lithium diisopropylamide solution (4.5 mL) was added. After stirring was for an additional 30 min, methyliodide (75 μL, 1.2 mmol) was added, and the mixture was allowed to attain −10° C. over 1 hr. Afterward, the mixture was acidified to a pH of 3 with the aid of 1 N HCl. The mixture was then diluted with water (4 mL). The aqueous solution was extracted with ethyl acetate (2×20 mL), and the combined organic layers were washed with brine (2×5 mL), dried over magnesium sulfate, and concentrated. Purification by column chromatography (ethyl acetate/cyclohexanes, 1:1, 21:1, and, finally, 3:1) afforded the desired product as a yellow solid (376 mg, 62% yield). The structure was confirmed using Protocol I-B. Calculated mass=603; observed mass=603; HPLC retention time=5.94 min.

In many instances, the method of Example 14 can be adapted to make other compounds (and salts thereof) of this invention. An illustrative generic scheme is as follows:

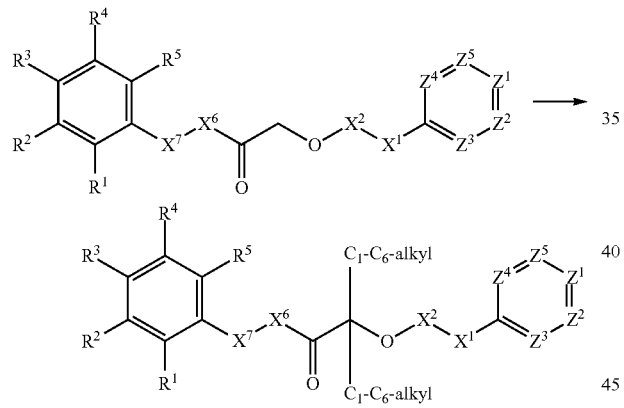

Here, $R^1$, $R^2$, $R^3$, $R^4$, $R^5$, $X^1$, $X^2$, $X^6$, $X^7$, $Z^1$, $Z^2$, $Z^3$, $Z^4$, and $Z^5$ are as defined above for the compounds of this invention. Determining the suitability of the method (and any necessary routine adaptations) for making a particular compound (or salt thereof) is generally within the skill of those in the art after reading this patent.

Example 15

Preparation of 1-[4-(4-tert-butyl-phenyl)-piperazin-1-yl]-2-[trans-4-(4-nitro-3-trifluoromethyl-phenylamino)-cyclohexyloxy]-ethanone

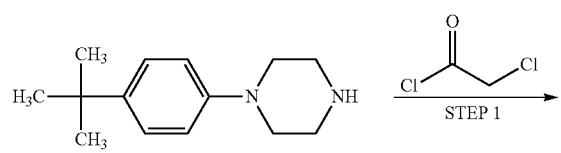

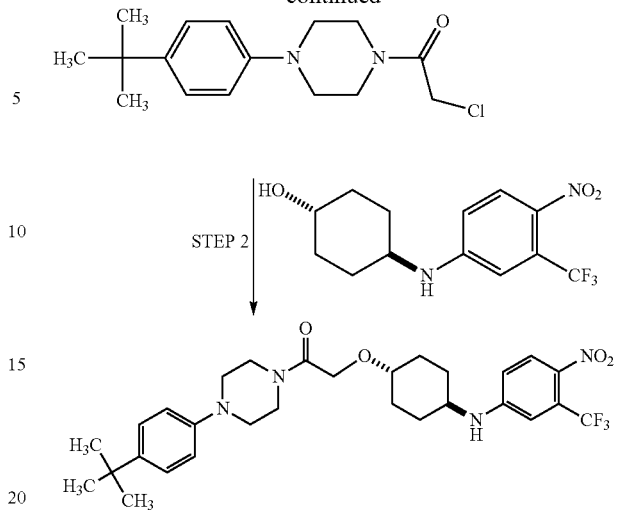

1-[4-(4-Tert-butyl-phenyl)-piperazin-1-yl]-2-[trans-4-(4-nitro-3-trifluoromethyl-phenylamino)-cyclohexyloxy]-ethanone was prepared using a two-step synthesis. In the first step, 1-chloracetyl-4-(4-Tert-butyl-phenyl)-piperazine was prepared with a 92% yield from 1-(4-Tert-butyl-phenyl)-piperazine and chloroacetyl chloride using the procedure illustrated in Example 4. In the second step, the 1-[4-(4-tert-butyl-phenyl)-piperazin-1-yl]-2-[trans-4-(4-nitro-3-trifluoromethyl-phenylamino)-cyclohexyloxy]-ethanone was prepared from the trans-4-(4-nitro-3-trifluoromethyl-phenylamino)-cyclohexanol (prepared in accordance with Example 5) using the procedure illustrated in Example 11. This afforded the product as a yellow solid (32% yield). The structure was confirmed using Protocol II-A. Calculated mass=563; observed mass=563; HPLC retention time=4.79 min.

Example 16

Preparation of 4-(4-{2-[trans-4-(4-nitro-3-trifluoromethyl-phenylamino)-cyclohexyloxy]-acetyl}-piperazin-1-yl)-benzonitrile

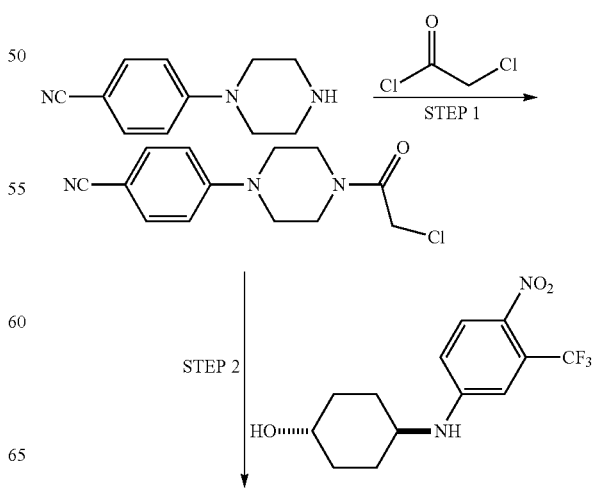

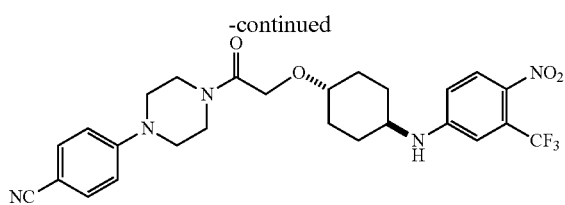

4-(4-{2-[Trans-4-(4-nitro-3-trifluoromethyl-phenylamino)-cyclohexyloxy]-acetyl}-piperazin-1-yl)-benzonitrile was prepared using a two-step synthesis. In the first step, 1-chloracetyl-4-(4-benzonitrile)-piperazine (also known as 4-[4-(2-chloroacetyl)-piperazin-1-yl]-benzonitrile) was prepared from 4-(piperazin-1-yl)-benzonitrile and chloroacetyl chloride using the procedure illustrated in Example 4. In the second step, the 4-(4-{2-[trans-4-(4-nitro-3-trifluoromethyl-phenylamino)-cyclohexyloxy]-acetyl]-piperazin-1-yl)-benzonitrile was prepared from the 1-chloracetyl-4-(4-benzonitrile)-piperazine and trans-4-(4-nitro-3-trifluoromethyl-phenylamino)-cyclohexanol (prepared in accordance with Example 5) using the procedure illustrated in Example 11. This afforded the product as a yellow solid (39% yield). The structure was confirmed using Protocol II-A. Calculated mass=532; observed mass=532; HPLC retention time=4.14 min.

Example 17

Preparation of 1-[4-(4-methoxy-phenyl)-piperazin-1-yl]-2-[trans-4-(4-nitro-3-trifluoromethyl-phenylamino)-cyclohexyloxy]-ethanone

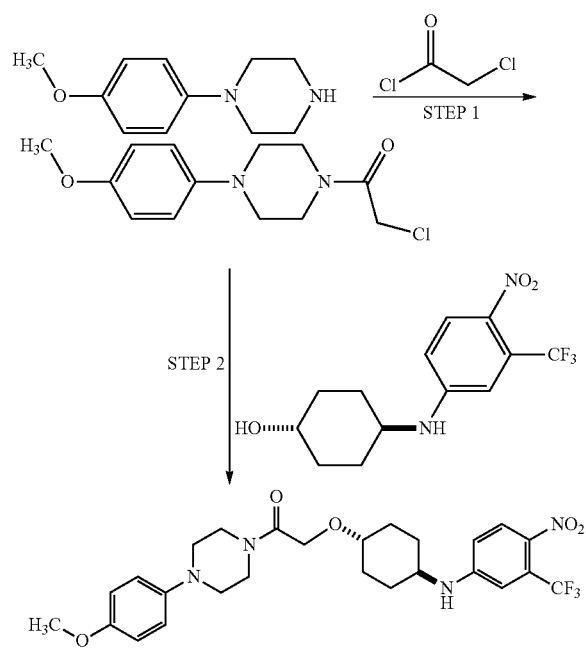

1-[4-(4-Methoxy-phenyl)-piperazin-1-yl]-2-[trans-4-(4-nitro-3-trifluoromethyl-phenylamino)-cyclohexyloxy]-ethanone was prepared using a two-step synthesis. In the first step, 1-chloracetyl-4-(4-methoxy-phenyl)-piperazine (also known as 2-chloro-1-[4-(4-methoxy-phenyl)-piperazin-1-yl]-ethanone) was prepared with a 78% yield from 1-(4-methoxy-phenyl)-piperazine and chloroacetyl chloride using the procedure illustrated in Example 4. In the second step, the 1-[4-(4-methoxy-phenyl)-piperazin-1-yl]-2-[trans-4-(4-nitro-3-trifluoromethyl-phenylamino)-cyclohexyloxy]-ethanone was prepared from the 1-chloracetyl-4-(4-methoxy-phenyl)-piperazine and trans-4-(4-nitro-3-trifluoromethyl-phenylamino)-cyclohexanol (prepared in accordance with Example 5) using the procedure illustrated in Example 11. This afforded the product as a yellow solid (24% yield). The structure was confirmed using Protocol II-A. Calculated mass=537; observed mass=537; HPLC retention time=4.05 min.

Example 18

Preparation of 1-[4-(4-chloro-2-fluoro-phenyl)-piperazin-1-yl]-2-[trans-4-(4-nitro-3-trifluoromethyl-phenylamino)-cyclohexyloxy]-ethanone

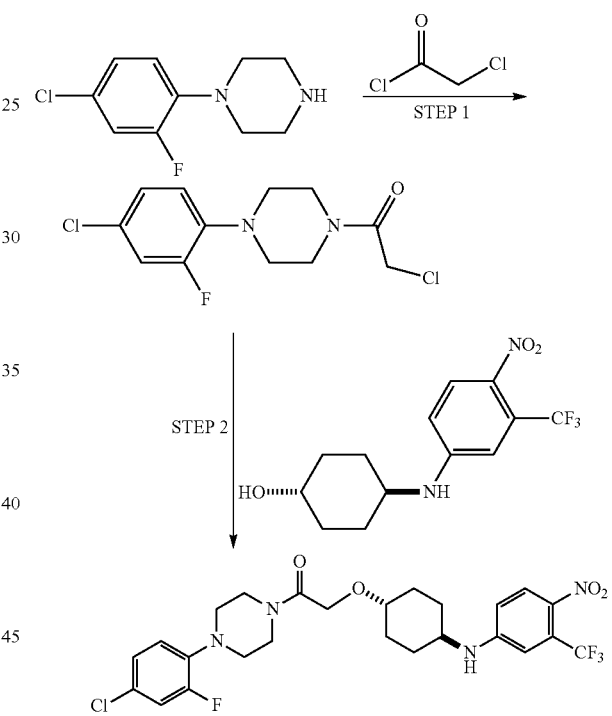

1-[4-(4-Chloro-2-fluoro-phenyl)-piperazin-1-yl]-2-[trans-4-(4-nitro-3-trifluoromethyl-phenylamino)-cyclohexyloxy]-ethanone was prepared using a two-step synthesis. In the first step, 1-chloracetyl-4-(4-chloro-2-fluoro-phenyl)-piperazine (also known as 2-chloro-1-[4-(4-chloro-2-fluoro-phenyl)-piperazin-1-yl]-ethanone) was prepared from 1-(4-chloro-2-fluoro-phenyl)-piperazine and chloroacetyl chloride using the procedure illustrated in Example 4. In the second step, the 1-[4-(4-chloro-2-fluoro-phenyl)-piperazin-1-yl]-2-[trans-4-(4-nitro-3-trifluoromethyl-phenylamino)-cyclohexyloxy]-ethanone was prepared from the 1-chloracetyl-4-(4-chloro-2-fluoro-phenyl)-piperazine and trans-4-(4-nitro-3-trifluoromethyl-phenylamino)-cyclohexanol (prepared in accordance with Example 5) using the procedure illustrated in Example 11. This afforded the product as a yellow solid (13% yield). The structure was confirmed using Protocol II-A. Calculated mass=559; observed mass=559; HPLC retention time=4.57 min.

Example 19

Preparation of 1-(4-(4-trifluoromethyl-benzyloxy)-phenyl)-piperazine Intermediate

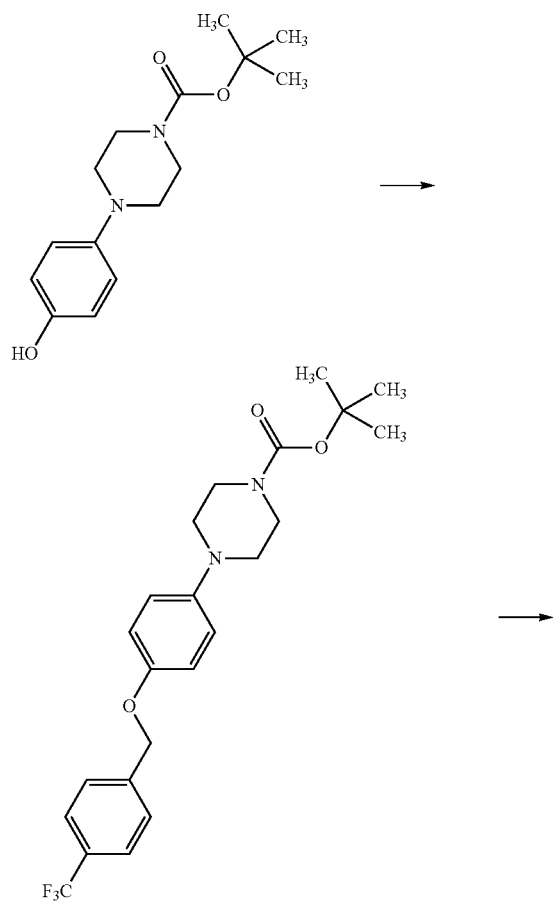

A solution of 4-(4-hydroxy-phenyl)-piperazine-1-carboxylic acid tent-butyl ester (1.5 g, 5.4 mmol) in dry tetrahydrofuran (5 mL) was added to a suspension of sodium hydride (431 mg, 60% in oil, 10.8 mmol) in dry tetrahydrofuran (35 mL). After 15 min, a solution of 1-bromomethyl-4-trifluoromethyl-benzene (1.9 g, 8.1 mmol) in tetrahydrofuran (5 mL) was added. The mixture was stirred for 16 hr at room temperature, filtered, and concentrated under vacuum. The resulting residue was diluted in ethyl acetate (40 mL), and the organic layer was washed with water (3×20 mL), dried over magnesium sulfate, filtered, and concentrated under vacuum. The resulting residue was dissolved in a 1:1 mixture of dichloromethane and trifluoroacetic acid (30 mL). The mixture was then stirred for 30 min. Afterward, the mixture was concentrated under vacuum, taken up in dichloromethane (30 mL), and evaporated to dryness. The resulting residue was diluted in diethylether (5 mL) and then combined with a molar solution of HCl in diethylether (10 mL, 1M). A precipitate formed, which was filtered, washed with diethylether (10 mL), and dried under vacuum. The desired product was isolated as a hydrochloride salt with traces of solvent.

Example 20

Preparation of 2-[trans-4-(4-nitro-3-trifluoromethyl-phenylamino)-cyclohexyloxy]-1-{4-[4-(4-trifluoromethyl-benzyloxy)-phenyl]-piperazin-1-yl}-ethanone

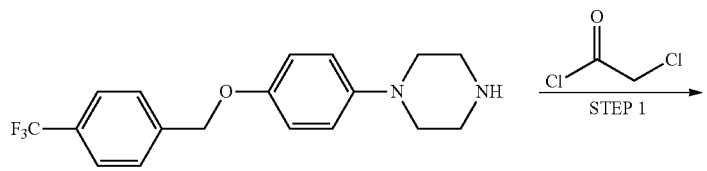

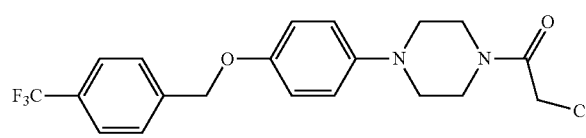

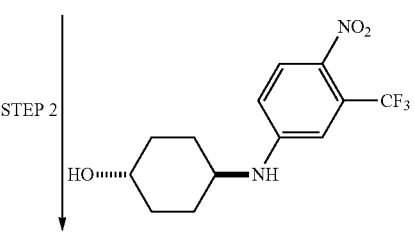

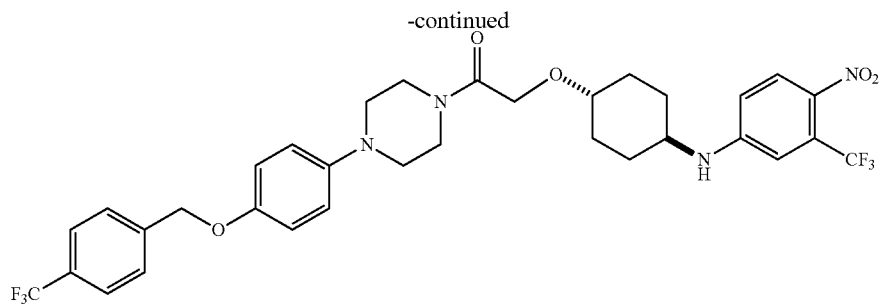

2-[Trans-4-(4-nitro-3-trifluoromethyl-phenylamino)-cyclohexyloxy]-1-{4-[4-(4-trifluoromethyl-benzyloxy)-phenyl]-piperazin-1-yl}-ethanone was prepared using a two-step synthesis. In the first step, 1-chloracetyl-4-[4-(4-trifluoromethyl-benzyloxy)-phenyl]-piperazine (also known as 2-chloro-1-{4-[4-(4-trifluoromethyl-benzyloxy)-phenyl]-piperazin-1-yl}-ethanone) was prepared with a 46% yield from 1-[4-(4-trifluoromethyl-benzyloxy)-phenyl]-piperazine (prepared in accordance with Example 19) and chloroacetyl chloride using the procedure illustrated in Example 4. In the second step, the 2-[trans-4-(4-nitro-3-trifluoromethyl-phenylamino)-cyclohexyloxy]-1-{4-[4-(4-trifluoromethyl-benzyloxy)-phenyl]-piperazin-1-yl}-ethanone was prepared from the 1-chloracetyl-4-[4-(4-trifluoromethyl-benzyloxy)-phenyl]-piperazine and trans-4-(4-nitro-3-trifluoromethyl-phenylamino)-cyclohexanol (prepared in accordance with Example 5) using the procedure illustrated in Example 11. This afforded the product as a yellow solid (10% yield). The structure was confirmed using Protocol II-A. Calculated mass=681; observed mass=681; HPLC retention time=4.75 min.

Example 21

Preparation of 1-[4-(4-butyl-phenyl)-piperidin-1-yl]-2-[trans-4-(4-nitro-3-trifluoromethyl-phenylamino)-cyclohexyloxy]-ethanone 1-[4-(4-Butyl-phenyl)-piperidin-1-yl]-2-[trans-4-(4-nitro-3-trifluoromethyl-phenylamino)-cyclohexyloxy]-ethanone was prepared using a two-step synthesis. In the first step, 1-chloracetyl-4-(4-butyl-phenyl)-piperidine (also known as 1-[4-(4-butyl-phenyl)-piperidin-1-yl]-2-chloroethanone) was prepared with a 72% yield from 4-(4-butyl-phenyl)-piperidine (prepared in accordance with Example 9) and chloroacetyl chloride using the procedure illustrated in Example 4. In the second step, the 1-[4-(4-butyl-phenyl)-piperidin-1-yl]-2-[trans-4-(4-nitro-3-trifluoromethyl-phenylamino)-cyclohexyloxy]-ethanone was prepared from the 1-chloracetyl-4-(4-butyl-phenyl)-piperidine and trans-4-(4-nitro-3-trifluoromethyl-phenylamino)-cyclohexanol (prepared in accordance with Example 5) using the procedure illustrated in Example 11. This afforded the product as a yellow solid (36% yield). The structure was confirmed using Protocol II-A. Calculated mass=548; observed mass=548; HPLC retention time=4.92 min.

Example 22

Preparation of 1-[4-(2,4-difluoro-phenyl)-piperidin-1-yl]-2-[trans-4-(4-nitro-3-trifluoromethyl-phenylamino)-cyclohexyloxy]-ethanone

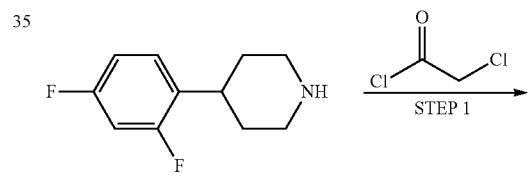

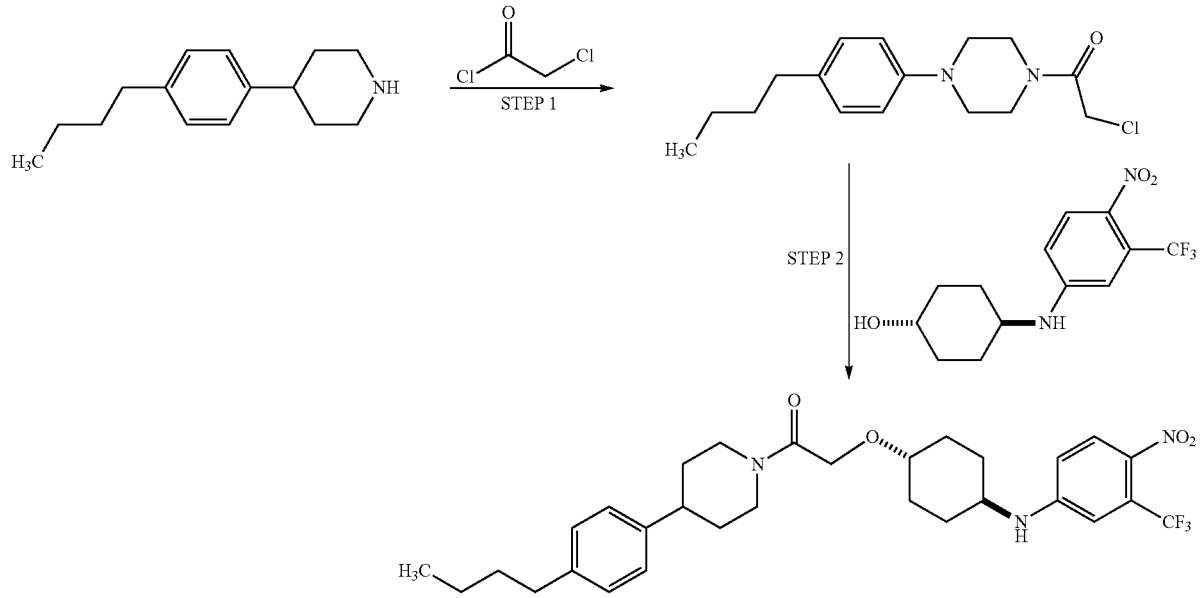

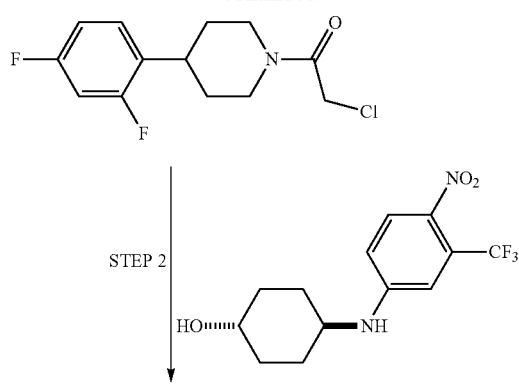

1-[4-(2,4-Difluoro-phenyl)-piperidin-1-yl]-2-[trans-4-(4-nitro-3-trifluoromethyl-phenylamino)-cyclohexyloxy]-ethanone was prepared using a two-step synthesis. In the first step, 1-chloracetyl-4-(2,4-difluoro-phenyl)-piperidine (also known as 2-chloro-1-[4-(2,4-difluoro-phenyl)-piperidin-1-yl]-ethanone) was prepared from 4-(2,4-difluoro-phenyl)-piperidine and chloroacetyl chloride using the procedure illustrated in Example 4. In the second step, the 1-[4-(2,4-difluoro-phenyl)-piperidin-1-yl]-2-[trans-4-(4-nitro-3-trifluoromethyl-phenylamino)-cyclohexyloxy]-ethanone was prepared from the 1-chloracetyl-4-(2,4-difluoro-phenyl)-piperidine and trans-4-(4-nitro-3-trifluoromethyl-phenylamino)-cyclohexanol (prepared in accordance with Example 5) using the procedure illustrated in Example 11. This afforded the product as a yellow solid (16% yield). The structure was confirmed using Protocol II-A. Calculated mass=542; observed mass=543; HPLC retention time=4.36 min.

Example 23

Preparation of 2-[trans-4-(4-nitro-3-trifluoromethyl-phenylamino)-cyclohexyloxy]-1-[4-(4-phenoxy-phenyl)-piperidin-1-yl]-ethanone

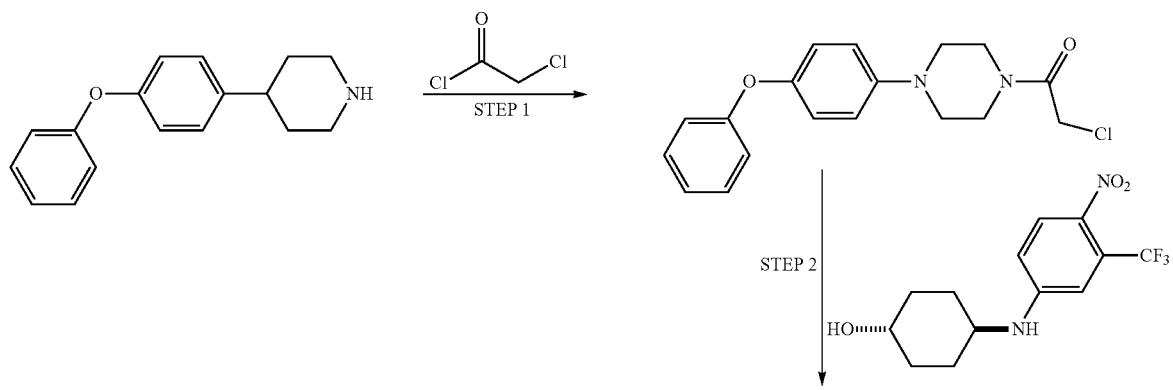

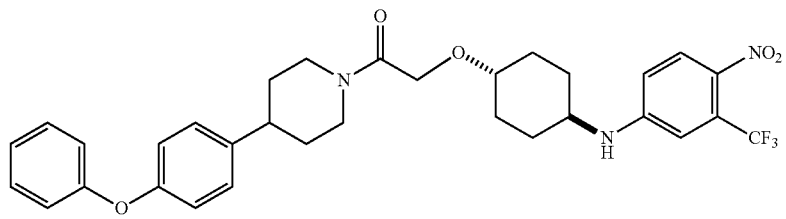

2-[Trans-4-(4-nitro-3-trifluoromethyl-phenylamino)-cyclohexyloxy]-1-[4-(4-phenoxy-phenyl)-piperidin-1-yl]-ethanone was prepared using a two-step synthesis. In the first step, 1-chloracetyl-4-(4-phenoxy-phenyl)-piperidine (also known as 2-chloro-1-[4-(4-phenoxy-phenyl)-piperidin-1-yl]-ethanone) was prepared with a 74% yield from 4-(4-phenoxy-phenyl)-piperidine (prepared in accordance with Example 8) and chloroacetyl chloride using the procedure illustrated in Example 4. In the second step, the 2-[trans-4-(4-nitro-3-trifluoromethyl-phenylamino)-cyclohexyloxy]-1-[4-(4-phenoxy-phenyl)-piperidin-1-yl]-ethanone was prepared from the 1-chloracetyl-4-(4-phenoxy-phenyl)-piperidine and trans-4-(4-nitro-3-trifluoromethyl-phenylamino)-cyclohexanol (prepared in accordance with Example 5) using the procedure illustrated in Example 11. This afforded the product as a yellow solid (14% yield). The structure was confirmed using Protocol I-A. Calculated mass=598; observed mass=598; HPLC retention time=4.81 min.

Example 24

Preparation of
1-chloracetyl-4-(4-benzyloxy-phenyl)-piperazine
Intermediate

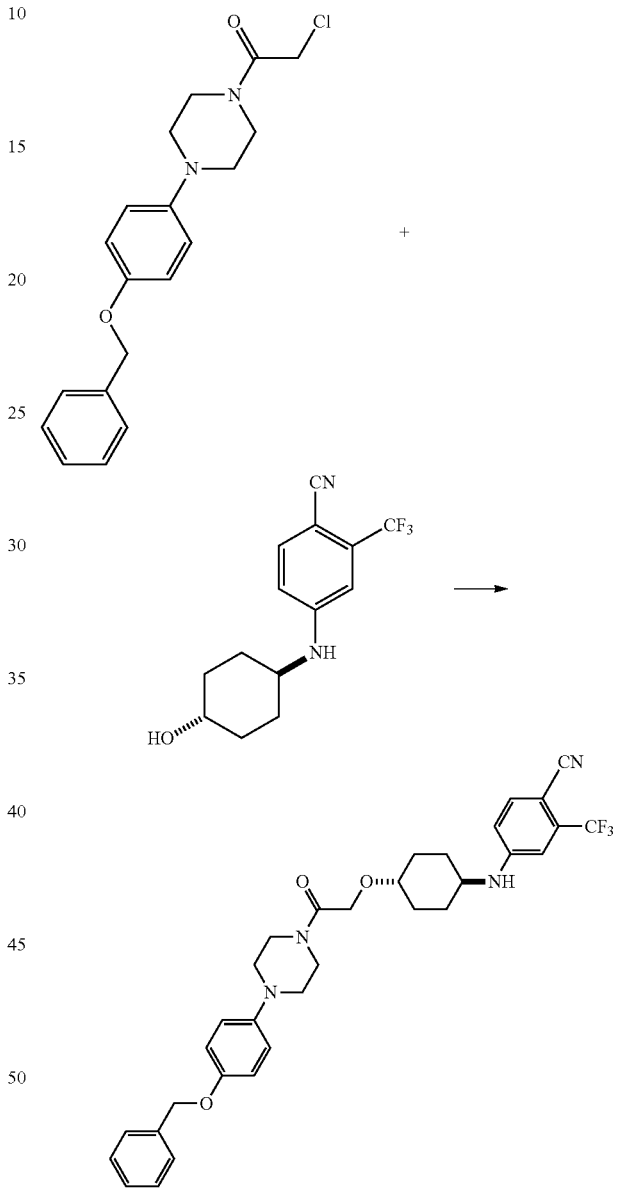

Crude 1-chloracetyl-4-(4-benzyloxy-phenyl)-piperazine (also known as 1-[4-(4-benzyloxy-phenyl)-piperazin-1-yl]-2-chloroethanone) was prepared from 1-(4-benzyloxy-phenyl)-piperazine and chloroacetyl chloride using the procedure illustrated in Example 4.

Example 25

Preparation of 4-(trans-4-{2-[4-(4-benzyloxy-phenyl)-piperazin-1-yl]-2-oxoethoxy}-cyclohexylamino)-2-trifluoromethyl-benzonitrile

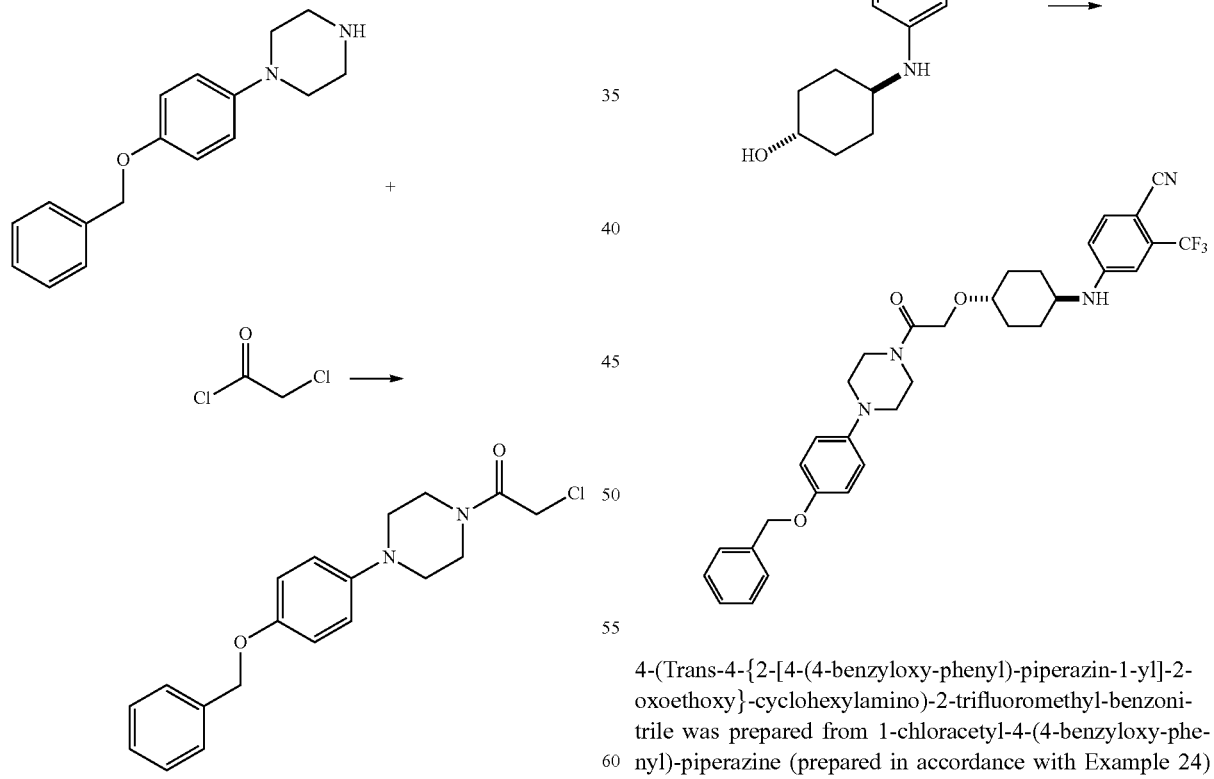

4-(Trans-4-{2-[4-(4-benzyloxy-phenyl)-piperazin-1-yl]-2-oxoethoxy}-cyclohexylamino)-2-trifluoromethyl-benzonitrile was prepared from 1-chloracetyl-4-(4-benzyloxy-phenyl)-piperazine (prepared in accordance with Example 24) and 4-(trans-4-hydroxy-cyclohexylamino)-2-trifluoromethyl-benzonitrile (prepared in accordance with Example 6) using the procedure illustrated in Example 11. This afforded the product as a yellow solid (51% yield). The structure was confirmed using Protocol II-A. Calculated mass=593; observed mass=593; HPLC retention time=4.41 min.

Example 26

Preparation of 1-chloracetyl-4-(4-tert-butyl-phenyl)-piperazine Intermediate

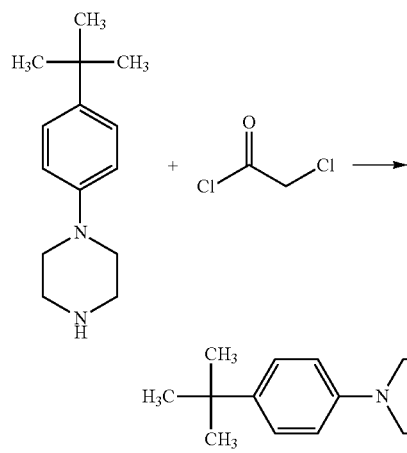

1-Chloracetyl-4-(4-Tert-butyl-phenyl)-piperazine (also known as 1-[4-(4-Tert-butyl-phenyl)-piperazin-1-yl]-2-chloroethanone) was prepared with a 92% yield from 1-(4-tert-butyl-phenyl)-piperazine and chloroacetyl chloride using the procedure illustrated in Example 4.

Example 27

Preparation of 4-(trans-4-{2-[4-(4-tert-butyl-phenyl)-piperazin-1-yl]-2-oxo-ethoxy}-cyclohexylamino)-2-trifluoromethyl-benzonitrile

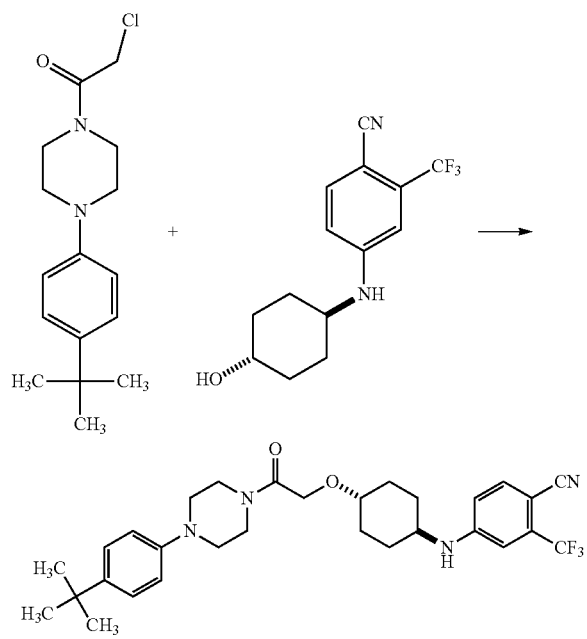

4-(Trans-4-{2-[4-(4-tert-butyl-phenyl)-piperazin-1-yl]-2-oxo-ethoxy}-cyclohexylamino)-2-trifluoromethyl-benzonitrile was prepared from 1-chloracetyl-4-(4-tert-butyl-phenyl)-piperazine (prepared in accordance with Example 26) and 4-(trans-4-hydroxy-cyclohexylamino)-2-trifluoromethyl-benzonitrile (prepared in accordance with Example 6) using the procedure illustrated in Example 11. This afforded the product as a colorless solid (39% yield). The structure was confirmed using Protocol II-A. Calculated mass=543; observed mass=543; HPLC retention time=4.68 min.

Example 28

Preparation of [trans-4-(tert-butyl-dimethyl-silyloxy)-cyclohexyl]-(4-trifluoromethylsulfanyl-phenyl)-amine Intermediate

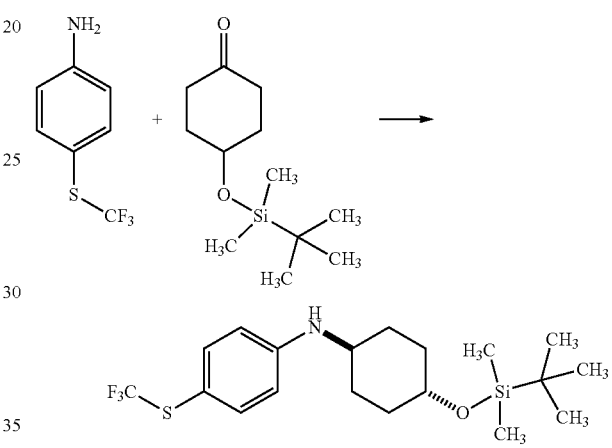

(4-Trifluoromethylsulfanyl-phenyl)-amine (386 mg, 2 mmol) and 4-Tert-butyl-dimethyl-silyloxy-cyclohexanone (457 mg, 2 mmol) were dissolved in acetonitrile (5 mL), and the resulting solution was refluxed for 1 hr. After cooling the mixture to room temperature, sodium triacetoxyborohydride (848 mg, 4 mmol) was added. The mixture was then stirred at room temperature for 18 hr. Afterward, the mixture was diluted with dichloromethane (20 mL) and washed with saturated aqueous sodium hydrogencarbonate (10 mL). The organic layer was collected, dried over magnesium sulfate, filtered, and concentrated under vacuum. An oily residue was obtained. This residue was purified by column chromatography on silica gel (cyclohexane/diethylether, 98:2). The trans isomer was isolated as a colorless oil (180 mg, 22% yield).

In many instances, the method of Example 28 can be adapted to make other compounds that are useful as intermediates for making compounds (and salts thereof) of this invention. An illustrative generic scheme is as follows:

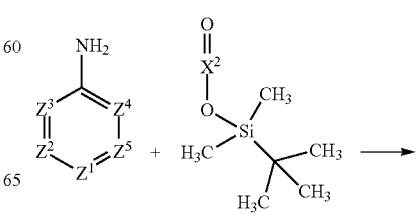

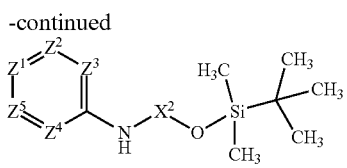

Here, $X^2$, $Z^1$, $Z^2$, $Z^3$, $Z^4$, and $Z^5$ are as defined above for the compounds of this invention. Another illustrative generic scheme is as follows:

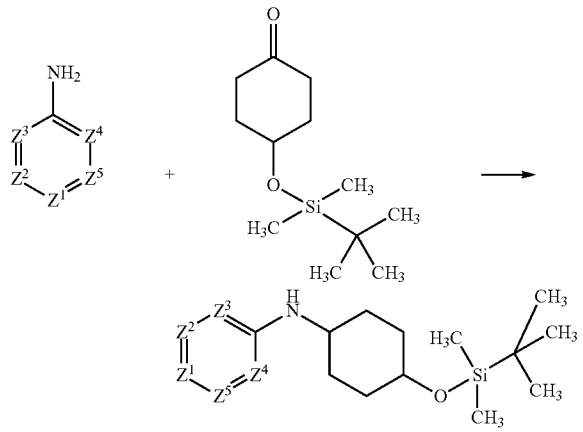

Determining the suitability of the methods (and any necessary routine adaptations) for making a particular intermediate is generally within the skill of those in the art after reading this patent.

Example 29

Preparation of trans-4-(4-trifluoromethylsulfanyl-phenylamino)-cyclohexanol Intermediate

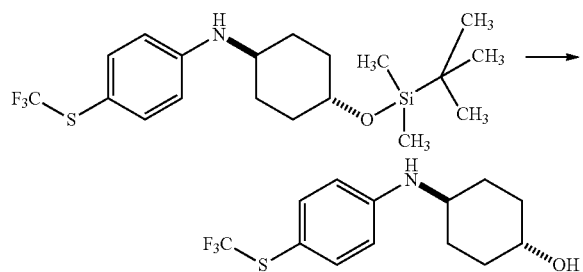

[Trans-4-(tert-butyl-dimethyl-silyloxy)-cyclohexyl]-(4-trifluoromethylsulfanyl-phenyl)-amine (180 mg, 0.44 mmol, prepared in accordance with Example 28) was dissolved in tetrahydrofuran (3 mL). A molar solution of tetrabutylammonium fluoride (500 μL, 5 mmol) was then added. The resulting mixture was heated to 40° C. and then maintained at that temperature for 4 hr. After cooling to room temperature, the mixture was diluted with diethylether (20 mL), washed with water (10 mL), and washed with saturated aqueous hydrogencarbonate (10 mL). The organic layer was collected, dried over magnesium sulfate, filtered, and concentrated under vacuum. The oily residue obtained was purified by column chromatography on silica gel (dichloromethane and then dichloromethane/methanol, 95:5). The desired product was isolated as a colorless oil with traces of tetrabutylammonium fluoride.

In many instances, the method of Example 29 can be adapted to make other compounds that are useful as intermediates for making compounds (and salts thereof) of this invention. An illustrative generic scheme is as follows:

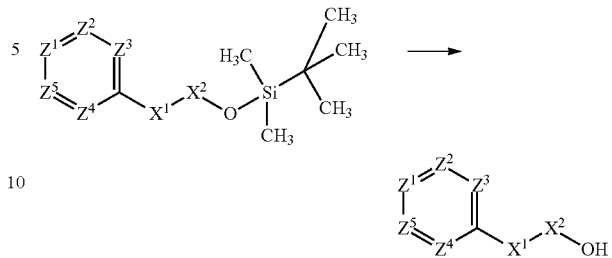

Here, $X^1$, $X^2$, $Z^1$, $Z^2$, $Z^3$, $Z^4$, and $Z^5$ are as defined above for the compounds of this invention. Another illustrative generic scheme is as follows:

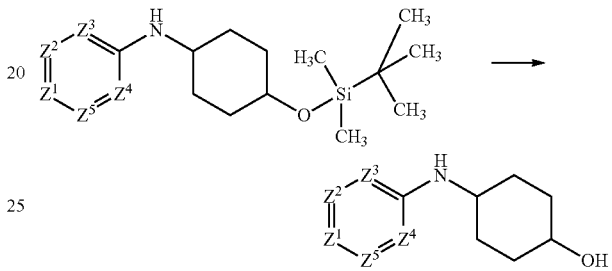

Determining the suitability of the methods (and any necessary routine adaptations) for making a particular intermediate is generally within the skill of those in the art after reading this patent.

Example 30

Preparation of [trans-4-(4-(trifluoromethylsulfanyl)-phenylamino)-cyclohexyloxy]-acetic acid Intermediate

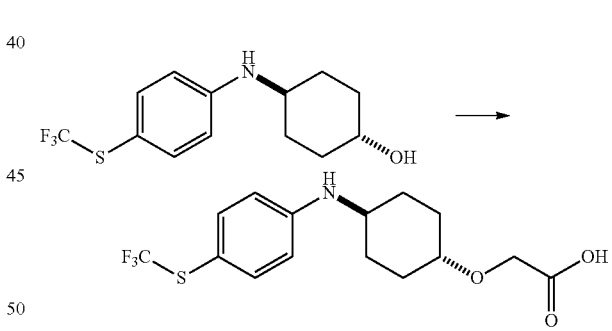

Trans-4-(4-trifluoromethylsulfanyl-phenylamino)-cyclohexanol (160 mg, 0.55 mmol, prepared in accordance with Example 29) was placed under an inert atmosphere and dissolved in dry tetrahydrofuran (2 mL). A molar solution of lithium bis(trimethylsilyl)-amide (1 mL, 1.0 mmol) was added. After 15 min, tert-butyl-bromoacetate (75 μL, 0.55 mmol) was added. After two additional hours, more lithium bis-(trimethylsilyl)-amide solution (500 μL, 0.50 mmol) and tert-butyl-bromoacetate (37 μL, 0.28 mmol) was added. After 4 hr, the mixture was diluted with diethylether (20 mL), washed with water (10 mL), and washed with saturated aqueous hydrogencarbonate (10 mL). The organic layer was collected, dried over magnesium sulfate, filtered, and concentrated under vacuum to afford an oil. This crude product was diluted in dichloromethane (4 mL) and treated with trifluoroacetic acid (3 mL) at room temperature. After 3 hr, the mixture was diluted with diethylether (20 mL) and washed with water (3×10 mL), and washed with aqueous saturated hydrogencarbonate (2×10 mL). The organic layer was collected, dried over magnesium sulfate, filtered, and concentrated under vacuum. The oily residue obtained was purified by column chromatography on silica gel (dichloromethane followed by dichloromethane/methanol, 95:5). The desired product was isolated as a yellow solid (68 mg, 35% yield).

In many instances, the method of Example 30 can be adapted to make other compounds that are useful as intermediates for making compounds (and salts thereof) of this invention. An illustrative generic scheme is as follows:

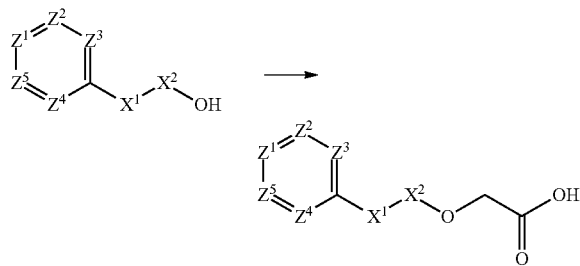

Here, $X^1$, $X^2$, $Z^1$, $Z^2$, $Z^3$, $Z^4$, and $Z^5$ are as defined above for the compounds of this invention. Another illustrative generic scheme is as follows:

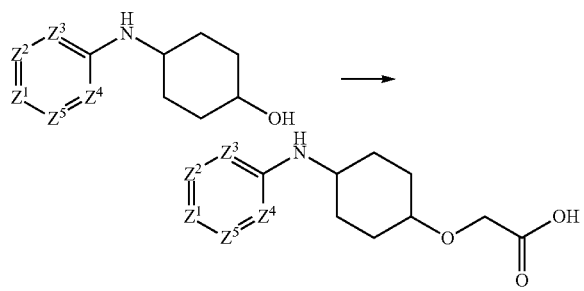

Determining the suitability of the methods (and any necessary routine adaptations) for making a particular intermediate is generally within the skill of those in the art after reading this patent.

Example 31

Preparation of 1-[4-(4-trifluoromethyl-phenyl)-piperazin-1-yl]-2-[trans-4-(4-trifluoromethylsulfanyl-phenylamino)-cyclohexyloxy]-ethanone

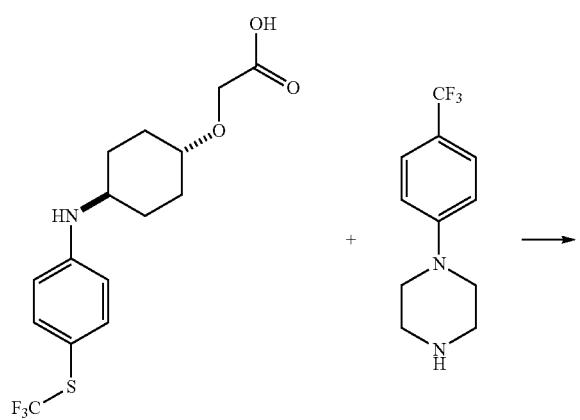

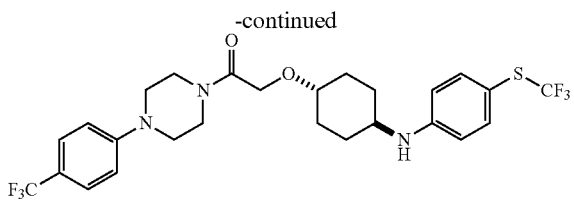

2-[Trans-4-(4-trifluoromethylsulfanyl-phenylamino)-cyclohexyloxy]-acetic acid (18 mg, 0.05 mmol, prepared in accordance with Example 30) and 2-(1H-benzotriazol-1-yl)-1,1,3,3-tetramethyluronium hexafluorophosphate (19 mg, 0.05 mmol) were dissolved in dry tetrahydrofuran (2 mL) and stirred at room temperature for 10 min. 1-(4-Trifluormethylphenyl)-piperazine (12 mg, 0.05 mmol) and diisopropylethylamine (18 μL, 0.10 mmol) were then added, and the solution was stirred at room temperature for 1.5 hr. Aluminium oxide was then added (1 spatula). Afterward, the mixture was diluted with diethylether (10 mL) and filtered. The filtrate was concentrated under vacuum. The crude product was purified by preparative HPLC. Following lyophilization of the fractions of interest, the desired product was isolated as a solid (16 mg, 57% yield). The structure was confirmed using Protocol I-B. Calculated mass=562; observed mass=562; HPLC retention time=6.03 min.

In many instances, the method of Example 31 can be adapted to make other compounds (and salts thereof) of this invention. An illustrative generic scheme is as follows:

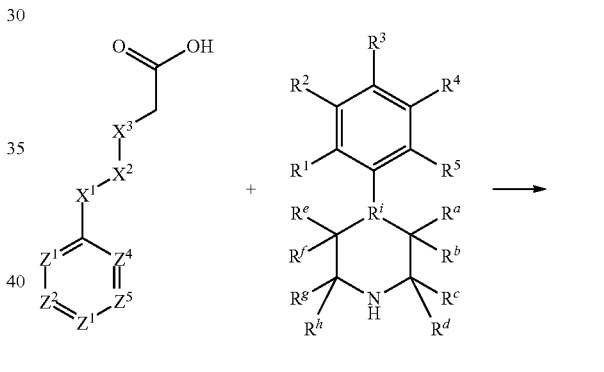

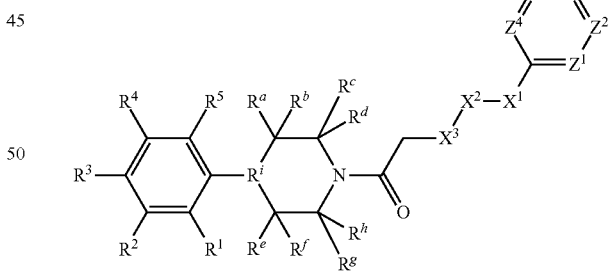

Here, $R^1$, $R^2$, $R^3$, $R^4$, $R^5$, $X^1$, $X^2$, $X^3$, $Z^1$, $Z^2$, $Z^3$, $Z^4$, and $Z^5$ are as defined above for the compounds of this invention. $R^a$, $R^b$, $R^c$, $R^d$, $R^e$, $R^f$, $R^g$, and $R^h$ are independently selected from the group consisting of hydrogen, halogen, hydroxy, alkyl, and alkoxy. And $R^i$ is either

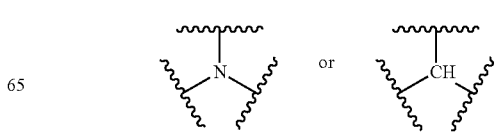

optionally substituted with halogen, hydroxy, alkyl, and alkoxy. Another illustrative generic scheme is as follows:

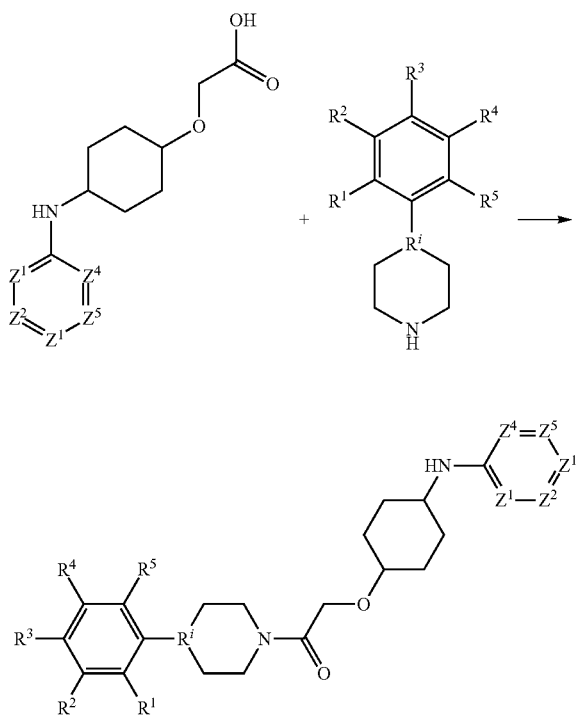

Determining the suitability of the methods (and any necessary routine adaptations) for making a particular compound (or salt thereof) is generally within the skill of those in the art after reading this patent.

Example 32

Preparation of [4-(tert-butyl-dimethyl-silyloxy)-cyclohexyl]-(4-chloro-3-trifluoromethyl-phenyl)-amine Intermediate

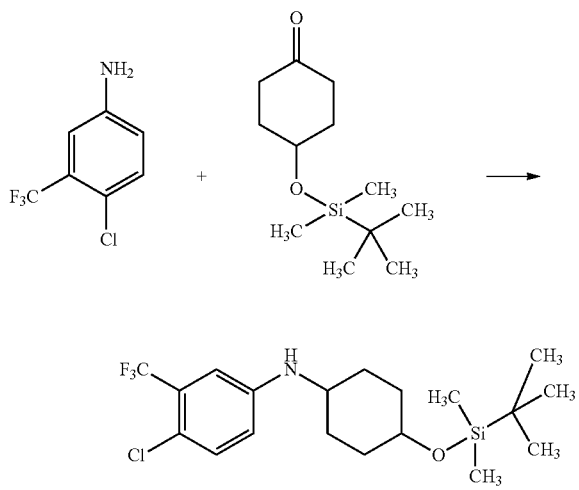

(4-Chloro-3-trifluoromethyl-phenyl)-amine (782 mg, 4 mmol) and 4-(tent-butyl-dimethyl-silyloxy)-cyclohexanone (913 mg, 4 mmol) were dissolved in dichloromethane (35 mL). Next, sodium triacetoxyborohydride (1.69 g, 8 mmol) was added, and the mixture was stirred at room temperature for 6 days. The mixture was then diluted with dichloromethane (35 mL), washed with water (25 mL), washed with HCl 1N (25 mL), washed with water (25 mL), and washed with brine (25 mL). The organic layer was collected, dried over magnesium sulfate, filtered, and concentrated under vacuum. This afforded an oily residue, which was purified by column chromatography on silica gel (pentane/ether gradient). The desired product was isolated as a yellow oil (1.3 g of 1:1 mixtures of cis and trans isomers, 80% yield).

Example 33

Preparation of trans-4-(4-chloro-3-trifluoromethyl-phenylamino)-cyclohexanol and cis-4-(4-chloro-3-trifluoromethyl-phenylamino)-cyclohexanol Intermediates

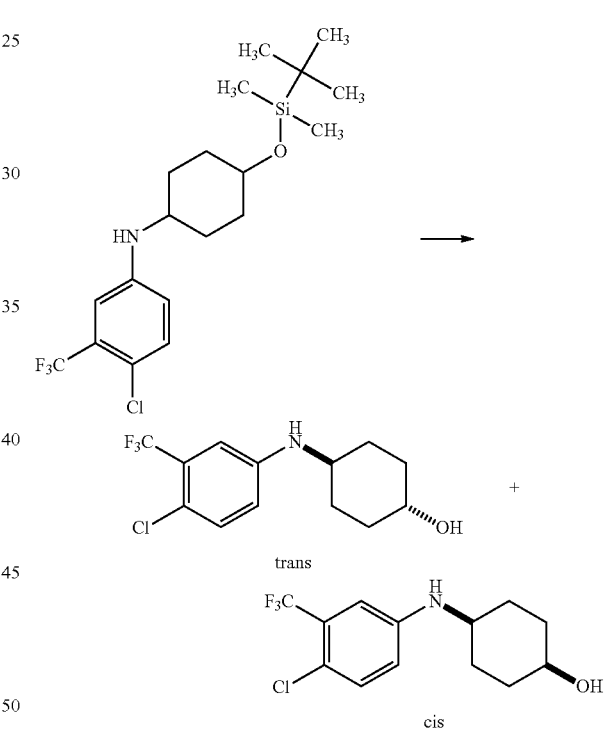

[4-(Tert-butyl-dimethyl-silyloxy)-cyclohexyl]-(4-chloro-3-trifluoromethyl-phenyl)-amine (1.3 g, 3.2 mmol, prepared in accordance with Example 32) was dissolved in tetrahydrofuran (25 mL). Next, a molar solution of tetrabutylammonium fluoride was added (3.2 mL, 3.2 mmol). The resulting mixture was heated to 40° C., and then maintained at this temperature for 8 hr. Afterward, the mixture was cooled to room temperature and then stirred at room temperature for 3 days. The resulting solution was concentrated under vacuum and purified by preparative HPLC. The fractions corresponding to the cis and trans isomers were isolated separately, partly evaporated under vacuum, and lyophilized.

In many instances, the method of Example 31 can be adapted to make other compounds that are useful as intermediates for making compounds (and salts thereof) of this invention. An illustrative generic scheme is as follows:

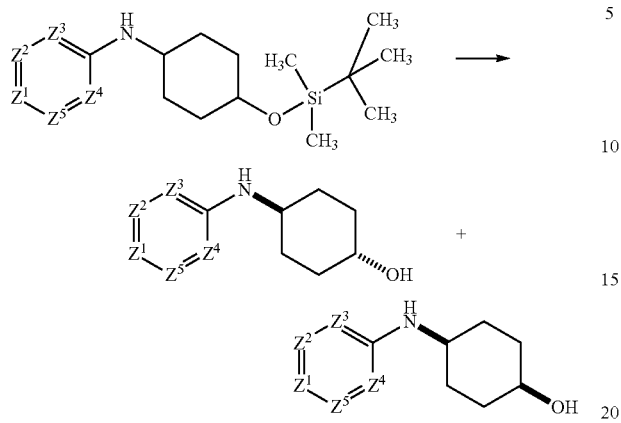

Here, $X^1$, $X^2$, $Z^1$, $Z^2$, $Z^3$, $Z^4$, and $Z^5$ are as defined above for the compounds of this invention. Determining the suitability of the methods (and any necessary routine adaptations) for making a particular intermediate is generally within the skill of those in the art after reading this patent.

Example 34

Preparation of [4-(tert-butyl-dimethyl-silyloxy)-cyclohexyl]-(4-trifluoromethoxy-3-trifluoromethyl-phenyl)-amine Intermediate

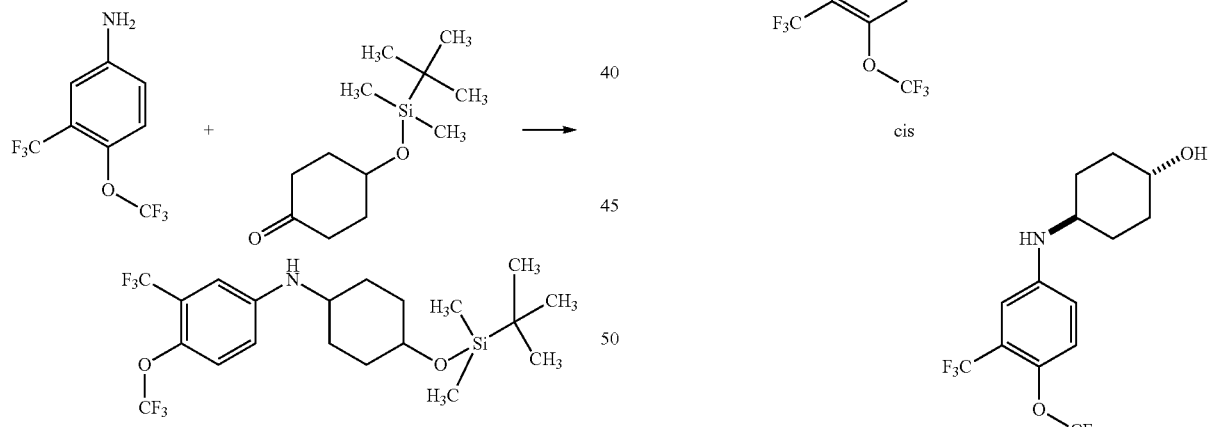

(4-Trifluoromethoxy-3-trifluoromethyl-phenyl)-amine (735 mg, 3 mmol) and 4-(tert-butyl-dimethyl-silyloxy)-cyclohexanone (685 mg, 3 mmol) were dissolved in dichloromethane (25 mL). Next, sodium triacetoxyborohydride (1.27 g, 6 mmol) was added. The resulting mixture was stirred at room temperature for 6 days. Afterward, the mixture was diluted with dichloromethane (25 mL), washed with water (20 mL), washed with HCl 1N (20 mL), washed with water (20 mL), and washed with brine (20 mL). The organic layer was collected, dried over magnesium sulfate, filtered, and concentrated under vacuum to afford an oily residue. The residue was purified by column chromatography on silica gel (pentane/ether gradient). The desired product was isolated as a colorless oil (900 mg of 1:1 mixtures of cis and trans isomers, 66% yield).

Example 35

Preparation of cis-4-(4-trifluoromethoxy-3-trifluoromethyl-phenylamino)-cyclohexanol and trans-4-(4-trifluoromethoxy-3-trifluoromethyl-phenylamino)-cyclohexanol Intermediates

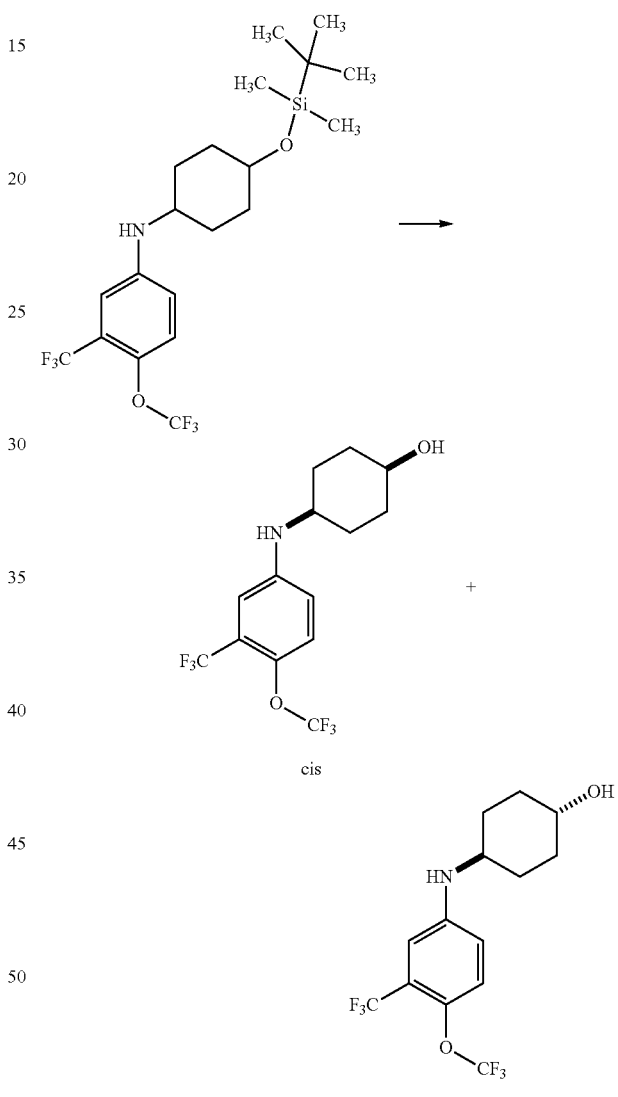

[4-(Tert-butyl-dimethyl-silyloxy)-cyclohexyl]-(4-trifluoromethoxy-3-trifluoromethyl-phenyl)-amine (1.3 g, 3.2 mmol, prepared in accordance with Example 34) was dissolved in tetrahydrofuran (25 mL). Next, a molar solution of tetrabutylammonium fluoride was added (3.2 mL, 3.2 mmol). The resulting mixture was heated to 40° C., and then maintained at that temperature for 8 hr. Afterward, the mixture was cooled to room temperature and then stirred at that temperature for 3 days. The resulting solution was concentrated under vacuum and purified by preparative HPLC. The fractions corresponding to the cis and trans isomers were isolated separately, partly evaporated under vacuum, and lyophilized.

Example 36

Preparation of 1-[4-(4-benzyloxy-phenyl)-piperazin-1-yl]-2-[trans-4-(4-trifluoromethoxy-3-trifluoromethyl-phenylamino)-cyclohexyloxy]-ethanone

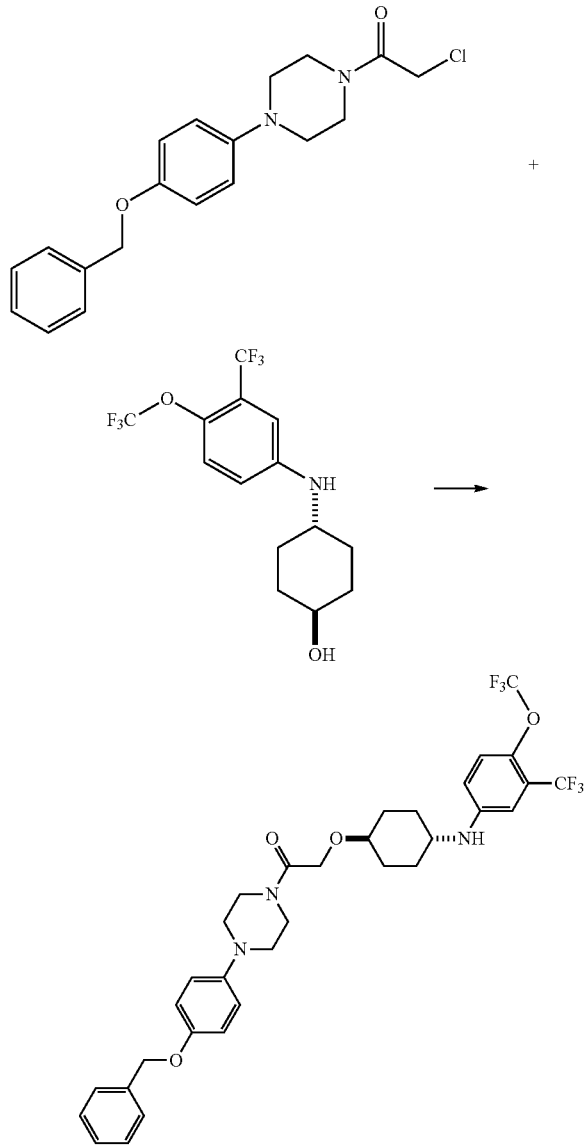

1-[4-(4-Benzyloxy-phenyl)-piperazin-1-yl]-2-[trans-4-(4-trifluoromethoxy-3-trifluoromethyl-phenylamino)-cyclohexyloxy]-ethanone was prepared from crude 1-chloracetyl-4-(4-benzyloxy-phenyl)-piperazine (prepared in accordance with Example 24) and trans-4-(4-trifluoromethoxy-3-trifluoromethyl-phenylamino)-cyclohexanol (prepared in accordance with Example 35) using the procedure illustrated in Example 11. This afforded the desired product as a colorless solid with a 37% yield. The structure was confirmed using Protocol I-B. Calculated mass=652; observed mass=652; HPLC retention time=6.17 min.

Example 37

Preparation of 1-[4-(4-tert-butyl-phenyl)-piperazin-1-yl]-2-[trans-4-(4-trifluoromethoxy-3-trifluoromethyl-phenylamino)-cyclohexyloxy]-ethanone

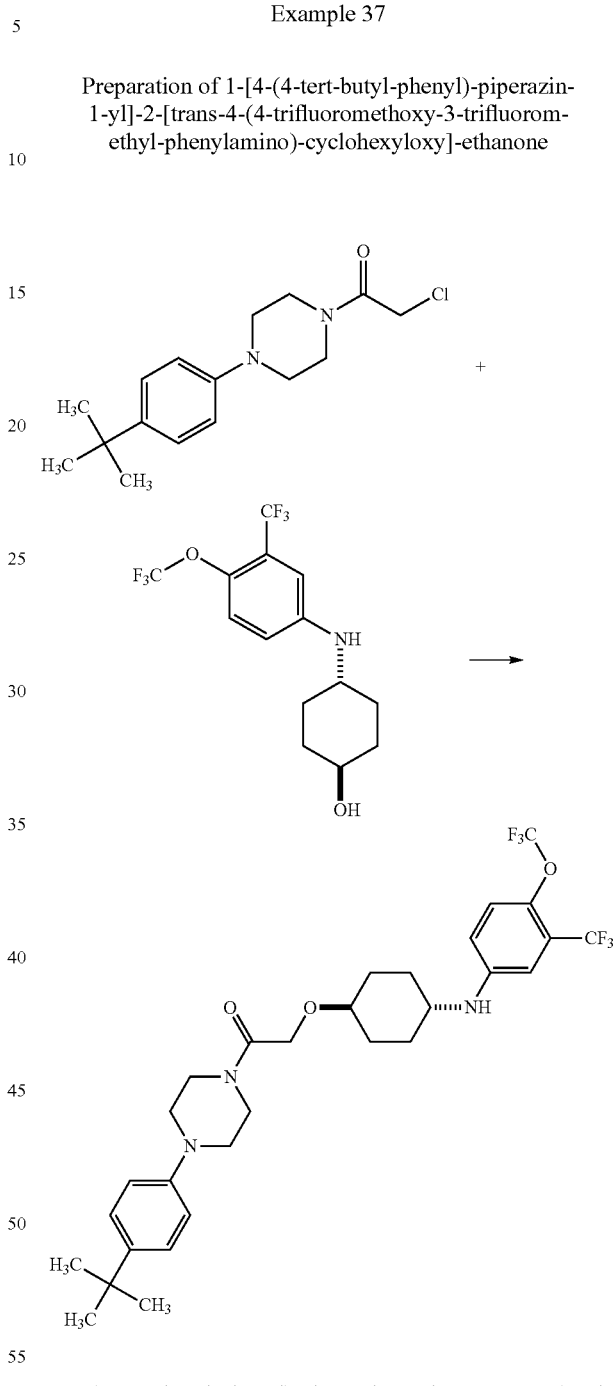

1-[4-(4-Tert-butyl-phenyl)-piperazin-1-yl]-2-[trans-4-(4-trifluoromethoxy-3-trifluoromethyl-phenylamino)-cyclohexyloxy]-ethanone was prepared from 1-chloracetyl-4-(4-tert-butyl-phenyl)-piperazine (prepared in accordance with Example 26) and trans-4-(4-trifluoromethoxy-3-trifluoromethyl-phenylamino)-cyclohexanol (prepared in accordance with Example 35) using the procedure illustrated in Example 11. This afforded the desired product as a colorless solid with a 39% yield. The structure was confirmed using Protocol I-B. Calculated mass=602; observed mass=602; HPLC retention time=6.35 min.

Example 38

Preparation of 1-[4-(4-tert-butyl-phenyl)-piperazin-1-yl]-2-[trans-4-(4-chloro-3-trifluoromethyl-phenylamino)-cyclohexyloxy]-ethanone

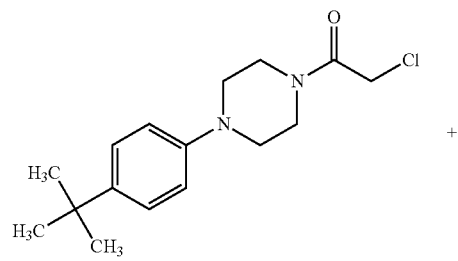
+
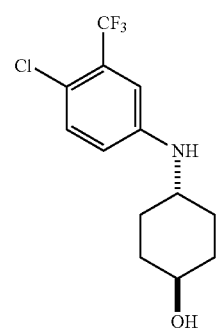
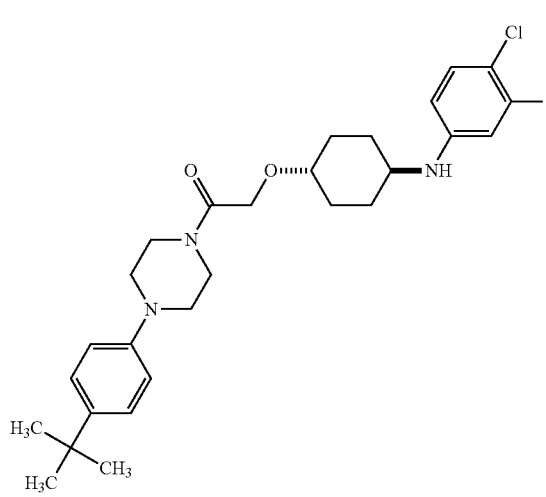

1-[4-(4-Tert-butyl-phenyl)-piperazin-1-yl]-2-[trans-4-(4-chloro-3-trifluoromethyl-phenylamino)-cyclohexyloxy]-ethanone was prepared from 1-chloracetyl-4-(4-tert-butyl-phenyl)-piperazine (prepared in accordance with Example 26) and trans-4-(4-chloro-3-trifluoromethyl-phenylamino)-cyclohexanol (prepared in accordance with Example 35) using the procedure illustrated in Example 11. This afforded the desired product as a colorless solid with a 47% yield. The structure was confirmed using Protocol I-B. Calculated mass=552; observed mass=552; HPLC retention time=6.26 min.

Example 39

Preparation of 1-[4-(4-benzyloxy-phenyl)-piperazin-1-yl]-2-[trans-4-(4-chloro-3-trifluoromethyl-phenylamino)-cyclohexyloxy]-ethanone

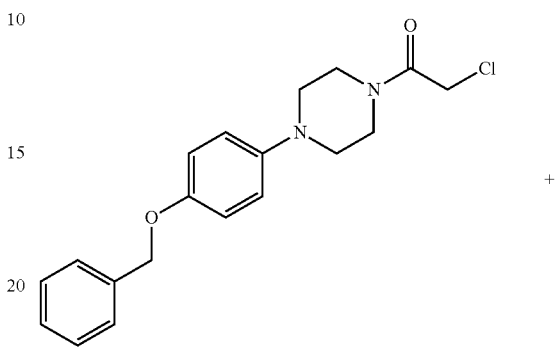
+
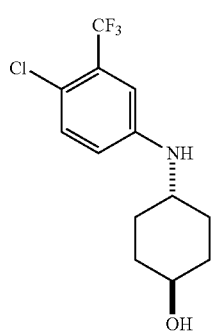
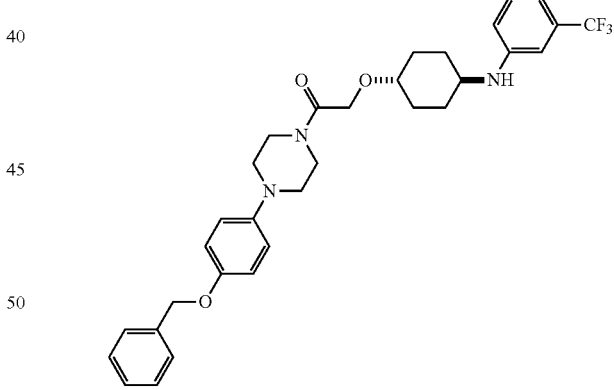

1-[4-(4-Benzyloxy-phenyl)-piperazin-1-yl]-2-[trans-4-(4-chloro-3-trifluoromethyl-phenylamino)-cyclohexyloxy]-ethanone was prepared from crude 1-chloracetyl-4-(4-tert-butyl-phenyl)-piperazine (prepared in accordance with Example 24) and trans-4-(4-chloro-3-trifluoromethyl-phenylamino)-cyclohexanol (prepared in accordance with Example 35) using the procedure illustrated in Example 11. This afforded the desired product as a colorless solid with a 45% yield. The structure was confirmed using Protocol I-B. Calculated mass=602; observed mass=602; HPLC retention time=6.12 min.

Example 40

Preparation of (trans-4-{3-oxo-3-[4-(4-trifluoromethyl-phenyl)-piperazin-1-yl]-propyl}-cyclohexyl)-carbamic acid tent-butyl ester Intermediate

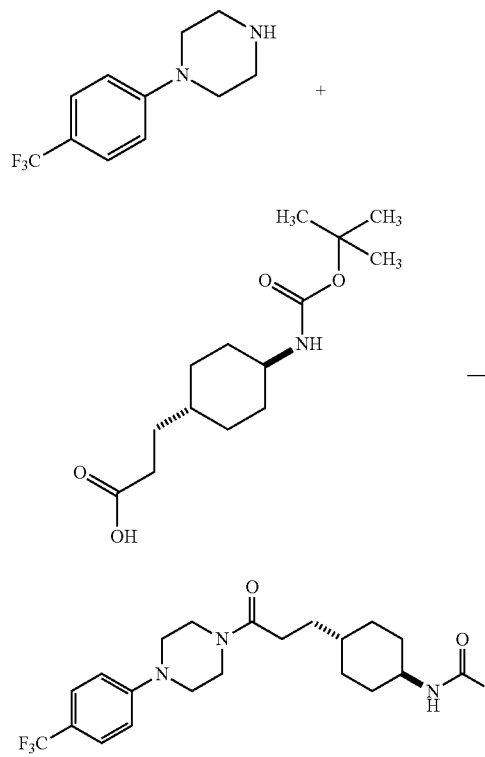

3-(Trans-4-tert-butoxycarbonylamino-cyclohexyl)-propanoic acid (50 mg, 0.18 mmol) and 2-(1H-benzotriazol-1-yl)-1,1,3,3-tetramethyluronium hexafluorophosphate (140 mg, 0.37 mmol) were dissolved in a mixture of dimethylacetamide (1.2 mL) and dichloromethane (0.3 mL). Next, diisopropylethylamine (100 µL, 0.55 mmol) was added. After 5 min, a solution of 1-(4-trifluormethyl-phenyl)-piperazine (50 mg, 0.22 mmol) in dimethylacetamide (1.2 mL) and dichloromethane (0.3 mL) was added, and the resulting mixture was stirred at room temperature for 30 min. The mixture was then diluted with dichloromethane (40 mL), and the organic layer was washed with water (2×20 mL), washed with saturated aqueous ammonium chloride (20 mL), washed with water (10 mL), washed with saturated aqueous hydrogencarbonate (2×20 mL), and washed with water (10 mL). The organic phase was dried over magnesium sulfate, filtered, and concentrated under vacuum. The crude product was purified by column chromatography on silica gel (pentane/ethyl acetate, 5:1), and the desired product was isolated as a light yellow solid (68 mg, 76% yield).

In many instances, the method of Example 40 can be adapted to make other compounds that are useful as intermediates for making compounds (and salts thereof) of this invention. An illustrative generic scheme is as follows:

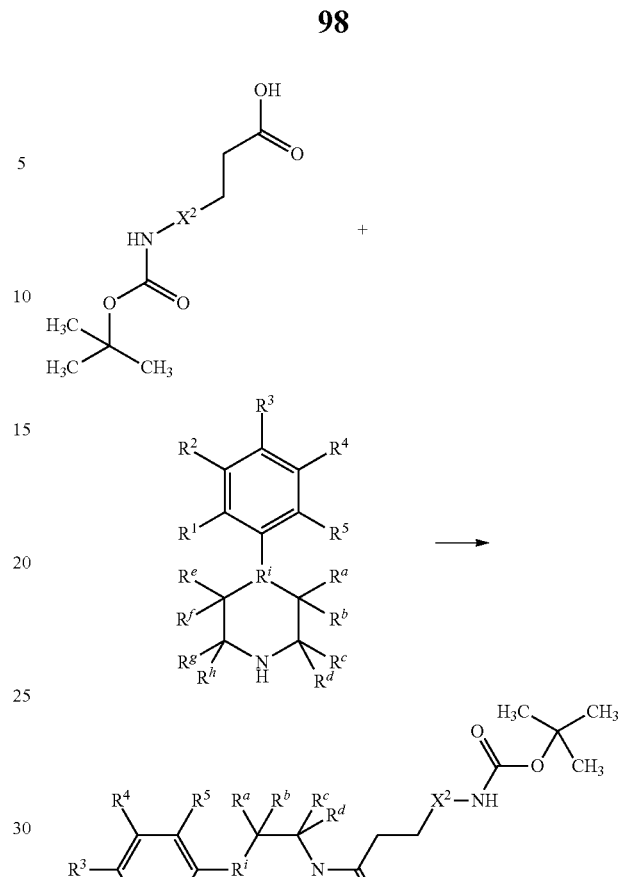

Here, $R^1$, $R^2$, $R^3$, $R^4$, $R^5$, and $X^2$ are as defined above for the compounds of this invention. $R^a$, $R^b$, $R^c$, $R^d$, $R^e$, $R^f$, $R^g$, and $R^h$ are independently selected from the group consisting of hydrogen, halogen, hydroxy, alkyl, and alkoxy. And $R^i$ is either

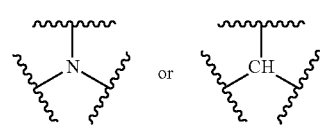

optionally substituted with halogen, hydroxy, alkyl, and alkoxy. Another illustrative generic scheme is as follows:

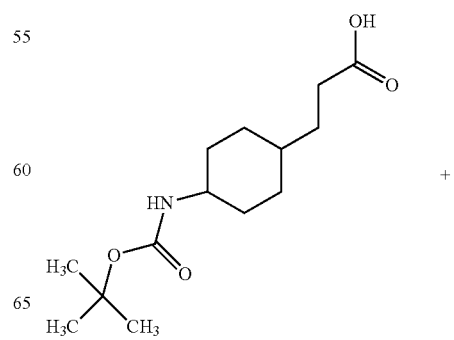

-continued

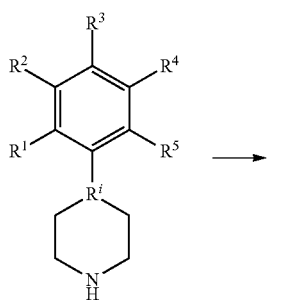

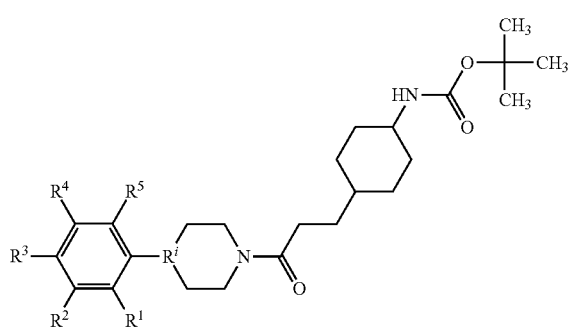

Determining the suitability of the methods (and any necessary routine adaptations) for making a particular intermediate is generally within the skill of those in the art after reading this patent.

Example 41

Preparation of 3-(trans-4-(4-nitro-3-trifluoromethyl-phenylamino)-cyclohexyl)-1-(4-(4-trifluoromethyl-phenyl)-piperazin-1-yl)-propan-1-one

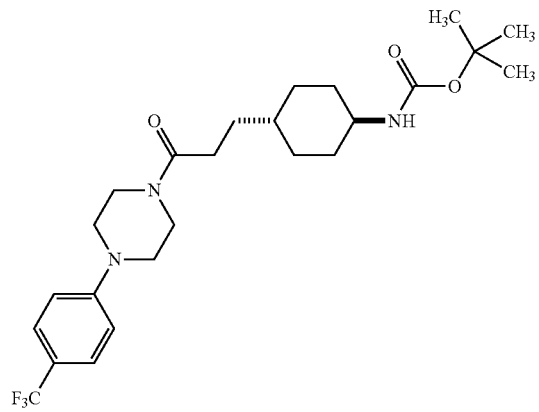

+

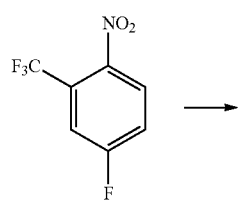

→

-continued

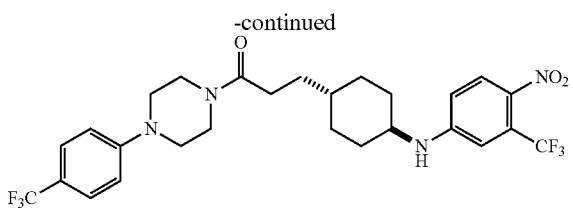

(Trans-4-{3-oxo-3-[4-(4-trifluoromethyl-phenyl)-piperazin-1-yl]-propyl}-cyclohexyl)-carbamic acid tert-butyl ester (23 mg, 0.06 mmol, prepared in accordance with Example 40) was combined with a 50% (vol/vol) solution of trifluoroacetic acid and dichloromethane (3 mL). The resulting mixture was stirred for 30 min at room temperature. The mixture was then concentrated under vacuum to form a crude residue. The crude residue was dissolved in dimethylsulfoxide (3 mL). Afterward, potassium carbonate was added (17 mg, 0.12 mmol). 5-Fluoro-2-nitrobenzotrifluoride (15 mg, 0.07 mmol) was then added. The resulting mixture was reacted at 120° C. for 18 hr. The mixture was then cooled to room temperature, diluted with dichloromethane (15 mL), washed with water (4×8 mL), washed with saturated aqueous ammonium chloride (8 mL), washed with water (8 mL), washed with saturated aqueous hydrogencarbonate (2×8 mL), and washed with water (2×8 mL). The organic phase was collected, dried over magnesium sulfate, and concentrated under vacuum to form a crude residue. The crude residue was purified by preparative HPLC. Following lyophilization of the fractions of interest, the desired product was isolated as a solid (17 mg, 48% yield). The structure was confirmed using Protocol I-A. Calculated mass=573; observed mass=553; HPLC retention time=4.98 min. It is believed that the discrepancy between the actual and observed masses stems from a loss of HF upon ionization.

In many instances, the method of Example 41 can be adapted to make other compounds (and salts thereof) of this invention. An illustrative generic scheme is as follows:

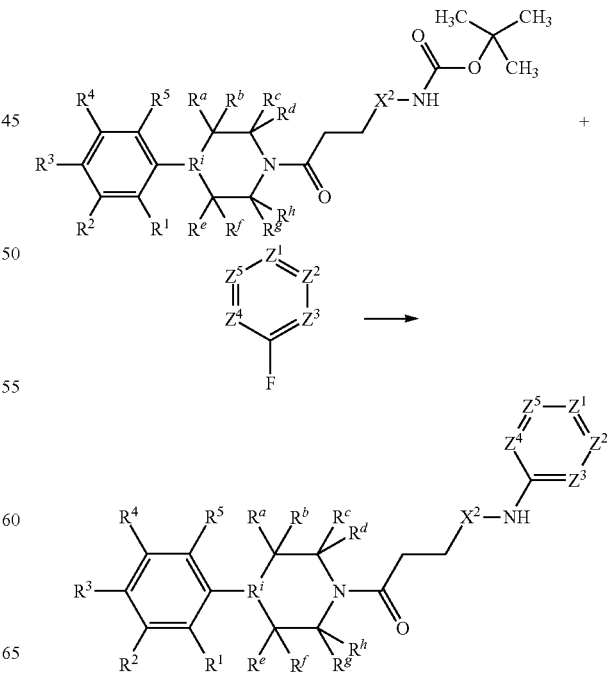

Here, $R^1$, $R^2$, $R^3$, $R^4$, $R^5$, $X^2$, $Z^1$, $Z^2$, $Z^3$, $Z^4$, and $Z^5$ are as defined above for the compounds of this invention. $R^a$, $R^b$, $R^c$, $R^d$, $R^e$, $R^f$, $R^g$, and $R^h$ are independently selected from the group consisting of hydrogen, halogen, hydroxy, alkyl, and alkoxy. And $R^i$ is either

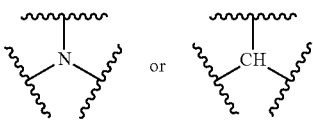

optionally substituted with halogen, hydroxy, alkyl, and alkoxy. Another illustrative generic scheme is as follows:

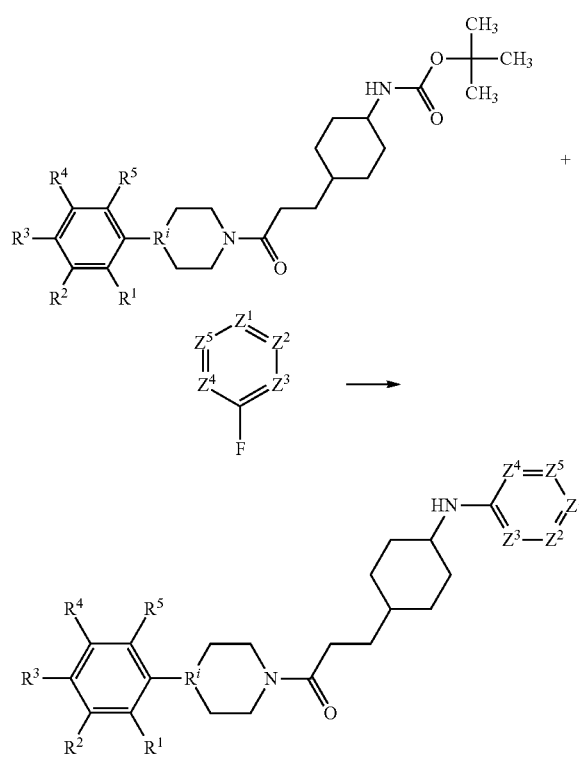

Determining the suitability of the methods (and any necessary routine adaptations) for making a particular compound (or salt thereof) is generally within the skill of those in the art after reading this patent.

Example 42

Preparation of trans-4-(4-nitro-3-trifluoromethyl-phenylamino)-cyclohexanecarboxylic acid Intermediate

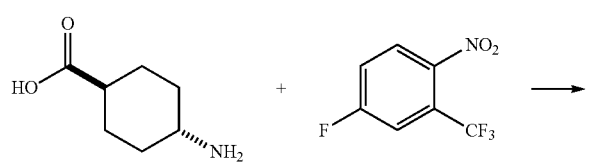

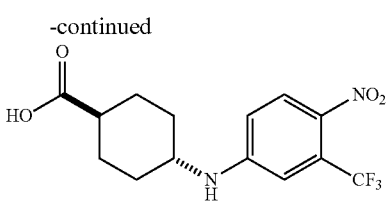

5-Fluoro-2-nitrobenzotrifluoride (1.46 g, 7.0 mmol) and trans-4-aminocyclohexane carboxylic acid (1.0 g, 7.0 mmol) were dissolved in a mixture of acetonitrile (42 mL), dimethylformamide (21 mL), and water (7 mL). The resulting solution was heated to 85° C. and then maintained at this temperature overnight. After cooling to room temperature, the mixture was partly concentrated under vacuum, diluted with ethyl acetate (50 mL), and washed with water (30 mL). The aqueous phase was acidified to pH 4 by the addition of 1 M HCl. This formed a precipitate, which was isolated by filtration. The filtrate was extracted with ethyl acetate (2×10 mL). The combined organic phases were dried over magnesium sulfate, filtered, and concentrated under vacuum to afford a solid. Both solids were combined and dried under vacuum. The desired product was isolated as a yellow solid (2.4 g, quantitative yield).

In many instances, the method of Example 42 can be adapted to make other compounds that are useful as intermediates for making compounds (and salts thereof) of this invention. An illustrative generic scheme is as follows:

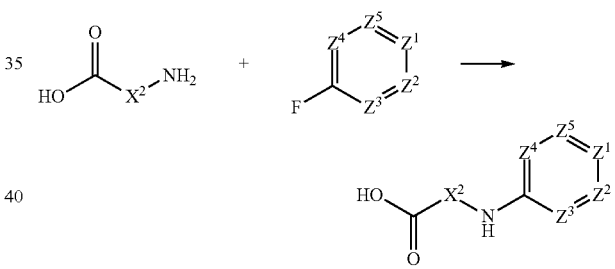

Here, $X^2$, $Z^1$, $Z^2$, $Z^3$, $Z^4$, and $Z^5$ are as defined above for the compounds of this invention. Another illustrative generic scheme is as follows:

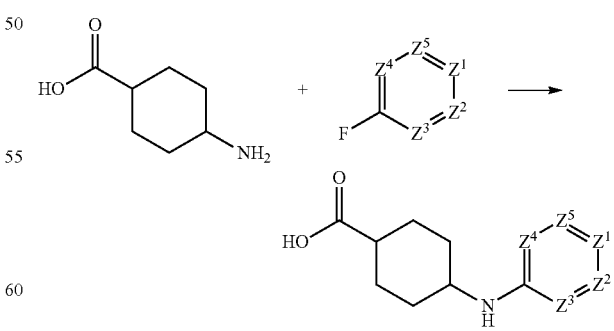

Determining the suitability of the methods (and any necessary routine adaptations) for making a particular intermediate is generally within the skill of those in the art after reading this patent.

Example 43

Preparation of [trans-4-(4-nitro-3-trifluoromethyl-phenylamino)-cyclohexyl]-methanol Intermediate

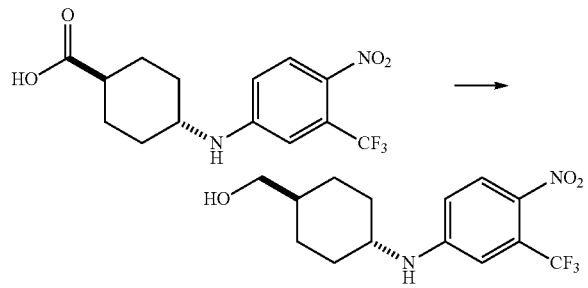

Trans-4-(4-nitro-3-trifluoromethyl-phenylamino)-cyclohexanecarboxylic acid (1.63 g, 4.9 mmol, prepared in accordance with Example 42) was suspended in tetrahydrofuran (40 mL). The resulting suspension was cooled to 0° C. with an ice bath. Afterward, a solution of lithium aluminium hydride in tetrahydrofuran (4.9 mL, 1 M in THF) was added under stirring. The resulting solution was allowed to reach room temperature, and then sonicated for 3 hr. After allowing the mixture to react overnight at room temperature, the mixture was heated to 60° C. to ensure complete conversion of the starting material. After cooling to room temperature, the mixture was acidified with 1M HCl and then diluted with ethyl acetate (50 mL). This formed a precipitate. The suspension was centrifuged, and the supernatant was collected and washed with water (10 mL). The organic layer was washed with saturated aqueous ammonium chloride (20 mL), dried over magnesium sulfate, filtered, and concentrated under vacuum. The desired product was obtained as a solid (1.3 g, 83% yield).

In many instances, the method of Example 43 can be adapted to make other compounds that are useful as intermediates for making compounds (and salts thereof) of this invention. An illustrative generic scheme is as follows:

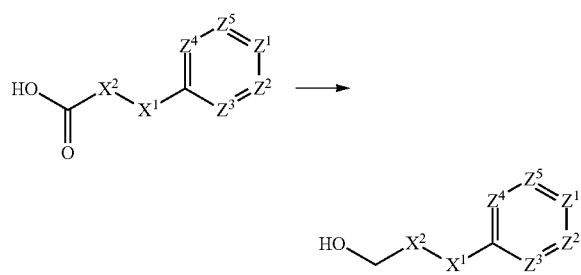

Here, $X^1$, $X^2$, $Z^1$, $Z^2$, $Z^3$, $Z^4$, and $Z^5$ are as defined above for the compounds of this invention. Another illustrative generic scheme is as follows:

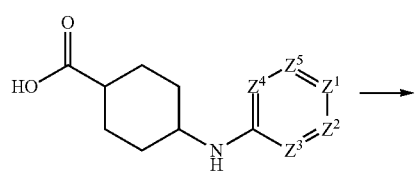

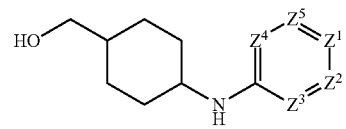

Determining the suitability of the methods (and any necessary routine adaptations) for making a particular intermediate is generally within the skill of those in the art after reading this patent.

Example 44

Preparation of trans-4-(4-nitro-3-trifluoromethyl-phenylamino)-cyclohexylmethyl toluene-4-sulfonic acid ester Intermediate

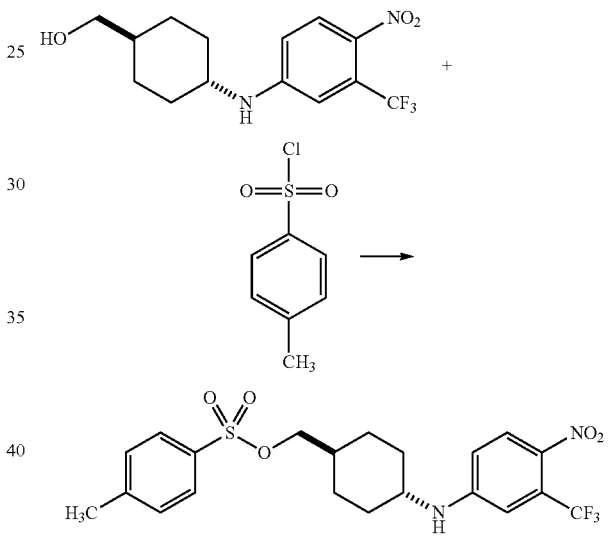

[Trans-4-(4-nitro-3-trifluoromethyl-phenylamino)-cyclohexyl]-methanol (700 mg, 2.2 mmol, prepared in accordance with Example 43 without any further purification) was diluted in dichloromethane (20 mL). Triethylamine (1.11 mL, 11.0 mmol) was then added, and the resulting mixture was cooled to 0° C. Para-toluenesulfonyl chloride (719 mg, 2.2 mmol) was then added. The mixture was stirred overnight at room temperature, and then diluted with dichloromethane (20 mL). The resulting mixture was treated with a half-saturated aqueous hydrogencarbonate (25 mL) solution. The two phases were stirred for one hr and then separated. The organic phase was washed with saturated aqueous ammonium chloride (20 mL), dried over magnesium sulfate, filtered, and concentrated under vacuum. The residue obtained was purified by chromatography on a short silica gel column (dichloromethane) to afford the desired product as a yellow solid (517 mg, 50% yield).

In many instances, the method of Example 44 can be adapted to make other compounds that are useful as intermediates for making compounds (and salts thereof) of this invention. An illustrative generic scheme is as follows:

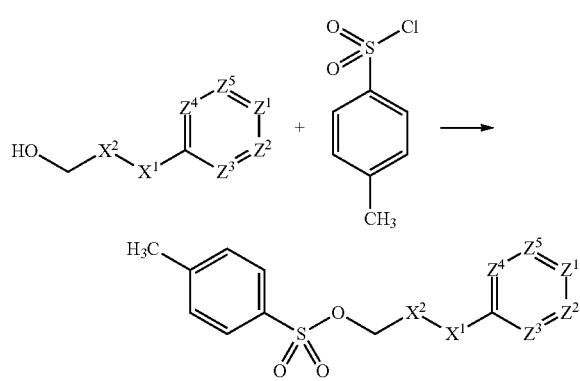

Here, $X^1$, $X^2$, $Z^1$, $Z^2$, $Z^3$, $Z^4$, and $Z^5$ are as defined above for the compounds of this invention. Another illustrative generic scheme is as follows:

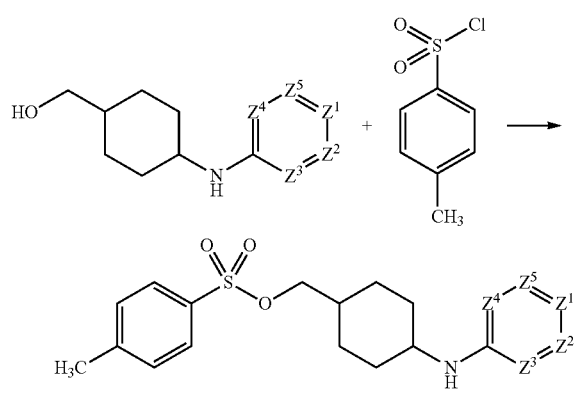

Determining the suitability of the methods (and any necessary routine adaptations) for making a particular intermediate is generally within the skill of those in the art after reading this patent.

Example 45

Preparation of (trans-4-aminomethyl-cyclohexyl)-4-nitro-3-trifluoromethyl-phenyl)-amine Intermediate

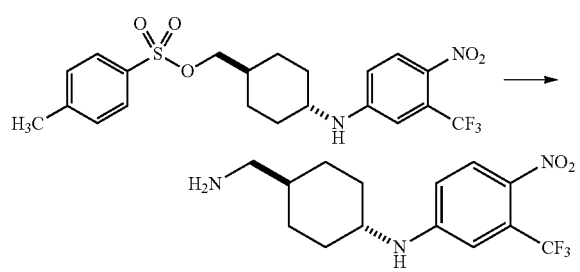

Trans-4-(4-nitro-3-trifluoromethyl-phenylamino)-cyclohexylmethyl toluene-4-sulfonic acid ester (715 mg, 1.51 mmol, prepared in accordance with Example 44) was dissolved in tetrahydrofuran (25 mL). An aqueous ammonia solution (1.5 mL, 25% wt/wt, 9.63 mmol) was then added. The resulting mixture was irradiated for 30 min at 150° C. in a microwave oven. After cooling to room temperature, the mixture was diluted with ethyl acetate (25 mL) and washed with water (30 mL). The organic phase was dried over magnesium sulfate, filtered, and concentrated under vacuum. The resulting residue was diluted in dioxane (5 mL). Afterward, a concentrated solution of HCl in dioxane was added (10 mL, 4N). A precipitate formed. The precipitate was triturated for 10 min in the solution, filtered, washed with diethylether (2×10 mL), and dried under vacuum. The desired product was isolated as a dihydrochloride (650 mg, quantitative yield).

In many instances, the method of Example 45 can be adapted to make other compounds that are useful as intermediates for making compounds (and salts thereof) of this invention. An illustrative generic scheme is as follows:

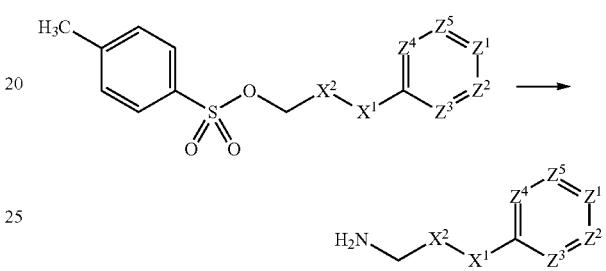

Here, $X^1$, $X^2$, $Z^1$, $Z^2$, $Z^3$, $Z^4$, and $Z^5$ are as defined above for the compounds of this invention. Another illustrative generic scheme is as follows:

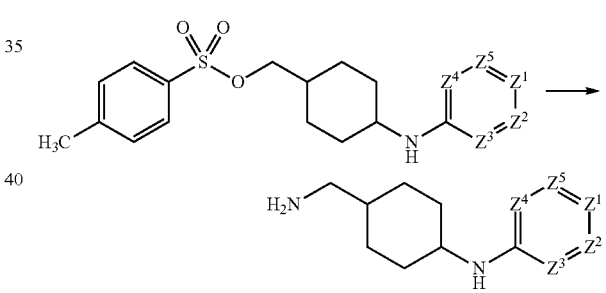

Determining the suitability of the methods (and any necessary routine adaptations) for making a particular intermediate is generally within the skill of those in the art after reading this patent.

Example 46

Preparation of trans-4-(4-nitro-3-trifluoromethyl-phenylamino)-cyclohexanecarboxilic acid methylamide Intermediate

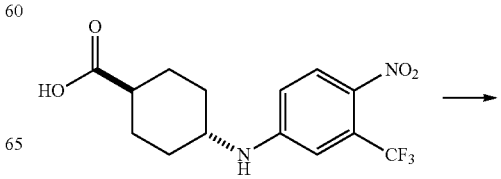

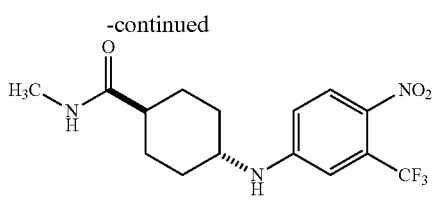

Trans-4-(4-nitro-3-trifluoromethyl-phenylamino)-cyclohexanecarboxylic acid (500 mg, 1.50 mmol, prepared in accordance with Example 42), 2-(1H-benzotriazol-1-yl)-1,1,3,3-tetramethyluronium hexafluorophosphate (570 mg, 1.5 mmol), and diisopropylethylamine (600 μL, 3.30 mmol) were dissolved in dry tetrahydrofuran (10 mL). The resulting mixture was stirred at room temperature for 10 min, and then cooled to 0° C. A solution of methylamine in tetrahydrofuran (750 μL, 2M, 1.50 mmol) and dimethylformamide (1 mL) was added, and the resulting mixture was stirred at room temperature for 3 hr. The mixture was then concentrated under vacuum. The resulting residue was taken up in dichloromethane (25 mL), and the organic phase was washed with water (10 mL), and then with aqueous saturated hydrogencarbonate (3×10 mL). The organic layer was collected, dried over magnesium sulfate, filtered, and concentrated under vacuum. The residue was diluted in dioxane (5 mL), and a concentrated solution of HCl in dioxane was added (10 mL, 4N). A precipitate formed, which was then washed with diethylether (10 mL) and dried under vacuum. The desired product was isolated as a yellow solid (498 mg, 87% yield).

In many instances, the method of Example 46 can be adapted to make other compounds that are useful as intermediates for making compounds (and salts thereof) of this invention. An illustrative generic scheme is as follows:

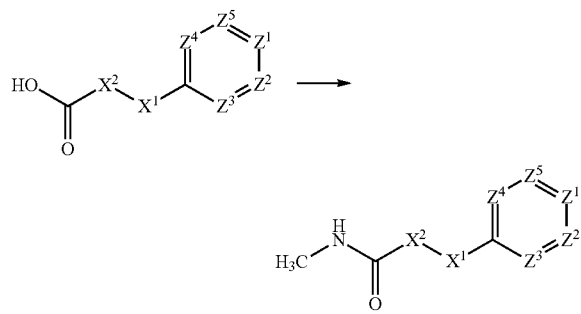

Here, $X^1$, $X^2$, $Z^1$, $Z^2$, $Z^3$, $Z^4$, and $Z^5$ are as defined above for the compounds of this invention. Another illustrative generic scheme is as follows:

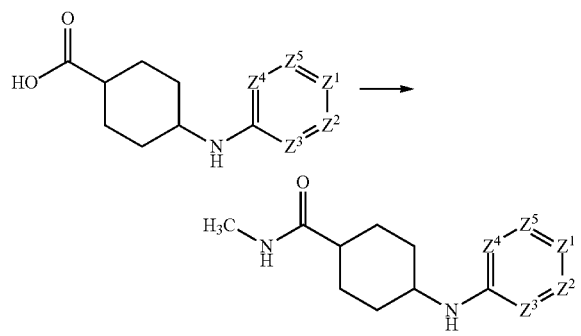

Determining the suitability of the methods (and any necessary routine adaptations) for making a particular intermediate is generally within the skill of those in the art after reading this patent.

Example 47

Preparation of (trans-4-methylaminomethyl-cyclohexyl)-4-nitro-3-trifluoromethyl-phenyl)-amine Intermediate

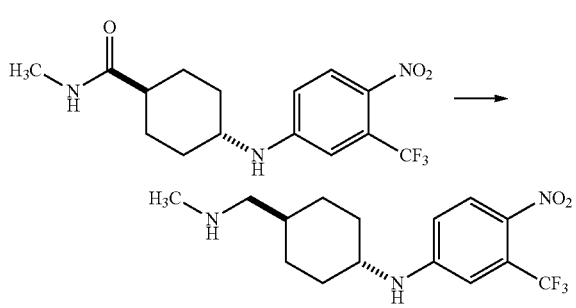

Trans-4-(4-nitro-3-trifluoromethyl-phenylamino)-cyclohexanecarboxilic acid methylamide (690 mg, 2.00 mmol, prepared in accordance with Example 46) was diluted in tetrahydrofuran (2 mL). The resulting solution was heated to reflux. A solution of borane-dimethylsulfide complex in tetrahydrofuran (4 mL, 2M, 8.00 mmol) was added. The mixture was then stirred for 10 min, acidified with 0.5 M HCl, and extracted with dichloromethane (10 mL). The aqueous phase was neutralized with aqueous saturated hydrogencarbonate, and extracted with dichloromethane (2×15 mL). The organic layer was collected, dried over magnesium sulfate, filtered, and concentrated under vacuum. The resulting residue was diluted in diethylether (5 mL) and then combined with a molar solution of HCl in diethylether (10 mL, 1M). A precipitate formed, which was filtered, washed with diethylether (10 mL), and dried under vacuum. The desired product was isolated as a yellow solid (256 mg, 35% yield).

In many instances, the method of Example 47 can be adapted to make other compounds that are useful as intermediates for making compounds (and salts thereof) of this invention. An illustrative generic scheme is as follows:

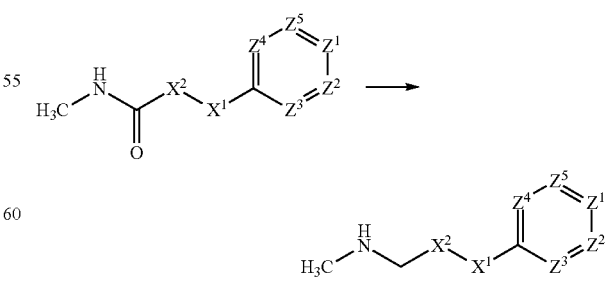

Here, $X^1$, $X^2$, $Z^1$, $Z^2$, $Z^3$, $Z^4$, and $Z^5$ are as defined above for the compounds of this invention. Another illustrative generic scheme is as follows:

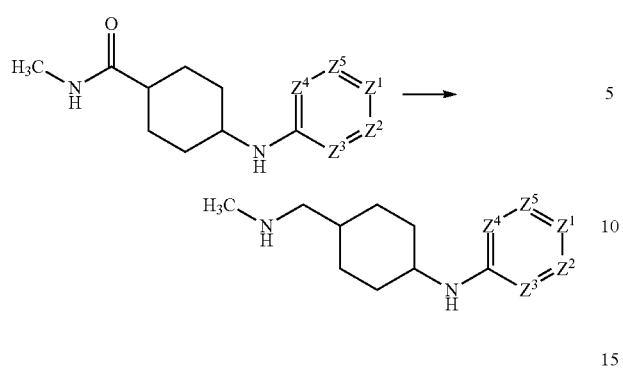

Determining the suitability of the methods (and any necessary routine adaptations) for making a particular intermediate is generally within the skill of those in the art after reading this patent.

Example 48

Preparation of
1-(4-Tert-butyl-phenyl)-piperidine-4-carboxylic acid ethyl ester Intermediate

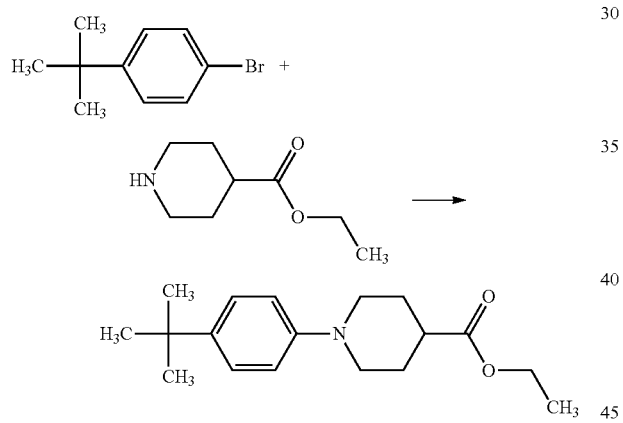

4-Bromobenzotrifluoride (572 µL, 3.30 mmol), piperidine-4-carboxylic acid ethyl ester (985 µL, 6.00 mmol), tris-(dibenzylideneacetone)-dipalladium (62 mg, 0.07 mmol), 2,2'-bis-(diphenylphosphino)-1,1'-binaphthalin (121 mg, 0.19 mmol), and sodium tert-butoxide (576 mg, 6.0 mmol) were dissolved in toluene (5 mL). The resulting mixture was irradiated at 120° C. for 30 min in a microwave oven. The mixture was then cooled to room temperature and diluted with ethyl acetate (20 mL). This resulted in a precipitate. The precipitate was separated by filtration, and the filtrate was concentrated under vacuum. Purification by column chromatography on silica gel (dichloromethane/diethylether; first eluting with a 1:0 mixture (i.e., all dichloromethane), and then with a 6:1 mixture) afforded the desired product as an oil (110 mg, 12% yield).

In many instances, the method of Example 48 can be adapted to make other compounds that are useful as intermediates for making compounds (and salts thereof) of this invention. An illustrative generic scheme is as follows:

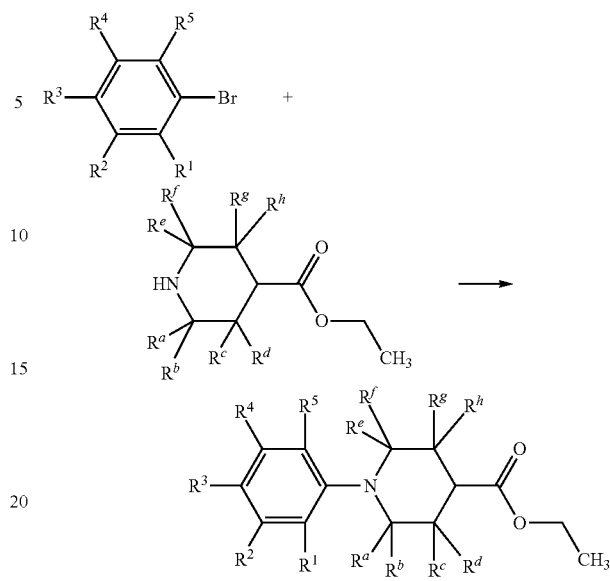

Here, $R^1$, $R^2$, $R^3$, $R^4$, and $R^5$ are as defined above for the compounds of this invention. $R^a$, $R^b$, $R^c$, $R^d$, $R^e$, $R^f$, $R^g$, and $R^h$ are independently selected from the group consisting of hydrogen, halogen, hydroxy, alkyl, and alkoxy. Another illustrative generic scheme is as follows:

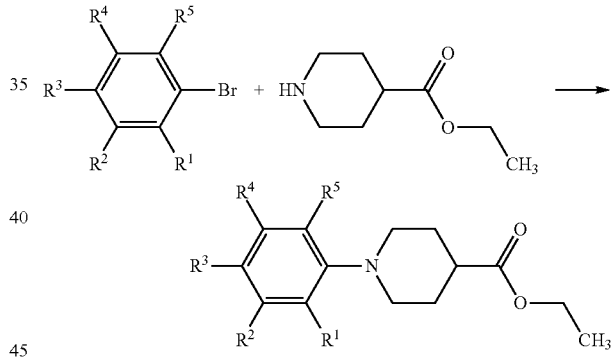

Determining the suitability of the methods (and any necessary routine adaptations) for making a particular intermediate is generally within the skill of those in the art after reading this patent.

Example 49

Preparation of
1-(4-Tert-butyl-phenyl)-piperidine-4-carboxylic acid Intermediate

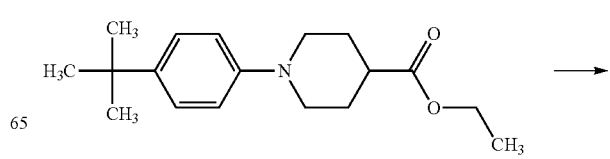

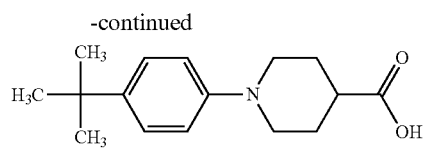

1-(4-Tert-butyl-phenyl)-piperidine-4-carboxylic acid ethyl ester (120 mg, 0.41 mmol, prepared in accordance with Example 48) was diluted in methanol (4 mL). An aqueous solution of sodium hydroxide (2 mL, 4M, 8.00 mmol) was then added. The resulting mixture was heated to 90° C., and then maintained at that temperature for 3 hr. After cooling to room temperature, the mixture was filtered. The filtrate was diluted with water (10 mL), and the aqueous phase was washed with ethyl acetate (10 mL). The aqueous phase was then acidified to a pH of 4 with 1 M HCl and then extracted with ethyl acetate (2×10 mL). The organic layer was collected, dried over magnesium sulfate, filtered, and concentrated under vacuum. The desired product was isolated as a solid (28 mg, 26% yield).

In many instances, the method of Example 49 can be adapted to make other compounds that are useful as intermediates for making compounds (and salts thereof) of this invention. An illustrative generic scheme is as follows:

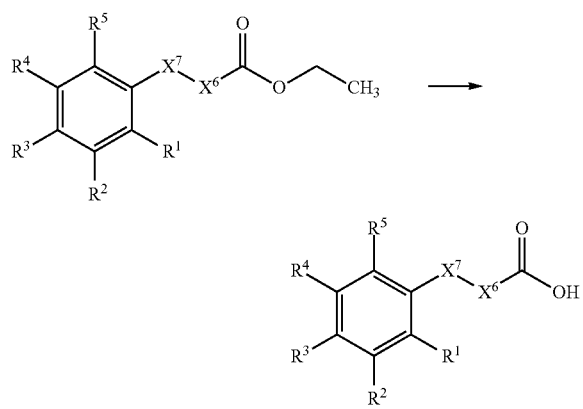

Here, $R^1$, $R^2$, $R^3$, $R^4$, $R^5$, $X^6$, and $X^7$ are as defined above for the compounds of this invention. Another illustrative generic scheme is as follows:

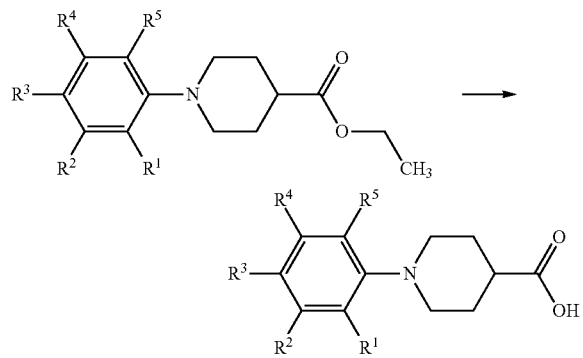

Determining the suitability of the methods (and any necessary routine adaptations) for making a particular intermediate is generally within the skill of those in the art after reading this patent.

Example 50

Preparation of 1-(4-Tert-butyl-phenyl)-4-methyl-piperidine-4-carboxylic acid ethyl ester Intermediate

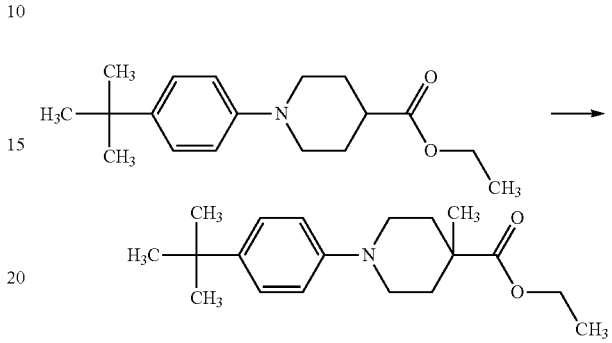

Diisopropylamine (113 µL, 0.81 mmol) was diluted with tetrahydrofuran (1 mL). The resulting solution was cooled to 0° C., and a solution of n-butyllithium in cyclohexane (400 µL, 2M, 0.80 mmol) was then added. The mixture was stirred at 0° C. for 30 min. The mixture was then cooled to −78° C., and a solution of the 1-(4-Tert-butyl-phenyl)-piperidine-4-carboxylic acid ethyl ester (118 mg, 0.41 mmol, prepared in accordance with Example 48) in tetrahydrofuran (3 mL) was added. After 30 min, methyl iodide (57 µL, 0.41 mmol) was added. Afterward, the mixture was maintained at −78° C. for 1 hr. The mixture was then allowed to increase to room temperature, and maintained at that temperature for 1 hr. The mixture was then quenched with saturated aqueous ammonium chloride (15 mL). The organic phase was extracted with ethyl acetate (20 mL). The organic phase was then dried over magnesium sulfate, filtered, and concentrated under vacuum. The desired product was isolated as an oil (155 mg, quantitative yield).

In many instances, the method of Example 50 can be adapted to make other compounds that are useful as intermediates for making compounds (and salts thereof) of this invention. An illustrative generic scheme is as follows:

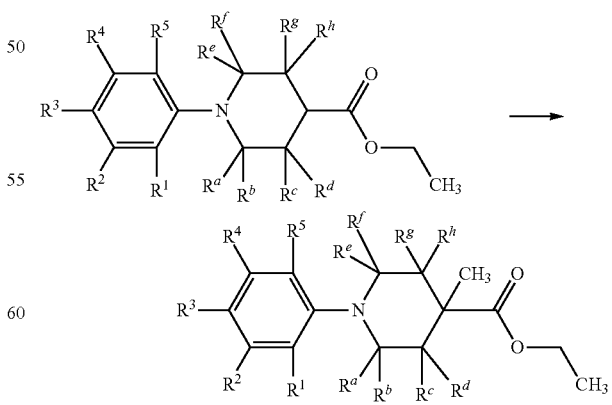

Here, $R^1$, $R^2$, $R^3$, $R^4$, and $R^5$ are as defined above for the compounds of this invention. $R^a$, $R^b$, $R^c$, $R^d$, $R^e$, $R^f$, $R^g$, and $R^h$ are independently selected from the group consisting of hydrogen, halogen, hydroxy, alkyl, and alkoxy. Another illustrative generic scheme is as follows:

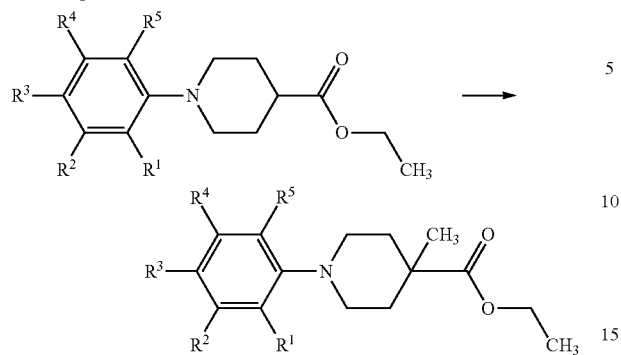

Determining the suitability of the methods (and any necessary routine adaptations) for making a particular intermediate is generally within the skill of those in the art after reading this patent.

Example 51

Preparation of 1-(4-tert-butyl-phenyl)-4-methylpiperidine-4-carboxylic acid Intermediate

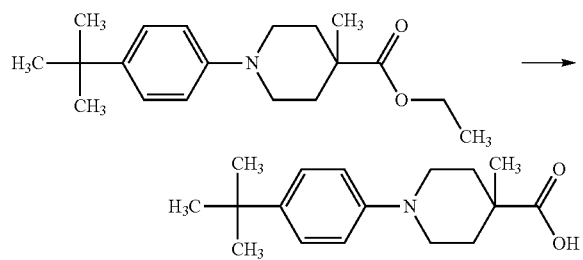

1-(4-Tert-butyl-phenyl)-4-methyl-piperidine-4-carboxylic acid ethyl ester (155 mg, 0.62 mmol, prepared in accordance with Example 50 without any further purification) was diluted in methanol (4 mL). An aqueous sodium hydroxide solution was then added (2 mL, 4M, 8.00 mmol). The resulting mixture was heated to 90° C. and then maintained at that temperature for 1 hr. After cooling to room temperature, the mixture was filtered. The filtrate was diluted with water (10 mL), and the aqueous phase was washed with ethyl acetate (10 mL). The aqueous phase was then acidified to a pH of 4 with 1 M HCl and extracted with ethyl acetate (2×10 mL). The organic layer was collected, dried over magnesium sulfate, filtered, and concentrated under vacuum. The desired product was isolated as a solid (81 mg, 48% yield).

Example 52

Preparation of 1-(4-tert-butyl-phenyl)-N-methyl-N-[trans-4-(4-nitro-3-trifluoromethyl-phenylamino)-cyclohexylmethyl]-piperidine-4-carboxamide

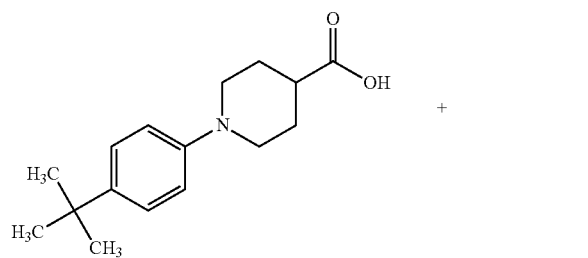

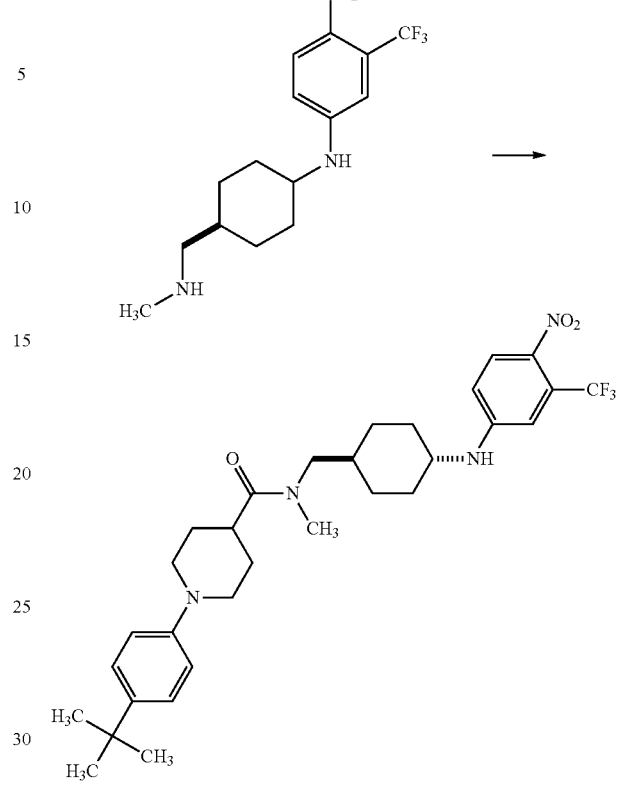

1-(4-Tert-butyl-phenyl)-piperidine-4-carboxylic acid (29 mg, 0.11 mmol, prepared in accordance with Example 49), 2-(1H-benzotriazol-1-yl)-1,1,3,3-tetramethyluronium hexafluorophosphate (38 mg, 0.11 mmol), and diisopropylethylamine (87 μL, 0.50 mmol) were dissolved in a 1:1 mixture of dry tetrahydrofuran (0.5 mL) and dry dimethylformamide (0.5 mL). The resulting mixture was stirred at room temperature for 5 min. A solution of (trans-4-methylaminomethyl-cyclohexyl)-4-nitro-3-trifluoromethyl-phenyl)-amine (35 mg, 0.10 mmol, prepared in accordance with Example 47) in a 1:1 mixture of dry tetrahydrofuran (0.5 mL) and dry dimethylformamide (0.5 mL) was then added. The resulting mixture was stirred at room temperature for 3 hr. The mixture was then diluted with dichloromethane (10 mL), and the organic phase was washed with water (5 mL), and then aqueous saturated hydrogencarbonate (2×5 mL). The organic layer was collected, dried over magnesium sulfate, filtered, and concentrated under vacuum. The residue obtained was purified by preparative HPLC. Following lyophilization of the fractions of interest, the desired product was isolated as a yellow solid (40 mg, 63% yield). The structure was confirmed using Protocol II-A. Calculated mass=575; observed mass=575; HPLC retention time=4.32 min.

Example 53

Preparation of 1-(4-tert-butyl-phenyl)-N-dimethyl-N-[trans-4-(4-nitro-3-trifluoromethyl-phenylamino)-cyclohexylmethyl]-4-methyl-piperidine-4-carboxamide

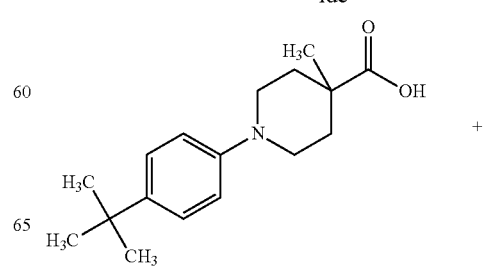

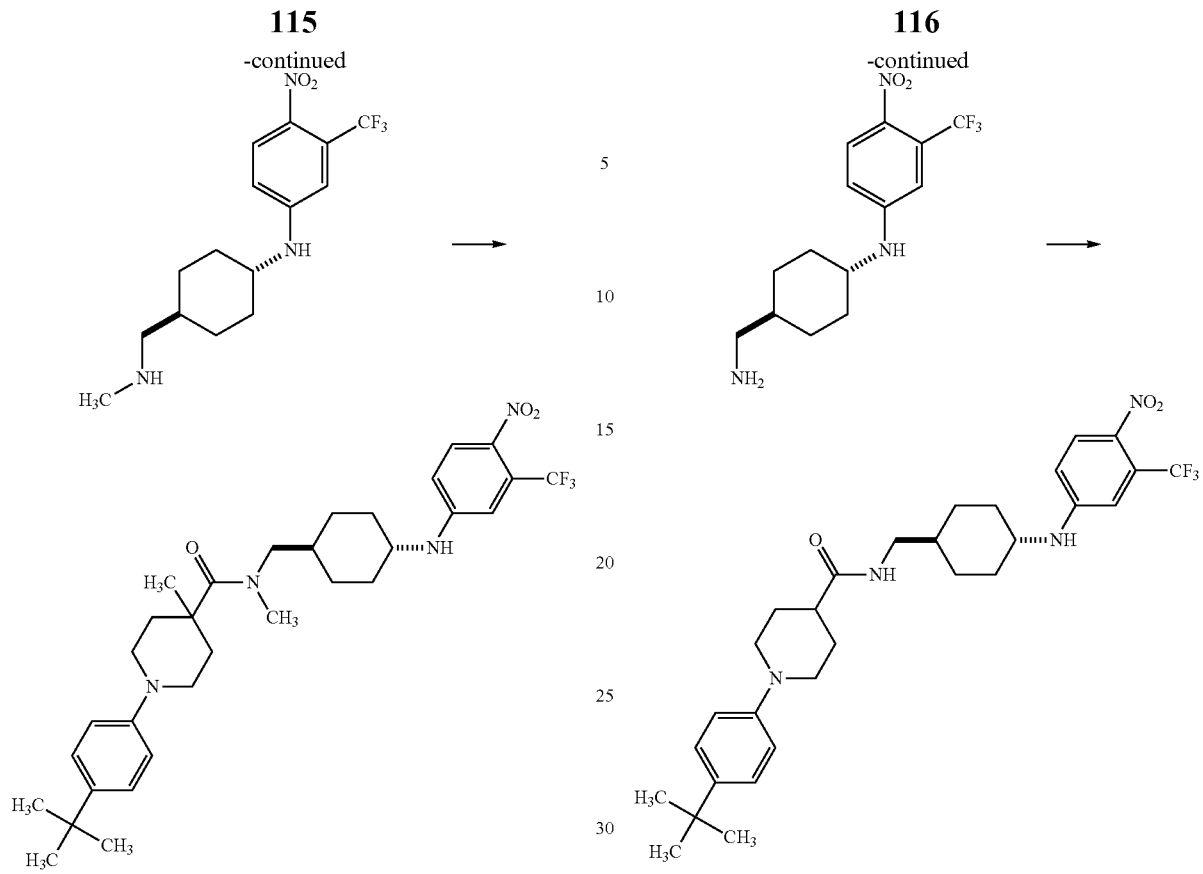

1-(4-Tert-butyl-phenyl)-4-methylpiperidine-4-carboxylic acid (30 mg, 0.11 mmol, prepared in accordance with Example 51), 2-(1H-benzotriazol-1-yl)-1,1,3,3-tetramethyluronium hexafluorophosphate (38 mg, 0.11 mmol), and diisopropylethylamine (87 μL, 0.50 mmol) were dissolved in a 1:1 mixture of dry tetrahydrofuran (0.5 mL) and dry dimethylformamide (0.5 mL). The resulting mixture was stirred at room temperature for 5 min. A solution of (trans-4-methylaminomethyl-cyclohexyl)-4-nitro-3-trifluoromethyl-phenyl)-amine (35 mg, 0.10 mmol, prepared in accordance with Example 47) in a 1:1 mixture of dry tetrahydrofuran (0.5 mL) and dry dimethylformamide (0.5 mL) was then added. The mixture was then stirred at room temperature for 3 hr. Afterward, the mixture was diluted with dichloromethane (10 mL), and the organic phase was washed with water (5 mL), and then aqueous saturated hydrogencarbonate (2×5 mL). The organic layer was collected, dried over magnesium sulfate, filtered, and concentrated under vacuum. The resulting residue was purified by preparative HPLC. Following lyophilization of the fractions of interest, the desired product was isolated as a yellow solid (10 mg, 15% yield). The structure was confirmed using Protocol II-A. Calculated mass=589; observed mass=589; HPLC retention time=4.59 min.

Example 54

Preparation of 1-(4-tert-butyl-phenyl)-N-[trans-4-(4-nitro-3-trifluoromethyl-phenylamino)-cyclohexylmethyl]-piperidine-4-carboxamide 1-(4-Tert-butyl-phenyl)-piperidine-4-carboxylic acid (29 mg, 0.11 mmol, prepared in accordance with Example 49), 2-(1H-benzotriazol-1-yl)-1,1,3,3-tetramethyluronium hexafluorophosphate (38 mg, 0.11 mmol), and diisopropylethylamine (87 μL, 0.50 mmol) were dissolved in a 1:1 mixture of dry tetrahydrofuran (0.5 mL) and dry dimethylformamide (0.5 mL). The resulting mixture was stirred at room temperature for 5 min. A solution of (trans-4-aminomethyl-cyclohexyl)-4-nitro-3-trifluoromethyl-phenyl)-amine (35 mg, 0.11 mmol, prepared in accordance with Example 45) in a 1:1 mixture of dry tetrahydrofuran (0.5 mL) and dry dimethylformamide (0.5 mL) was then added. The resulting mixture was stirred at room temperature for 3 hr. The mixture was then diluted with dichloromethane (10 mL), and the organic phase was washed with water (5 mL) and then aqueous saturated hydrogencarbonate (2×5 mL). The organic layer was collected, dried over magnesium sulfate, filtered, and concentrated under vacuum. The resulting residue was purified by preparative HPLC. Following lyophilization of the fractions of interest, the desired product was isolated as a yellow solid (4 mg, 9% yield). The structure was confirmed using Protocol II-B. Calculated mass=561; observed mass=561; HPLC retention time=5.21 min.

In many instances, the methods of Examples 52-54 can be adapted to make other compounds (and salts thereof) of this invention. An illustrative generic scheme is as follows:

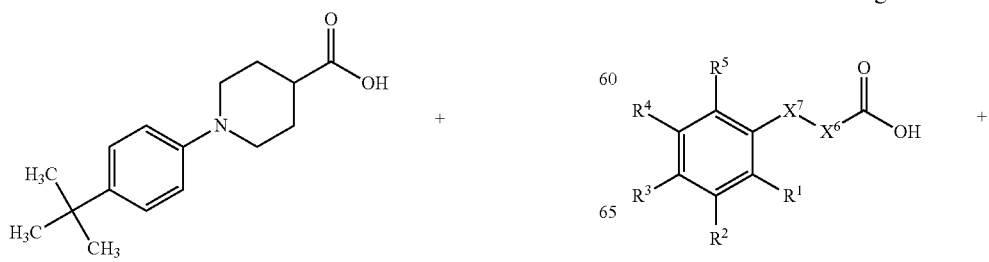

117

-continued

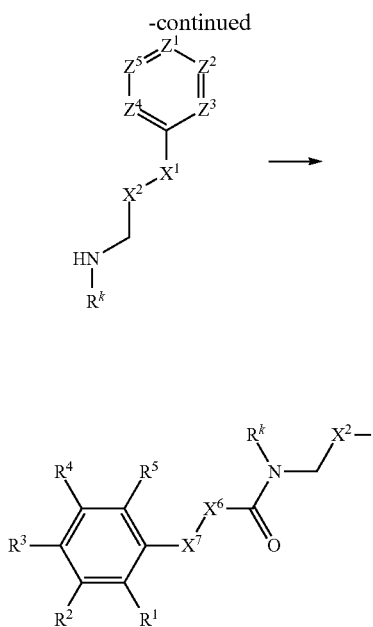

Here, $R^1$, $R^2$, $R^3$, $R^4$, $R^5$, $X^1$, $X^2$, $X^6$, $X^7$, $Z^1$, $Z^2$, $Z^3$, $Z^4$, and $Z^5$ are as defined above for the compounds of this invention. And $R^k$ is selected from the group consisting of hydrogen, $C_1$-$C_6$-alkyl, $C_2$-$C_6$-alkenyl, and $C_2$-$C_6$-alkynyl. The $C_1$-$C_6$-alkyl, $C_2$-$C_6$-alkenyl, and $C_2$-$C_6$-alkynyl are optionally substituted with one or more independently selected halogen. Another illustrative generic scheme is as follows:

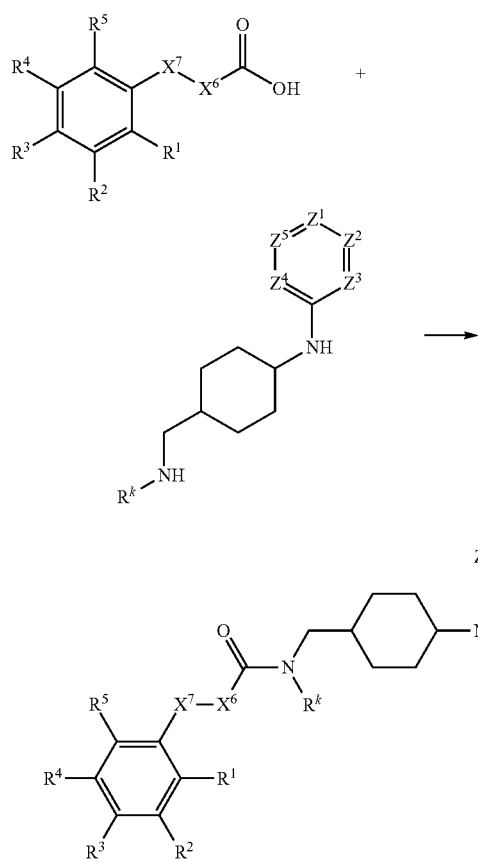

118

Determining the suitability of the methods (and any necessary routine adaptations) for making a particular compound (or salt thereof) is generally within the skill of those in the art after reading this patent.

Example 55

Preparation of [1-(4-trifluoromethyl-phenyl)-piperidin-4-ylmethyl]-carbamic acid tert-butyl ester

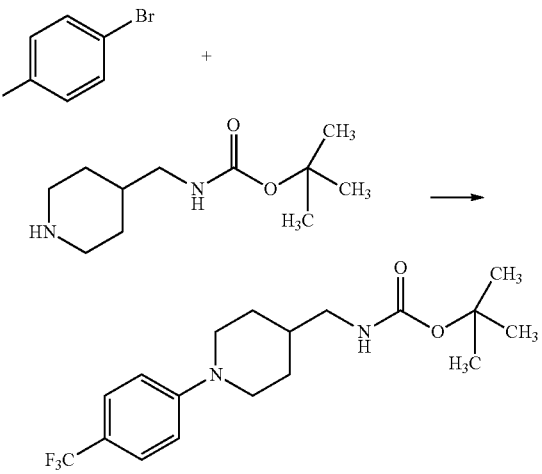

A solution of 1-bromo-4-trifluoromethyl-benzene (50.0 g; 220 mmol) and piperidin-4-ylmethyl-carbamic acid tert-butyl ester (48.1 g; 220 mmol) in dioxane (1 L) was added to a suspension of palladium (II) acetate (7.41 g; 33 mmol), cesium carbonate (144.8 g; 440 mmol), and 2,2'-bis(diphenylphosphino)-1,1'-binaphthyl (31.8 g; 45 mmol) in dioxane (1 L). The resulting mixture was heated to 110° C., and then maintained at that temperature for 28 hr with stirring. The mixture was then allowed to cool to room temperature. Afterward, the reaction mixture was treated with water (2 L) and extracted with dichloromethane (2×1 L). The combined organic phases were dried over sodium sulfate and filtered, and then the solvents were removed under reduced pressure. The resulting residue was dissolved in acetonitrile (1.5 L). Water (1.5 L) was then added with stirring. This resulting in a precipitate, which was filtered and then dried overnight at 40° C. at a pressure of 3 mbar to afford the desired product (48.9 g; 136 mmol).

Example 56

Preparation of methyl-[1-(4-trifluoromethyl-phenyl)-piperidin-4-ylmethyl]-amine

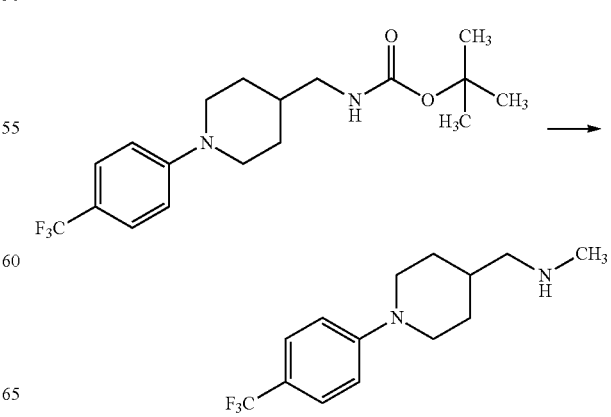

A solution of [1-(4-trifluoromethyl-phenyl)-piperidin-4-yl-methyl]-carbamic acid tert-butyl ester (45 g; 126 mmol, prepared in accordance with Example 55) in tetrahydrofuran (450 mL) was added over 7 min to a molar solution of lithium aluminium hydride in tetrahydrofuran (377 mL). The resulting mixture was heated to 100° C., and then maintained at that temperature for 195 min. Afterward, the mixture was allowed to cool to room temperature and then poured onto a mixture of ice (500 g) and of 2 N aqueous HCl (350 mL). The organic solvents were removed by evaporation under reduced pressure, and the aqueous phase was basified to a pH of 11 by adding 2 N aqueous NaOH. This resulting in a precipitate, which was filtered and dried at 40° C. under a pressure of 3 mbar to afford the desired product (17.7 g; 65 mmol).

Example 57

Preparation of trans-N-methyl-4-(4-nitro-3-(trifluoromethyl)phenylamino)-N-((1-(4-(trifluoromethyl)phenyl)piperidin-4-yl)methyl)cyclohexanecarboxamide

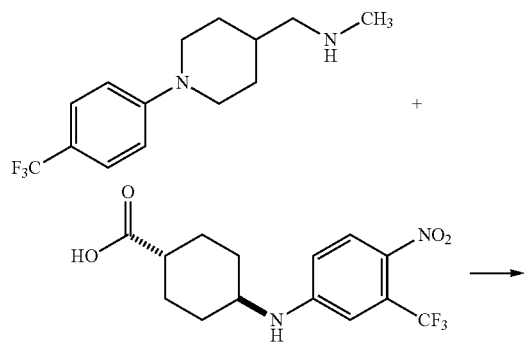

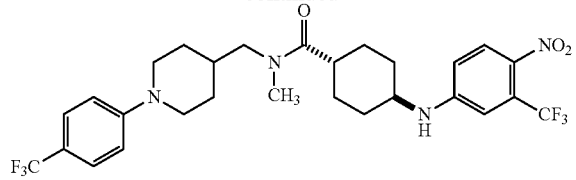

A suspension of trans-4-(4-nitro-3-trifluoromethyl-phenylamino)-cyclohexanecarboxylic acid (7.88 g; 23.7 mmol, prepared in accordance with Example 42), diisopropylethyl amine (8.56 mL; 47.4 mmol), and tetramethyl-O-(1H-benzotriazol-1-yl)uronium hexafluorophosphate (8.74 g; 22.6 mmol) in a mixture of dichloromethane (300 mL) and dimethylsulfoxide (5 mL) was stirred for 20 min. Afterward, methyl-[1-(4-trifluoromethyl-phenyl)-piperidin-4-ylmethyl]-amine (6.15 g; 22.6 mmol, prepared in accordance with Example 56) was added. The resulting suspension was stirred for 15.5 hr at room temperature. This resulted in a clear solution, which was extracted with water (1 L). The organic phase was dried over sodium sulfate. After concentrating under reduced pressure, the resulting residue obtained was dissolved in a small volume of acetonitrile and filtered over a silica gel pad. The solvent was removed under reduced pressure, and the resulting solid was dried at 40° C. under a pressure of 3 mbar to afford the desired product (12.9; 22.0 mmol).

Examples 58-265

Examples of Additional Compounds Prepared by Applicants in Accordance with this Invention Applicants have prepared various other compounds using the above protocols alone or in combination methods generally known in the art. Such compounds include those listed in the following Table II. Table II also provides the protocol used to confirm each compound structure, as well as the calculated mass, the observed mass, and the HPLC retention time.

TABLE II

Additional Compounds Prepared by Applicants in Accordance with this Invention

| Compound Structure | Analysis Method | Retention Time (min) | Calc. Mass | Obs. Mass |
|---|---|---|---|---|
| 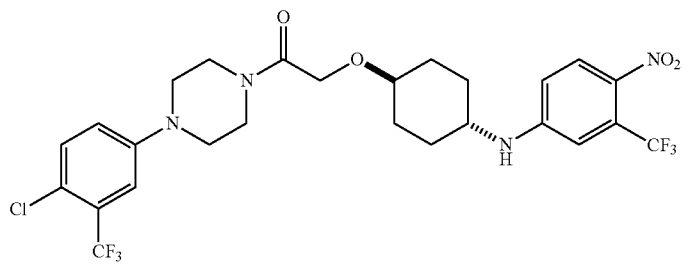<br>Example 58 | Protocol II-A | 4.57 | 575 | 575 |
| Example 59 | Protocol II-A | 4.70 | 609 | 609 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 60 | Protocol II-A | 4.70 | 575 | 575 |
| Example 61 | Protocol II-A | 4.53 | 541 | 541 |
| Example 62 | Protocol II-A | 4.64 | 575 | 575 |
| Example 63 | Protocol II-A | 4.45 | 541 | 541 |
| Example 64 | Protocol II-A | 4.35 | 600 | 600 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 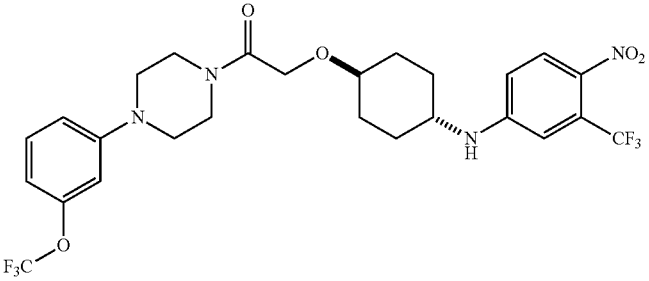 Example 65 | Protocol II-A | 4.64 | 591 | 591 |
| 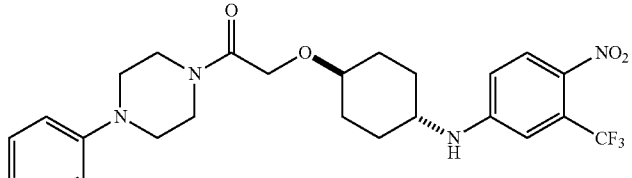 Example 66 | Protocol I-C | 3.45 | 507 | 507 |
| 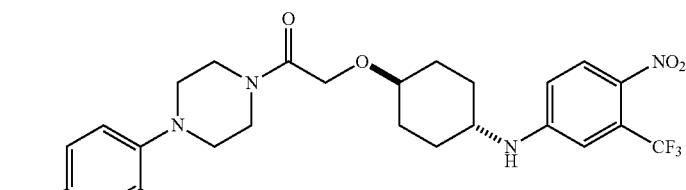 Example 67 | Protocol II-A | 4.71 | 535 | 535 |
| 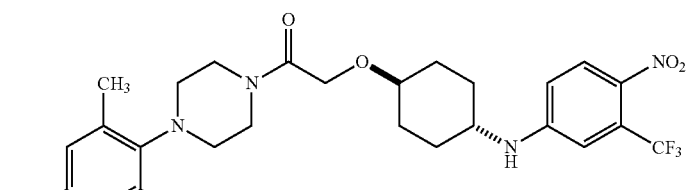 Example 68 | Protocol II-A | 4.89 | 549 | 549 |
| 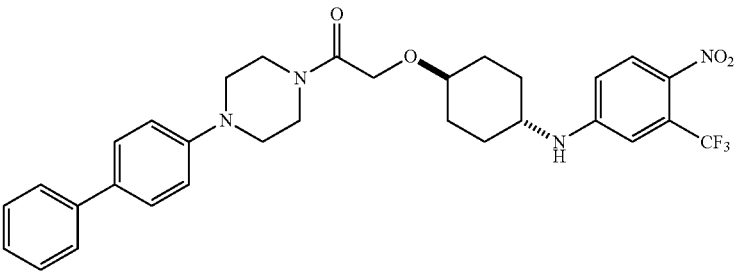 Example 69 | Protocol II-A | 4.67 | 583 | 583 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 70 | Protocol II-A | 4.36 | 521 | 521 |
| Example 71 | Protocol II-A | 4.36 | 543 | 543 |
| Example 72 | Protocol II-A | 4.60 | 520 | 520 |
| Example 73 | Protocol II-A | 4.61 | 540 | 540 |
| Example 74 | Protocol II-A | 4.37 | 536 | 536 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 75 | Protocol II-A | 4.83 | 582 | 582 |
| Example 76 | Protocol II-A | 4.97 | 562 | 562 |
| Example 77 | Protocol II-A | 4.56 | 613 | 613 |
| Example 78 | Protocol II-A | 3.89 | 567 | 567 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 79 | Protocol II-A | 4.71 | 535 | 535 |
| Example 80 | Protocol II-A | 4.62 | 575 | 575 |
| Example 81 | Protocol II-A | 4.85 | 583 | 583 |
| Example 82 | Protocol II-A | 4.67 | 579 | 579 |
| Example 83 | Protocol II-A | 3.93 | 567 | 567 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 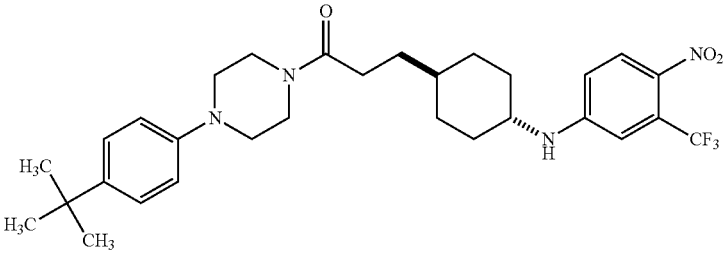<br>Example 84 | Protocol I-A | 5.21 | 561 | 561 |
| 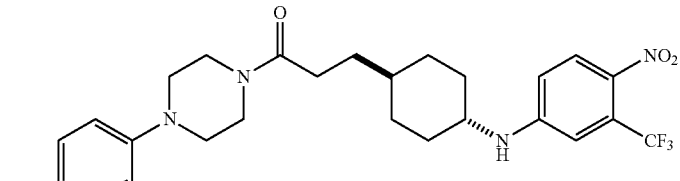<br>Example 85 | Protocol I-A | 4.97 | 539 | 539 |
| 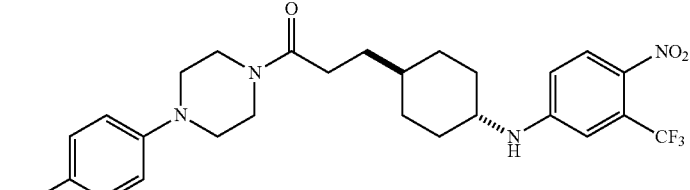<br>Example 86 | Protocol I-C | 3.65 | 519 | 519 |
| 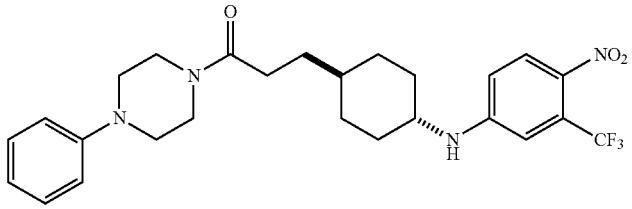<br>Example 87 | Protocol I-A | 4.74 | 505 | 505 |
| 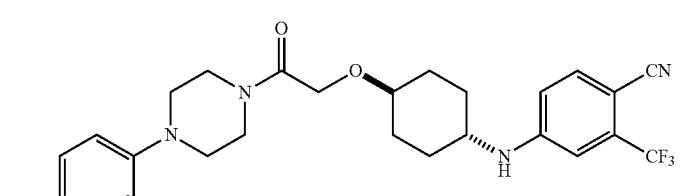<br>Example 88 | Protocol II-A | 4.38 | 521 | 521 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 89 | Protocol II-A | 4.46 | 555 | 555 |
| Example 90 | Protocol I-B | 6.13 | 580 | 580 |
| Example 91 | Protocol I-B | 6.14 | 614 | 614 |
| Example 92 | Protocol I-B | 6.07 | 580 | 580 |
| Example 93 | Protocol I-B | 6.09 | 614 | 614 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 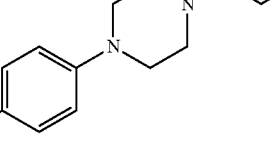<br>Example 94 | Protocol I-B | 6.30 | 602 | 602 |
| 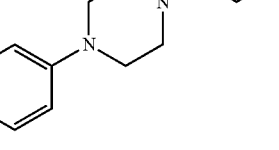<br>Example 95 | Protocol I-B | 6.02 | 530 | 530 |
| 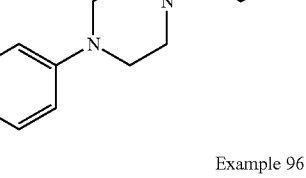<br>Example 96 | Protocol I-B | 6.04 | 564 | 564 |
| 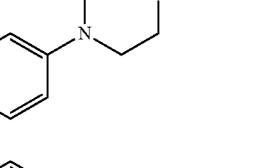<br>Example 97 | Protocol I-B | 6.05 | 602 | 602 |
| 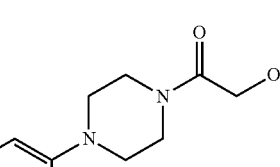<br>Example 98 | Protocol I-B | 6.07 | 530 | 530 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 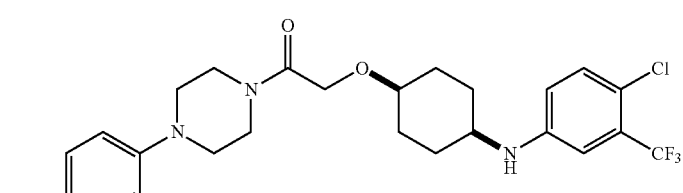<br>Example 99 | Protocol I-B | 6.09 | 564 | 564 |
| 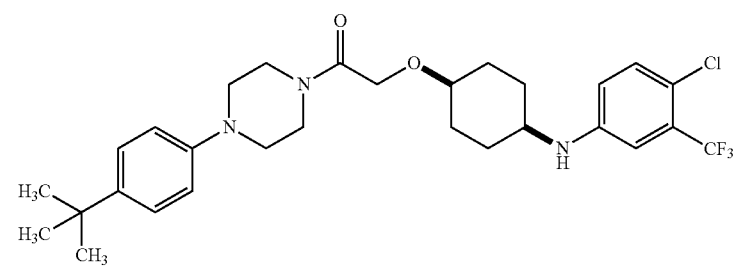<br>Example 100 | Protocol I-B | 6.32 | 552 | 552 |
| 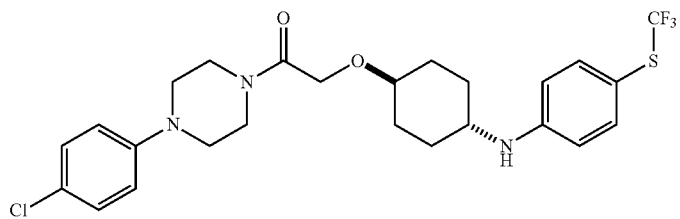<br>Example 101 | Protocol I-B | 6.02 | 528 | 528 |
| 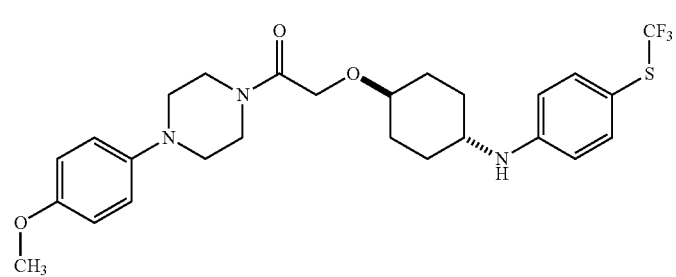<br>Example 102 | Protocol I-B | 5.76 | 524 | 524 |
| 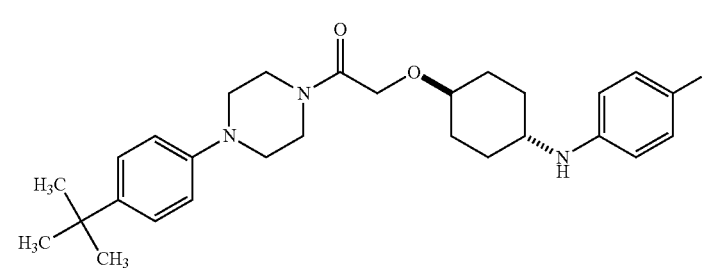<br>Example 103 | Protocol I-B | 6.27 | 550 | 550 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 104 | Protocol II-B | 4.90 | 573 | 573 |
| Example 105 | Protocol II-B | 5.11 | 587 | 587 |
| Example 106 | Protocol II-B | 5.02 | 553 | 553 |
| Example 107 | Protocol II-B | 4.79 | 539 | 539 |
| Example 108 | Protocol I-A | 4.80 | 567 | 567 |
| Example 109 | Protocol I-A | 4.52 | 553 | 553 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 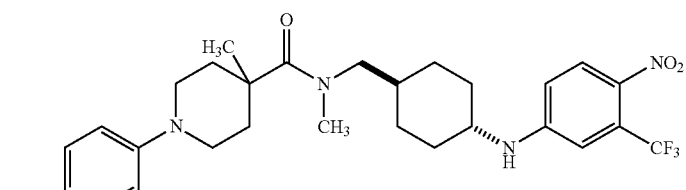 Example 110 | Protocol I-A | 4.99 | 601 | 601 |
| 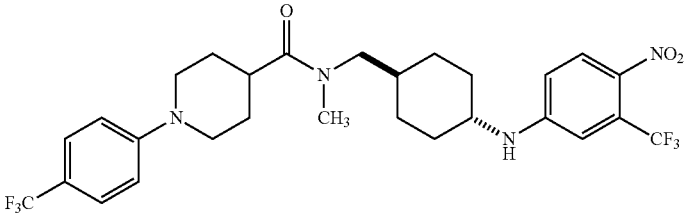 Example 111 | Protocol I-A | 4.75 | 587 | 587 |
| 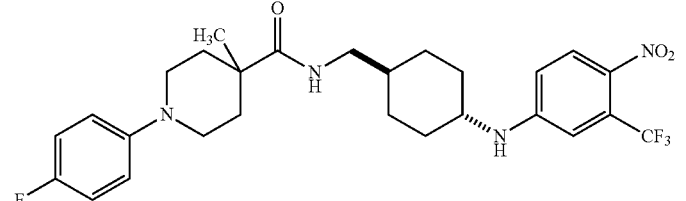 Example 112 | Protocol I-A | 4.00 | 537 | 537 |
| 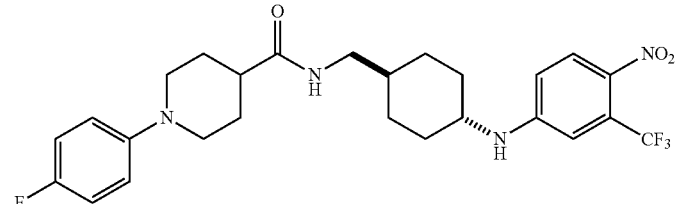 Example 113 | Protocol I-A | 3.75 | 523 | 523 |
| 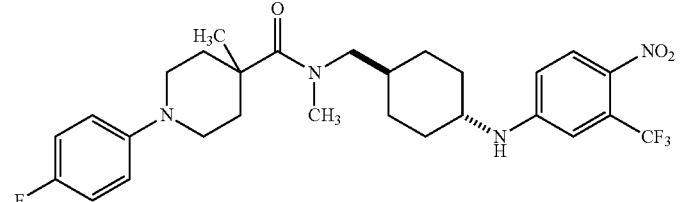 Example 114 | Protocol II-A | 4.28 | 551 | 551 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 115 | Protocol II-A | 3.99 | 537 | 537 |
| Example 116 | Protocol I-C | 3.21 | 549 | 549 |
| Example 117 | Protocol I-C | 3.06 | 527 | 527 |
| Example 118 | Protocol I-C | 3.04 | 507 | 507 |
| Example 119 | Protocol I-A | 4.15 | 561 | 561 |
| Example 120 | Protocol II-A | 4.47 | 572.5 | 572.8 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 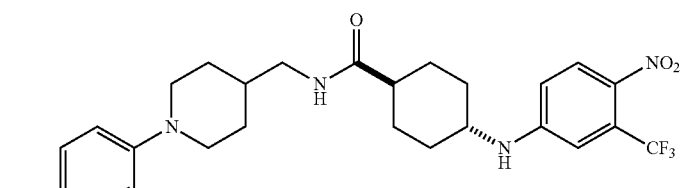 Example 121 | Protocol II-A | 4.12 | 539.0 | 538.8 |
| 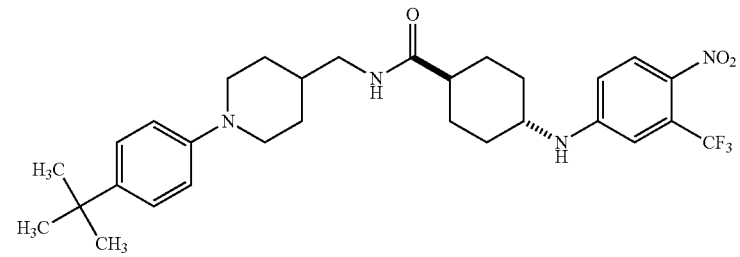 Example 122 | Protocol II-A | 3.69 | 560.7 | 560.9 |
| 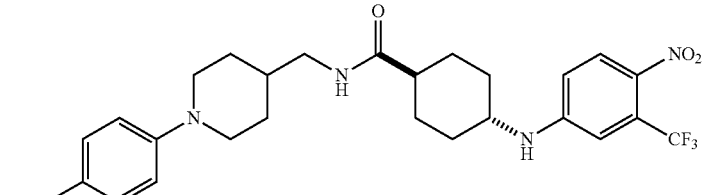 Example 123 | Protocol II-A | 3.36 | 518.6 | 518.9 |
| 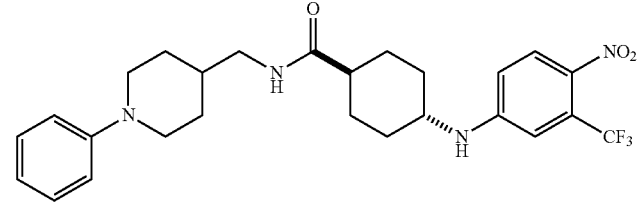 Example 124 | Protocol II-A | 3.24 | 504.5 | 504.9 |
| 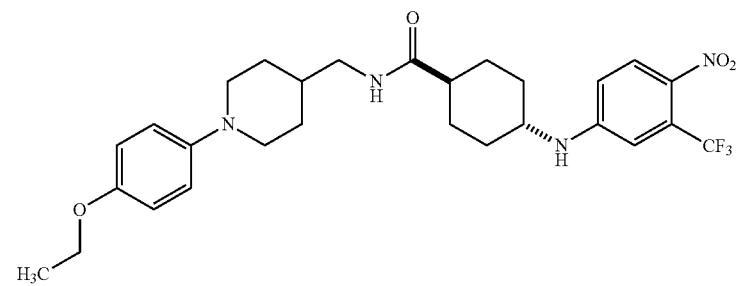 Example 125 | Protocol II-A | 3.42 | 548.6 | 549.3 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 126 | Protocol II-C | 3.75 | 504.5 | 505.2 |
| Example 127 | Protocol II-C | 3.55 | 518.6 | 519.2 |
| Example 128 | Protocol II-C | 4.10 | 560.7 | 561.2 |
| Example 129 | Protocol II-C | 4.89 | 572.5 | 573.2 |
| Example 130 | Protocol II-C | 4.78 | 539.0 | 539.2 |

TABLE II-continued

Additional Compounds Prepared by Applicants in Accordance with this Invention

| Compound Structure | Analysis Method | Retention Time (min) | Calc. Mass | Obs. Mass |
| --- | --- | --- | --- | --- |
| Example 131 | Protocol II-C | 3.31 | 548.6 | 549.2 |
| Example 132 | Protocol II-A | 3.88 | 574.7 | 574.9 |
| Example 133 | Protocol II-A | 3.38 | 562.6 | 562.9 |
| Example 134 | Protocol II-A | 4.01 | 518.6 | 518.7 |
| Example 135 | Protocol II-A | 4.74 | 532.6 | 532.9 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 136 | Protocol I-B | 5.48 | 553.0 | 553.1 |
| Example 137 | Protocol II-B | 4.32 | 530.5 | 531.3 |
| Example 138 | Protocol I-B | 5.96 | 587.6 | 588.2 |
| Example 139 | Protocol I-B | 5.95 | 554.0 | 554.2 |
| Example 140 | Protocol I-B | 5.78 | 537.6 | 538.2 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 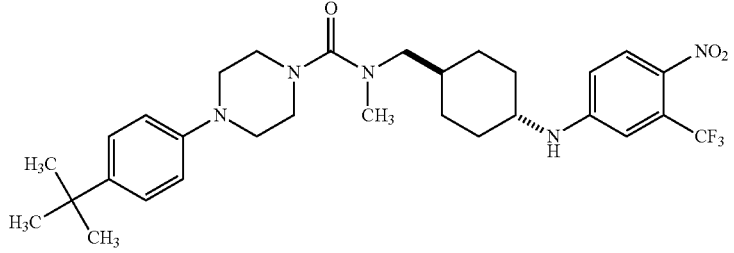<br>Example 141 | Protocol I-B | 6.18 | 575.7 | 576.3 |
| 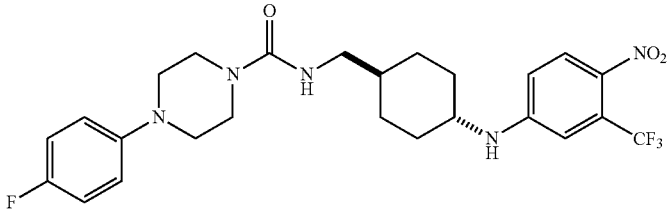<br>Example 142 | Protocol I-B | 5.54 | 523.5 | 524.2 |
| 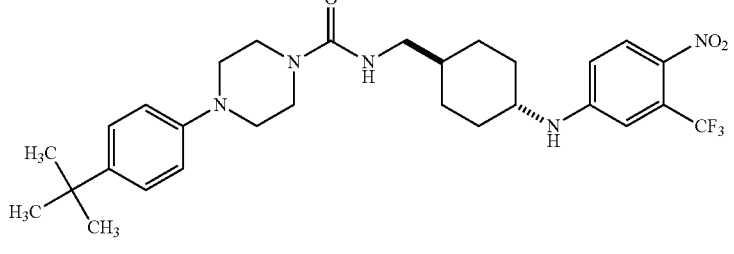<br>Example 143 | Protocol I-B | 5.88 | 561.6 | 562.3 |
| 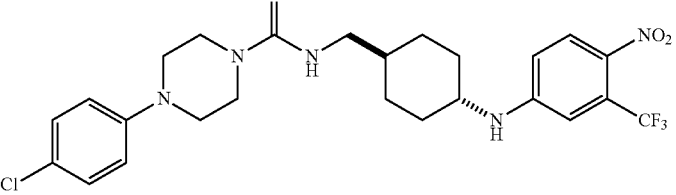<br>Example 144 | Protocol I-B | 5.70 | 540.0 | 540.2 |
| 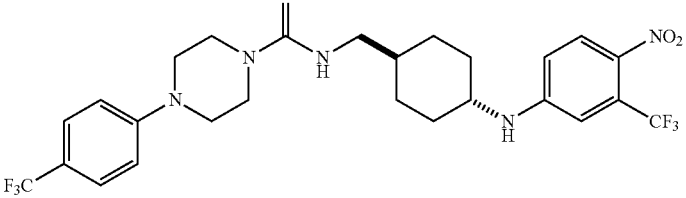<br>Example 145 | Protocol I-B | 5.73 | 573.5 | 574.2 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 146 | Protocol I-B | 5.91 | 586.5 | 587.2 |
| Example 147 | Protocol I-B | 5.88 | 553.0 | 553.2 |
| Example 148 | Protocol I-B | 5.73 | 518.5 | 519.2 |
| Example 149 | Protocol I-B | 5.95 | 588.5 | 589.2 |
| Example 150 | Protocol I-B | 5.94 | 555.0 | 555.2 |
| Example 151 | Protocol I-B | 5.80 | 520.5 | 521.2 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 152 | Protocol I-B | 5.89 | 562.5 | 563.2 |
| Example 153 | Protocol I-B | 5.81 | 529.0 | 529.2 |
| Example 154 | Protocol I-B | 5.77 | 514.9 | 515.2 |
| Example 155 | Protocol I-B | 5.82 | 548.5 | 549.2 |
| Example 156 | Protocol I-B | 5.57 | 480.5 | 481.2 |
| Example 157 | Protocol I-B | 5.51 | 555.0 | 555.2 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 158 | Protocol I-B | 5.60 | 588.5 | 589.2 |
| Example 159 | Protocol I-B | 5.33 | 520.5 | 521.2 |
| Example 160 | Protocol I-B | 6.08 | 600.6 | 601.2 |
| Example 161 | Protocol I-B | 5.74 | 613.6 | 614.2 |
| Example 162 | Protocol I-B | 5.68 | 593.6 | 594.2 |
| Example 163 | Protocol I-B | 5.86 | 613.6 | 614.2 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 164 | Protocol I-B | 5.80 | 593.6 | 594.2 |
| Example 165 | Protocol I-B | 6.04 | 582.6 | 583.2 |
| Example 166 | Protocol I-B | 6.33 | 541.7 | 542.3 |
| Example 167 | Protocol I-B | 6.22 | 561.6 | 562.3 |
| Example 168 | Protocol I-B | 6.29 | 527.6 | 528.3 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 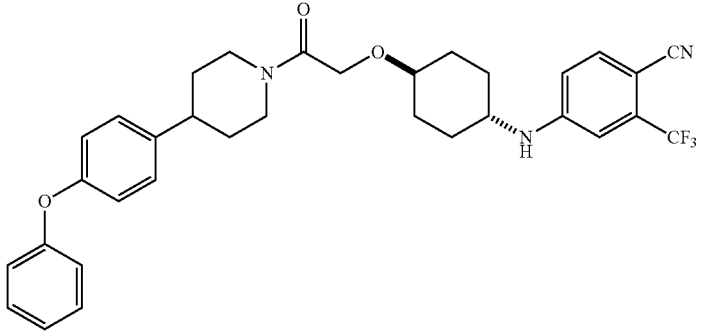<br>Example 169 | Protocol I-B | 6.19 | 577.6 | 578.3 |
| 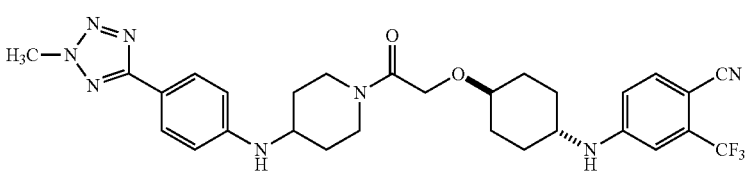<br>Example 170 | Protocol I-B | 5.48 | 582.6 | 583.3 |
| 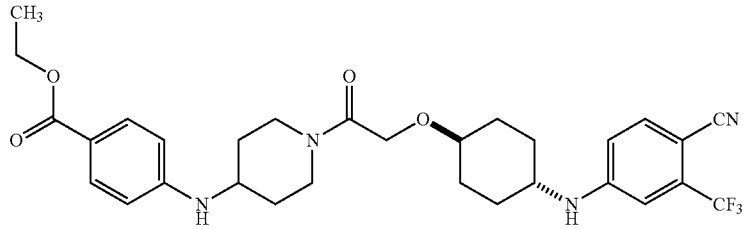<br>Example 171 | Protocol I-B | 5.72 | 572.6 | 572.1 |
| 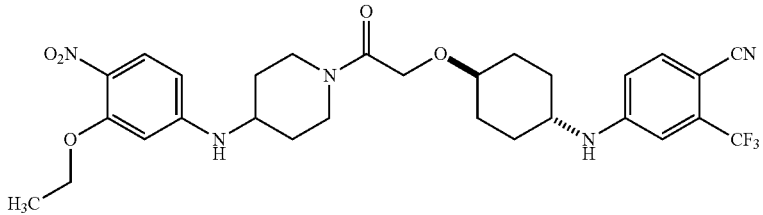<br>Example 172 | Protocol I-B | 5.59 | 589.6 | 590.3 |
| 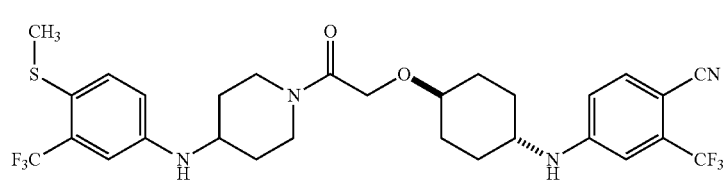<br>Example 173 | Protocol I-B | 5.97 | 614.7 | 615.2 |
| 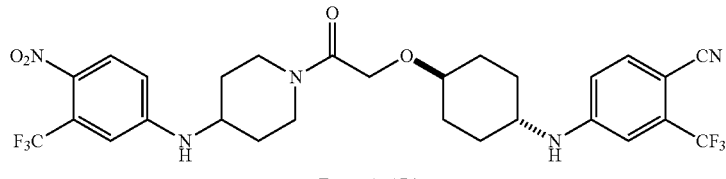<br>Example 174 | Protocol I-B | 5.77 | 613.6 | 614.2 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 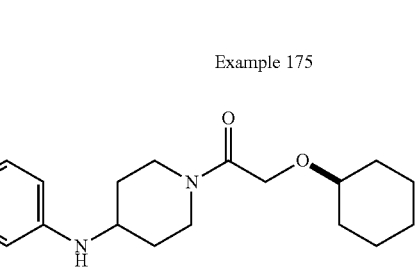<br>Example 175 | Protocol I-B | 5.86 | 617.7 | 618.3 |
| 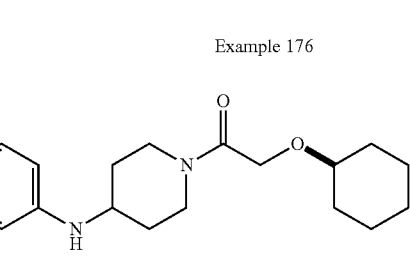<br>Example 176 | Protocol I-B | 5.45 | 575.6 | 576.2 |
| 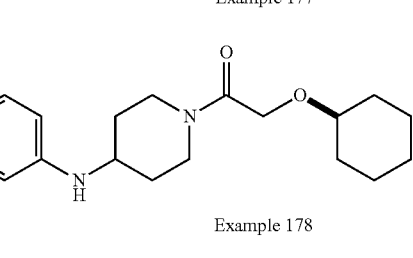<br>Example 177 | Protocol I-B | 6.19 | 635.1 | 635.2 |
| 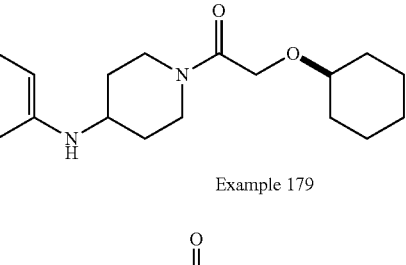<br>Example 178 | Protocol I-B | 5.71 | 593.6 | 594.2 |
| 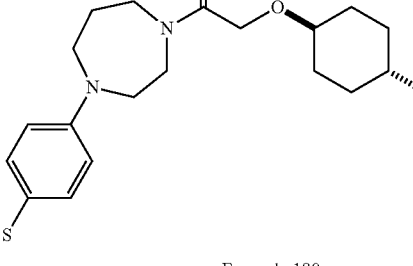<br>Example 179 | Protocol I-B | 5.92 | 584.6 | 585.2 |
| 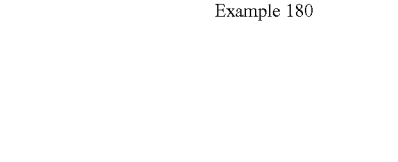<br>Example 180 | Protocol I-B | 6.13 | 620.6 | 621.2 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| 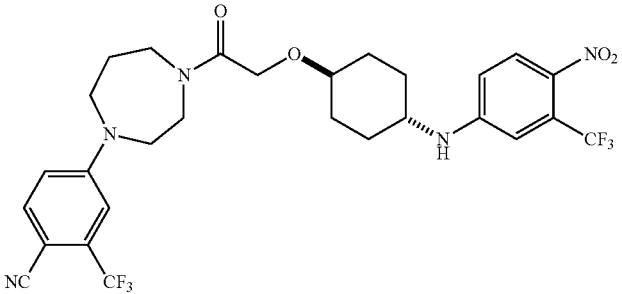 Example 181 | Protocol I-B | 5.75 | 613.6 | 614.2 |
| 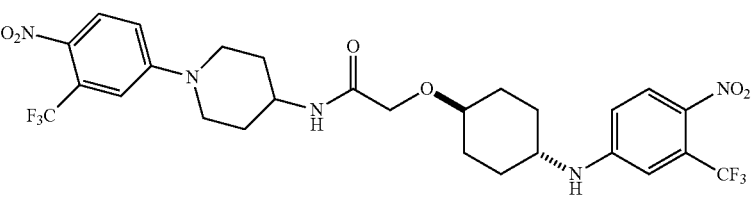 Example 182 | Protocol I-B | 5.91 | 633.5 | 634.2 |
| 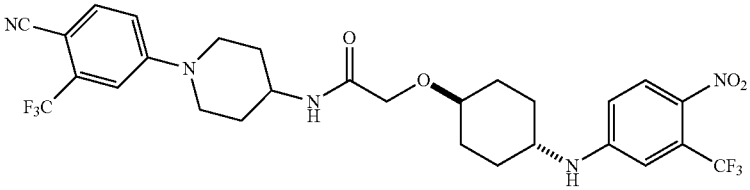 Example 183 | Protocol I-B | 5.86 | 613.6 | 614.2 |
| 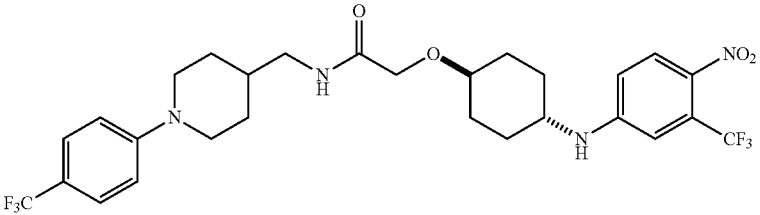 Example 184 | Protocol I-B | 6.10 | 602.6 | 603.2 |
| 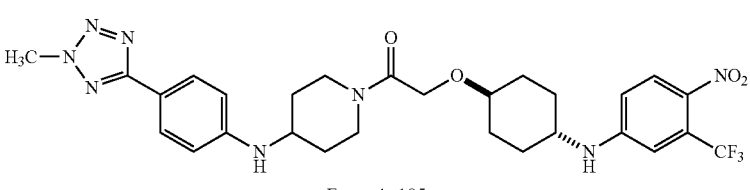 Example 185 | Protocol I-B | 5.56 | 602.6 | 603.2 |
| 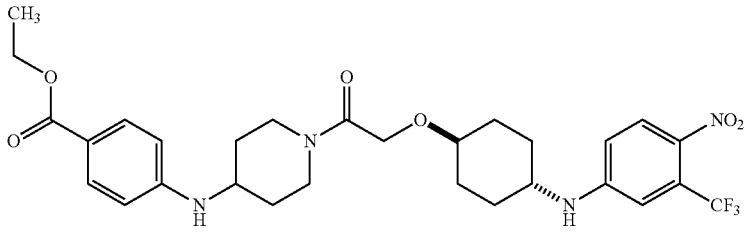 Example 186 | Protocol I-B | 5.78 | 592.6 | 547.2 (it is believed that this compound fragmented during analysis) |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 187 | Protocol I-B | 5.66 | 609.6 | 610.2 |
| Example 188 | Protocol I-B | 6.02 | 634.6 | 635.2 |
| Example 189 | Protocol I-B | 5.83 | 633.5 | 634.2 |
| Example 190 | Protocol I-B | 5.92 | 637.7 | 638.3 |
| Example 191 | Protocol I-B | 5.53 | 595.6 | 596.2 |
| Example 192 | Protocol I-B | 6.23 | 655.1 | 655.1 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 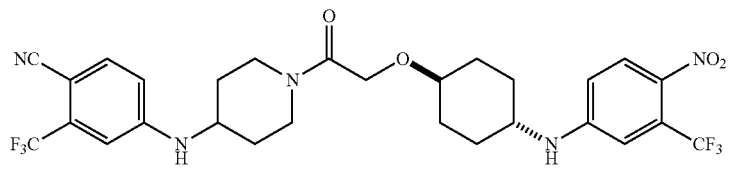<br>Example 193 | Protocol I-B | 5.77 | 613.6 | 614.2 |
| 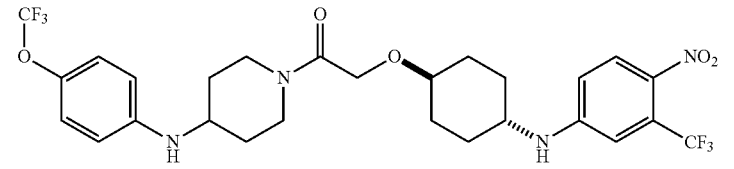<br>Example 194 | Protocol I-B | 5.98 | 604.5 | 605.2 |
| 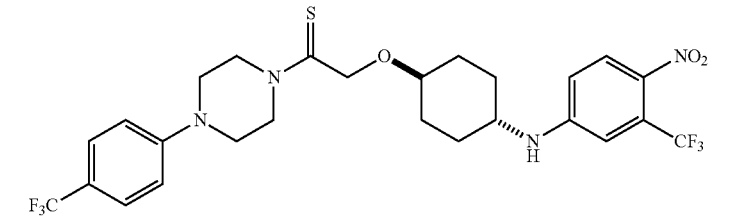<br>Example 195 | Protocol II-A | 4.85 | 590.6 | 590.8 |
| 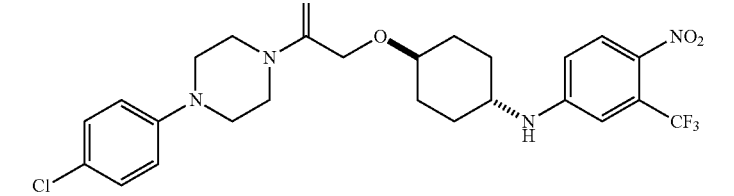<br>Example 196 | Protocol II-A | 4.85 | 557.0 | 556.8 |
| 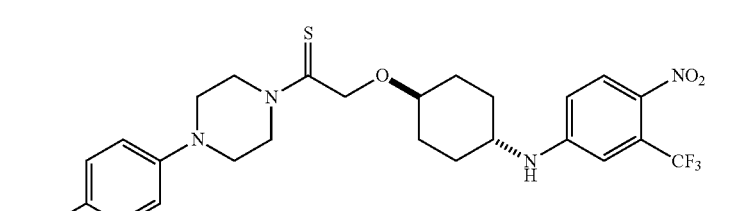<br>Example 197 | Protocol II-A | 4.50 | 547.6 | 547.9 |
| 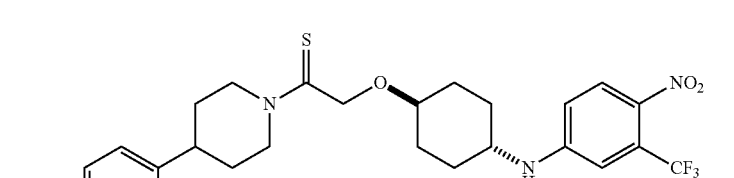<br>Example 198 | Protocol II-A | 4.96 | 556.0 | 555.8 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 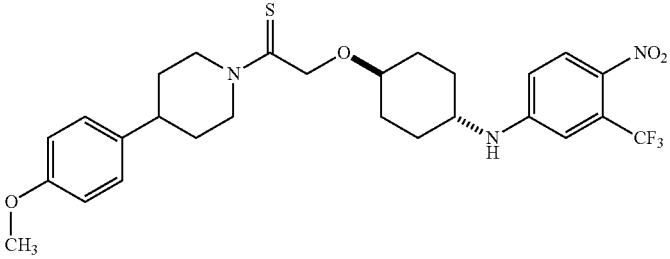 Example 199 | Protocol II-A | 4.76 | 551.6 | 551.9 |
| 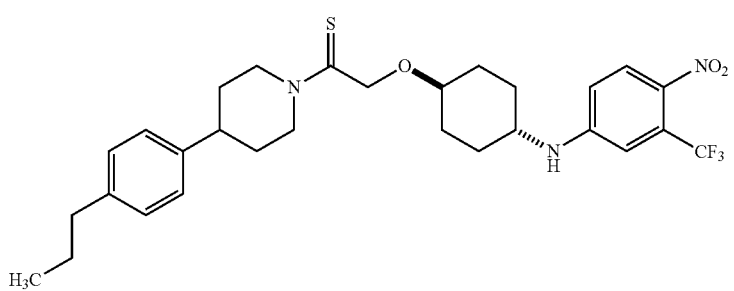 Example 200 | Protocol II-A | 5.20 | 563.7 | 563.9 |
| 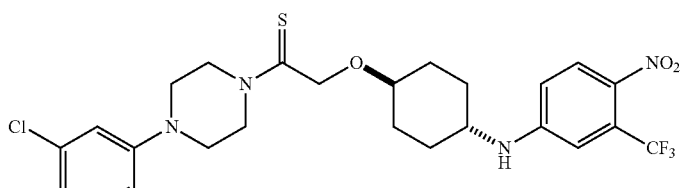 Example 201 | Protocol II-A | 4.99 | 591.5 | 590.8 |
| 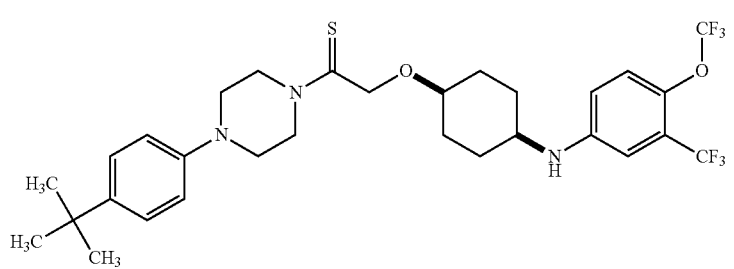 Example 202 | Protocol II-A | 5.50 | 617.7 | 618.1 |
| 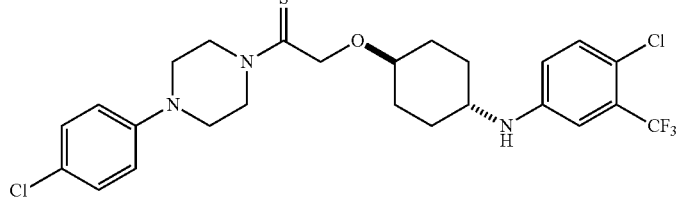 Example 203 | Protocol II-A | 5.15 | 546.5 | 545.9 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 204 | Protocol II-A | 5.15 | 580.0 | 579.8 |
| Example 205 | Protocol II-A | 5.18 | 596.0 | 595.9 |
| Example 206 | Protocol II-A | 5.45 | 617.7 | 618.0 |
| Example 207 | Protocol II-A | 4.48 | 582.6 | 582.9 |
| Example 208 | Protocol II-A | 5.06 | 550.6 | 550.9 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 209 | Protocol II-A | 4.80 | 537.0 | 536.8 |
| Example 210 | Protocol II-A | 4.82 | 570.6 | 570.8 |
| Example 211 | Protocol II-A | 5.47 | 568.1 | 567.9 |
| Example 212 | Protocol II-A | 4.71 | 522.6 | 522.9 |
| Example 213 | Protocol II-A | 4.97 | 588.6 | 588.9 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 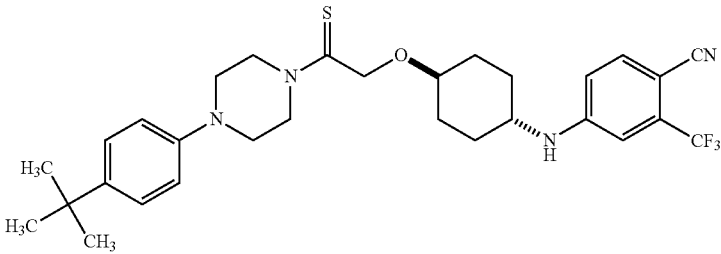 Example 214 | Protocol II-A | 5.14 | 558.7 | 559.0 |
| 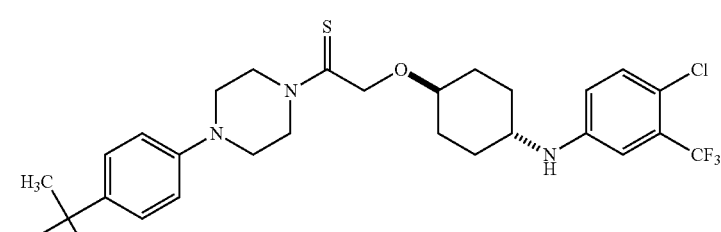 Example 215 | Protocol II-A | 5.42 | 568.1 | 567.9 |
| 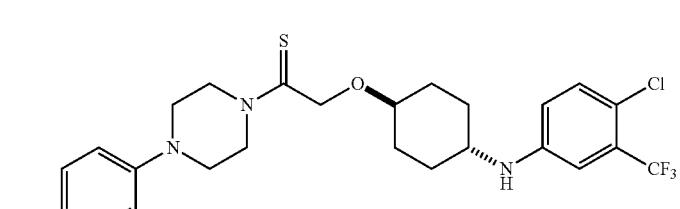 Example 216 | Protocol I-D | 3.90 | 546.5 | 545.9 |
| 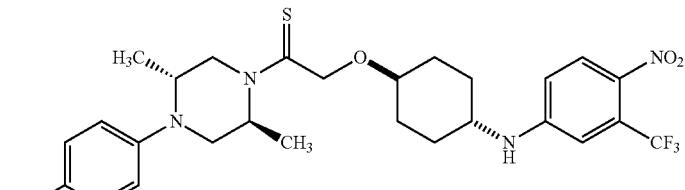 Example 217 | Protocol II-A | 5.04 | 618.6 | 619.0 |
| 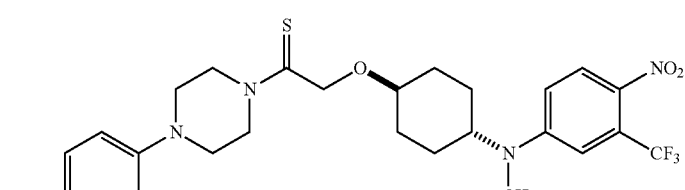 Example 218 | Protocol II-A | 4.99 | 604.6 | 604.9 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 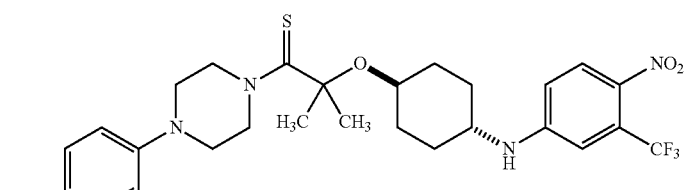<br>Example 219 | Protocol II-A | 5.12 | 618.6 | 618.8 |
| 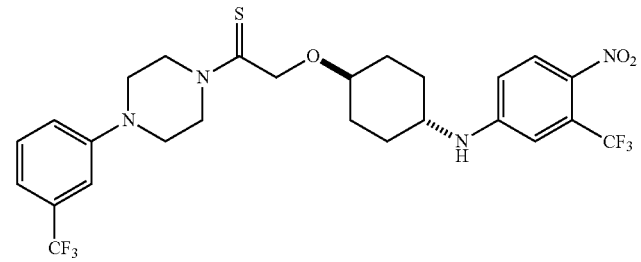<br>Example 220 | Protocol II-A | 4.88 | 590.6 | 591.0 |
| 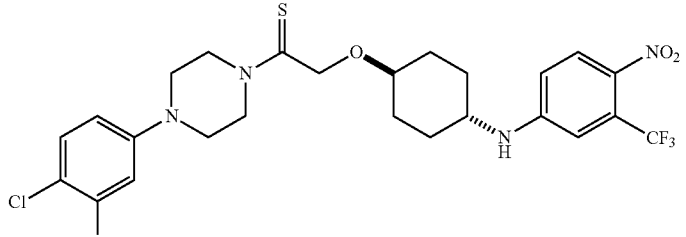<br>Example 221 | Protocol II-A | 4.99 | 625.0 | 624.9 |
| 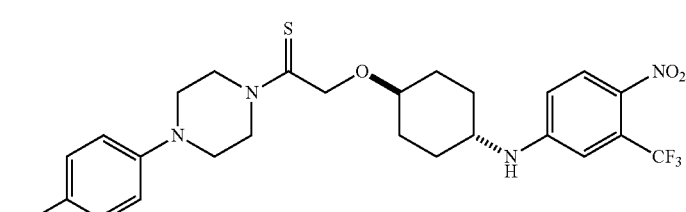<br>Example 222 | Protocol II-A | 4.85 | 536.6 | 537.1 |
| 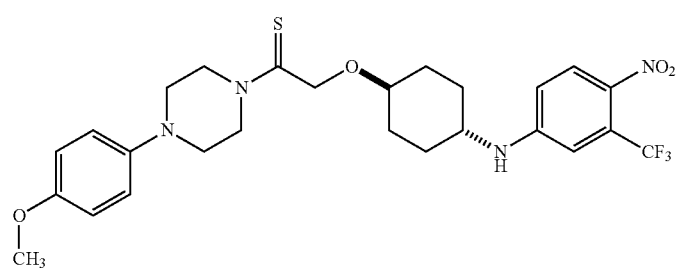<br>Example 223 | Protocol II-A | 4.65 | 552.6 | 553.1 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 224 | Protocol II-A | 4.78 | 604.6 | 559.0 |
| Example 225 | Protocol II-A | 4.77 | 614.6 | 615.2 |
| Example 226 | Protocol II-A | 4.74 | 602.6 | 602.8 |
| Example 227 | Protocol I-B | 6.14 | 568.5 | 569.2 |
| Example 228 | Protocol I-B | 6.07 | 569.5 | 570.2 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 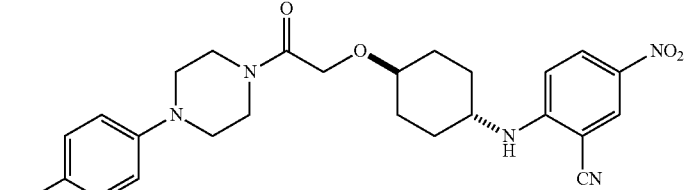 Example 229 | Protocol I-B | 5.79 | 531.5 | 532.2 |
| 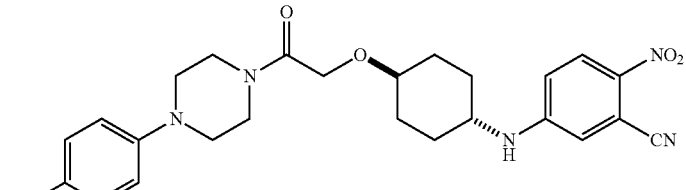 Example 230 | Protocol I-B | 5.69 | 531.5 | 532.2 |
| 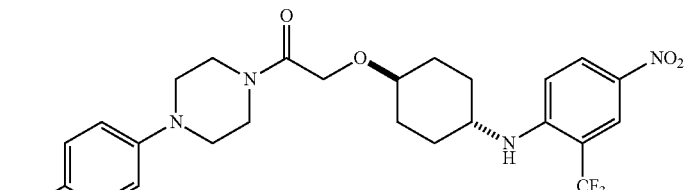 Example 231 | Protocol I-B | 6.08 | 574.5 | 575.2 |
| 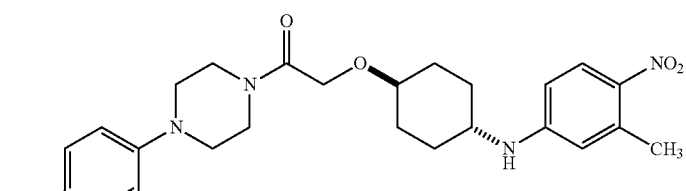 Example 232 | Protocol I-B | 5.84 | 520.5 | 521.2 |
| 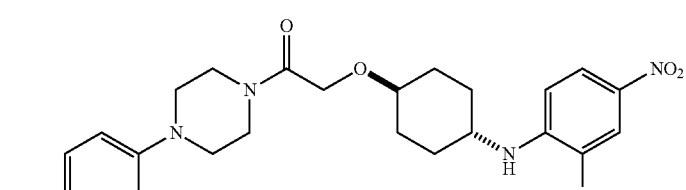 Example 233 | Protocol I-B | 5.90 | 520.5 | 521.2 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 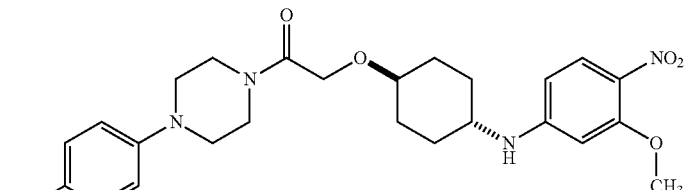<br>Example 234 | Protocol I-B | 5.61 | 536.5 | 537.2 |
| 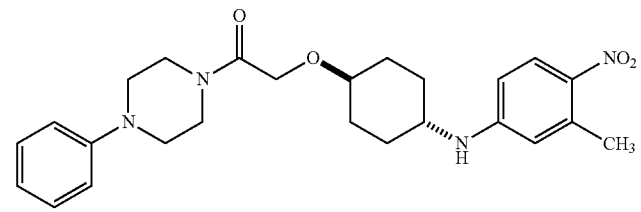<br>Example 235 | Protocol I-B | 5.58 | 452.6 | 453.2 |
| 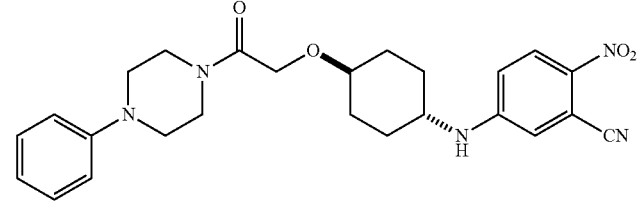<br>Example 236 | Protocol I-B | 5.40 | 463.5 | 464.2 |
| 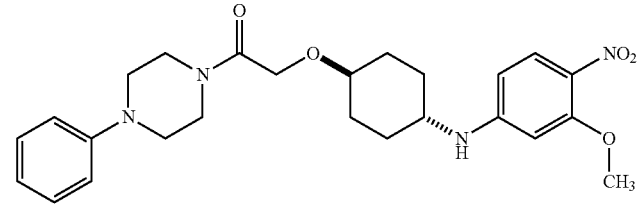<br>Example 237 | Protocol I-B | 5.30 | 468.6 | 469.2 |
| 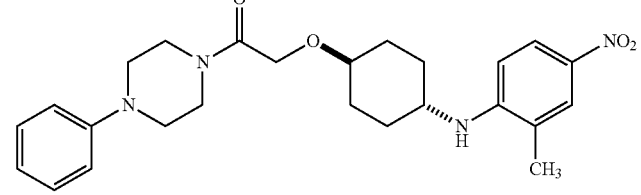<br>Example 238 | Protocol I-B | 5.64 | 452.6 | 453.3 |
| 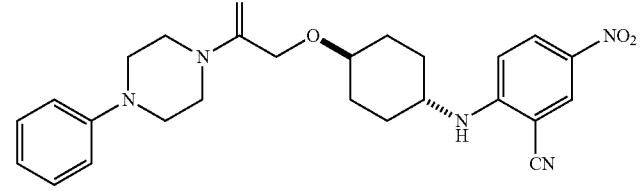<br>Example 239 | Protocol I-B | 5.51 | 463.5 | 464.2 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 240 | Protocol I-B | 5.86 | 506.5 | 507.2 |
| Example 241 | Protocol I-B | 5.80 | 487.0 | 487.2 |
| Example 242 | Protocol I-B | 5.62 | 498.0 | 4.98 |
| Example 243 | Protocol I-B | 5.54 | 503.0 | 530.2 |
| Example 244 | Protocol I-B | 5.85 | 487.0 | 487.2 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 245 | Protocol I-B | 5.73 | 498.0 | 498.2 |
| Example 246 | Protocol I-B | 6.04 | 541.0 | 541.2 |
| Example 247 | Protocol I-B | 6.10 | 508.7 | 509.3 |
| Example 248 | Protocol I-B | 5.91 | 519.6 | 520.3 |
| Example 249 | Protocol I-B | 5.84 | 524.7 | 525.3 |

TABLE II-continued
Additional Compounds Prepared by Applicants in Accordance with this Invention
| Compound Structure | Analysis Method | Retention Time (min) | Calc. Mass | Obs. Mass |
|---|---|---|---|---|
| 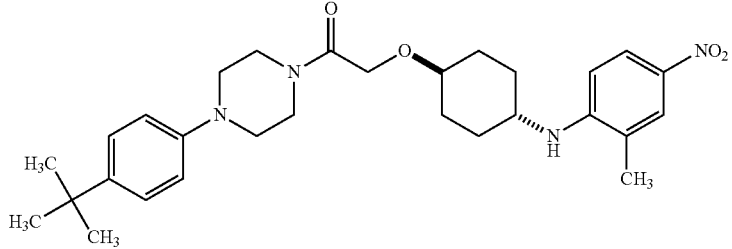  Example 250 | Protocol I-B | 6.15 | 508.7 | 509.3 |
| 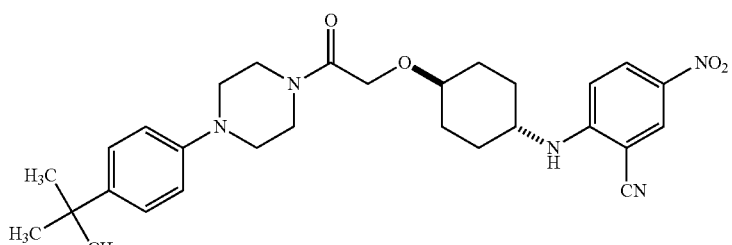  Example 251 | Protocol I-B | 6.02 | 519.6 | 520.3 |
| 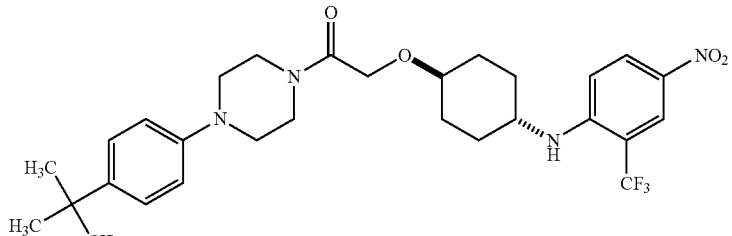  Example 252 | Protocol I-B | 6.32 | 562.6 | 563.3 |
| 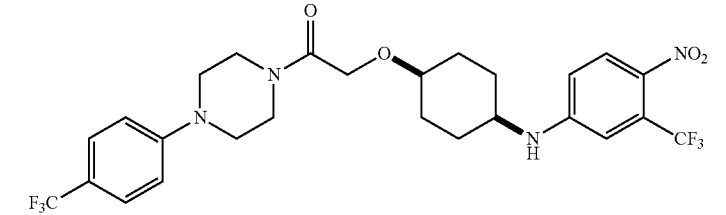  Example 253 | Protocol I-B | 5.97 | 574.5 | 575.2 |
| 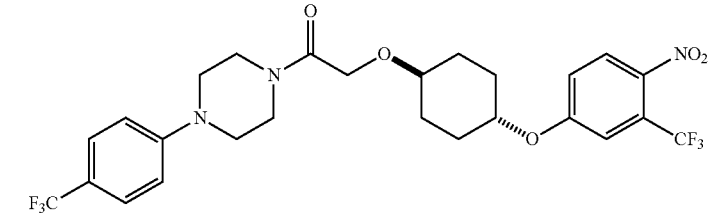  Example 254 | Protocol I-B | 5.88 | 575.5 | 576.1 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 255 | Protocol I-B | 5.08 | 542.0 | 542.0 |
| Example 256 | Protocol I-B | 5.88 | 560.5 | 561.2 |
| Example 257 | Protocol I-B | 6.18 | 548.6 | 549.3 |
| Example 258 | Protocol I-B | 5.87 | 526.9 | 527.2 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 259 | Protocol I-B | 6.11 | 546.6 | 547.3 |
| Example 260 | Protocol I-B | 6.38 | 563.6 | 564.3 |
| Example 261 | Protocol I-B | 6.28 | 588.7 | 589.3 |
| Example 262 | Protocol I-B | 5.96 | 567.0 | 567.2 |
| Example 263 | Protocol I-B | 5.80 | 534.5 | 535.1 |

TABLE II-continued

Additional Compounds Prepared by Applicants in Accordance with this Invention

| Compound Structure | Analysis Method | Retention Time (min) | Calc. Mass | Obs. Mass |
|---|---|---|---|---|
| Example 264 | Protocol I-B | 6.06 | 522.6 | 523.2 |
| Example 265 | Protocol I-B | 5.76 | 500.9 | 501.1 |

Example 266

Determining Activity Against *Ascaridia galli* and *Oesophagostomum dentatum*

Anthelmintic effects of compounds of this invention were tested in vitro using gut-welling larval stages of two parasitic nematode species: *A. galli* (intestinal roundworm of chicken), larval stage 3 ("L3"); and *O. dentatum* (nodular worm of swine), larval stages 3 and 4 (respectively "L3" and "L4"). When conducting these experiments, various concentrations of the compounds were incubated in 96-well microtiter plates. Parasites were then distributed at 20 larvae per well. The anthelmintic effects were classified by microscopic examination. The microscopic examination included assessing mortality, damage, motility, progression of development, and neutral red uptake by the larvae in comparison to a DMSO-control and standard anthelmintics. The anthelmintic effects were defined by the minimum effective concentration ("MEC"). Nearly all the tested compounds showed at least some activity against one or more of the nematodes. The following compounds exhibited an MEC of less than 7 µM against one or more of the tested nematodes: Examples 10-18, 20-23, 25, 27, 31, 36-39, 41, 52-54, 57-65, 67-105, 107, 109-111, 113, 115-120, 122-125, 127-153, 155, 157-226, 228-235, 241-243, 245, 247-252, and 254-265. The following compounds exhibited an MEC of less than 1 µM against one or more of the tested nematodes: Examples 10-18, 20-23, 25, 27, 31, 36-39, 41, 52-54, 57-64, 67, 69-71, 73, 75-79, 82-84, 88, 90, 92-98, 100-105, 111, 116, 119, 120, 122, 123, 125, 128, 129, 132, 133, 136-138, 141, 143, 145, 146, 149, 150, 152, 155, 157-198, 200-204, 206, 207, 209, 211-219, 221, 222, 224-226, 228-232, 234, 241, 247-252, 254-257, and 259-264. The following compounds exhibited an MEC of less than 1 µM against two or more of the tested nematodes: Examples 10-18, 20, 22, 25, 27, 36-38, 41, 54, 57-59, 63, 64, 71, 82, 97, 103, 120, 122, 132, 133, 136, 145, 149, 150, 158, 160, 162-164, 166, 168, 170-172, 174-186, 188, 189, 191-197, 202, 213, 215, 218, 226, 248, 249, 259, 260, and 262. Applicants observed no detectable activity against the tested nematodes with the compound of Example 240.

Example 267

Determining Resistance-Breaking Activity Against *Haemonchus contortus*

Anthelmintic resistance-breaking effects of compounds of this invention were tested in vitro using larval stage 4 ("L4") of the parasitic nematode species *Haemonchus contortus* (Barber's pole worm in ruminants). One isolate of *Haemonchus contortus* with a resistance to benzimidazoles and ivermectin was tested in comparison to the anthelmintic-sensitive isolate of *Haemonchus contortus*. When conducting these experiments, various concentrations of the compounds were incubated in 96-well microtiter plates. Parasites were then distributed at 20 larvae per well. The anthelmintic effects were classified by microscopic examination. The microscopic examination included assessing mortality, damage, motility, progression of development, and neutral red uptake by the larvae in comparison to a DMSO-control and standard anthelmintics. The anthelmintic effects were defined by the minimum effective concentration ("MEC"). Compounds from Examples 11 and 57 demonstrated the same activity against the resistant and the sensitive isolate of *Haemonchus contortus*, whereas benzimidazoles and ivermectin were less sensitive against the resistant isolate of *Haemonchus contortus*.

Example 268

Determining Efficacy Against *Haemonchus contortus* in Jirds

Anthelmintic effects of compounds of this invention were tested in vivo using *Haemonchus contuortus* in jirds (*Meri-

*ones unguiculatus*). The jirds were orally infected with approximately 750-3,000 third-stage larvae of *Haemonchus contortus*. Ten days after infection, the jirds in the treatment groups were treated once orally or subcutaneously at a dose of 2, 10, and/or 50 mg per kg bodyweight. Three days after treatment, the jirds were necropsied, and the larvae burden in the stomach was determined. The efficacy was defined as the reduction of the mean larvae count in the jirds of the treatment groups in comparison to the infected jirds in the untreated negative control group. All the compounds of this invention tested using this protocol reduced the *Haemonchus contortus* count in both the oral and subcutaneous experiments. As shown in Table III, the compounds of Examples 10-14 reduced the *Haemonchus contortus* count by at least 60% when administered orally and by at least 73% when administered subcutaneously at 10 mg/kg:

TABLE III

Efficacy against *Haemonchus contortus* in Jirds

| Compound | Dose (mg/kg) | Administration Route | % Reduction in *H. contortus* count |
| --- | --- | --- | --- |
| Example 10 | 10 | subcutaneous | 99 |
| Example 10 | 10 | oral | 99 |
| Example 11 | 2 | subcutaneous | 69 |
| Example 11 | 2 | oral | 84 |
| Example 11 | 10 | subcutaneous | 99 |
| Example 11 | 10 | oral | 97 |
| Example 11 | 50 | subcutaneous | 99 |
| Example 11 | 50 | oral | 98 |
| Example 12 | 10 | subcutaneous | 100 |
| Example 12 | 10 | oral | 95 |
| Example 13 | 10 | subcutaneous | 93 |
| Example 13 | 10 | oral | 94 |
| Example 14 | 10 | subcutaneous | 73 |
| Example 14 | 10 | oral | 60 |

Example 269

Determining Efficacy Against *Haemonchus contortus* in Sheep

Anthelmintic effects of compounds of this invention were tested in vivo using *Haemonchus contortus* in sheep. The sheep were orally infected with approximately 5,000 third-stage larvae of *Haemonchus contortus*. Thirty-five days after infection, the sheep in the treatment groups were treated once orally or subcutaneously at a dose of 2, 5, 10, and/or 50 mg per kg bodyweight. Seven days after treatment, the sheep were necropsied, and the worm burden in the abomasum was determined. The efficacy was defined as the reduction of the mean worm count in the infected sheep of the treatment groups in comparison to the infected sheep in the untreated negative control group. Results for the compounds of Examples are shown in Table IV:

TABLE IV

Efficacy against *Haemonchus contortus* in sheep

| Compound | Dose (mg/kg) | Administration Route | % Reduction in *H. contortus* count |
| --- | --- | --- | --- |
| Example 11 | 2 | oral | 0 |
| Example 11 | 5 | oral | 95 |
| Example 11 | 10 | oral | 100 |
| Example 12 | 10 | oral | 53 |
| Example 12 | 10 | subcutaneous | 0 |
| Example 57 | 10 | oral | 83 |
| Example 57 | 10 | subcutaneous | 0 |

Example 270

Determining Efficacy Against *Haemonchus contortus* and *Trichostrongylus colubriformis* in Cattle Anthelmintic effects of compounds of this invention were tested in vivo using *Haemonchus contortus* and *Trichostrongylus colubriformis* in cattle. The cattle were orally infected with approximately 10,000 third-stage larvae of *Haemonchus contortus* and approximately 30,000 third-stage larvae of *Trichostrongylus colubriformis*. Thirty-two days after infection, the cattle in the treatment group were treated once orally with the compound of Example 11 at a dose of 10 mg/kg bodyweight. Seven days after treatment, the cattle were necropsied, and the worm burden in the abomasum and the small intestine was determined. The efficacy was defined as the reduction of the mean worm count in the infected cattle of the treatment group in comparison to the infected cattle in the untreated negative control group. Efficacy against *H. contortus* was observed to be 98%, and efficacy against *T. axei* was observed to be 99%.

DEFINITIONS

The term "alkyl" (alone or in combination with another term(s)) means a straight- or branched-chain saturated hydrocarbyl substituent (i.e., a substituent containing only carbon and hydrogen) typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, iso-butyl, sec-butyl, tent-butyl, pentyl, iso-amyl, hexyl, and octyl.

The term "alkenyl" (alone or in combination with another term(s)) means a straight- or branched-chain hydrocarbyl substituent containing one or more double bonds and typically from 2 to about 20 carbon atoms, more typically from about 2 to about 20 carbon atoms, even more typically from about 2 to about 8 carbon atoms, and still even more typically from about 2 to about 6 carbon atoms. Examples of such substituents include ethenyl(vinyl); 2-propenyl; 3-propenyl; 1,4-pentadienyl; 1,4-butadienyl; 1-butenyl; 2-butenyl; 3-butenyl; and decenyl.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, decynyl, 1-butynyl, 2-butynyl, and 3-butynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent typically containing from 3 to 14 carbon ring atoms ("ring atoms" are the atoms bound together to form the ring or rings of a cyclic moiety). A carbocyclyl may be a single ring, which typically contains from 3 to 6 ring atoms. Examples of such single-ring carbocyclyls include cyclopropanyl, cyclobutanyl, cyclopentyl, cyclopentenyl, cyclopentadienyl, cyclohexyl, cyclohexenyl, cyclohexadienyl, and phenyl. A carbocyclyl alternatively may be multiple (typically 2 or 3) rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluoreneyl, decalinyl, and norpinanyl.

The term "cycloalkyl" (alone or in combination with another term(s)) means a saturated cyclic hydrocarbyl substituent typically containing from 3 to 14 carbon ring atoms. A cycloalkyl may be a single carbon ring, which typically contains from 3 to 6 carbon ring atoms. Examples of single-ring cycloalkyls include cyclopropyl (or "cyclopropanyl"), cyclobutyl (or "cyclobutanyl"), cyclopentyl (or "cyclopentanyl"), and cyclohexyl (or "cyclohexanyl"). A cycloalkyl alternatively may be multiple (typically 2 or 3) carbon rings fused together, such as, decalinyl or norpinanyl.

The term "aryl" (alone or in combination with another term(s)) means an aromatic carbocyclyl typically containing from 6 to 14 carbon ring atoms. Examples of aryls include phenyl, naphthalenyl, and indenyl.

In some instances, the number of carbon atoms in a hydrocarbyl group (e.g., alkyl, alkenyl, alkynyl, or cycloalkyl) is indicated by the prefix "$C_x$-$C_y$-", wherein x is the minimum and y is the maximum number of carbon atoms in the group. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical (or "hydrido"), and may be depicted as —H.

The term "hydroxy" (alone or in combination with another term(s)) means —OH.

The term "nitro" (alone or in combination with another term(s)) means —$NO_2$.

The term "cyano" (alone or in combination with another term(s)) means —CN, which also may be depicted:

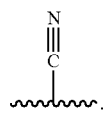

The term "oxo" (alone or in combination with another term(s)) means an oxo radical, and may be depicted as:

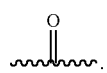 [SMILES: *=O]

The term "carboxy" (alone or in combination with another term(s)) means —C(O)—OH, which also may be depicted as:

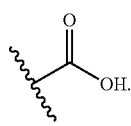

The term "amino" (alone or in combination with another term(s)) means —$NH_2$.

The term "halogen" (alone or in combination with another term(s)) means a fluorine radical ("fluoro", which may be depicted as —F), chlorine radical ("chloro", which may be depicted as —Cl), bromine radical ("bromo", which may be depicted as —Br), or iodine radical ("iodo", which may be depicted as —I). Typically, fluoro or chloro is preferred, with fluoro often being particularly preferred.

If a substituent is described as being "substituted", a non-hydrogen substituent is in the place of a hydrogen on a carbon, nitrogen, oxygen, or sulfur of the substituent. Thus, for example, a substituted alkyl substituent is an alkyl substituent wherein at least one non-hydrogen substituent is in the place of a hydrogen on the alkyl substituent. To illustrate, mono fluoroalkyl is alkyl substituted with a fluoro, and difluoroalkyl is alkyl substituted with two fluoros. It should be recognized that if there are more than one substitutions on a substituent, each non-hydrogen substituent may be identical or different (unless otherwise stated).

If a substituent is described as being "optionally substituted", the substituent may be either (1) not substituted or (2) substituted. If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 substituents, then any heteroaryl with less than 3 substitutable positions would be optionally substituted by up to only as many non-hydrogen substituents as the heteroaryl has substitutable positions. To illustrate, tetrazolyl (which has only one substitutable position when it is bonded to a single non-hydrogen moiety by a single bond) would be optionally substituted with up to one non-hydrogen substituent. To illustrate further, if an amino nitrogen is described as being optionally substituted with up to 2 non-hydrogen substituents, then a primary amino nitrogen will be optionally substituted with up to 2 non-hydrogen substituents, whereas a secondary amino nitrogen will be optionally substituted with up to only one non-hydrogen substituent.

The prefix "halo" indicates that the substituent to which the prefix is attached is substituted with one or more independently selected halogens. For example, haloalkyl means an alkyl substituent having a halogen in the place of a hydrogen, or multiple halogens in the place of the same number of hydrogens. Examples of haloalkyls include chloromethyl, 1-bromoethyl, fluoromethyl, difluoromethyl, trifluoromethyl, and 1,1,1-trifluoroethyl. Illustrating further, "haloalkoxy" means an alkoxy substituent wherein a halogen is in the place of a hydrogen, or multiple halogens are in the place of the same number of hydrogens. Examples of haloalkoxy substituents include chloromethoxy, 1-bromoethoxy, fluoromethoxy, difluoromethoxy, trifluoromethoxy (also known as "perfluoromethyloxy"), and 1,1,1,-trifluoroethoxy. It should be recognized that if a substituent is substituted by more than one halogen, the halogens may be identical or different (unless otherwise stated).

The term "carbonyl" (alone or in combination with another term(s)) means —C(O)—, which also may be depicted as:

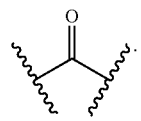

This term also is intended to encompass a hydrated carbonyl substituent, i.e., —C(OH)$_2$—.

The term "aminocarbonyl" (alone or in combination with another term(s)) means —C(O)—NH$_2$, which also may be depicted as:

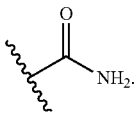

The term "oxy" (alone or in combination with another term(s)) means an ether substituent, and may be depicted as —O—.

The term "alkoxy" (alone or in combination with another term(s)) means an alkylether substituent, i.e., —O-alkyl. Examples of such a substituent include methoxy (—O—CH$_3$), ethoxy, n-propoxy, iso-propoxy, n-butoxy, iso-butoxy, sec-butoxy, and tert-butoxy.

The term "alkylcarbonyl" (alone or in combination with another term(s)) means —C(O)-alkyl. For example, "ethylcarbonyl" may be depicted as:

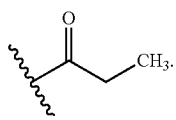

The term "alkoxycarbonyl" (alone or in combination with another term(s)) means —C(O)—O-alkyl. For example, "ethoxycarbonyl" may be depicted as:

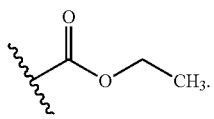 [SMILES: *C(=O)OCC]

The term "carbocyclylcarbonyl" (alone or in combination with another term(s)) means —C(O)-carbocyclyl. For example, "phenylcarbonyl" may be depicted as:

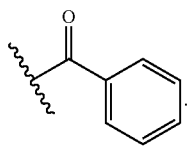 [SMILES: *C(=O)c1ccccc1]

Similarly, the term "heterocyclylcarbonyl" (alone or in combination with another term(s)) means —C(O)-heterocyclyl.

The term "sulfanyl" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-sulfanyl-alkyl" means alkyl-S-alkyl.

The term "thiol" or "mercapto" (alone or in combination with another term(s)) means a sulfhydryl substituent, and may be depicted as —SH.

The term "thiocarbonyl" (alone or in combination with another term(s)) means a carbonyl wherein a sulfur is in the place of the oxygen. Such a substituent may be depicted as —C(S)—, and also may be depicted as:

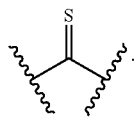

The term "sulfonyl" (alone or in combination with another term(s)) means —S(O)$_2$—, which also may be depicted as:

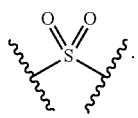

Thus, for example, "alkyl-sulfonyl-alkyl" means alkyl-S(O)$_2$-alkyl.

The term "aminosulfonyl" (alone or in combination with another term(s)) means —S(O)$_2$—NH$_2$, which also may be depicted as:

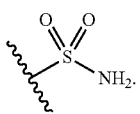

The term "sulfinyl" (alone or in combination with another term(s)) means —S(O)—, which also may be depicted as:

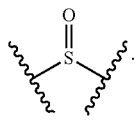

Thus, for example, "alkyl-sulfinyl-alkyl" means alkyl-S(O)-alkyl.

The term "heterocyclyl" (alone or in combination with another term(s)) means a saturated (i.e., "heterocycloalkyl"), non-aromatic partially-saturated (i.e., "heterocycloalkenyl"), or heterocyclic aromatic (i.e., "heteroaryl") ring structure typically containing a total of 3 to 14 ring atoms. At least one of the ring atoms is a heteroatom (typically oxygen, nitrogen, or sulfur), with the remaining ring atoms generally being independently selected from the group typically consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, thienyl (also known as "thiophenyl" and "thiofuranyl"), oxazolyl, isoxazolyl, thiazolyl, isothiazolyl, thiodiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), pyrrolyl, pyrazolyl, imidazolyl, triazolyl, tetrazolyl, oxathiazolyl, oxatriazolyl (including 1,2,3,4-oxatriazolyl and 1,2,3,5-oxatriazolyl), pyridinyl, diazinyl (including pyridazinyl (also known as "1,2-diazinyl"), pyrimidinyl (also known as "1,3-diazinyl"), and pyrazinyl (also known as "1,4-diazinyl")), triazinyl (including s-triazinyl (also known as "1,3,5-triazinyl"), as-triazinyl (also known 1,2,4-triazinyl), and v-triazinyl (also known as "1,2,3-triazinyl")), oxathiazinyl (including 1,2,5-oxathiazinyl and 1,2,6- oxathiazinyl), oxepinyl, thiepinyl, dihydrofuranyl, tetrahydrofuranyl, dihydrothienyl (also known as "dihydrothiophenyl"), tetrahydrothienyl (also known as "tetrahydrothiophenyl"), isopyrrolyl, pyrrolinyl, pyrrolidinyl, isoimidazolyl, imidazolinyl, imidazolidinyl, pyrazolinyl, pyrazolidinyl, dithiolyl, oxathiolyl, oxathiolanyl, oxazolidinyl, isoxazolidinyl, thiazolinyl, isothiazolinyl, thiazolidinyl, isothiazolidinyl, dioxazolyl (including 1,2,3-dioxazolyl, 1,2,4-dioxazolyl, 1,3,2-dioxazolyl, and 1,3,4-dioxazolyl), pyranyl (including 1,2-pyranyl and 1,4-pyranyl), dihydropyranyl, tetrahydropyranyl, piperidinyl, piperazinyl, oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxadiazinyl (including 1,4,2-oxadiazinyl and 1,3,5,2-oxadiazinyl), morpholinyl, azepinyl, and diazepinyl.

A heterocyclyl alternatively may be 2 or 3 rings fused together, such as, for example, indolizinyl, pyranopyrrolyl, purinyl, imidazopyrazinyl, imidazolopyridazyl, pyridopyridinyl (including pyrido[3,4-b]-pyridinyl, pyrido[3,2-b]-pyridinyl, pyrido[4,3-b]-pyridinyl, and naphthyridinyl), pteridinyl, pyridazinotetrazinyl, pyrazinotetrazinyl, pyrimidinotetrazinyl, pyrindinyl, pyrazolopyrimidinyl, pyrazolopyrazinyl, pyrazolopyridazyl, or 4H-quinolizinyl. In some embodiments, the preferred multi-ring heterocyclyls are indolizinyl, pyranopyrrolyl, purinyl, pyridopyridinyl, pyrindinyl, and 4H-quinolizinyl.

Other examples of fused-ring heterocyclyls include benzo-fused heterocyclyls, such as, for example, benzofuranyl (also known as "coumaronyl"), isobenzofuranyl, benzoxazolyl, benzoisoxazolyl (also known as "indoxazinyl"), anthranilyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzoisothiazolyl, benzothiadiazolyl, benzoxadiazolyl, indolyl, isoindazolyl (also known as "benzpyrazolyl"), benzoimidazolyl, benzotriazolyl, benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzoimidazothiazolyl, carbazolyl, acridinyl, isoindolyl, indoleninyl (also known as "pseudoindolyl"), benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, benzoxazinyl (including 1,3,2-benzoxazinyl, 1,4,2-benzoxazinyl, 2,3,1-benzoxazinyl, and 3,1,4-benzoxazinyl), benzoisoxazinyl (including 1,2-benzisoxazinyl and 1,4-benzisoxazinyl), benzoxadiazinyl, and xanthenyl. In some embodiments, the preferred benzo-fused heterocyclyls are benzofuranyl, isobenzofuranyl, benzoxazolyl, benzoisoxazolyl, anthranilyl, benzothienyl, isobenzothienyl, benzothiazolyl, benzothiadiazolyl, benzoxadiazolyl, indolyl, isoindazolyl, benzoimidazolyl, benzotriazolyl, benzazinyl, phthalazinyl, quinoxalinyl, benzodiazinyl, carbazolyl, acridinyl, isoindolyl, indoleninyl, benzodioxolyl, chromanyl, isochromanyl, thiochromanyl, benzodioxanyl, tetrahydroisoquinolinyl, benzoxazinyl, benzoisoxazinyl, and xanthenyl.

The term "2-fused-ring" heterocyclyl (alone or in combination with another term(s)) means a saturated, non-aromatic partially-saturated, or heteroaryl containing two fused rings. Such heterocyclyls include, for example, benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, imidazolopyridazyl, quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, pyrindinyl, isoindolyl, indoleninyl, pyrazolopyrimidinyl, pyrazolopyrazinyl, pyrazolopyridazyl, benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, 4H-quinolizinyl, benzoxazinyl, and benzoisoxazinyl. In some embodiments, preferred 2-fused-ring heterocyclyls include benzofuranyl, isobenzofuranyl, benzoxazolyl, benzoisoxazolyl, anthranilyl, benzothienyl, isobenzothienyl, benzothiazolyl, benzothiadiazolyl, indolizinyl, pyranopyrrolyl, benzoxadiazolyl, indolyl, isoindazolyl, benzoimidazolyl, benzotriazolyl, purinyl, quinolinyl, isoquinolinyl, pyridopyridinyl, phthalazinyl, quinoxalinyl, benzodiazinyl, pteridinyl, pyrindinyl, isoindolyl, indoleninyl, benzodioxolyl, benzodioxanyl, tetrahydroisoquinolinyl, 4H-quinolizinyl, benzoxazinyl, and benzoisoxazinyl.

The term "heteroaryl" (alone or in combination with another term(s)) means an aromatic heterocyclyl typically containing from 5 to 14 ring atoms. A heteroaryl may be a single ring or multiple (typically 2 or 3) fused rings. Such moieties include, for example, 5-membered rings such as furanyl, thienyl, oxazolyl, isoxazolyl, thiazolyl, isothiazolyl, thiodiazolyl, oxadiazolyl, pyrrolyl, pyrazolyl, imidazolyl, triazolyl, tetrazolyl, oxathiazolyl, and oxatriazolyl; 6-membered rings such as pyridinyl, pyrazinyl, pyrimidinyl, pyridazinyl, triazinyl, and oxathiazinyl; 7-membered rings such as oxepinyl and thiepinyl; 6/5-membered fused-ring systems such as benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, and imidazolopyridazyl; and 6/6-membered fused-ring systems such as quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, benzoimidazothiazolyl, carbazolyl, and acridinyl. In some embodiments, the preferred 5-membered rings include furanyl, thienyl, oxazolyl, isoxazolyl, thiazolyl, isothiazolyl, oxadiazolyl, pyrazolyl, and imidazolyl; the preferred 6-membered rings include pyridinyl, pyrazinyl, pyrimidinyl, pyridazinyl, and triazinyl; the preferred 6/5-membered fused-ring systems include benzoxazolyl, benzoisoxazolyl, anthranilyl, benzothienyl, isobenzothienyl, and purinyl; and the preferred 6/6-membered fused-ring systems include quinolinyl, isoquinolinyl, and benzodiazinyl.

A carbocyclyl or heterocyclyl can optionally be substituted with, for example, one or more substituents independently selected from the group consisting of halogen, hydroxy, carboxy, oxo, alkyl, alkoxy, alkoxyalkyl, alkylcarbonyl, aryl, arylalkyl, arylalkoxy, arylalkoxyalkyl, arylalkoxycarbonyl, cycloalkyl, cycloalkylalkyl, cycloalkylalkoxy, cycloalkylalkoxyalkyl, and cycloalkylalkoxycarbonyl. More typically, a carbocyclyl or heterocyclyl may optionally be substituted with, for example, one or more substituents independently selected from the group consisting of halogen, —OH, —C(O)—OH, oxo, $C_1$-$C_6$-alkyl, $C_1$-$C_6$-alkoxy, $C_1$-$C_6$-alkoxy-$C_1$-$C_6$-alkyl, $C_1$-$C_6$-alkylcarbonyl, aryl, aryl-$C_1$-$C_6$-alkyl, aryl-$C_1$-$C_6$-alkoxy, aryl-$C_1$-$C_6$-alkoxy-$C_1$-$C_6$-alkyl, aryl-$C_1$-$C_6$-alkoxycarbonyl, cycloalkyl, cycloalkyl-$C_1$-$C_6$-alkyl, cycloalkyl-$C_1$-$C_6$-alkoxy, cycloalkyl-$C_1$-$C_6$-alkoxy-$C_1$-$C_6$-alkyl, and cycloalkyl-$C_1$-$C_6$-alkoxycarbonyl. The alkyl, alkoxy, alkoxyalkyl, alkylcarbonyl, aryl, arylalkyl, arylalkoxy, arylalkoxyalkyl, or arylalkoxycarbonyl substituent(s) may further be substituted with, for example, one or more halogen. The aryl and cycloalkyl portions of such optional substituents are typically single-rings containing from 3 to 6 ring atoms, and more typically from 5 to 6 ring atoms.

An aryl or heteroaryl can optionally be substituted with, for example, one or more substituents independently selected from the group consisting of halogen, —OH, —CN, —NO$_2$, —SH, —C(O)—OH, amino, aminoalkyl, alkyl, alkylsulfanyl, carboxyalkylsulfanyl, alkylcarbonyloxy, alkoxy, alkoxyalkyl, alkoxycarbonylalkoxy, alkoxyalkylsulfanyl, alkoxycarbonylalkylsulfanyl, carboxyalkoxy, alkoxycarbonylalkoxy, carbocyclyl, carbocyclylalkyl, carbocyclyloxy, carbocyclylsulfanyl, carbocyclylalkylsulfanyl, carbocyclylamino, carbocyclylalkylamino, carbocyclylcarbonylamino, carbocyclylalkyl, carbocyclylcarbonyloxy, carbocyclyloxyalkoxycarbocyclyl, carbocyclylsulfanylalkylsulfanylcarbocyclyl, carbocyclylsulfanylalkoxycarbocyclyl, carbocyclyloxyalkylsulfanylcarbocyclyl, heterocyclyl, heterocyclylalkyl, heterocyclyloxy, heterocyclylsulfanyl, heterocyclylalkylsulfanyl, heterocyclylamino, heterocyclylalkylamino, heterocyclylcarbonylamino, heterocyclylcarbonyloxy, heterocyclyloxyalkoxyheterocyclyl, heterocyclylsulfanylalkylsulfanylheterocyclyl, heterocyclylsulfanylalkoxyheterocyclyl, and heterocyclyloxyalkylsulfanylheterocyclyl. More typically, an aryl or heteroaryl may, for example, optionally be substituted with one or more substituents independently selected from the group consisting of halogen, —OH, —CN, —NO$_2$, —SH, —C(O)—OH, amino, amino-C$_1$-C$_6$-alkyl, C$_1$-C$_6$-alkyl, C$_1$-C$_6$-alkylsulfanyl, carboxy-C$_1$-C$_6$-alkylsulfanyl, C$_1$-C$_6$-alkylcarbonyloxy, C$_1$-C$_6$-alkoxy, C$_1$-C$_6$-alkoxy-C$_1$-C$_6$-alkyl, C$_1$-C$_6$-alkoxycarbonyl-C$_1$-C$_6$-alkoxy, C$_1$-C$_6$-alkoxy-C$_1$-C$_6$-alkylsulfanyl, C$_1$-C$_6$-alkoxycarbonyl-C$_1$-C$_6$-alkylsulfanyl, carboxy-C$_1$-C$_6$-alkoxy, C$_1$-C$_6$-alkoxycarbonyl-C$_1$-C$_6$-alkoxy, aryl, aryl-C$_1$-C$_6$-alkyl, aryloxy, arylsulfanyl, aryl-C$_1$-C$_6$-alkylsulfanyl, arylamino, aryl-C$_1$-C$_6$-alkylamino, arylcarbonylamino, arylcarbonyloxy, aryloxy-C$_1$-C$_6$-alkoxyaryl, arylsulfanyl-C$_1$-C$_6$-alkylsulfanylaryl, arylsulfanyl-C$_1$-C$_6$-alkoxyaryl, aryloxy-C$_1$-C$_6$-alkylsulfanylaryl, cycloalkyl, cycloalkyl-C$_1$-C$_6$-alkyl, cycloalkyloxy, cycloalkylsulfanyl, cycloalkyl-C$_1$-C$_6$-alkylsulfanyl, cycloalkylamino, cycloalkyl-C$_1$-C$_6$-alkylamino, cycloalkylcarbonylamino, cycloalkylcarbonyloxy, heteroaryl, heteroaryl-C$_1$-C$_6$-alkyl, heteroaryloxy, heteroarylsulfanyl, heteroaryl-C$_1$-C$_6$-alkylsulfanyl, heteroarylamino, heteroaryl-C$_1$-C$_6$-alkylamino, heteroarylcarbonylamino, and heteroarylcarbonyloxy. Here, one or more hydrogens bound to a carbon in any such substituent may, for example, optionally be replaced with halogen. In addition, any cycloalkyl, aryl, and heteroaryl portions of such optional substituents are typically single-rings containing 3 to 6 ring atoms, and more typically 5 or 6 ring atoms.

A prefix attached to a multi-component substituent only applies to the first component. To illustrate, the term "alkylcycloalkyl" contains two components: alkyl and cycloalkyl. Thus, the C$_1$-C$_6$— prefix on C$_1$-C$_6$-alkylcycloalkyl means that the alkyl component of the alkylcycloalkyl contains from 1 to 6 carbon atoms; the C$_1$-C$_6$— prefix does not describe the cycloalkyl component.

If substituents are described as being "independently selected," each substituent is selected independent of the other. Each substituent, therefore, may be identical to or different from the other selected substituent(s).

When words are used to describe a substituent, the right-most-described component of the substituent is the component that has the free valence. To illustrate, benzene substituted with methoxyethyl has the following structure:

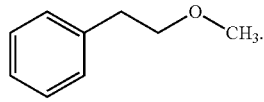

As can be seen, the ethyl is bound to the benzene, and the methoxy is the component of the substituent that is the component furthest from the benzene. As further illustration, benzene substituted with cyclohexanylsulfanylbutoxy has the following structure:

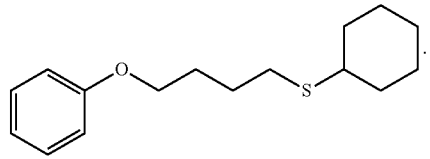 [SMILES: c1ccc(OCCCCSC2CCCCC2)cc1]

When a chemical formula is used to describe a monovalent substituent, the dash on the left side of the formula indicates the portion of the substituent that has the free valence. To illustrate, benzene substituted with —C(O)—OH has the following structure:

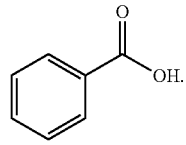

When a chemical formula is used to describe a di-valent (or "linking") component between two other components of a depicted chemical structure (the right and left components), the leftmost dash of the linking component indicates the portion of the linking component that is bound to the left component in the depicted structure. The rightmost dash, on the other hand, indicates the portion of the linking component that is bound to the right component in the depicted structure. To illustrate, if the depicted chemical structure is X-L-Y and L is described as —C(O)—N(H)—, then the chemical would be:

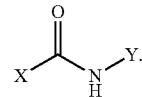

Dashes are not used to characterize a tri-valent component when standing alone. Thus, for example, a tri-valent nitrogen is identified as "N" and a tri-valent carbon bonded to hydrogen is identified as "CH" in this patent.

The words "comprise", "comprises", and "comprising" are to be interpreted inclusively rather than exclusively. This interpretation is intended to be the same as the interpretation that these words are given under United States patent law.

The term "pharmaceutically acceptable" is used adjectivally to mean that the modified noun is appropriate for use in a pharmaceutical product. When it is used, for example, to describe a salt or excipient, it characterizes the salt or excipient as being compatible with the other ingredients of the composition, and not deleterious to the intended recipient animal to the extent that the deleterious effect(s) outweighs the benefit(s) of the salt.

* * *

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

What is claimed:
1. A compound or salt thereof, wherein:
the compound corresponds in structure to:

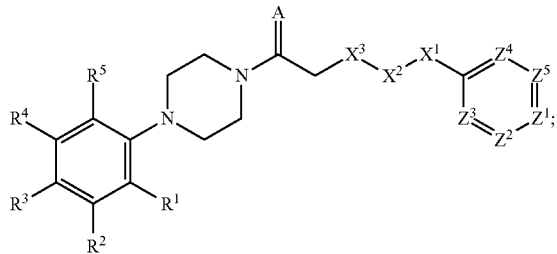

each of $R^1$, $R^2$, $R^3$, $R^4$, and $R^5$ is independently selected from the group consisting of hydrogen, halogen, cyano, alkyl, and alkoxy, wherein:
the alkyl, and alkoxy, are optionally substituted with one or more substituents independently selected from the group consisting of halogen, cyano, alkyl, alkoxy, haloalkyl, haloalkoxy, alkylsulfanyl, and haloalkylsulfanyl;
$X^1$ is selected from the group consisting of —O—, and —NH—, wherein:
the —NH— is optionally substituted with a substituent selected from the group consisting of alkyl, alkenyl, alkynyl, alkoxyalkyl, carbocyclyl, and carbocyclylalkyl, wherein:
any such substituent is optionally substituted with one or more independently selected halogen;
$X^2$ is selected from the group consisting of straight-chain $C_3$-$C_5$-alkyl, straight-chain $C_3$-$C_5$-alkenyl, straight-chain $C_3$-$C_5$-alkynyl, and $C_4$-$C_6$-carbocyclyl, wherein:
the straight-chain $C_3$-$C_5$-alkyl, straight-chain $C_3$-$C_5$-alkenyl, straight-chain $C_3$-$C_5$-alkynyl, and $C_4$-$C_6$-carbocyclyl are optionally substituted with one or more independently selected alkyl;
$X^3$ is selected from the group consisting of —CH$_2$—, —O—, —C(O)—, and —S—, wherein:
the —CH$_2$— is optionally substituted with up to two substituents independently selected from the group consisting of alkyl and carbocyclyl, and
wherein:
any such substituent is optionally substituted with one or more independently selected halogen;
$Z^1$ is CH, wherein:
the CH is substituted with a substituent selected from the group consisting of halogen, nitro, cyano, aminosulfonyl, alkyl, alkoxycarbonyl, alkylsulfanyl, alkylsulfinyl, alkylsulfonyl, aryl, arylsulfanyl, arylsulfinyl, arylsulfonyl, heteroaryl, heteroarylsulfanyl, heteroarylsulfinyl, and heteroarylsulfonyl, wherein:
the alkyl, alkoxycarbonyl, alkylsulfanyl, alkylsulfinyl, alkylsulfonyl, alkylsulfanyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl, and
the aminosulfonyl is optionally substituted with up to two independently selected alkyl;
$Z^2$ is CH, wherein:
the CH is optionally substituted with a substituent selected from the group consisting of cyano, halogen, nitro, alkyl, haloalkyl, and haloalkylsulfanyl; and
each of $Z^3$, $Z^4$, and $Z^5$ is CH, wherein:
the CH is optionally substituted with a substituent selected from the group consisting of halogen, cyano, nitro, alkyl, alkylsulfanyl, haloalkyl, haloalkoxy, and haloalkylsulfanyl; and
A is O or S.

2. A compound or salt of claim 1, wherein:
each of $R^1$, $R^2$, $R^3$, $R^4$, and $R^5$ is independently selected from the group consisting of hydrogen, halogen, cyano, $C_1$-$C_6$-alkyl, and $C_1$-$C_6$-alkoxy, wherein:
the $C_1$-$C_6$-alkyl, and $C_1$-$C_6$-alkoxy, are optionally substituted with one or more substituents independently selected from the group consisting of halogen, cyano, $C_1$-$C_6$-alkyl, $C_1$-$C_6$-alkoxy, halo-$C_1$-$C_6$-alkyl, halo-$C_1$-$C_6$-alkoxy, $C_1$-$C_6$-alkylsulfanyl, and halo-$C_1$-$C_6$-alkylsulfanyl;
$X^1$ is selected from the group consisting of —O—, and —NH—, wherein:
the —NH— is optionally substituted with a substituent selected from the group consisting of $C_1$-$C_6$-alkyl, $C_2$-$C_6$-alkenyl, $C_2$-$C_6$-alkynyl, $C_1$-$C_6$-alkoxy-C-$C_6$-alkyl, $C_3$-$C_6$-carbocyclyl, and $C_3$-$C_6$-carbocyclyl-$C_1$-$C_6$-alkyl, wherein:
any such substituent is optionally substituted with one or more independently selected halogen;
$X^2$ is selected from the group consisting of straight-chain $C_3$-$C_4$-alkyl, straight-chain $C_3$-$C_4$-alkenyl, straight-chain $C_3$-$C_4$-alkynyl, and $C_4$-$C_6$-carbocyclyl, wherein:
the straight-chain $C_3$-$C_4$-alkyl, straight-chain $C_3$-$C_4$-alkenyl, straight-chain $C_3$-$C_4$-alkynyl, and $C_3$-$C_4$-carbocyclyl are optionally substituted with one or more independently selected $C_1$-$C_6$-alkyl;
$X^3$ is selected from the group consisting of —CH$_2$—, —O—, —C(O)—, and —S—, wherein:
the —CH$_2$— is optionally substituted with up to two substituents independently selected from the group consisting of $C_1$-$C_6$-alkyl and cyclopropyl,
wherein:
any such substituent is optionally substituted with one or more independently selected halogen;
$Z^1$ is CH, wherein:
the CH is substituted with a substituent selected from the group consisting of halogen, nitro, cyano, aminosulfonyl, $C_1$-$C_6$-alkyl, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, phenyl, phenylsulfanyl, phenylsulfinyl, phenylsulfonyl, heteroaryl, heteroarylsulfanyl, heteroarylsulfinyl, and heteroarylsulfonyl, wherein:
the $C_1$-$C_6$-alkyl, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, $C_1$-$C_6$-alkylsulfanyl, phenyl, phenylsulfanyl, phenylsulfinyl, phenylsulfonyl, heteroaryl, heteroarylsulfanyl, heteroarylsulfinyl, and heteroarylsulfonyl are optionally substituted with one or more substituents independently selected from the group consisting of halogen and $C_1$-$C_6$-alkyl, and the aminosulfonyl is optionally substituted with up to two independently selected $C_1$-$C_6$-alkyl;

$Z^2$ is CH, wherein:
the CH is optionally substituted with a substituent selected from the group consisting of cyano, halogen, nitro, $C_1$-$C_6$-alkyl, halo-$C_1$-$C_6$-alkyl, and halo-$C_1$-$C_6$-alkylsulfanyl;

each of $Z^3$, $Z^4$, and $Z^5$ is independently CH, wherein:
the CH is optionally substituted with a substituent selected from the group consisting of halogen, cyano, nitro, $C_1$-$C_6$-alkyl, $C_1$-$C_6$-alkylsulfanyl, halo-$C_1$-$C_6$-alkyl, and halo-$C_1$-$C_6$-alkylsulfanyl; and each heteroaryl is a 5- to 6-member heteroaryl.

3. A compound or salt thereof, wherein: the compound corresponds in structure to:

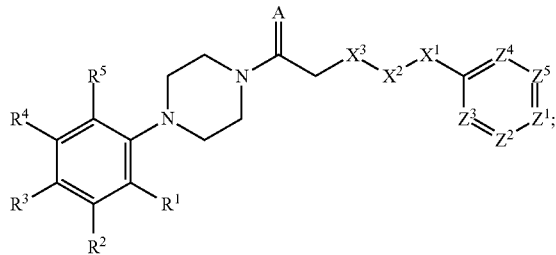

each of $R^1$, $R^2$, $R^3$, $R^4$, and $R^5$ is independently selected from the group consisting of hydrogen, halogen, cyano, $C_1$-$C_6$-alkyl, and $C_1$-$C_6$-alkoxy, wherein:
the $C_1$-$C_6$-alkyl, and $C_1$-$C_6$-alkoxy, are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy;

$X^1$ is selected from the group consisting of —O—, and —NH—, wherein:
the —NH— is optionally substituted with a substituent selected from the group consisting of alkyl, alkenyl, alkynyl, alkoxyalkyl, carbocyclyl, and carbocyclylalkyl, wherein:
any such substituent is optionally substituted with one or more independently selected halogen;

$X^2$ is $C_4$-$C_6$-carbocyclyl optionally substituted with one or more independently selected $C_1$-$C_6$-alkyl; and $X^3$ is selected from the group consisting of —CH$_2$—, —O—, —C(O)—, and —S—, wherein:
the —CH$_2$— is optionally substituted with up to two substituents independently selected from the group consisting of alkyl and carbocyclyl, and wherein:
any such substituent is optionally substituted with one or more independently selected halogen;

$Z^1$ is CH, wherein:
the CH is substituted with a substituent selected from the group consisting of halogen, nitro, cyano, aminosulfonyl, $C_1$-$C_6$-alkyl, $C_1$-$C_6$-alkoxy, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, phenylsulfonyl, and heteroaryl, wherein:
the $C_1$-$C_6$-alkyl, $C_1$-$C_6$-alkoxy, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, $C_1$-$C_6$-alkylsulfanyl, phenylsulfonyl, and heteroaryl are optionally substituted with one or more substituents independently selected from the group consisting of halogen and $C_1$-$C_6$-alkyl, and
the aminosulfonyl is optionally substituted with up to two independently selected $C_1$-$C_6$-alkyl;, $Z^2$ is CH, wherein:
the CH is optionally substituted with a substituent selected from the group consisting of cyano, halogen, nitro, alkyl, alkoxy, haloalkyl, and haloalkylsulfanyl; and each of $Z^3$, $Z^4$, and $Z^5$ is CH, wherein:
the CH is optionally substituted with a substituent selected from the group consisting of halogen, cyano, nitro, alkyl, alkoxy, alkylsulfanyl, haloalkyl, haloalkoxy, and haloalkylsulfanyl; and A is O or S.

4. A compound or salt thereof according to claim 1, wherein $X^6$ is selected from the group of linkers consisting of:

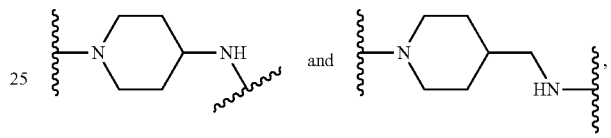

wherein
any such group is optionally substituted with one or more substituents independently selected from the group consisting of halogen, hydroxy, $C_1$-$C_6$-alkyl, $C_1$-$C_6$-alkoxy, oxo, and thiocarbonyl.

5. A compound or salt thereof according claim 1, wherein the compound is selected from the group consisting of:

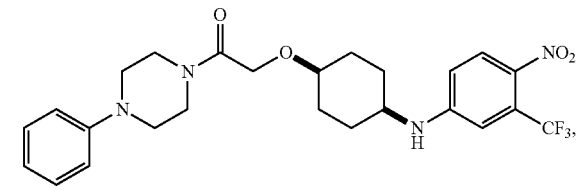

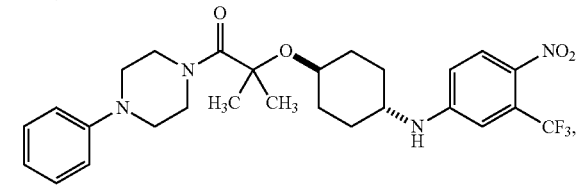

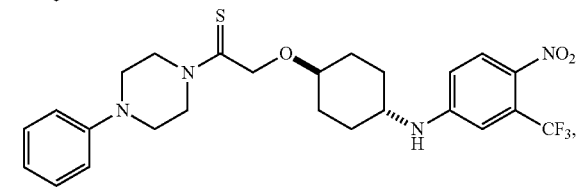

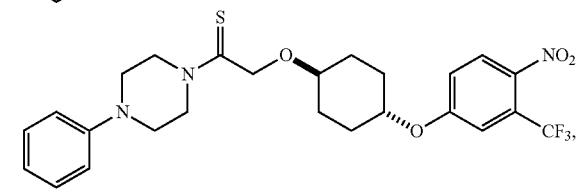

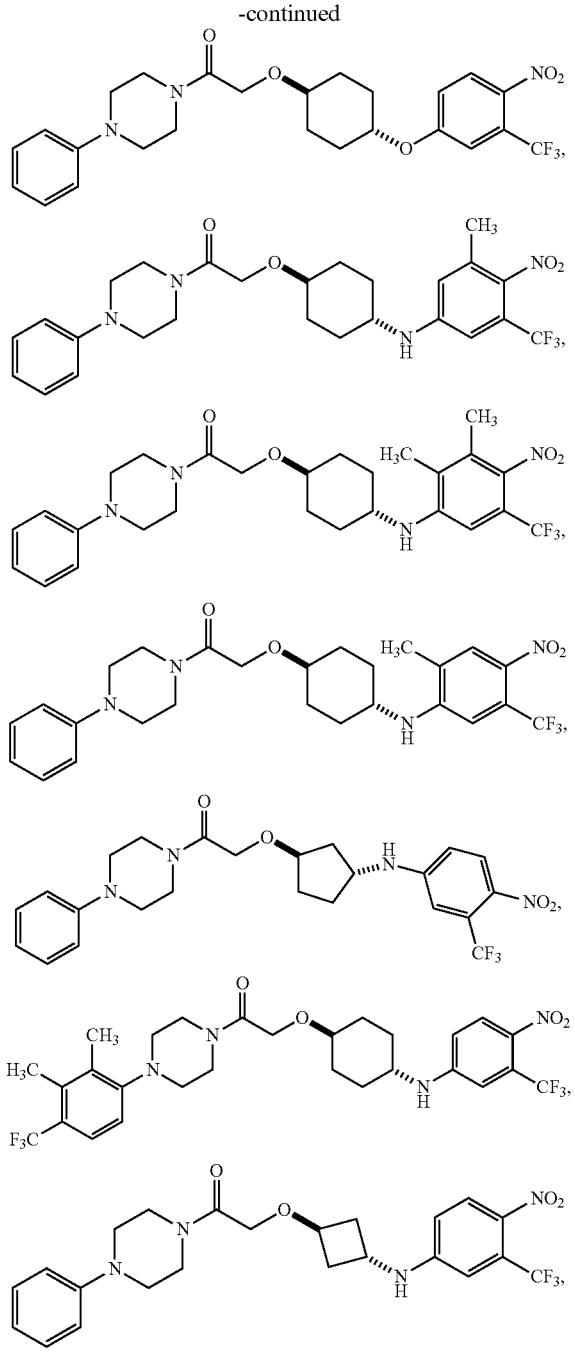
6. A compound or salt thereof according to claim 1, wherein the compound is selected from the group consisting of:

217
-continued
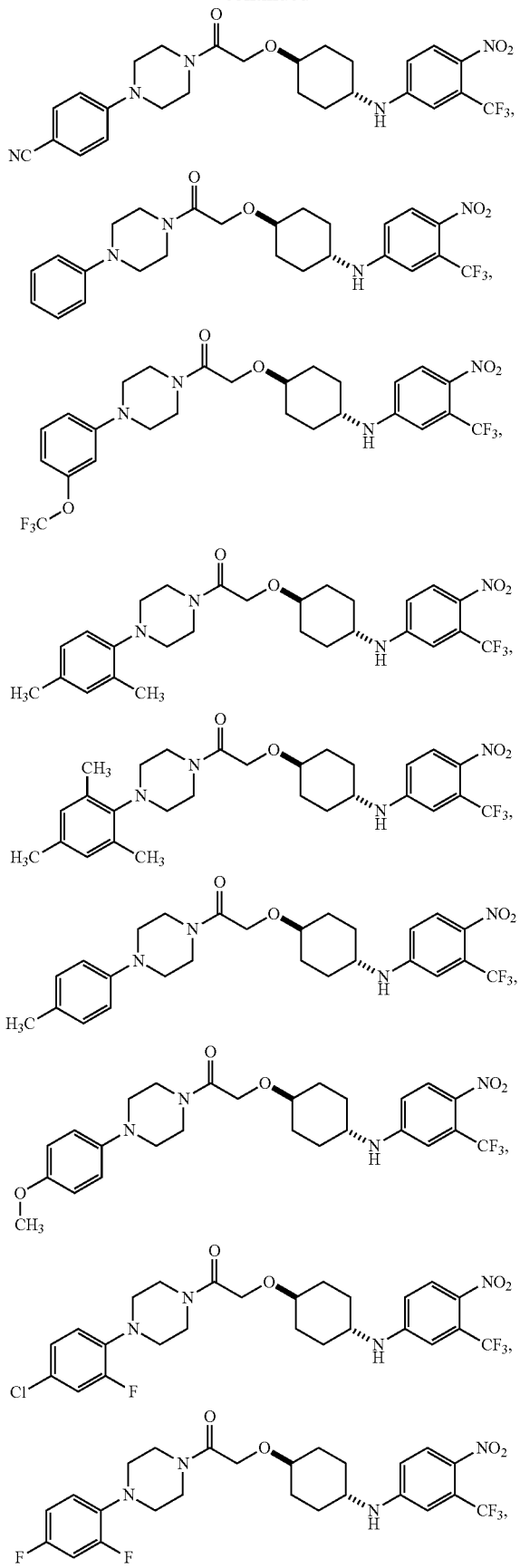
218
-continued
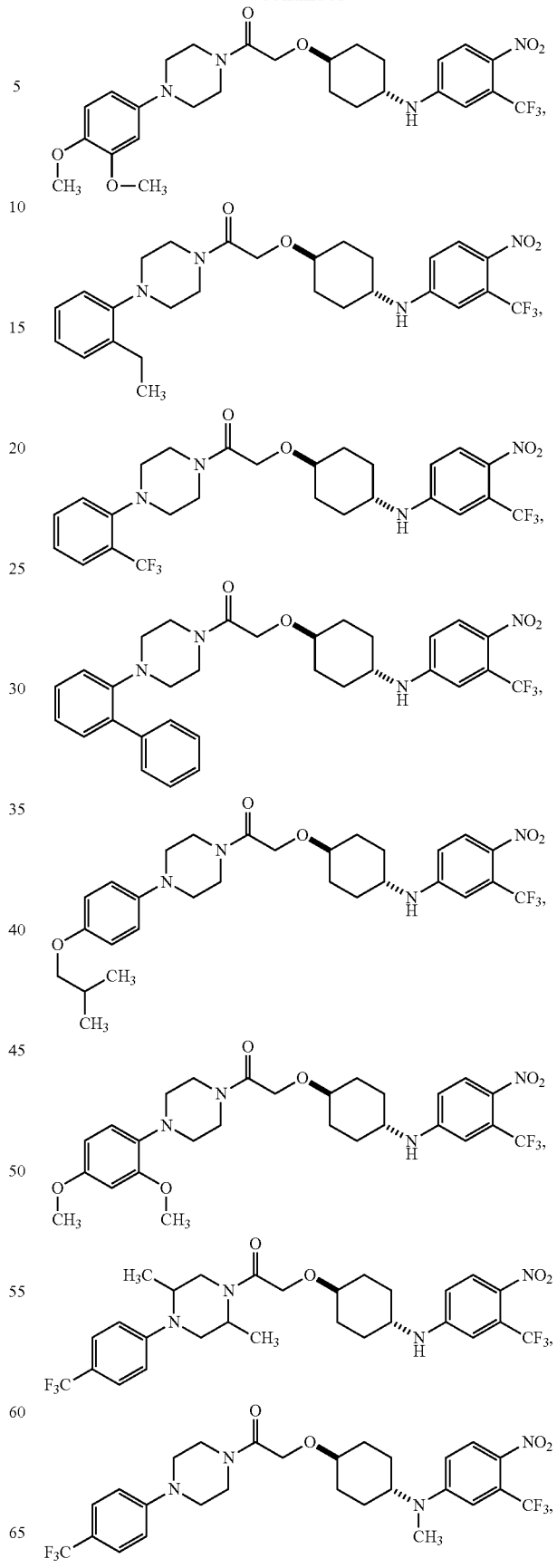

219 -continued
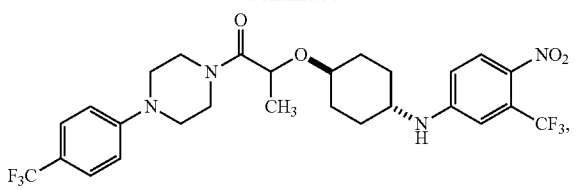
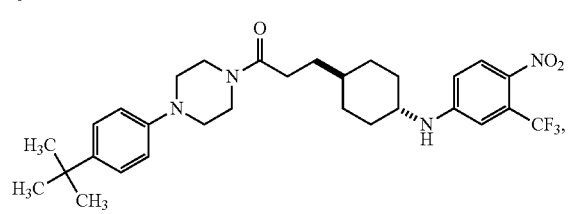
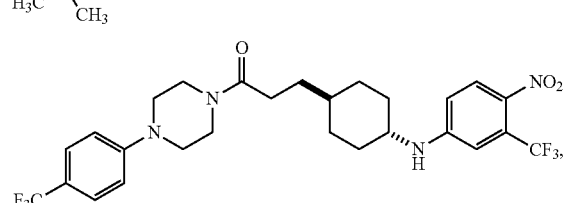
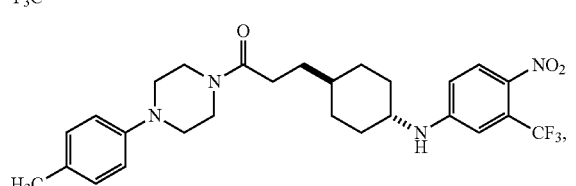
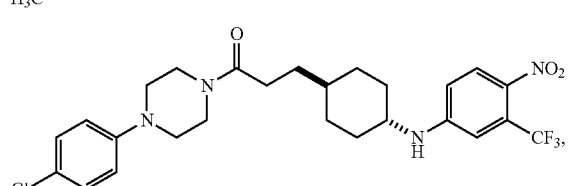
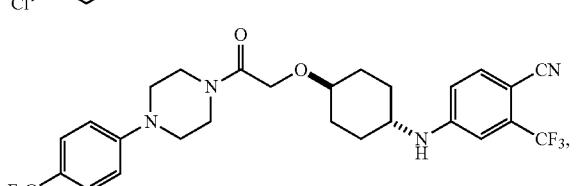
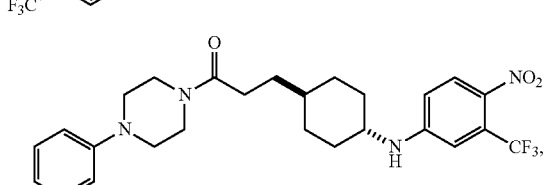
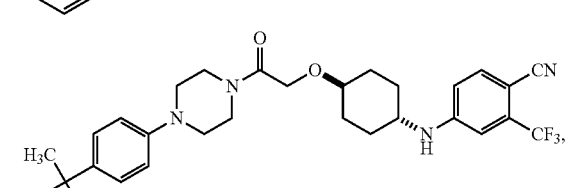
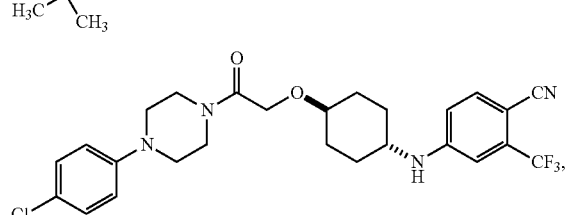
220 -continued
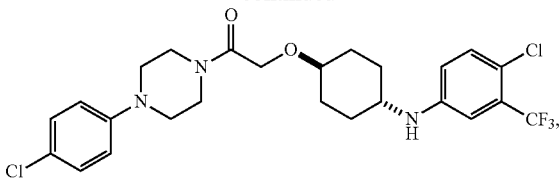
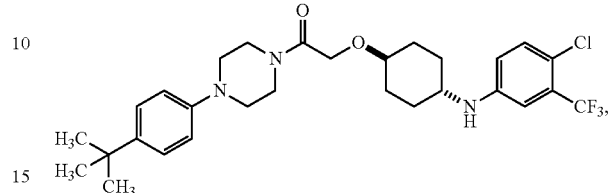
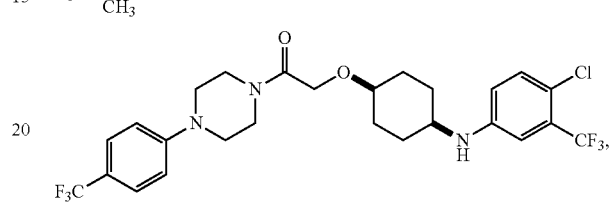
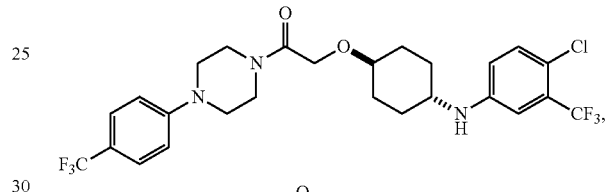
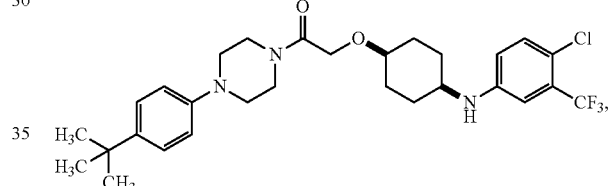
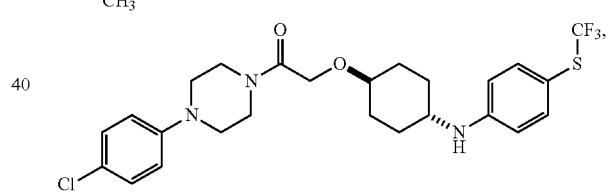
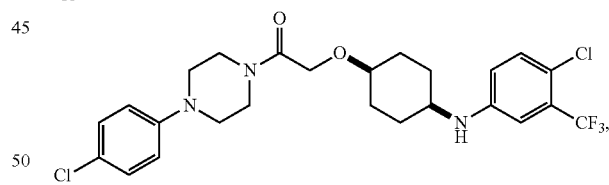
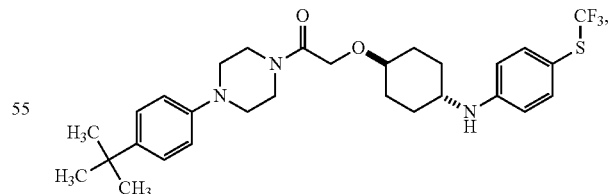
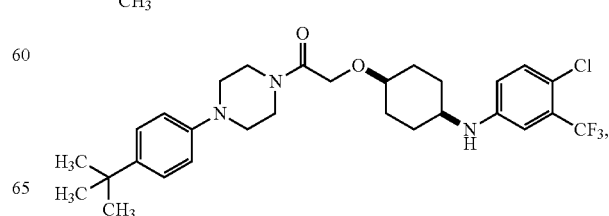

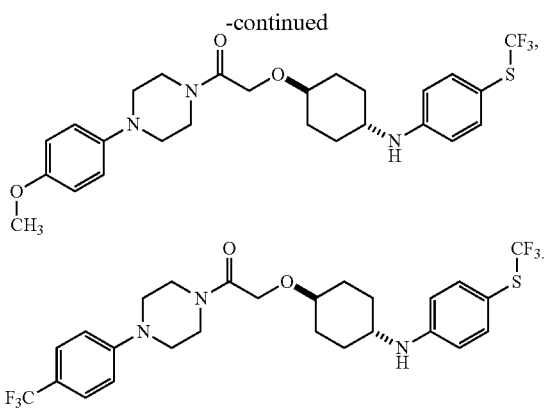

7. A compound or salt thereof according to claim 3, wherein $Z^2$ is CH substituted with a substituent selected from the group consisting of cyano, halogen, nitro, $C_1$-$C_6$-alkyl, $C_1$-$C_6$-alkoxy, halo-$C_1$-$C_6$-alkyl, and halo-$C_1$-$C_6$-alkylsulfanyl.

8. A compound or salt thereof according to claim 1, wherein $R^3$ is independently selected from the group consisting of halogen, cyano, $C_1$-$C_6$-alkyl, and $C_1$-$C_6$-alkoxy, wherein:
  the $C_1$-$C_6$-alkyl, $C_1$-$C_6$-alkoxy, phenyl, phenoxy, and benzyloxy are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy; and
  at least two of $R^1$, $R^2$, $R^4$, and $R^5$ are each hydrogen.

9. A compound or salt thereof according to claim 1, wherein the compound corresponds in structure to a formula consisting of:

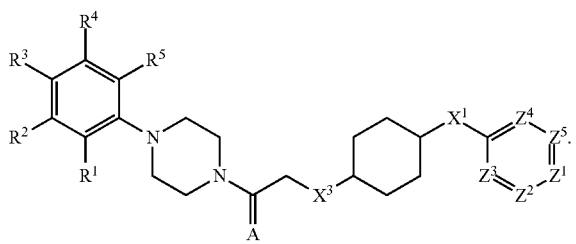

10. A compound or salt thereof according to claim 1, wherein the compound corresponds in structure to a formula consisting of:

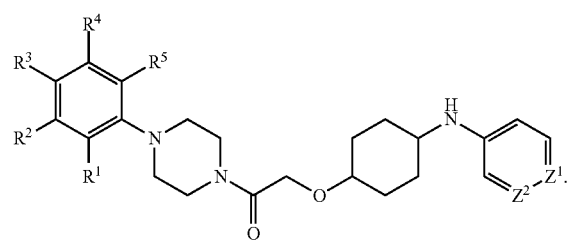

11. A compound or salt thereof according to claim 1, wherein:
  the compound corresponds in structure to a formula consisting of:

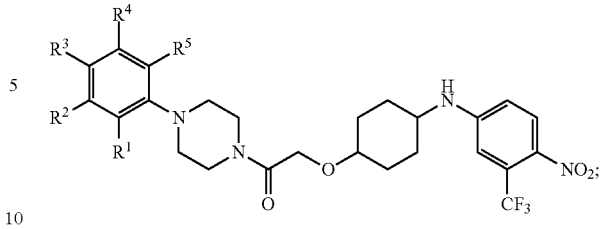

$R^3$ is selected from the group consisting of halogen, cyano, $C_1$-$C_6$-alkyl, and $C_1$-$C_6$-alkoxy, wherein:
  the $C_1$-$C_6$-alkyl, and $C_1$-$C_6$-alkoxy, are optionally substituted with one or more substituents independently selected from the group consisting of halogen, cyano, $C_1$-$C_6$-alkyl, $C_1$-$C_6$-alkoxy, halo-$C_1$-$C_6$-alkyl, and halo-$C_1$-$C_6$-alkoxy; and
at least two of $R^1$, $R^2$, $R^4$, and $R^5$ are each hydrogen.

12. A compound or salt thereof according to claim 1, wherein the compound is selected from the group consisting of:

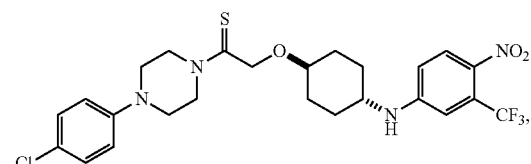

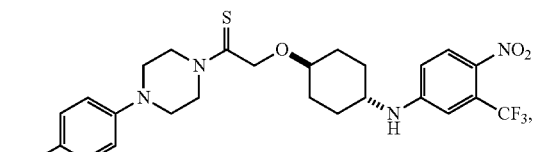

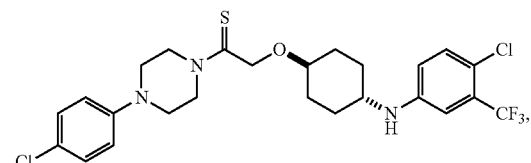

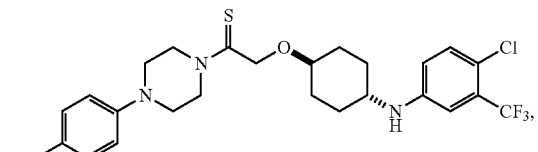

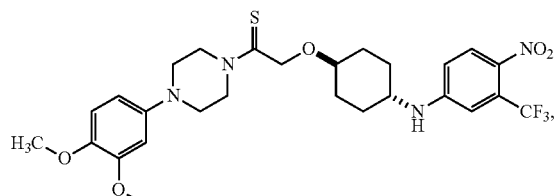

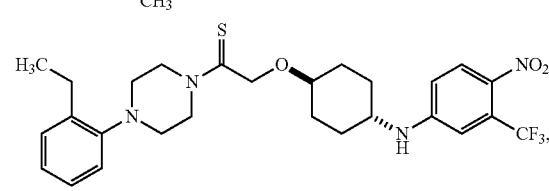

223
-continued
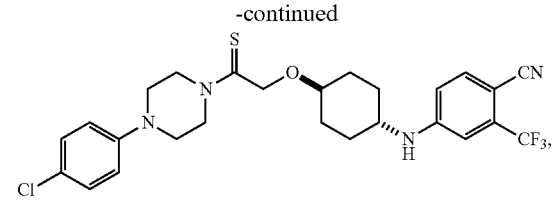
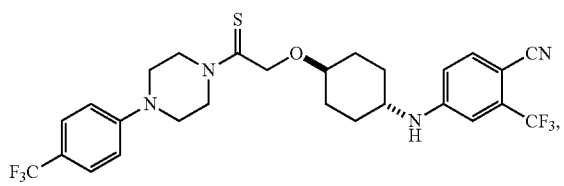
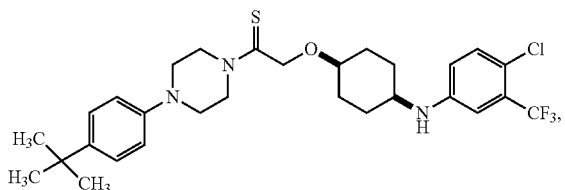
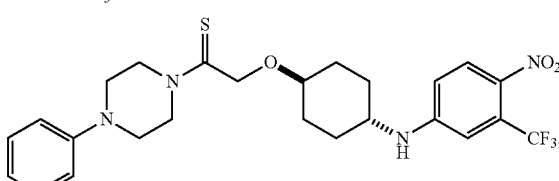
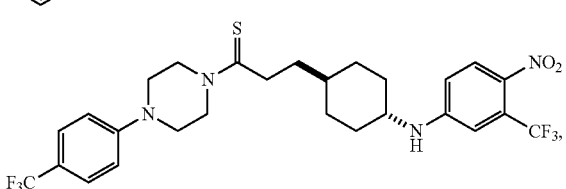
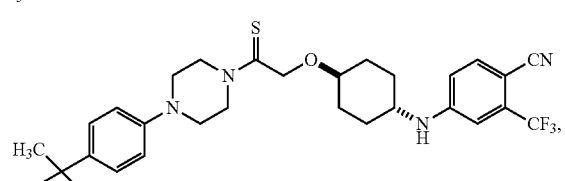
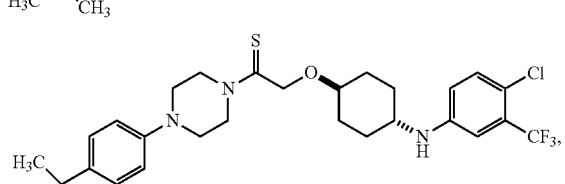
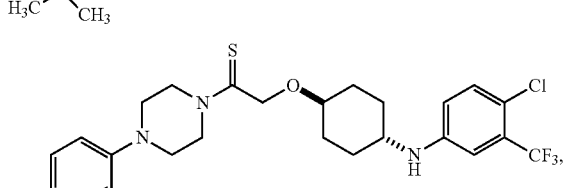
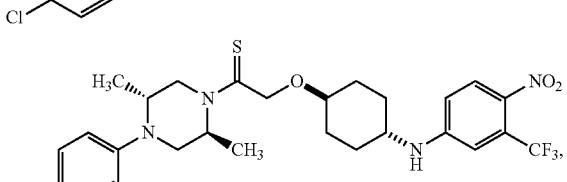
224
-continued
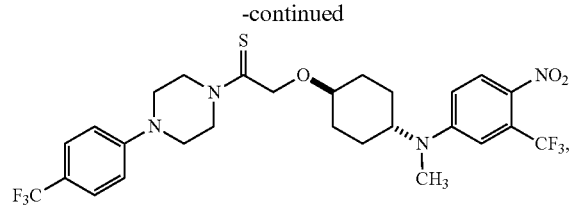
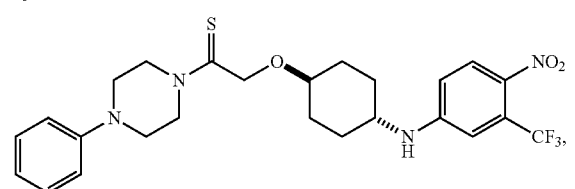
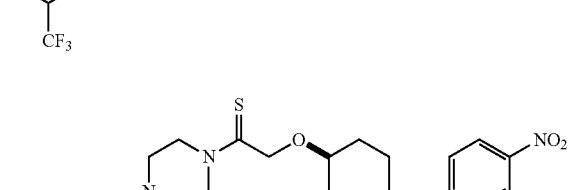
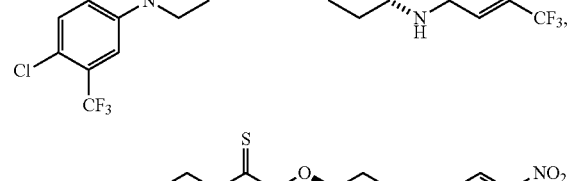
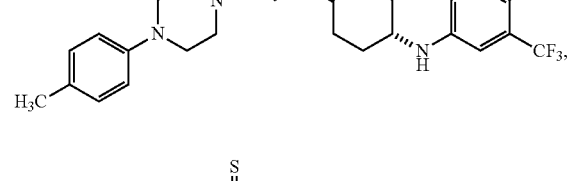
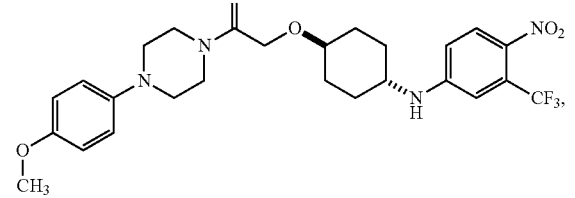
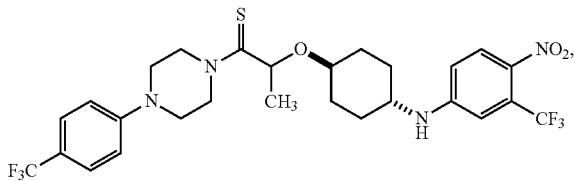
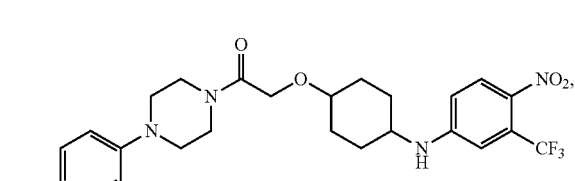
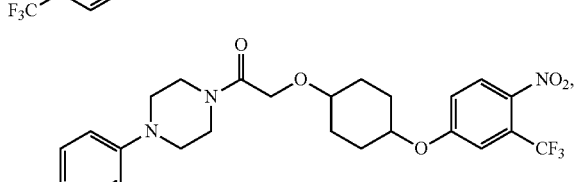

-continued

-continued

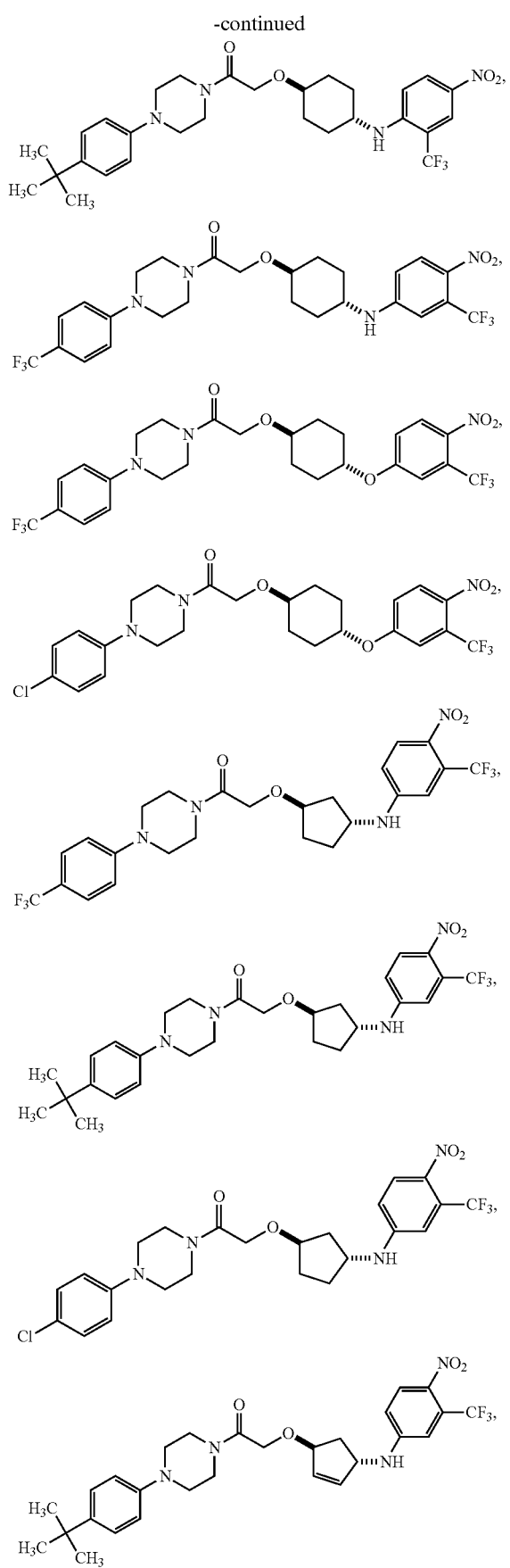

-continued

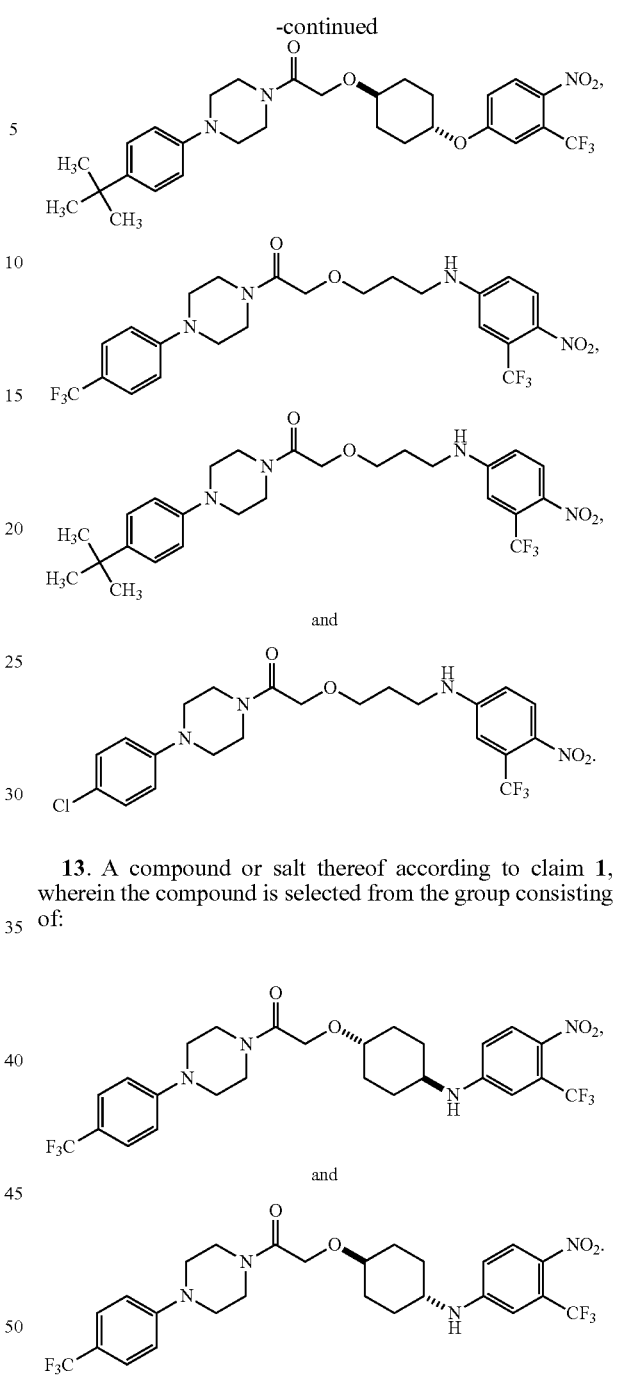

13. A compound or salt thereof according to claim 1, wherein the compound is selected from the group consisting of:

14. A compound or salt of claim 1, wherein the compound or salt is active against *Haemonchus contortus* resistant to one or more anthelmintic agents selected from the group consisting of an avermectin, a benzimidazole derivative, levamisole, and pyrantel.

15. A pharmaceutical composition, wherein the composition comprises:
    at least one compound or salt of claim 1, and
    at least one excipient.

16. A method of treating a nematode infection in an animal, wherein the method comprises administering at least one compound or salt of claim 1 to the animal.

17. A method of claim 16, wherein the nematode infection comprises an infection by at least one of *Trichostrongylus* axei, *Trichostrongylus colubriformis, Haemonchus contortus, Ascaridia galli,* and *Oesophagostomum dentatum.*

18. A method of claim 16, wherein the animal is a sheep.

19. A method of claim 16, wherein the animal is a bovine animal.

20. A kit, wherein the kit comprises:
   at least one compound or salt of claim 1, and
      at least one other component selected from the group consisting of an excipient, an active ingredient, instructions for combining the compound or salt with an excipient or active ingredient, an apparatus for combining the compound or salt with an excipient or active ingredient, instructions for administering the compound or salt to an animal, an apparatus for administering the compound or salt to an animal, and a diagnostic tool.

21. A compound of the formula

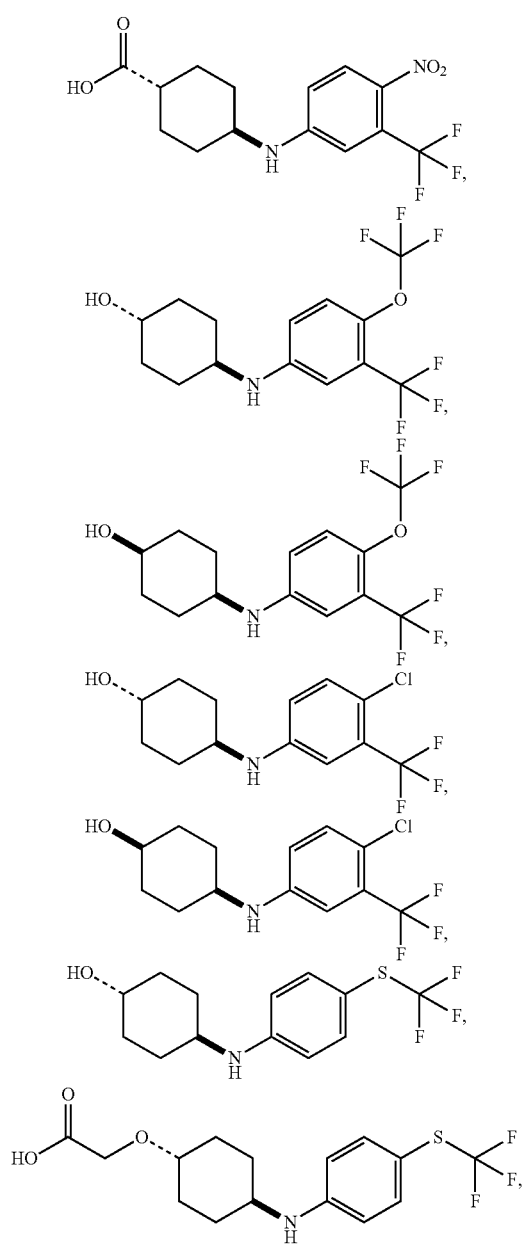

22. A process for preparing a compound of claim 1, wherein the process utilizes an intermediate compound selected from the group consisting of:

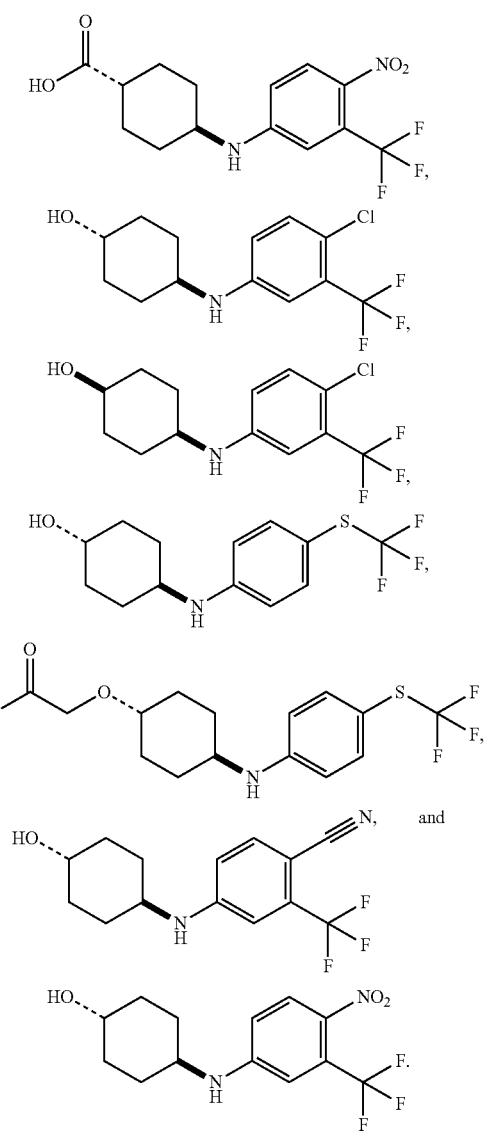

23. A compound or salt thereof according to claim 1, wherein the compound is

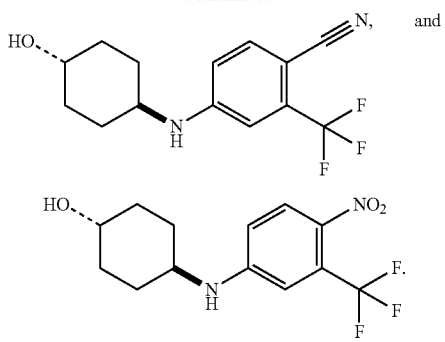

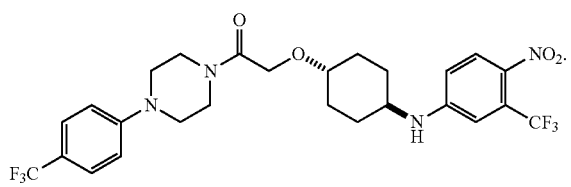

24. A compound or salt thereof according claim 3, wherein the compound is selected from the group consisting of:

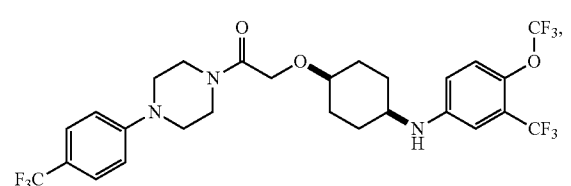

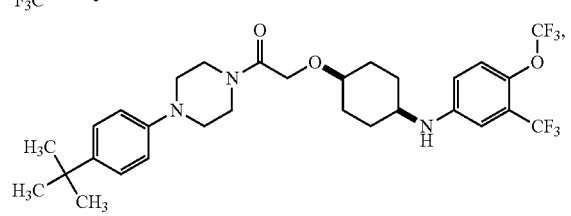

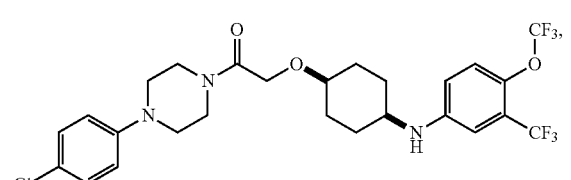

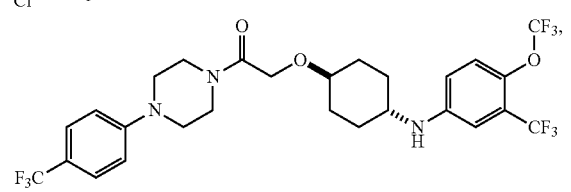

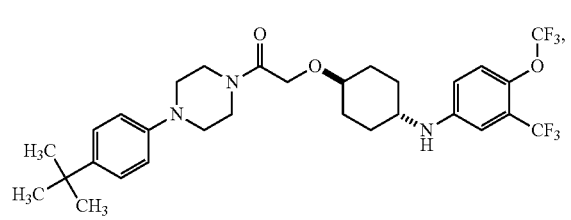

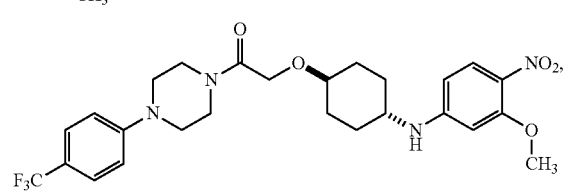

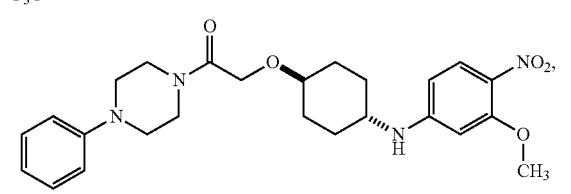

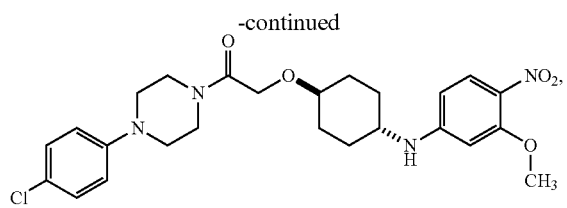

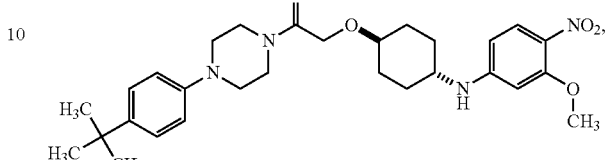

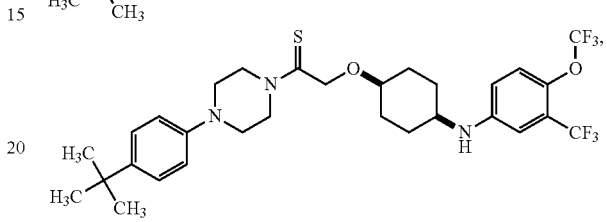

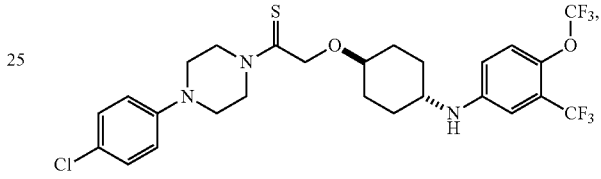

and

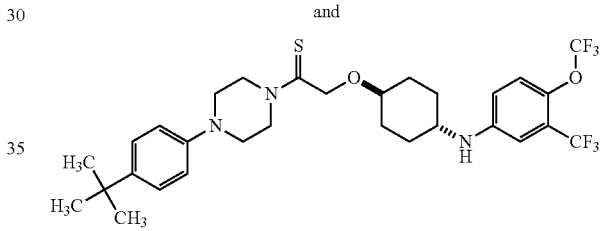

25. A compound or salt of claim 3, wherein the compound or salt is active against *Haemonchus contortus* resistant to one or more anthelmintic agents selected from the group consisting of an avermectin, a benzimidazole derivative, levamisole, and pyrantel.

26. A pharmaceutical composition, wherein the composition comprises at least one compound or salt of claim 3, and at least one excipient.

27. A method of treating a nematode infection in an animal, wherein the method comprises administering at least one compound or salt of claim 3 to the animal.

28. A method of claim 27, wherein the nematode infection comprises an infection by at least one of *Trichostrongylus axei, Trichostrongylus colubriformis, Haemonchus contortus, Ascaridia galli*, and *Oesophagostomum dentatum*.

29. A method of claim 27, wherein the animal is a sheep or a bovine animal.

30. A kit, wherein the kit comprises:
at least one compound or salt of claim 3, and
at least one other component selected from the group consisting of an excipient, an active ingredient, instructions for combining the compound or salt with an excipient or active ingredient, an apparatus for combining the compound or salt with an excipient or active ingredient, instructions for administering the compound or salt to an animal, an apparatus for administering the compound or salt to an animal, and a diagnostic tool.

31. A process for preparing a compound of claim 3, wherein the process utilizes an intermediate compound selected from the group consisting of:
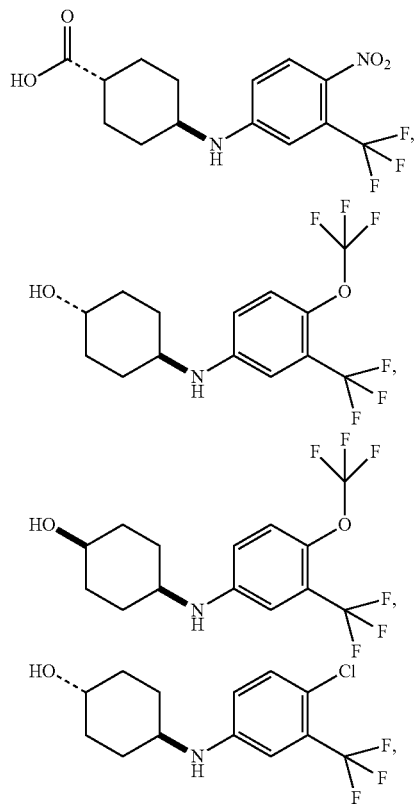
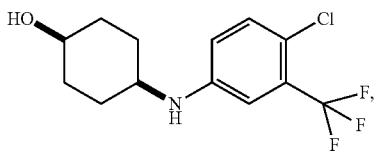
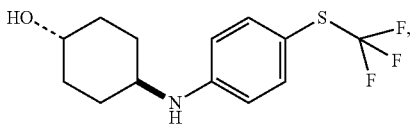
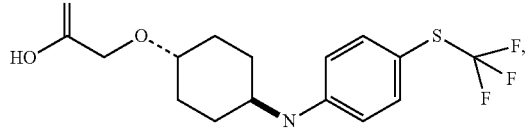
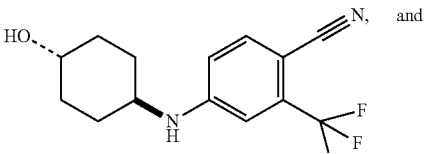
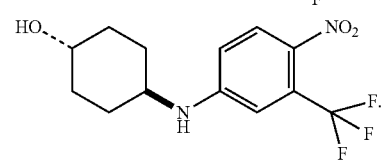
* * * * *